United States Patent
Leung et al.

(10) Patent No.: US 7,375,101 B2
(45) Date of Patent: May 20, 2008

(54) BENZODIAZEPINE DERIVATIVES, PREPARATION THEREOF AND USE THEREOF

(75) Inventors: Carmen Leung, Quebec (CA); Vijayaratnam Santhakumar, Quebec (CA); Miroslaw Tomaszewski, Quebec (CA); Simon Woo, Quebec (CA)

(73) Assignee: AstraZeneca AB, Sodertalje (SE)

( * ) Notice: Subject to any disclaimer, the term of this patent is extended or adjusted under 35 U.S.C. 154(b) by 109 days.

(21) Appl. No.: 10/497,565

(22) PCT Filed: Dec. 11, 2002

(86) PCT No.: PCT/SE02/02306

§ 371 (c)(1),
(2), (4) Date: Jun. 3, 2004

(87) PCT Pub. No.: WO03/051274

PCT Pub. Date: Jun. 26, 2003

(65) Prior Publication Data

US 2005/0176699 A1   Aug. 11, 2005

(30) Foreign Application Priority Data

Dec. 14, 2001   (SE)   .................... 0104250

(51) Int. Cl.
| C07D 243/24 | (2006.01) |
| C07D 401/14 | (2006.01) |
| C07D 403/14 | (2006.01) |
| C07D 405/14 | (2006.01) |
| A61K 31/5513 | (2006.01) |

(52) U.S. Cl. ...................... 514/221; 540/509
(58) Field of Classification Search .............. 540/509; 514/221
See application file for complete search history.

(56) References Cited

U.S. PATENT DOCUMENTS

| 4,820,834 A | * | 4/1989 | Evans et al. ................. 540/504 |
| 5,218,114 A | | 6/1993 | Bock et al. |
| 5,378,838 A | | 1/1995 | Bergman et al. |
| 5,478,933 A | | 12/1995 | Showell |
| 5,521,175 A | | 5/1996 | Pineiro et al. |
| 5,696,110 A | | 12/1997 | Bourrain et al. |

FOREIGN PATENT DOCUMENTS

| EP | 0434364 | 6/1991 |
| EP | 0549039 | 6/1993 |
| WO | WO 9319052 | 9/1993 |
| WO | WO 9604254 | 2/1996 |

* cited by examiner

*Primary Examiner*—Bruck Kifle
(74) *Attorney, Agent, or Firm*—Pepper Hamilton LLP

(57) ABSTRACT

Compounds of Formula (I) wherein $R^1$, $R^3$, $R^4$, $R^5$ and X are as defined in the specification, as well as salts, enantiomers thereof and pharmaceutical compositions including the compounds are prepared. They are useful in therapy, in particular in the management of pain (I)

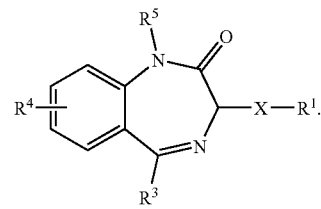

12 Claims, No Drawings

BENZODIAZEPINE DERIVATIVES, PREPARATION THEREOF AND USE THEREOF

CROSS-REFERENCE TO RELATED APPLICATIONS

This application is a US National Stage of International Application No. PCT/SE02/02306 that was filed on Dec. 11, 2002. The International Application claims priority under 35 U.S.C. § 119(a) to Swedish Application No. 0104250-6 filed Dec. 14, 2001.

BACKGROUND OF THE INVENTION

1. Field of the Invention

The present invention is directed to compounds that are useful in treating or preventing pain, septic shock, pancreatitis, edema, rhinitis, asthma, colitis, arthritis, hepatorenal syndrome, cancer, bacterial and viral infections, ulcerative colitis, and Alzheimer's Disease. More particularly, the present invention is directed to benzodiazepine derivatives that useful in treating pain.

2. Discussion of Relevant Art

Two types of bradykinin receptor are known: The B1 receptor and the B2 receptor. A number of reports indicate an important role for the B2 receptor in the pathophysiology of pain. [e.g. Hall, J. M., Morton, I. K. M. The pharmacology and immunopharmacology of kinin receptors. In: Farmer S G (Ed). The kinin system. London: Academic Press, 1997; 9-44]. Hence, compounds that are B2 antagonists are useful in the relief of pain, including chronic pain and acute pain, e.g., chronic inflammatory pain, neuropathic pain, back pain, migraine, cancer pain, visceral pain, arthritis pain and postoperative pain.

DETAILED DESCRIPTION OF THE INVENTION

Thus, the problem underlying the present invention was to develop new compounds that are novel kinin B2 antagonists.

Accordingly, in one aspect, the present invention provides compounds that are useful in treating pain.

Definitions

Unless specified otherwise within this specification, the nomenclature used in this specification generally follows the examples and rules stated in *Nomenclature of Organic Chemistry, Sections A, B, C, D, E, F, and H*, Pergamon Press, Oxford, 1979, which is incorporated by references herein for its exemplary chemical structure names and rules on naming chemical structures. Optionally, a name of a compound may be generated using a chemical naming program: ACD/ChemSketch, Version 5.09/September 2001, Advanced Chemistry Development, Inc., Toronto, Canada.

The term "$C_{m-n}$" or "$C_{m-n}$ group" used alone or as a prefix, refers to any group having m to n carbon atoms, and having 0 to n multivalent heteroatoms selected from O, S, N and P, wherein m and n are O or positive integers, and n>m. For example, "$C_{1-6}$" would refer to a chemical group having 1 to 6 carbon atoms, and having 0 to 6 multivalent heteroatoms selected from O, S, N and P.

The term "hydrocarbon" used alone or as a suffix or prefix, refers to any structure comprising only carbon and hydrogen atoms up to 14 carbon atoms.

The term "hydrocarbon radical" or "hydrocarbyl" used alone or as a suffix or prefix, refers to any structure as a result of removing one or more hydrogens from a hydrocarbon.

The term "alkyl" used alone or as a suffix or prefix, refers to monovalent straight or branched chain hydrocarbon radicals comprising 1 to about 12 carbon atoms. Unless otherwise specified, "alkyl" general includes both saturated alkyl and unsaturated alkyl.

The term "alkylene" used alone or as suffix or prefix, refers to divalent straight or branched chain hydrocarbon radicals comprising 1 to about 12 carbon atoms, which serves to links two structures together.

The term "alkenyl" used alone or as suffix or prefix, refers to a monovalent straight or branched chain hydrocarbon radical having at least one carbon-carbon double bond and comprising at least 2 up to about 12 carbon atoms.

The term "alkynyl" used alone or as suffix or prefix, refers to a monovalent straight or branched chain hydrocarbon radical having at least one carbon-carbon triple bond and comprising at least 2 up to about 12 carbon atoms.

The term "cycloalkyl," used alone or as suffix or prefix, refers to a monovalent ring-containing hydrocarbon radical comprising at least 3 up to about 12 carbon atoms.

The term "cycloalkenyl" used alone or as suffix or prefix, refers to a monovalent ring-containing hydrocarbon radical having at least one carbon-carbon double bond and comprising at least 3 up to about 12 carbon atoms.

The term "cycloalkenyl" used alone or as suffix or prefix, refers to a monovalent ring-containing hydrocarbon radical having at least one carbon-carbon triple bond and comprising about 7 up to about 12 carbon atoms.

The term "aryl" used alone or as suffix or prefix, refers to a monovalent hydrocarbon radical having one or more polyunsaturated carbon rings having aromatic character, (e.g., 4n+2 delocalized electrons) and comprising 5 up to about 14 carbon atoms.

The term "arylene" used alone or as suffix or prefix, refers to a divalent hydrocarbon radical having one or more polyunsaturated carbon rings having aromatic character, (e.g., 4n+2 delocalized electrons) and comprising 5 up to about 14 carbon atoms, which serves to links two structures together.

The term "heterocycle" used alone or as a suffix or prefix, refers to a ring-containing structure or molecule having one or more multivalent heteroatoms, independently selected from N, O, P and S, as a part of the ring structure and including at least 3 and up to about 20 atoms in the ring(s). Heterocycle may be saturated or unsaturated, containing one or more double bonds, and heterocycle may contain more than one ring. When a heterocycle contains more than one ring, the rings may be fused or unfused. Fused rings generally refer to at least two rings share two atoms therebetween. Heterocycle may have aromatic character or may not have aromatic character.

The term "heteroalkyl" used alone or as a suffix or prefix, refers to a radical formed as a result of replacing one or more carbon atom of an alkyl with one or more heteroatoms selected from N, O, P and S.

The term "heteroaromatic" used alone or as a suffix or prefix, refers to a ring-containing structure or molecule having one or more multivalent heteroatoms, independently selected from N, O, P and S, as a part of the ring structure and including at least 3 and up to about 20 atoms in the ring(s), wherein the ring-containing structure or molecule has an aromatic character (e.g., 4n+2 delocalized electrons).

The term "heterocyclic group," "heterocyclic moiety," "heterocyclic," or "heterocyclo" used alone or as a suffix or prefix, refers to a radical derived from a heterocycle by removing one or more hydrogens therefrom.

The term "heterocyclyl" used alone or as a suffix or prefix, refers a monovalent radical derived from a heterocycle by removing one hydrogen therefrom.

The term "heterocyclylene" used alone or as a suffix or prefix, refers to a divalent radical derived from a heterocycle by removing two hydrogens therefrom, which serves to links two structures together.

The term "heteroaryl" used alone or as a suffix or prefix, refers to a heterocyclyl having aromatic character.

The term "heterocylcoalkyl" used alone or as a suffix or prefix, refers to a heterocyclyl that does not have aromatic character.

The term "heteroarylene" used alone or as a suffix or prefix, refers to a heterocyclylene having aromatic character.

The term "heterocycloalkylene" used alone or as a suffix or prefix, refers to a heterocyclylene that does not have aromatic character.

The term "six-membered" used as prefix refers to a group having a ring that contains six ring atoms.

The term "five-membered" used as prefix refers to a group having a ring that contains five ring atoms.

A five-membered ring heteroaryl is a heteroaryl with a ring having five ring atoms wherein 1, 2 or 3 ring atoms are independently selected from N, O and S.

Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl.

A six-membered ring heteroaryl is a heteroaryl with a ring having six ring atoms wherein 1, 2 or 3 ring atoms are independently selected from N, O and S.

Exemplary six-membered ring heteroaryls are pyridyl, pyrazinyl, pyrimidinyl, triazinyl and pyridazinyl.

The term "substituted" used as a prefix refers to a structure, molecule or group, wherein one or more hydrogens are replaced with one or more $C_{1-12}$ hydrocarbon groups, or one or more chemical groups containing one or more heteroatoms selected from N, O, S, F, Cl, Br, I, and P. Exemplary chemical groups containing one or more heteroatoms include heterocyclyl, —$NO_2$, —OR, —Cl, —Br, —I, —F, —$CF_3$, —C(=O)R, —C(=O)OH, —$NH_2$, —SH, —NHR, —$NR_2$, —SR, —$SO_3H$, —$SO_2R$, —S(=O)R, —CN, —OH, —C(=O)OR, —C(=O)$NR_2$, NRC(=O)R, oxo (=O), imino (=NR), thio (=S), and oximino (=N—OR), wherein each "R" is a $C_{1-12}$ hydrocarbyl. For example, substituted phenyl may refer to nitrophenyl, pyridylphenyl, methoxyphenyl, chlorophenyl, aminophenyl, etc., wherein the nitro, pyridyl, methoxy, chloro, and amino groups may replace any suitable hydrogen on the phenyl ring.

The term "substituted" used as a suffix of a first structure, molecule or group, followed by one or more names of chemical groups refers to a second structure, molecule or group, which is a result of replacing one or more hydrogens of the first structure, molecule or group with the one or more named chemical groups. For example, a "phenyl substituted by nitro" refers to nitrophenyl.

The term "optionally substituted" refers to both groups, structures, or molecules that are substituted and those that are not substituted.

Heterocycle includes, for example, monocyclic heterocycles such as: aziridine, oxirane, thiirane, azetidine, oxetane, thietane, pyrrolidine, pyrroline, imidazolidine, pyrazolidine, pyrazoline, dioxolane, sulfolane 2,3-dihydrofuran, 2,5-dihydrofuran tetrahydrofuran, thiophane, piperidine, 1,2,3,6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide.

In addition, heterocycle includes aromatic heterocycles, for example, pyridine, pyrazine, pyrimidine, pyridazine, thiophene, furan, furazan, pyrrole, imidazole, thiazole, oxazole, pyrazole, isothiazole, isoxazole, 1,2,3-triazole, tetrazole, 1,2,3-thiadiazole, 1,2,3-oxadiazole, 1,2,4-triazole, 1,2,4-thiadiazole, 1,2,4-oxadiazole, 1,3,4-triazole, 1,3,4-thiadiazole, and 1,3,4-oxadiazole.

Additionally, heterocycle encompass polycyclic heterocycles, for example, indole, indoline, isoindoline, quinoline, tetrahydroquinoline, isoquinoline, tetrahydroisoquinoline, 1,4-benzodioxan, coumarin, dihydrocoumarin, benzofuran, 2,3-dihydrobenzofuran, isobenzofuran, chromene, chroman, isochroman, xanthene, phenoxathiin, thianthrene, indolizine, isoindole, indazole, purine, phthalazine, naphthyridine, quinoxaline, quinazoline, cinnoline, pteridine, phenanthridine, perimidine, phenanthroline, phenazine, phenothiazine, phenoxazine, 1,2-benzisoxazole, benzothiophene, benzoxazole, benzthiazole, benzimidazole, benztriazole, thioxanthine, carbazole, carboline, acridine, pyrolizidine, and quinolizidine.

In addition to the polycyclic heterocycles described above, heterocycle includes polycyclic heterocycles wherein the ring fusion between two or more rings includes more than one bond common to both rings and more than two atoms common to both rings. Examples of such bridged heterocycles include quinuclidine, diazabicyclo[2.2.1]heptane and 7-oxabicyclo[2.2.1]heptane.

Heterocyclyl includes, for example, monocyclic heterocyclyls, such as: aziridinyl, oxiranyl, thiiranyl, azetidinyl, oxetanyl, thietanyl, pyrrolidinyl, pyrrolinyl, imidazolidinyl, pyrazolidinyl, pyrazolinyl, dioxolanyl, sulfolanyl, 2,3-dihydrofuranyl, 2,5-dihydrofuranyl, tetrahydrofuranyl, thiophanyl, piperidinyl, 1,2,3,6-tetrahydro-pyridinyl, piperazinyl, morpholinyl, thiomorpholinyl, pyranyl, thiopyranyl, 2,3-dihydropyranyl, tetrahydropyranyl, 1,4-dihydropyridinyl, 1,4-dioxanyl, 1,3-dioxanyl, dioxanyl, homopiperidinyl, 2,3,4,7-tetrahydro-1H-azepinyl, homopiperazinyl, 1,3-dioxepanyl, 4,7-dihydro-1,3-dioxepinyl, and hexamethylene oxidyl.

In addition, heterocyclyl includes aromatic heterocyclyls or heteroaryl, for example, pyridinyl, pyrazinyl, pyrimidinyl, pyridazinyl, thienyl, furyl, furazanyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4 oxadiazolyl.

Additionally, heterocyclyl encompasses polycyclic heterocylyls (including both aromatic or non-aromatic), for example, indolyl, indolinyl, isoindolinyl, quinolinyl, tetrahydroquinolinyl, isoquinolinyl, tetrahydroisoquinolinyl, 1,4-benzodioxanyl, coumarinyl, dihydrocoumarinyl, benzofuranyl, 2,3-dihydrobenzofuranyl, isobenzofuranyl, chromenyl, chromanyl, isochromanyl, xanthenyl, phenoxathiinyl, thianthrenyl, indolizinyl, isoindolyl, indazolyl, purinyl, phthalazinyl, naphthyridinyl, quinoxalinyl, quinazolinyl, cinnolinyl, pteridinyl, phenanthridinyl, perimidinyl, phenanthrolinyl, phenazinyl, phenothiazinyl, phenoxazinyl, 1,2-benzisoxazolyl, benzothiophenyl, benzoxazolyl, benzthiazolyl, benzimidazolyl, benztriazolyl, thioxanthinyl, carbazolyl, carbolinyl, acridinyl, pyrolizidinyl, and quinolizidinyl.

In addition to the polycyclic heterocyclyls described above, heterocyclyl includes polycyclic heterocyclyls wherein the ring fusion between two or more rings includes more than one bond common to both rings and more than two atoms common to both rings. Examples of such bridged heterocycles include quinuclidinyl, diazabicyclo[2.2.1]heptyl; and 7-oxabicyclo[2.2.1]heptyl.

The term "alkoxy" used alone or as a suffix or prefix, refers to radicals of the general formula —O—R, wherein R is selected from a hydrocarbon radical. Exemplary alkoxy includes methoxy, ethoxy, propoxy, isopropoxy, butoxy, t-butoxy, isobutoxy, cyclopropylmethoxy, allyloxy, and propargyloxy.

The term "amine" or "amino" used alone or as a suffix or prefix, refers to radicals of the general formula —NRR', wherein R and R' are independently selected from hydrogen or a hydrocarbon radical.

"Acyl" used alone, as a prefix or suffix, means —C(=O)—R, wherein R is an optionally substituted hydrocarbyl, hydrogen, amino or alkoxy. Acyl groups include, for example, acetyl, propionyl, benzoyl, phenyl acetyl, carboethoxy, and dimethylcarbamoyl.

Halogen includes fluorine, chlorine, bromine and iodine.

"Halogenated," used as a prefix of a group, means one or more hydrogens on the group is replaced with one or more halogens.

"RT" or "rt" means room temperature.

A first ring group being "fused" with a second ring group means the first ring and the second ring share at least two atoms therebetween.

"Link," "linked," or "linking," unless otherwise specified, means covalently linked or bonded.

Description of Preferred Embodiments

In one aspect, the present invention provides a compound of formula (I), pharmaceutically acceptable salts thereof, diasteriomers thereof, enantiomers thereof, or mixtures thereof:

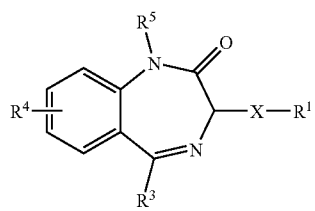
(I)

wherein $R^1$ is selected from optionally substituted acyl, optionally substituted alkyl-oxycarbonyl, optionally substituted alkyl, optionally substituted heteroalkyl, optionally substituted cycloalkyl, optionally substituted aryl; optionally substituted heterocyclyl; optionally substituted aryl-$C_{1-6}$alkyl, and optionally substituted heterocyclyl-$C_{1-6}$alkyl; or a divalent $C_{1-12}$ group that together with a second nitrogen of X to form a ring;

X is a divalent group including a first nitrogen atom and the second nitrogen atom, wherein a first group (e.g., the 2H,1,4benzodiazepin-2-one group of formula (I)) is linked to the first nitrogen atom and $R^1$ is linked to the second nitrogen atom, and wherein the first and second nitrogen atoms are separated by either one carbon atom, or two carbon atoms wherein said two carbon atoms have a double bond therebetween;

$R^3$ is optionally substituted aryl, optionally substituted $C_{1-12}$alkyl, optionally substituted $C_{3-12}$cycloalkyl, or optionally substituted heterocyclyl;

$R^4$ is, at each position, independently —H, halogen, optionally substituted alkyl, optionally substituted heteroalkyl, nitro, cyano, hydroxy, —$OR^6$, —$SR^6$, —$S(=O)R^6$, —$S(=O)_2R^6$, —$C(=O)R^6$, —$C(=S)R^6$, —$NR^7R^6$, —$C(=O)NR^7R^6$, —$NR^7C(=O)R^6$, —$SO_2NR^7R^6$, —$NR^7SO_2R^6$, or —$C(=O)OR^6$; and $R^5$, $R^6$ and $R^7$ are independently —H, optionally substituted $C_{1-6}$alkyl.

In another aspect, the compounds of the present invention are those of formula (I), pharmaceutically acceptable salts thereof, diasteriomers thereof, enantiomers thereof, or mixtures thereof, wherein $R^1$ is selected from optionally substituted acyl, optionally substituted alkyl-oxycarbonyl, optionally substituted alkyl, optionally substituted heteroalkyl, optionally substituted cycloalkyl, optionally substituted aryl; optionally substituted heterocyclyl; optionally substituted aryl-$C_{1-6}$alkyl, and optionally substituted heterocyclyl-$C_{1-6}$alkyl; or a divalent $C_{1-12}$ group that together with a divalent $R^2$ of X forms a portion of a ring;

X is represented by (i), (ii), (iii), (iv), (v), (vi), (vii), (viii), (ix), (x), (xi), (xii), (xiii), (xiv), (xv), (xvi), or (xvii) below:

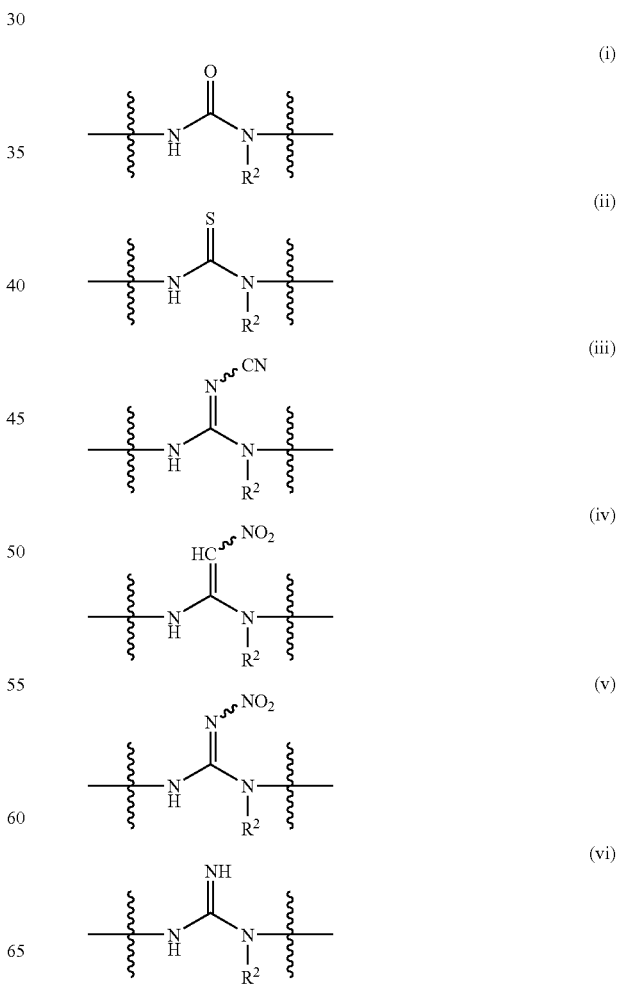

-continued (vii) 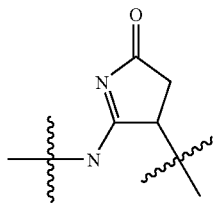

(viii) 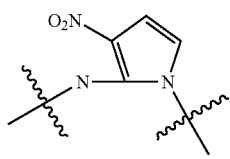

(ix) 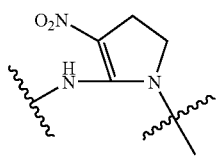

(x) 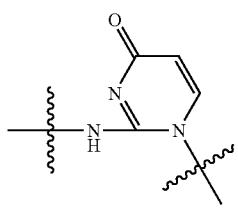

(xi) 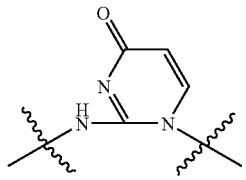

(xii) 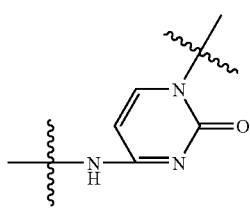

(xiii) 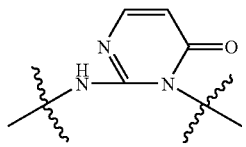

(xiv) 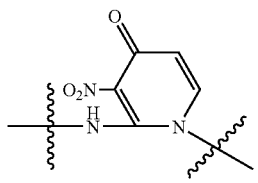

-continued (xv) 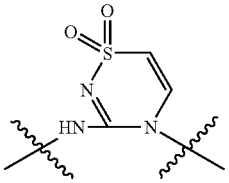

(xvi) 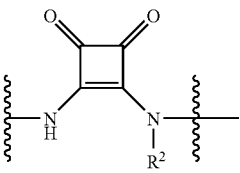

(xvii) 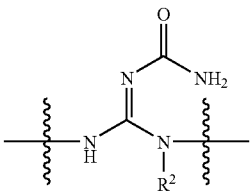

wherein R² is selected from —H, optionally substituted $C_{1-12}$alkyl, optionally substituted $C_{1-12}$heteroalkyl, optionally substituted aryl, optionally substituted heterocyclyl, and a divalent $C_{0-6}$group together with a divalent R¹ to form the portion of the ring, wherein said divalent $C_{0-6}$ group optionally includes one or more heteroatoms;

R³ is optionally substituted aryl, optionally substituted $C_{1-12}$alkyl, optionally substituted $C_{3-12}$cycloalkyl, or optionally substituted heterocyclyl;

R⁴ is, at each position, independently, —H, halogen, optionally substituted alkyl, optionally substituted heteroalkyl, nitro, cyano, hydroxy, —OR⁶, —SR⁶, —S(=O)R⁶, —S(=O)₂R⁶, —C(=O)R⁶, —C(=S)R⁶, —NR⁷R⁶, —C(=O)NR⁷R⁶, —NR⁷C(=O)R⁶, —SO₂NR⁷R⁶, —NR⁷SO₂R⁶, or —C(=O)OR⁶; and R⁵, R⁶ and R⁷ are independently —H, optionally substituted $C_{1-6}$alkyl.

More particularly, the compound of the present invention is a compound of formula (I), wherein R¹ is optionally substituted phenyl, optionally substituted naphthyl, optionally substituted isoquinolyl, optionally substituted acridinyl, optionally substituted coumarinyl, optionally substituted carbazolyl, or a first divalent group selected from optionally substituted $C_{1-12}$alkylene and optionally substituted $C_{1-12}$heteroalkylene; wherein said phenyl, naphthyl, isoquinolyl, acridinyl, coumarinyl, and carbazolyl are optionally substituted by $C_{1-6}$alkyl, $C_{1-6}$heterocyclyl or amino, wherein said $C_{1-12}$alkylene and $C_{1-12}$heteroalkylene are optionally substituted by $C_{1-6}$alkyl, aryl-$C_{1-6}$alkyl, aryl or heterocyclyl;

X is selected from formulas (i), (ii), (iii), (vi) and (xvii) below:

(i) 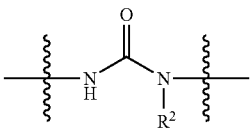

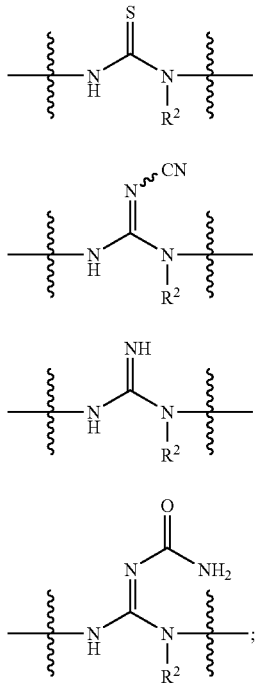

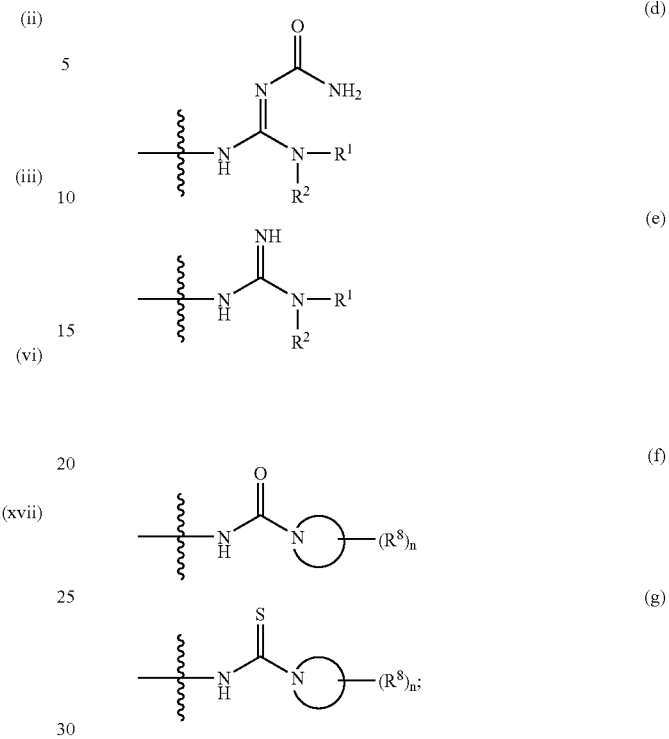

$R^2$ is —H, $C_{1-3}$alkyl, or a second divalent group selected from a single bond, an optionally substituted alkylene and an optionally substituted heteroalkylene; wherein said second divalent group together with said first divalent group forms a portion of a ring;

$R^3$ is optionally substituted aryl, optionally substituted heteroaryl or optionally substituted cycloalkyl;

$R^4$ is halogen, or $C_{1-3}$alkyl; and $R^5$ is $C_{1-3}$alkyl.

Most particularly, the compound of the present invention is a compound of formula (I), wherein —X—$R^1$ of formula (I) is selected from formulas (a), (b), (c), (d), (e), (f) and (g) below:

(a)
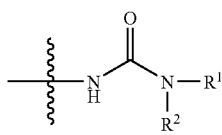

(b)
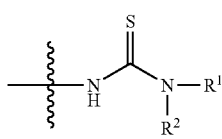

(c)
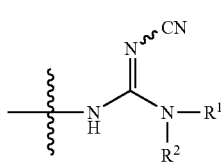

$R^1$ is optionally substituted phenyl, optionally substituted naphthyl, optionally substituted isoquinolyl, wherein said phenyl, naphthyl and isoquinolyl are optionally substituted by $C_{1-6}$alkyl, $C_{1-6}$heterocyclyl or amino;

$R^2$ is —H, or $C_{1-3}$alkyl;

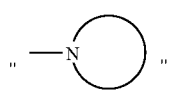

is a nitrogen containing heterocyclyl, which may be optionally substituted by one or more —$R^8$, and which includes a bond on the nitrogen that links to other group of formula (I). Exemplary nitrogen containing heterocyclyls include, but is not limited to, piperazinyl, morpholinyl, poperidyl, and pyrrolidinyl.

$R^8$ is —H, optionally substituted aryl, optionally substituted heterocyclyl, optionally substituted $C_{1-6}$alkyl, —OH, or $C_{1-6}$alkoxy, wherein $R^8$ is optionally fused with the ring of

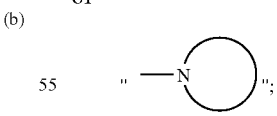

$R^3$ is optionally substituted cyclohexyl, optionally substituted phenyl, optionally substituted pyridyl, optionally substituted thienyl, or optionally substituted pyrimidinyl, wherein said cyclohexyl, phenyl, pyridyl, thienyl and pyrimidinyl are optionally substituted by halogen, methoxy, or $C_{1-3}$alkyl;

$R^4$ is halogen; and $R^5$ is methyl.

Specific examples of compounds of the present invention that may be used in practicing the present invention are listed in Table 1, below.

TABLE 1

Spreadsheet of combinatorially prepared compounds with LCMS analysis of the reaction product.

| Compound # | Structure | Target Mass | Mass Found? | Rtn Time (MS) |
|---|---|---|---|---|
| 1 | 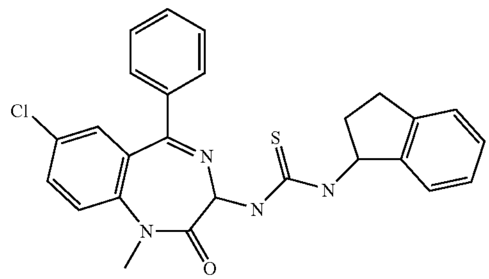 | 474.13 | Yes | 3.92 |
| 2 | 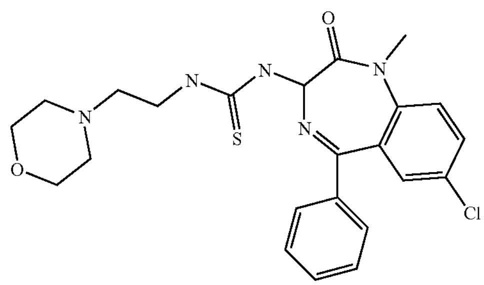 | 471.15 | Yes | 2.9 |
| 3 | 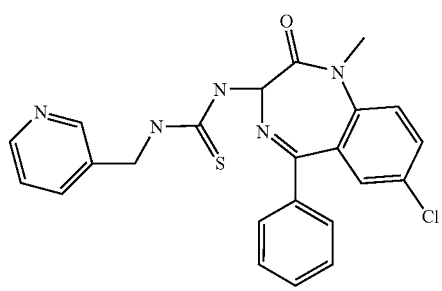 | 449.11 | Yes | 2.93 |
| 4 | 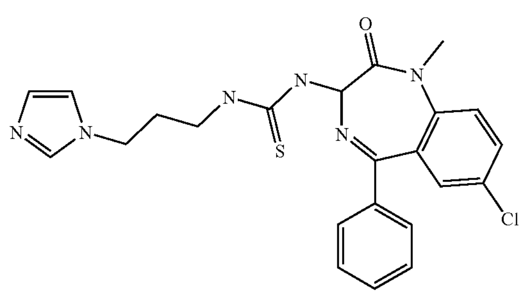 | 466.13 | No | |
| 5 | 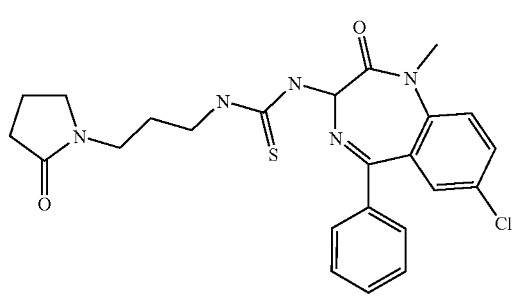 | 483.15 | Yes | 2.85 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 6 | 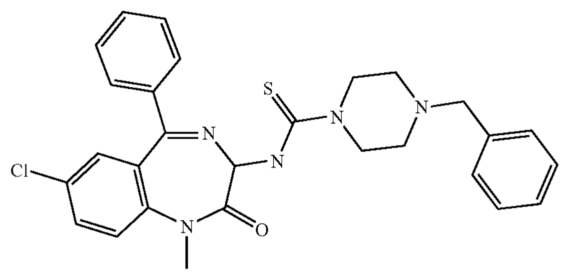 | 517.17 | Yes | 3.97 |
| 7 | 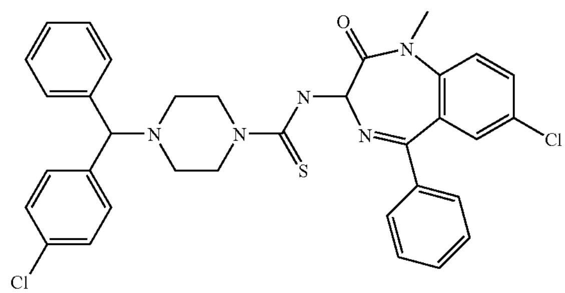 | 627.16 | No | |
| 8 | 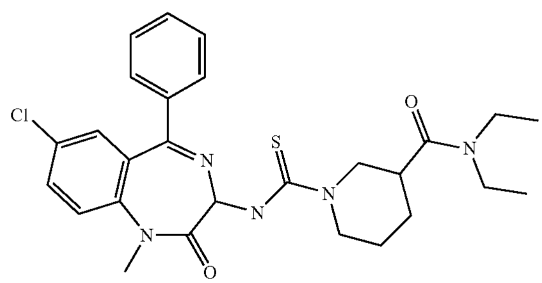 | 525.2 | Yes | 3.47 |
| 9 | 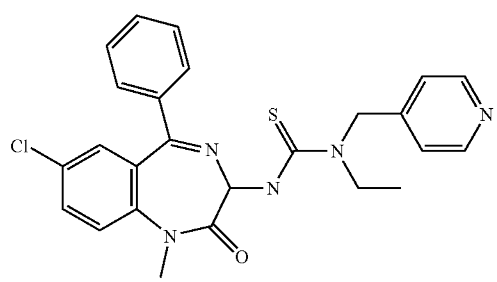 | 477.14 | Yes | 3.11 |
| 10 | 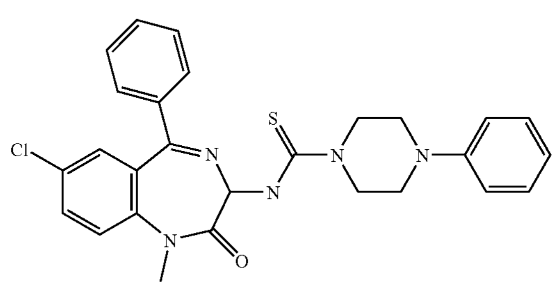 | 503.15 | No | |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 11 | 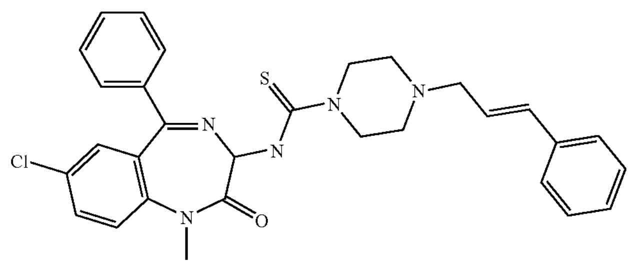 | 543.19 | Yes | 4.24 |
| 12 | 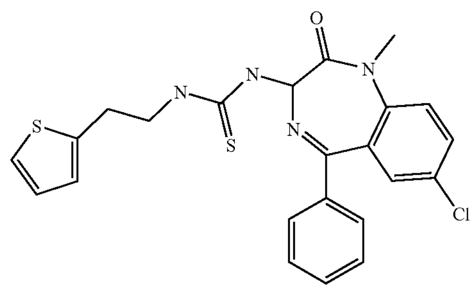 | 468.08 | Yes | 3.55 |
| 13 | 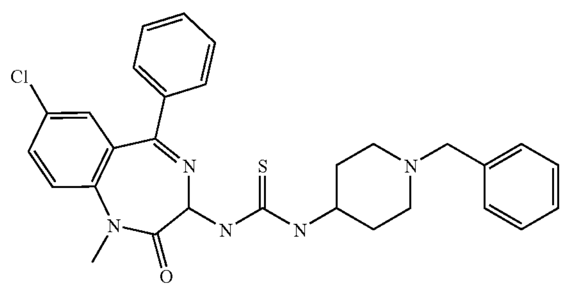 | 531.19 | No | |
| 14 | 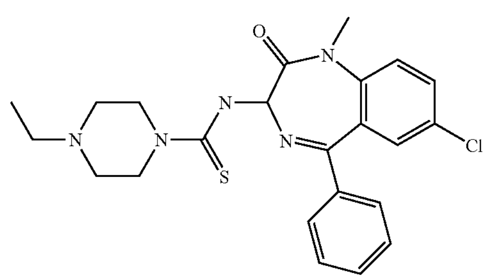 | 455.15 | Yes | 3.11 |
| 15 | 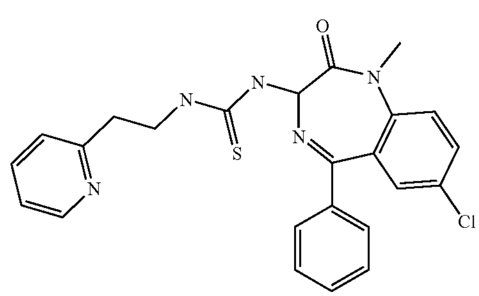 | 463.12 | Yes | 3.05 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 16 | 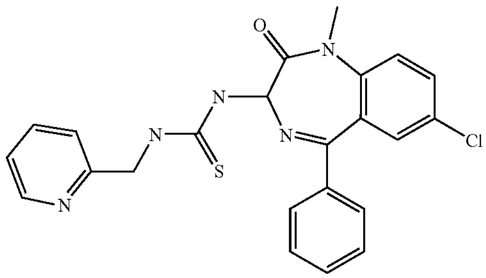 | 449.11 | Yes | 2.94 |
| 17 | 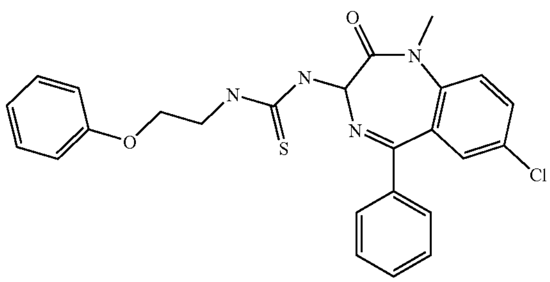 | 478.12 | Tentative | |
| 18 | 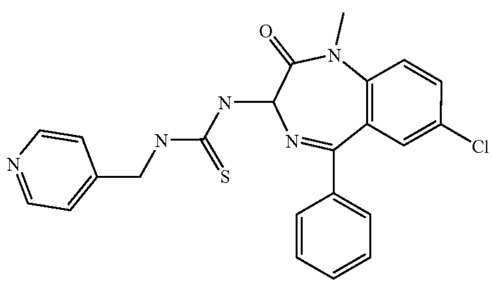 | 449.11 | Yes | 2.89 |
| 19 | 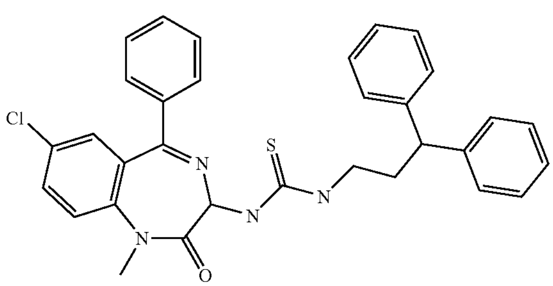 | 552.17 | Yes | 4.5 |
| 20 | 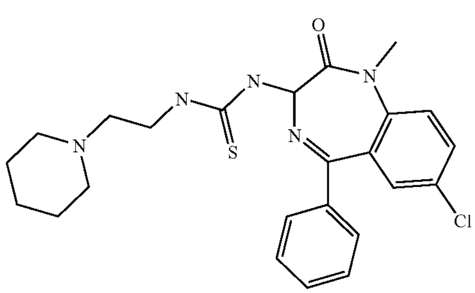 | 469.17 | Yes | 2.85 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 21 | 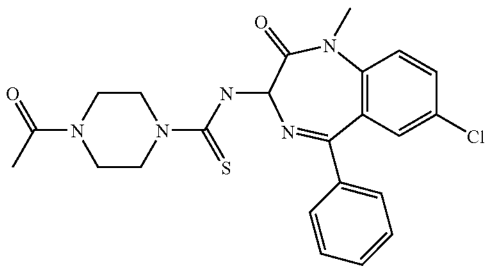 | 469.13 | Yes | 2.78 |
| 22 | 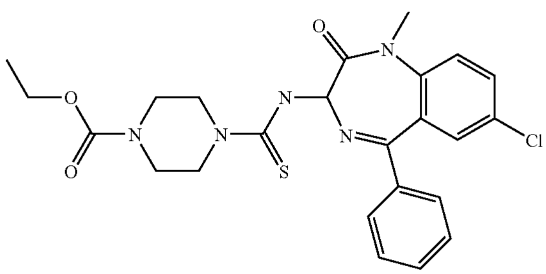 | 499.14 | Yes | 3.3 |
| 23 | 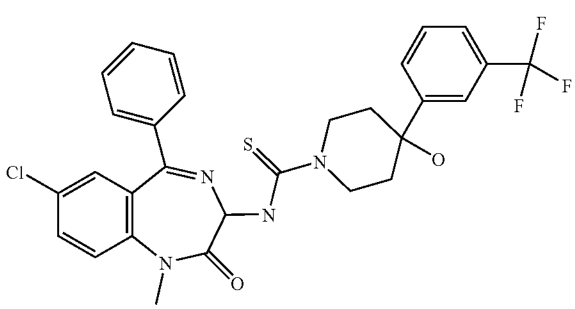 | 586.14 | Yes | 3.75 |
| 24 | 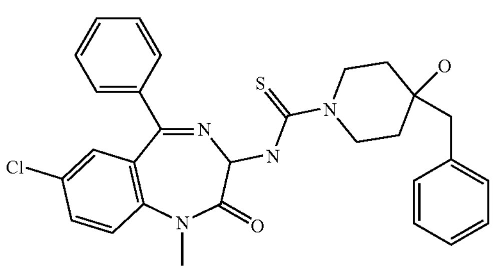 | 532.17 | Yes | 3.7 |
| 25 | 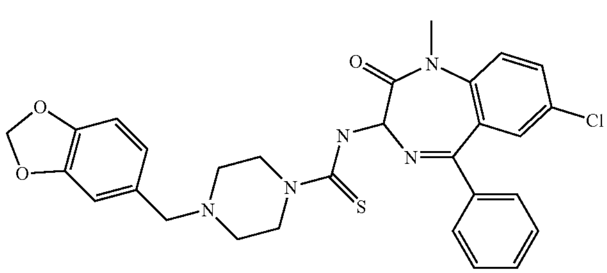 | 561.16 | Yes | 3.87 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 26 | 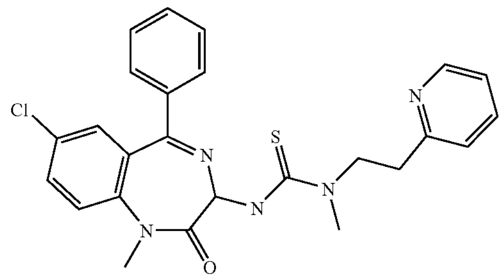 | 477.14 | Yes | 3.17 |
| 27 | 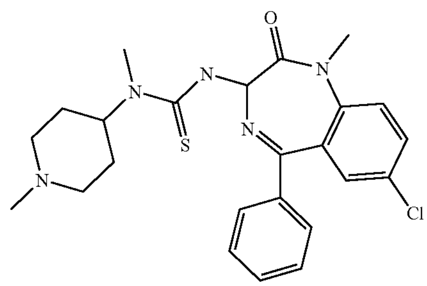 | 469.17 | Yes | 2.78 |
| 28 | 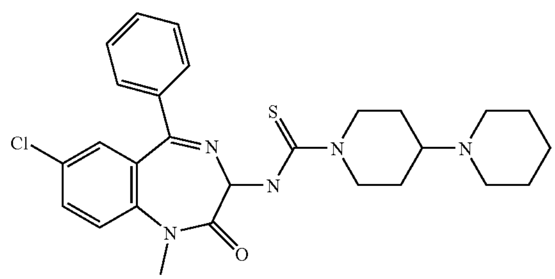 | 509.2 | Yes | 2.74 |
| 29 | 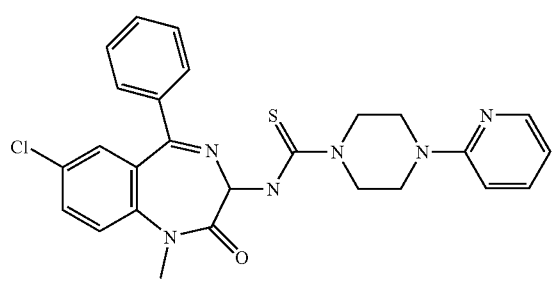 | 504.15 | Yes | 3.43 |
| 30 | 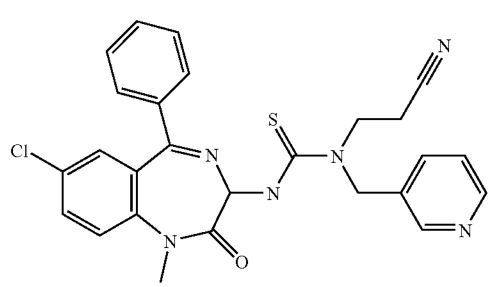 | 502.13 | Yes | 2.96 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 31 | 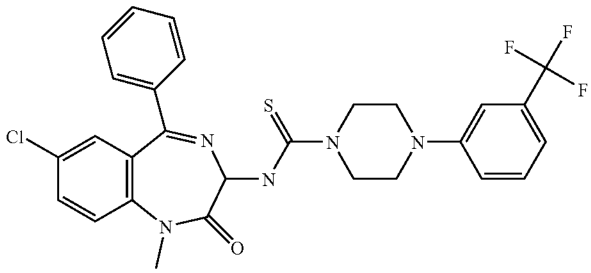 | 571.14 | Yes | |
| 32 | 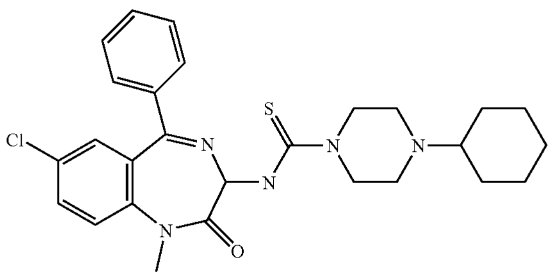 | 509.2 | Yes | 4.05 |
| 33 | 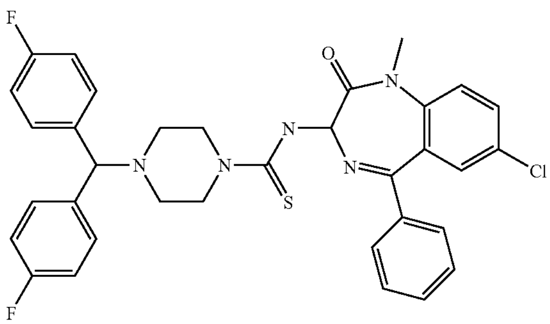 | 629.18 | Yes | |
| 34 | 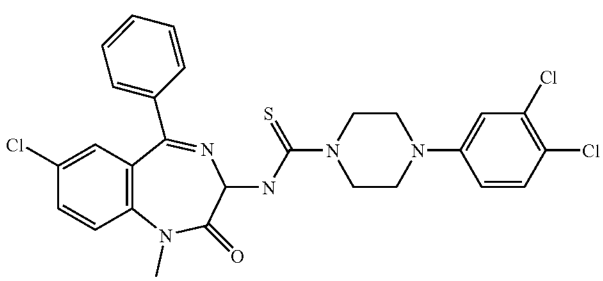 | 571.08 | No | |
| 35 | 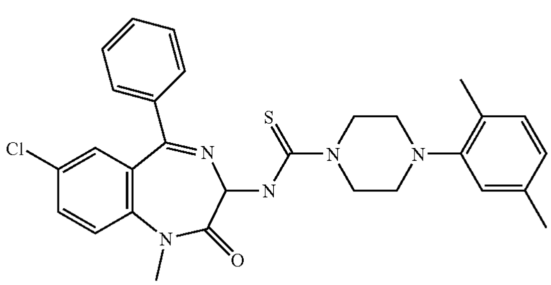 | 531.19 | Yes | 4.8 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 36 | 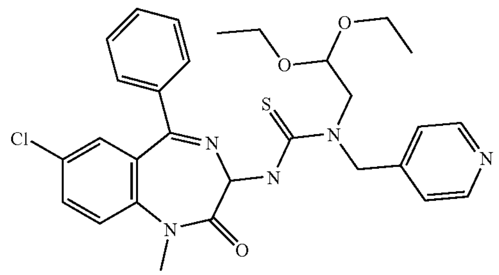 | 565.19 | No | |
| 37 | 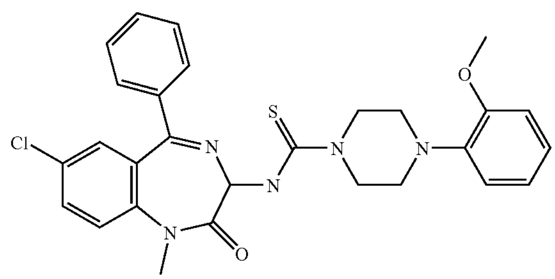 | 533.17 | Yes | 3.87 |
| 38 | 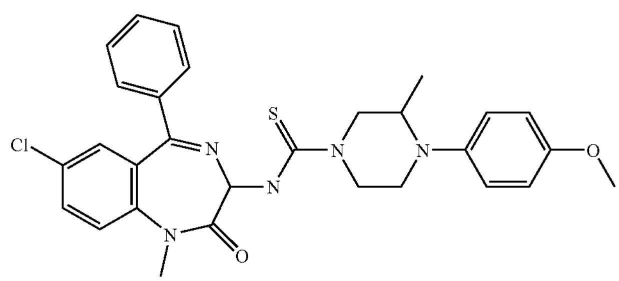 | 547.18 | Yes | 3.98 |
| 39 | 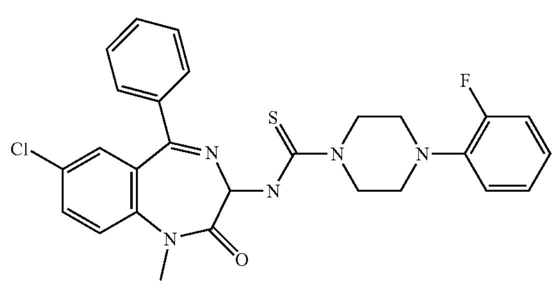 | 521.15 | Yes | 4.02 |
| 40 | 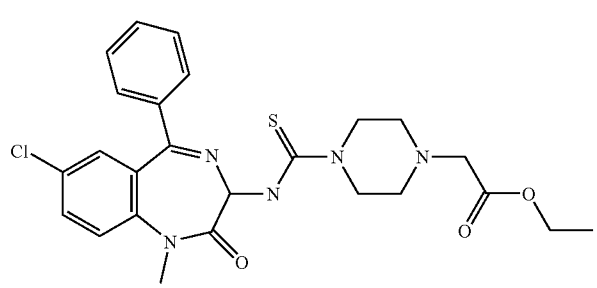 | 513.16 | Yes | 3.22 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 41 | 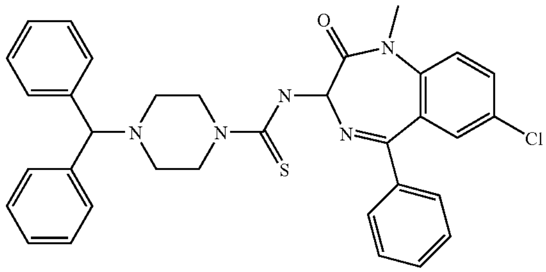 | 593.2 | Yes | |
| 42 | 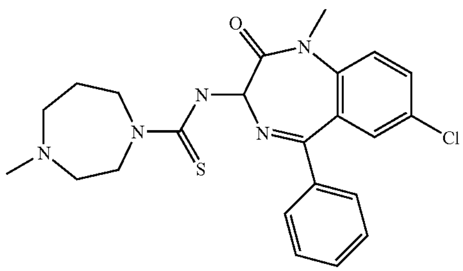 | 455.15 | Yes | 2.79 |
| 43 | 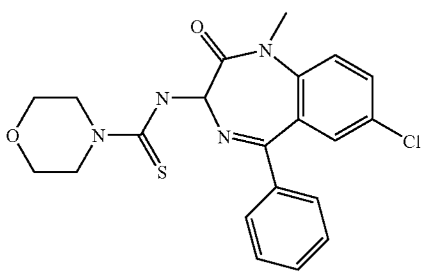 | 428.11 | Yes | 2.91 |
| 44 | 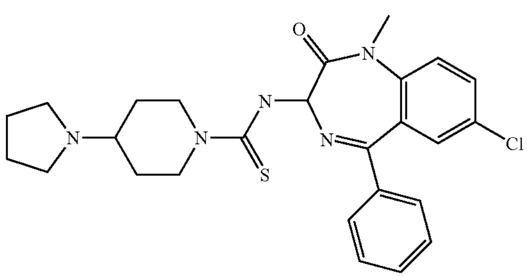 | 495.19 | Yes | 2.62 |
| 45 | 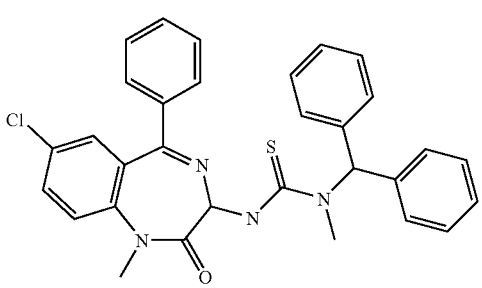 | 538.16 | Yes | 4.64 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 46 | 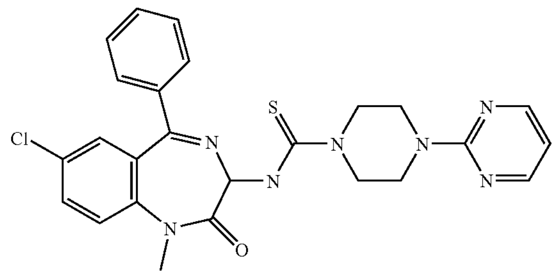 | 505.15 | Yes | 3.31 |
| 47 | 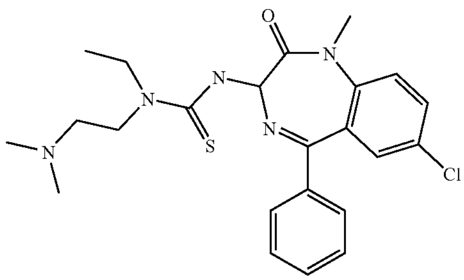 | 457.17 | Yes | 3.02 |
| 48 | 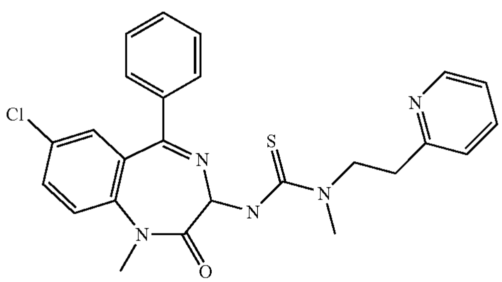 | 477.14 | Yes | 3.17 |
| 49 | 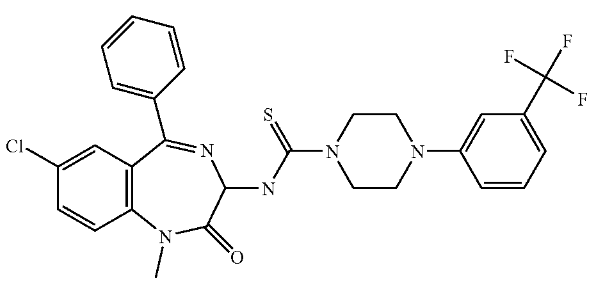 | 571.14 | Yes | 4.49 |
| 50 | 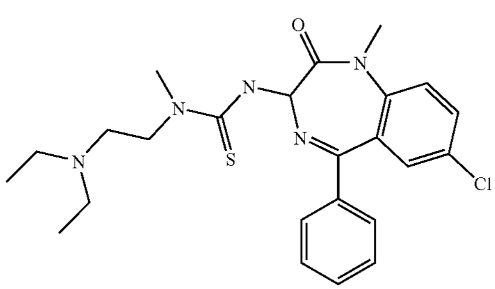 | 471.19 | Yes | 2.9 |

TABLE 1-continued

Spreadsheet of combinatorially prepared compounds with LCMS analysis of the reaction product.

| Compound # | Structure | Target Mass | Mass Found? | Rtn Time (MS) |
| --- | --- | --- | --- | --- |
| 51 | 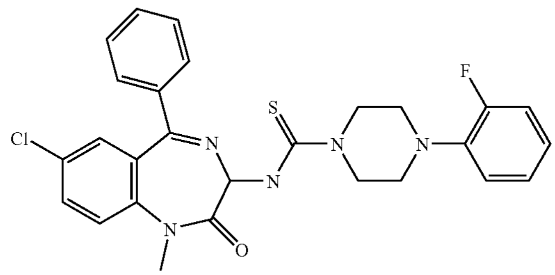 | 521.15 | Yes | 4.02 |
| 52 | 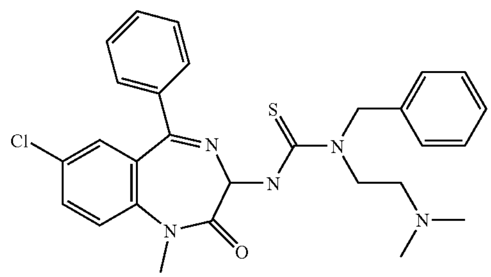 | 519.19 | Yes | 3.97 |
| 53 | 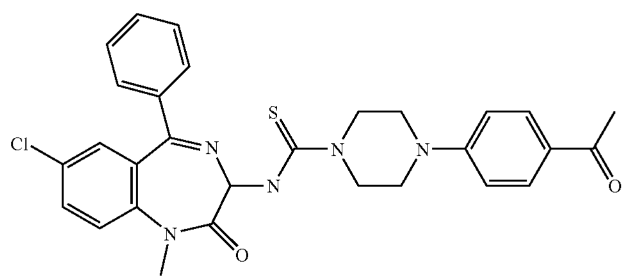 | 545.17 | Yes | 3.49 |
| 54 | 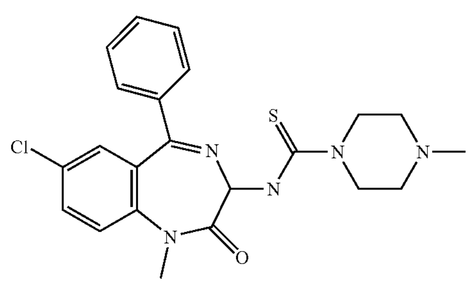 | 441.14 | Yes | 2.94 |
| 55 | 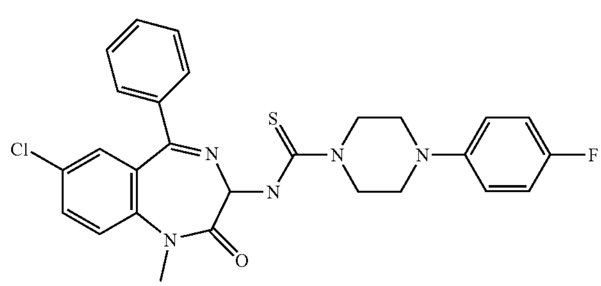 | 521.15 | Yes | 3.92 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 56 | 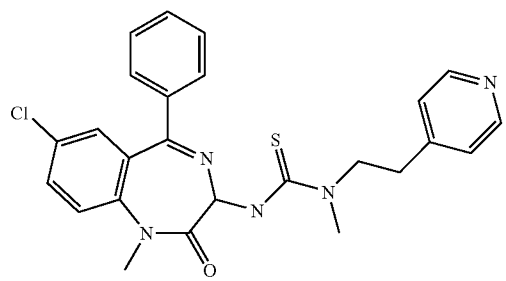 | 477.14 | Yes | 3.08 |
| 57 | 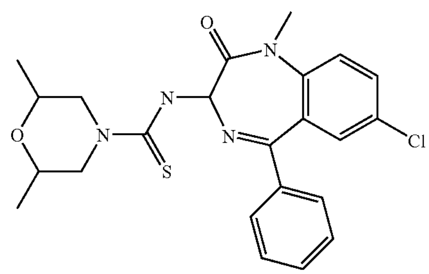 | 456.14 | Yes | 3.34 |
| 58 | 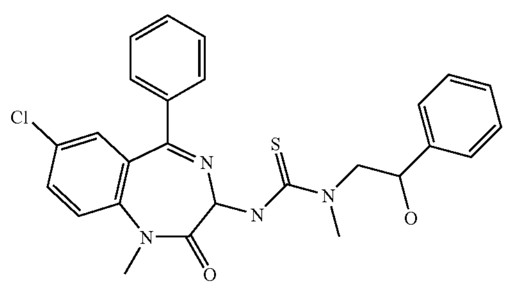 | 492.14 | Yes | 3.47 |
| 59 | 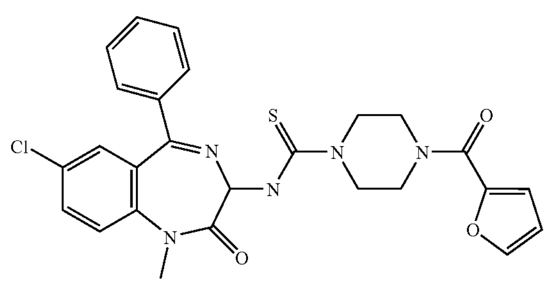 | 521.13 | Yes | 3.04 |
| 60 | 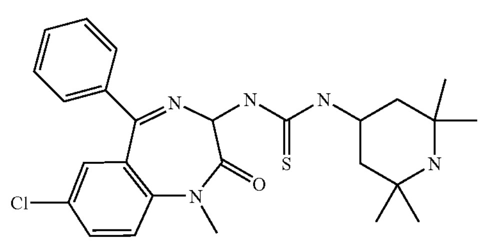 | 497.2 | Yes | 2.7 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 61 | 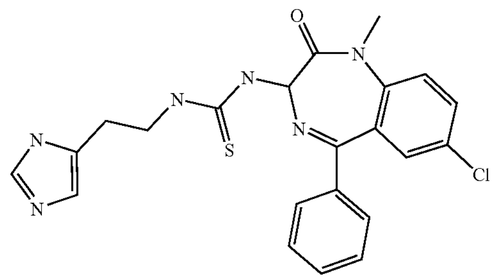 | 452.12 | Yes | 2.69 |
| 62 | 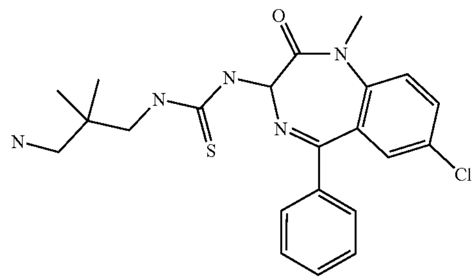 | 443.15 | Yes | 2.51 |
| 63 | 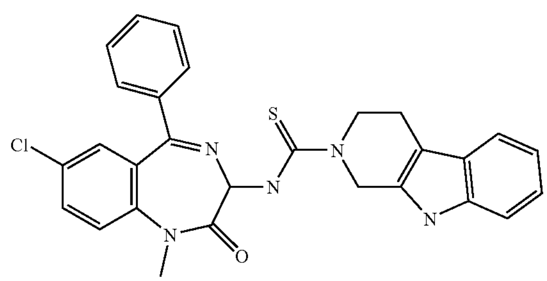 | 513.14 | Yes | 3.97 |
| 64 | 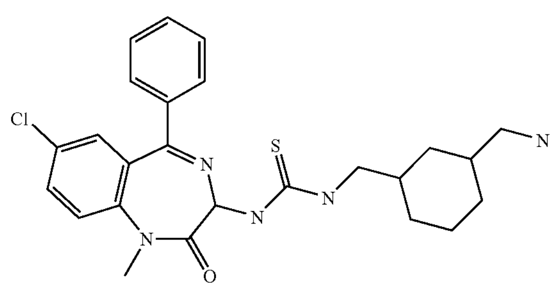 | 483.19 | Tentative | 1.63 |
| 65 | 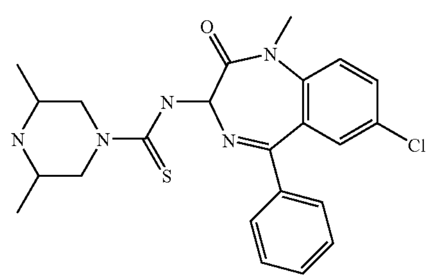 | 455.15 | Yes | 2.8 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 66 | 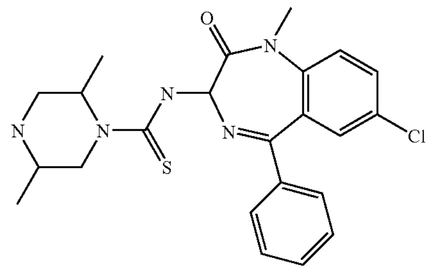 | 455.15 | Yes | 2.77 |
| 67 | 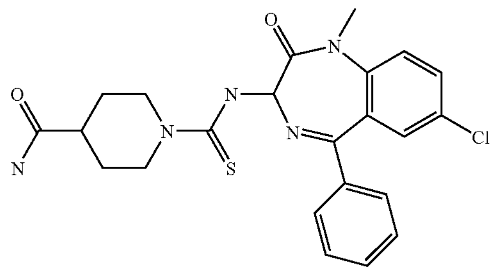 | 469.13 | Yes | 2.69 |
| 68 | 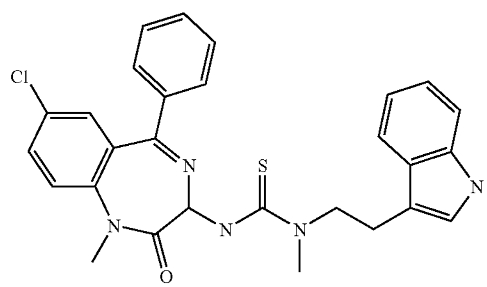 | 515.15 | Yes | 3.59 |
| 69 | 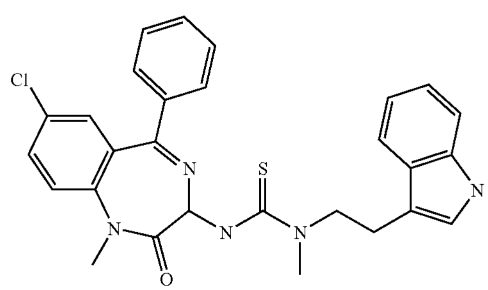 | 515.15 | Yes | 3.59 |
| 70 | 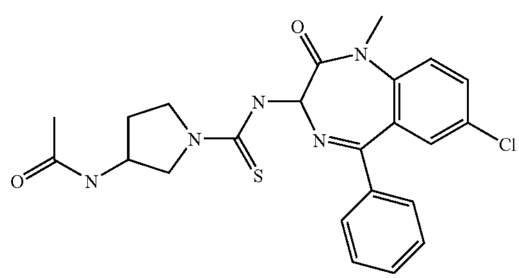 | 469.13 | Yes | 2.73 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 71 | 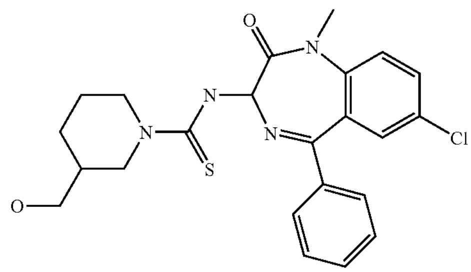 | 456.14 | Tentative | |
| 72 | 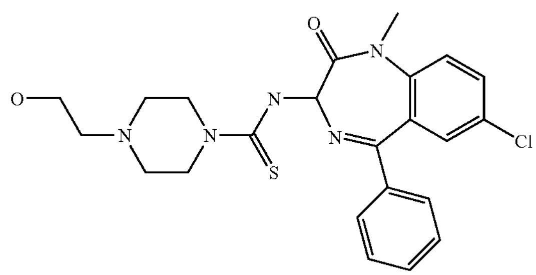 | 471.15 | Tentative | |
| 73 | 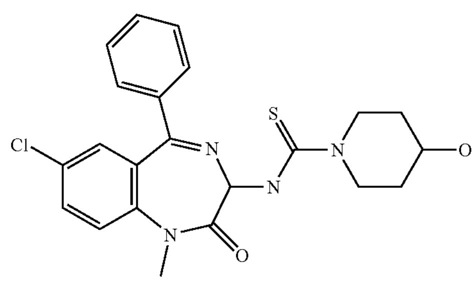 | 442.12 | No | |
| 74 | 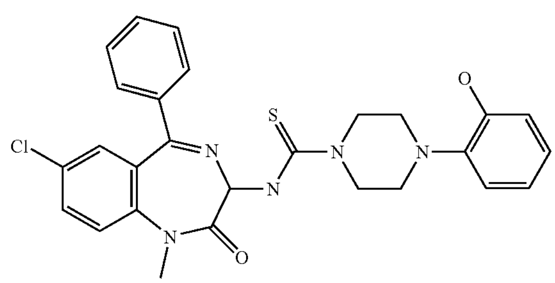 | 519.15 | Tentative | |
| 75 | 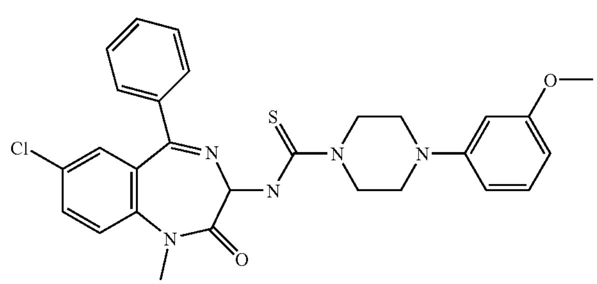 | 533.17 | No | |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 76 | 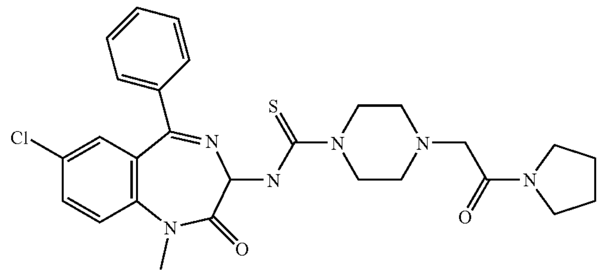 | 538.19 | No | |
| 77 | 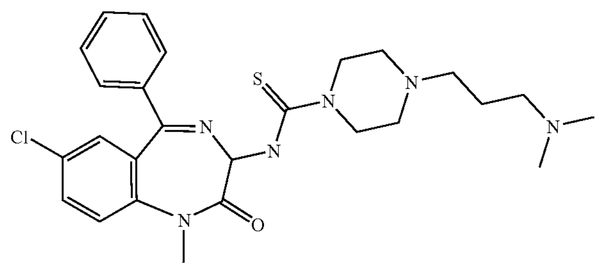 | 512.21 | No | |
| 78 | 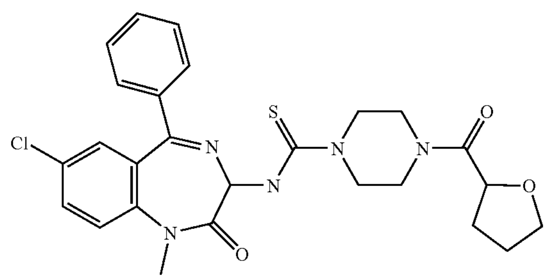 | 525.16 | Yes | 6.5 |
| 79 | 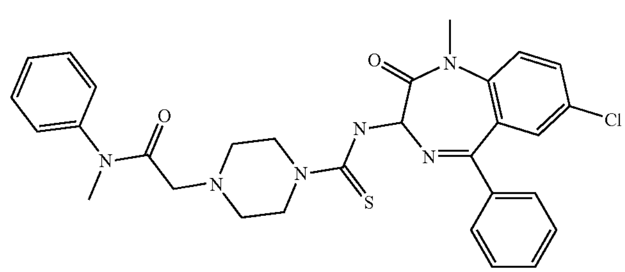 | 574.19 | No | |
| 80 | 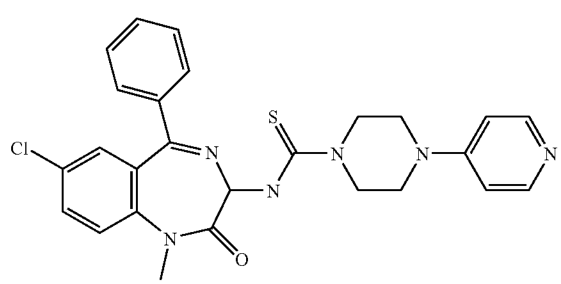 | 504.15 | Tentative | |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 81 | 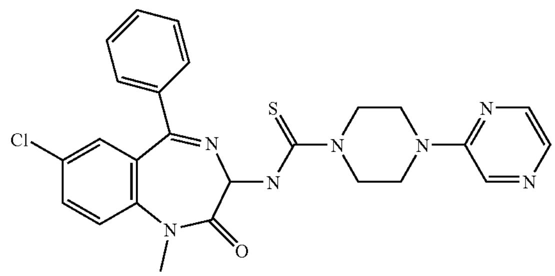 | 505.15 | No | |
| 82 | 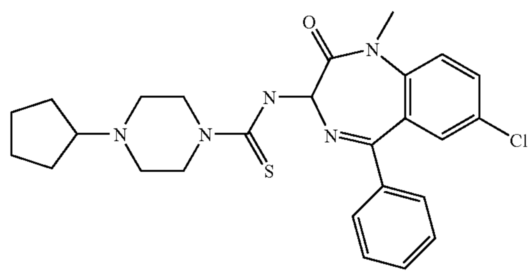 | 495.19 | No | |
| 83 | 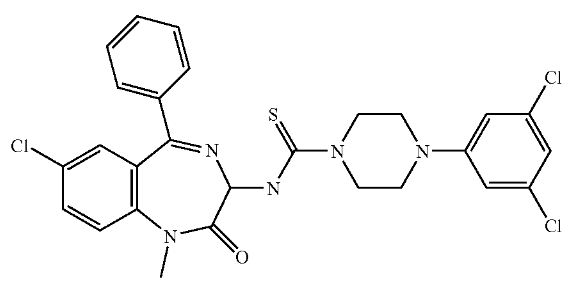 | 571.08 | No | |
| 84 | 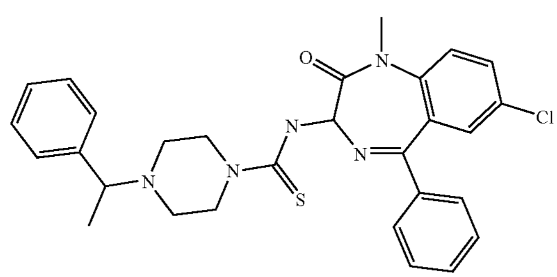 | 531.19 | Yes | 4.18 |
| 85 | 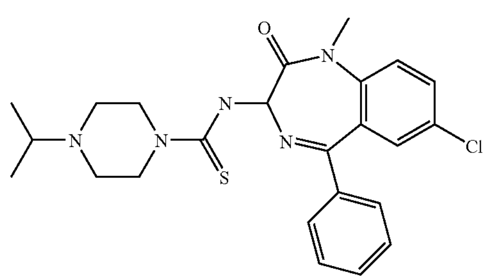 | 469.17 | Yes | 3.28 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 86 | | 616.13 | No | |
| 87 | | 455.15 | Yes | |
| 88 | | 503.15 | Yes | 5.38 |
| 89 | | 483.15 | No | |
| 90 | | 622.15 | Yes | 6.44 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 91 | 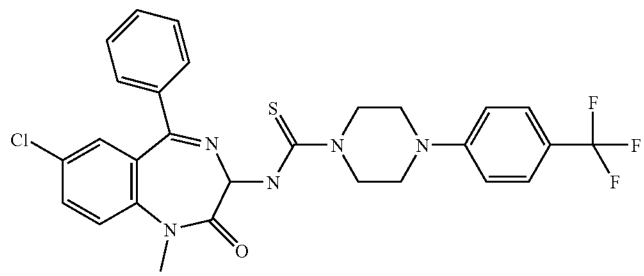 | 571.14 | No | |
| 92 | 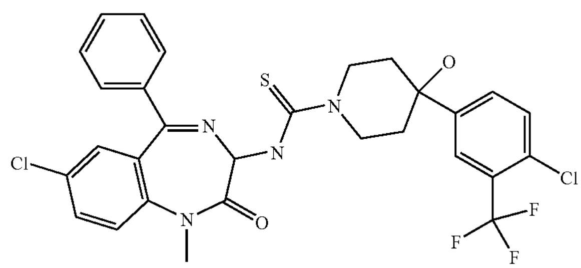 | 620.1 | Yes | 4.37 |
| 93 | 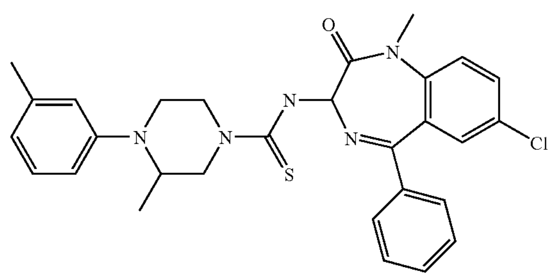 | 531.19 | No | |
| 94 | 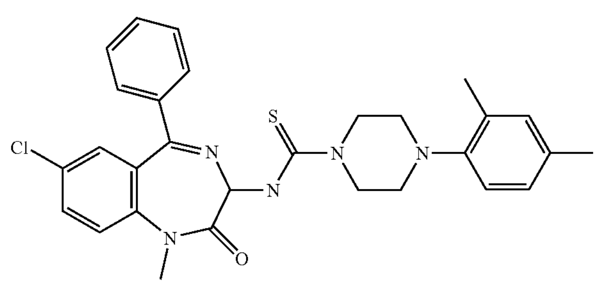 | 531.19 | No | |
| 95 | 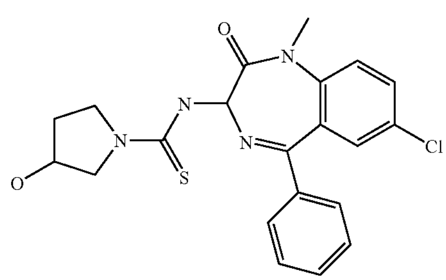 | 428.11 | Tentative | |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 96 | 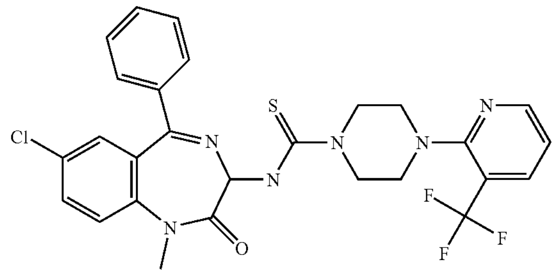 | 572.14 | Tentative | 6.45 |
| 97 | 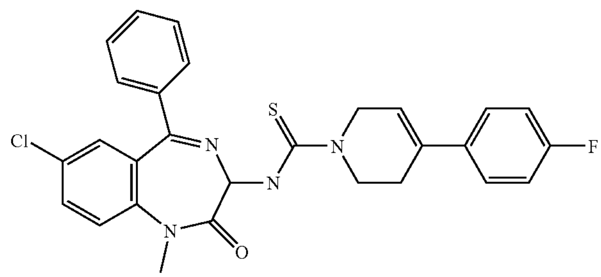 | 518.13 | No | |
| 98 | 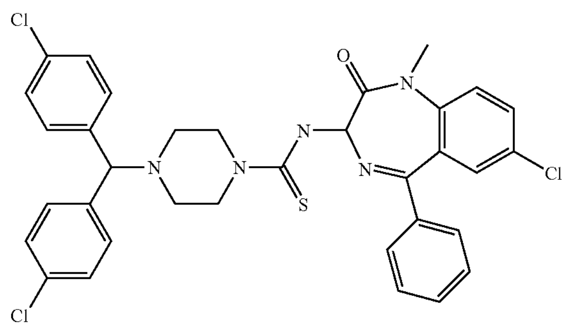 | 661.12 | Yes | |
| 99 | 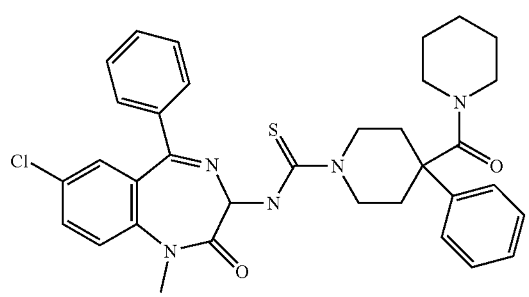 | 613.23 | Yes | 6.59 |
| 100 | 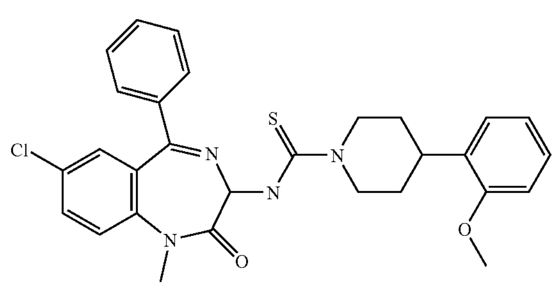 | 532.17 | No | |

TABLE 1-continued
Spreadsheet of combinatorially prepared compounds with LCMS analysis of the reaction product.
| Compound # | Structure | Target Mass | Mass Found? | Rtn Time (MS) |
|---|---|---|---|---|
| 101 | 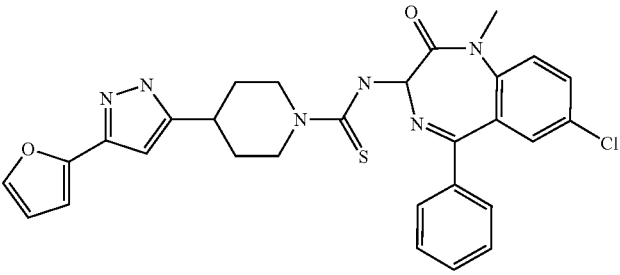 | 558.16 | No | |
| 102 | 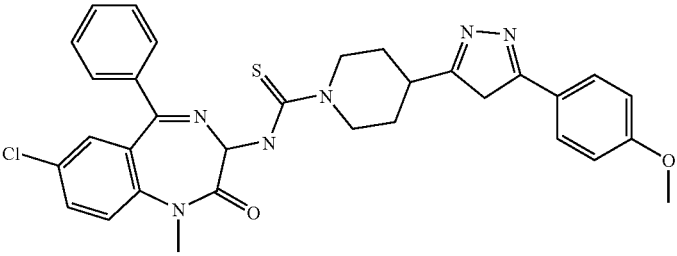 | 598.19 | No | |
| 103 | 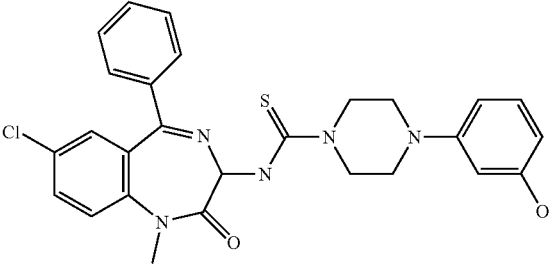 | 519.15 | No | |
| 104 | 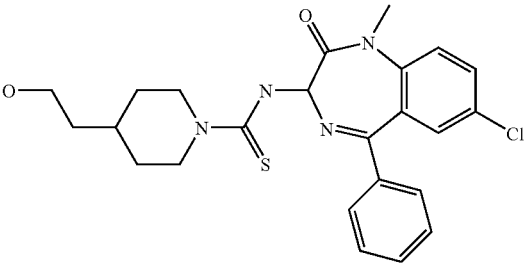 | 470.15 | Yes | |
| 105 | 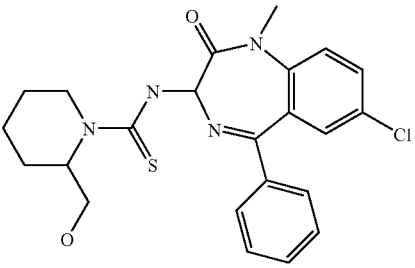 | 456.14 | Yes | |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 106 | 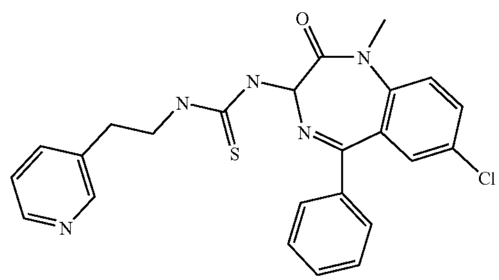 | 463.12 | Yes | |
| 107 | 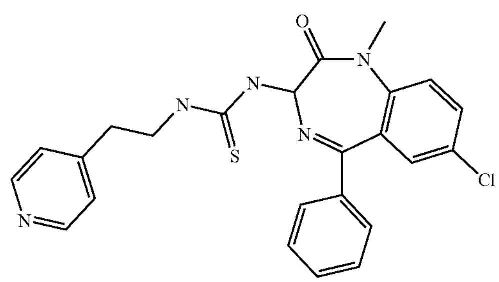 | 463.12 | Yes | 5.94 |
| 108 | 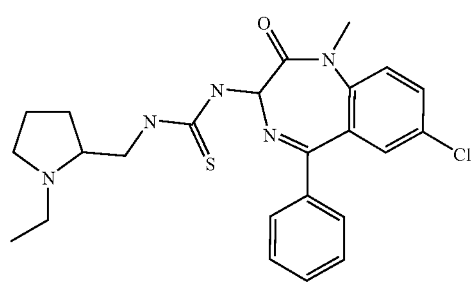 | 469.17 | Yes | 2.7 |
| 109 | 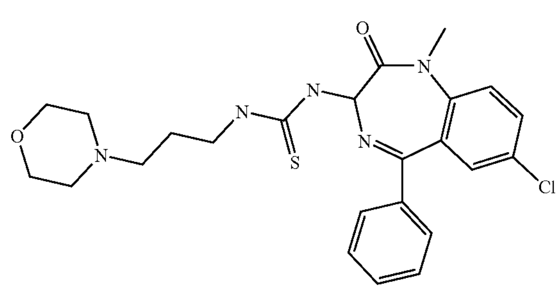 | 485.17 | No | |
| 110 | 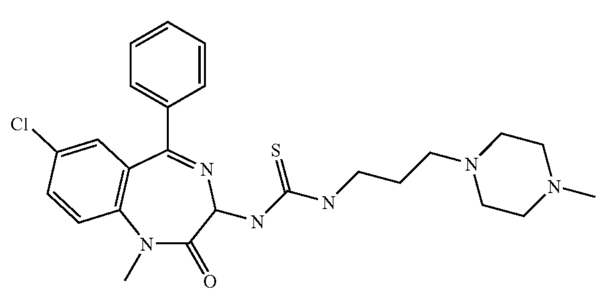 | 498.2 | No | |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 111 | 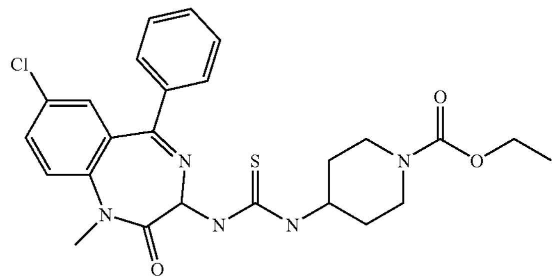 | 513.16 | Tentative | |
| 112 | 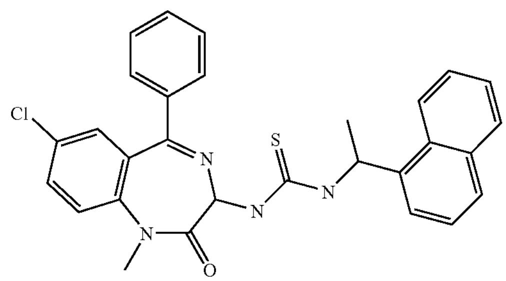 | 512.14 | Yes | 4.21 |
| 113 | 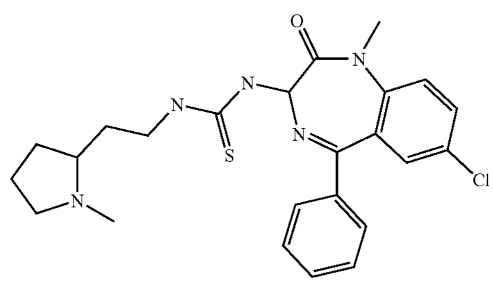 | 469.17 | Yes | 2.55 |
| 114 | 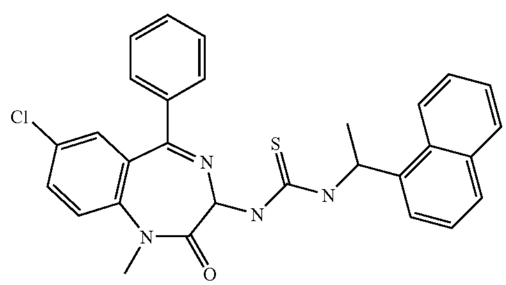 | 512.14 | No | |
| 115 | 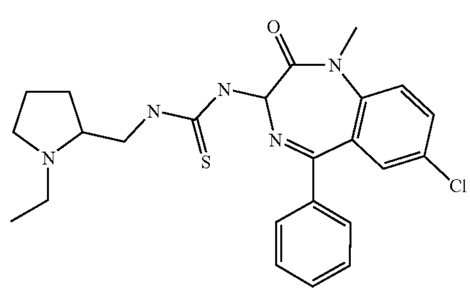 | 469.17 | No | |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 116 | 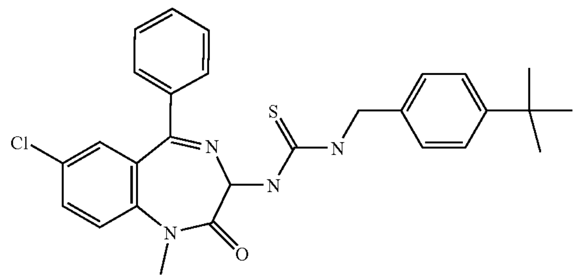 | 504.17 | No | |
| 117 | 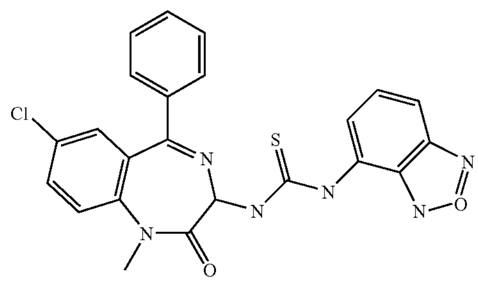 | 476.08 | Tentative | |
| 118 | 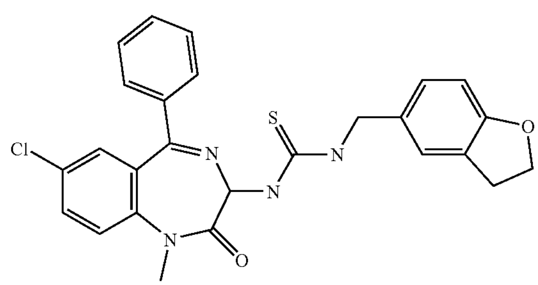 | 490.12 | No | |
| 119 | 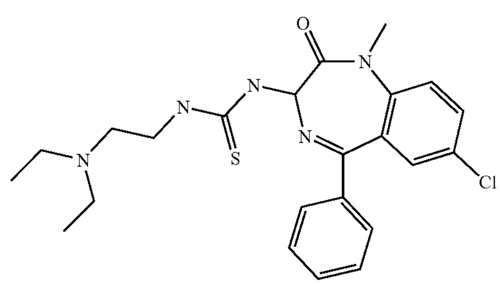 | 457.17 | Yes | 2.68 |
| 120 | 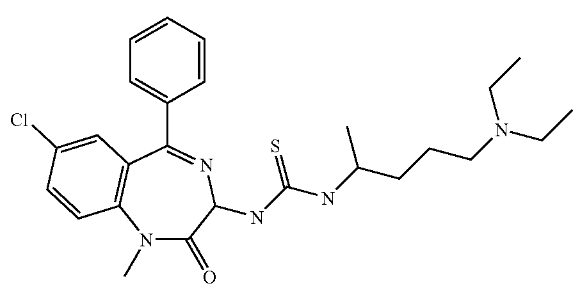 | 499.22 | No | |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 121 | 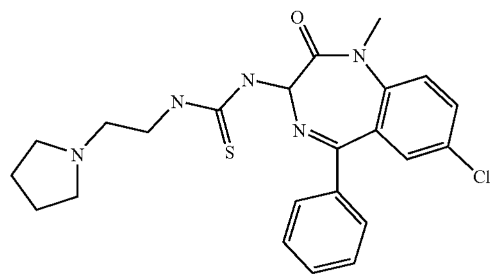 | 455.15 | Yes | 2.63 |
| 122 | 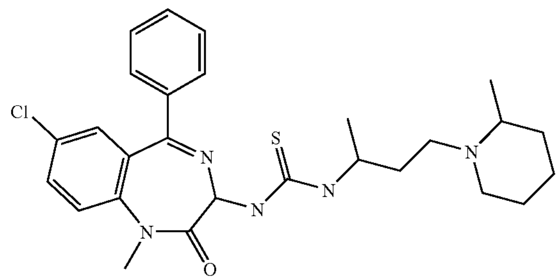 | 497.2 | No | |
| 123 | 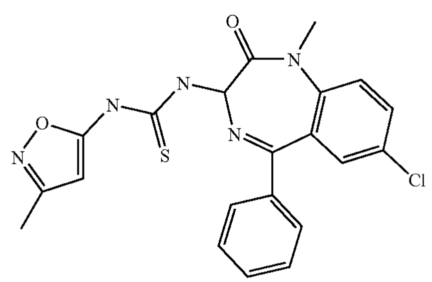 | 493.09 | Yes | 3.34 |
| 124 | 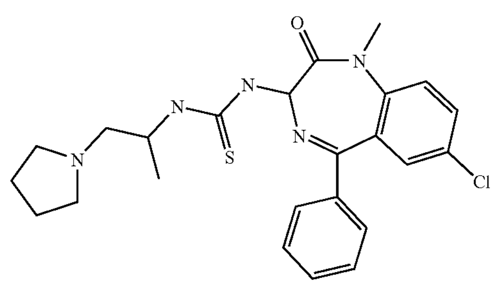 | 469.17 | No | |
| 125 | 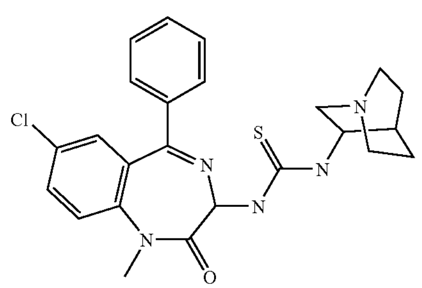 | 467.15 | No | |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 126 | 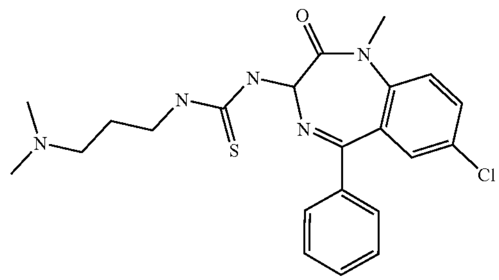 | 443.15 | No | |
| 127 | 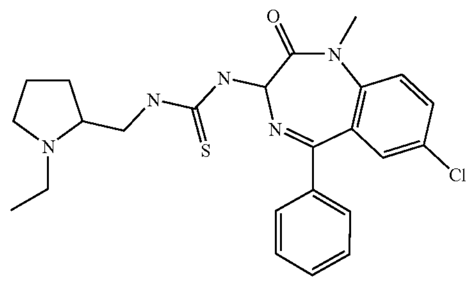 | 469.17 | No | |
| 128 | 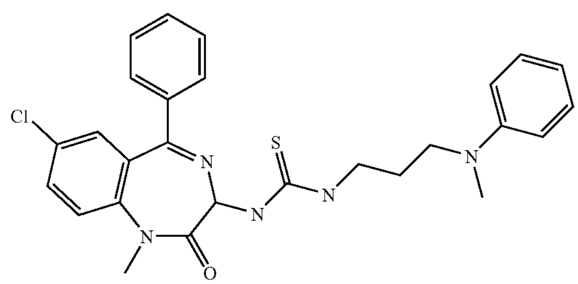 | 505.17 | No | |
| 129 | 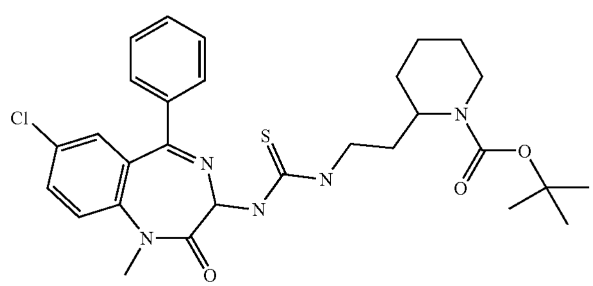 | 569.22 | No | |
| 130 | 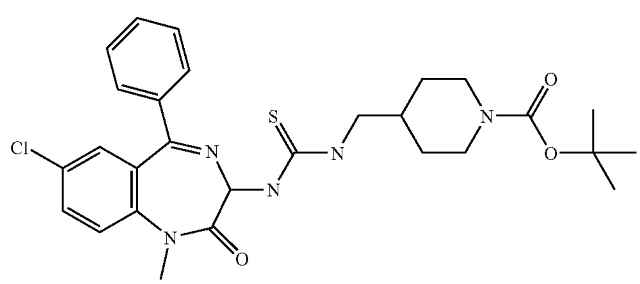 | 555.21 | Yes | 3.99 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 131 | 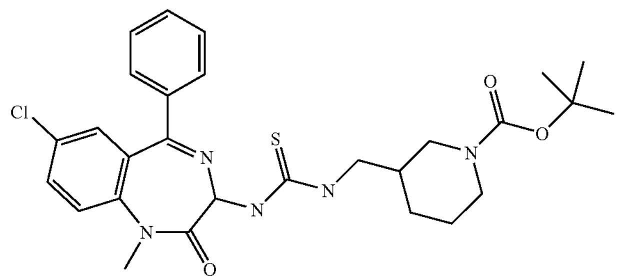 | 555.21 | Yes | 4.03 |
| 132 | 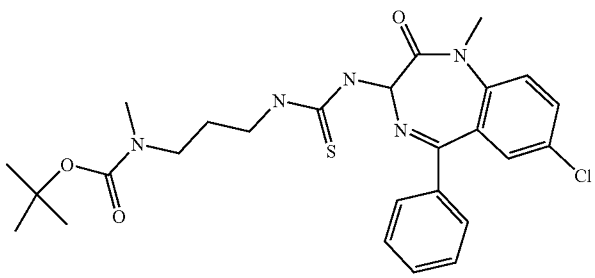 | 529.19 | Yes | 3.74 |
| 133 | 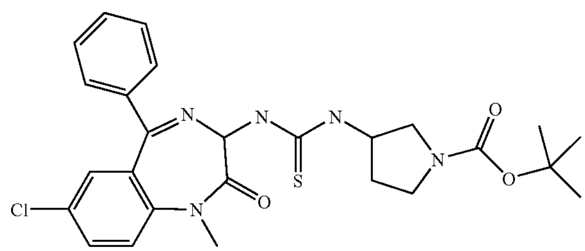 | 527.18 | No | |
| 134 | 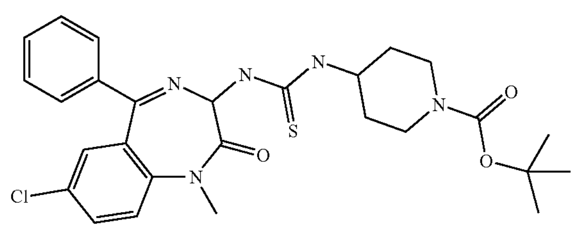 | 541.19 | No | |
| 135 | 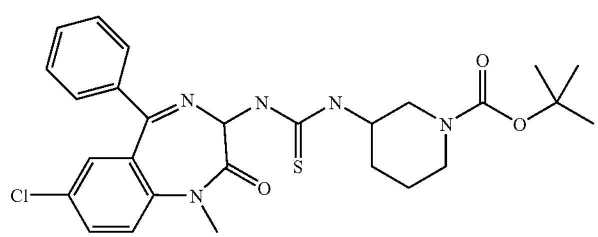 | 541.19 | Yes | 3.84 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 136 | 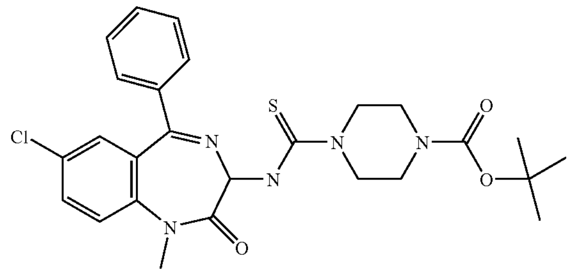 | 527.18 | Tentative | |
| 137 | 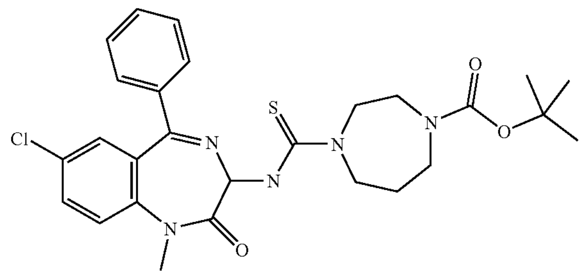 | 541.19 | Yes | 3.84 |
| 138 | 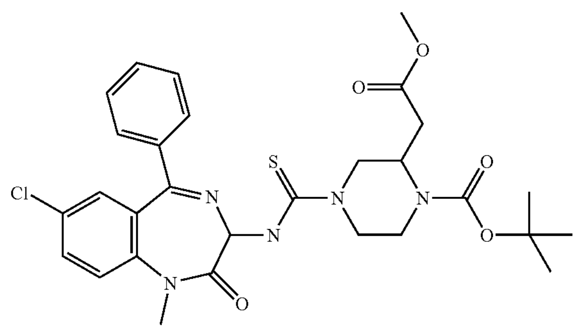 | 599.2 | Yes | 3.87 |
| 139 | 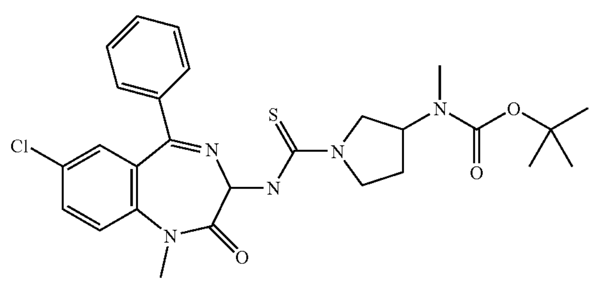 | 541.19 | Yes | 3.75 |
| 140 | 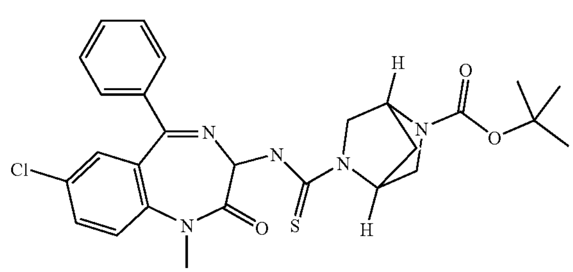 | 539.18 | No | |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 141 | 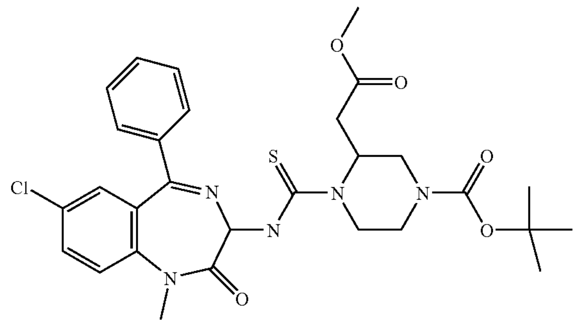 | 599.2 | Yes | 3.87 |
| 142 | 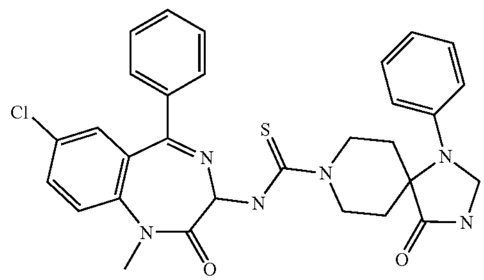 | 572.18 | No | |
| 143 | 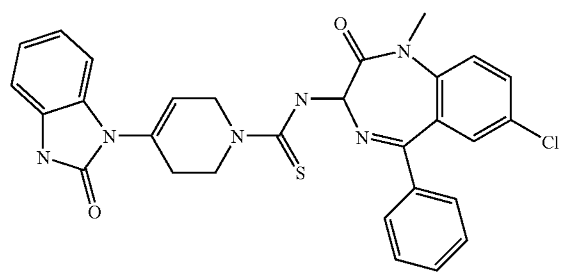 | 556.14 | No | |
| 144 | 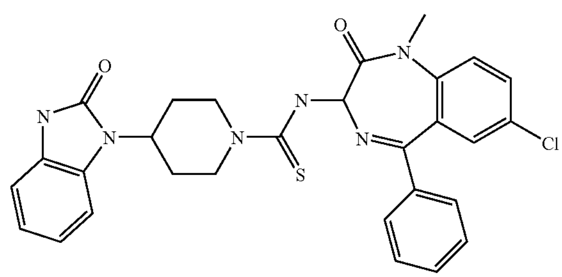 | 558.16 | No | |
| 145 | 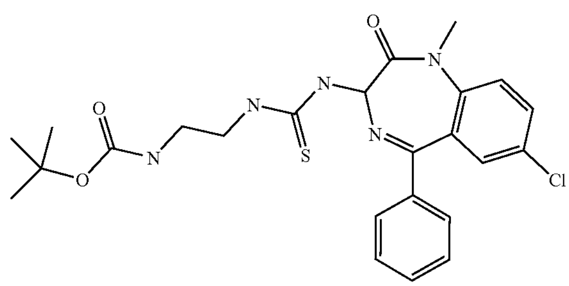 | 501.16 | No | |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 146 | 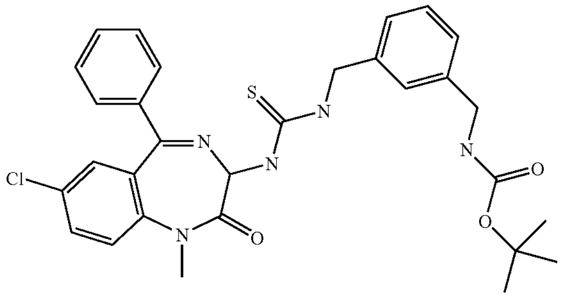 | 577.19 | No | |
| 147 | 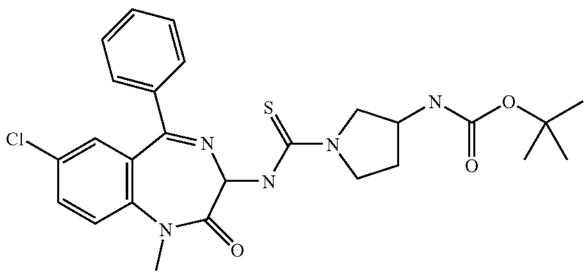 | 527.18 | Yes | 3.46 |
| 148 | 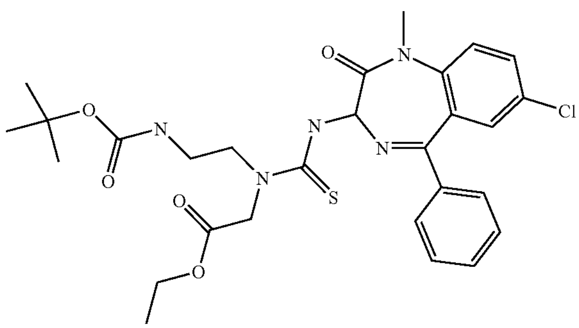 | 587.2 | No | |
| 149 | 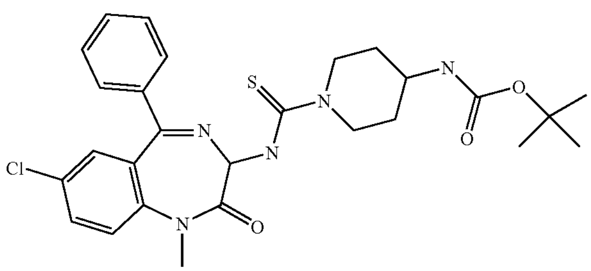 | 541.19 | Yes | 3.59 |
| 150 | 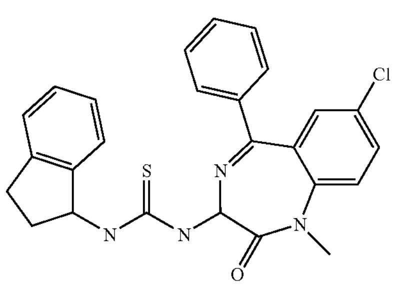 | 474.13 | No | |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 151 | 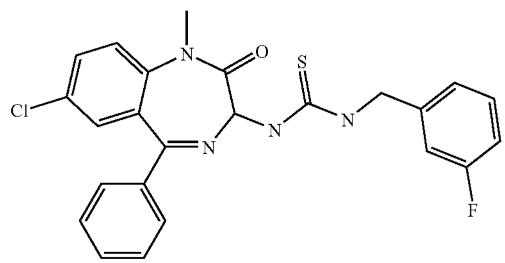 | 466.1 | Yes | 3.54 |
| 152 | 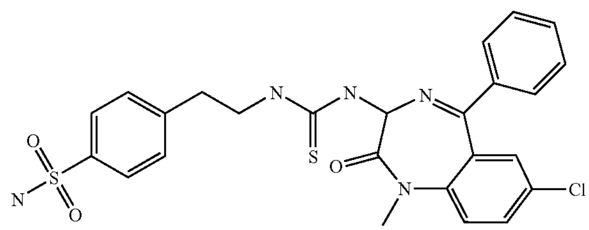 | 541.1 | Yes | 2.63, 2.81 |
| 153 | 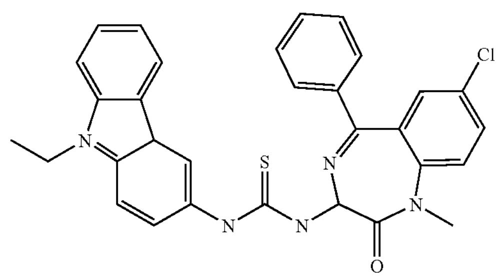 | 553.17 | Tentative | 4.13 |
| 154 | 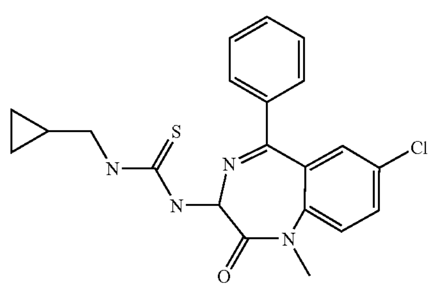 | 412.11 | Tentative | 2.21 |
| 155 | 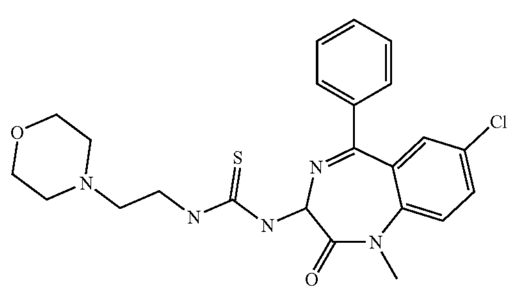 | 471.15 | Yes | 2.9 |

TABLE 1-continued
Spreadsheet of combinatorially prepared compounds with LCMS analysis of the reaction product.
| Compound # | Structure | Target Mass | Mass Found? | Rtn Time (MS) |
|---|---|---|---|---|
| 156 | 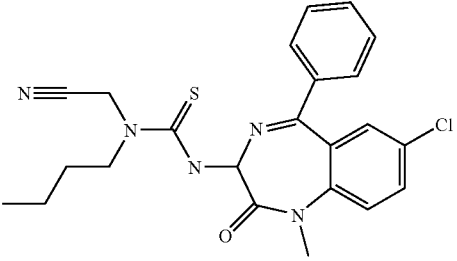 | 453.14 | Yes | 3.37, 4.15 |
| 157 | 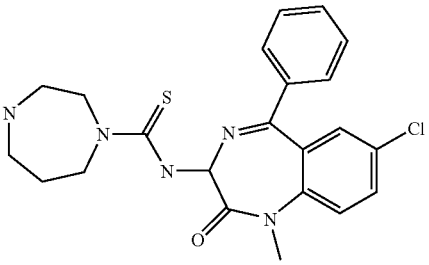 | 441.14 | Yes | 2.61 |
| 158 | 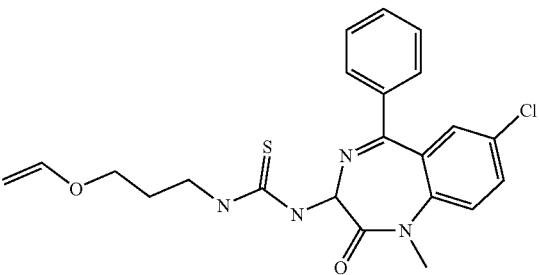 | 442.12 | No | |
| 159 | 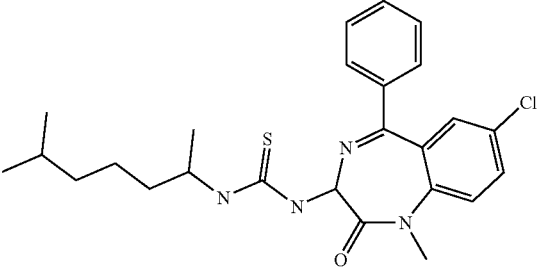 | 470.19 | Yes | 4.55, 4.66 |
| 160 | 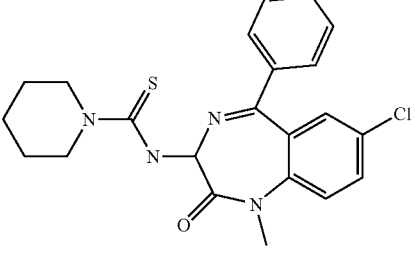 | 426.13 | Yes | 3.27 |

TABLE 1-continued

Spreadsheet of combinatorially prepared compounds with LCMS analysis of the reaction product.

| Compound # | Structure | Target Mass | Mass Found? | Rtn Time (MS) |
| --- | --- | --- | --- | --- |
| 161 | 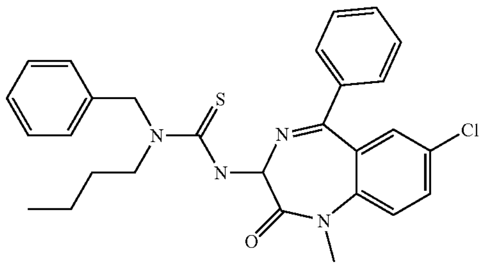 | 504.17 | Yes | 4.52 |
| 162 | 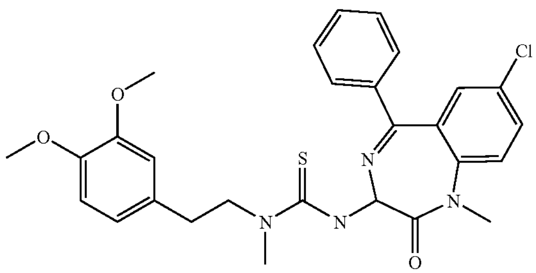 | 536.16 | Yes | 3.46 |
| 163 | 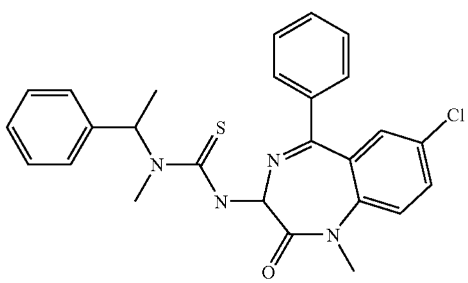 | 476.14 | Yes | 3.97 |
| 164 | 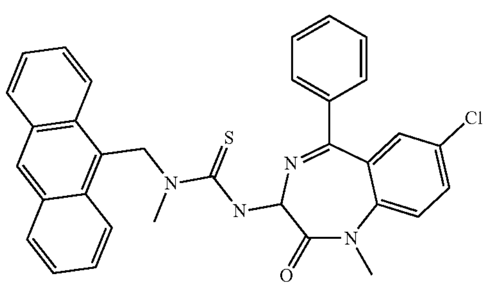 | 562.16 | Yes | 3.1, 3.35 |
| 165 | 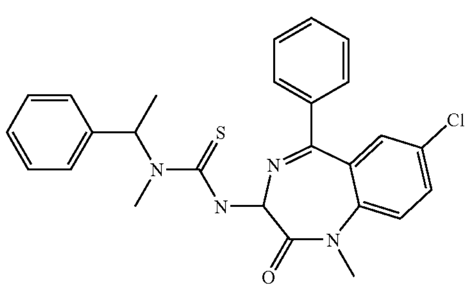 | 462.13 | Yes | 3.64 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 166 | 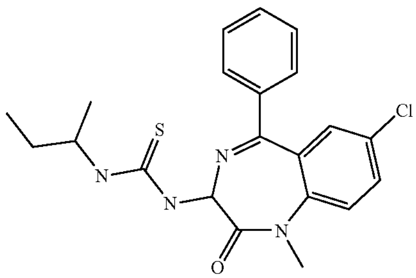 | 414.13 | No | |
| 167 | 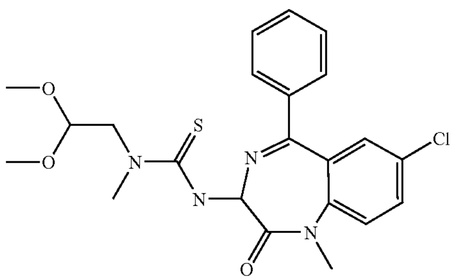 | 460.13 | Yes | 3.08 |
| 168 | 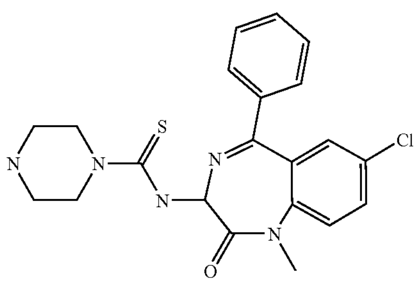 | 427.12 | Yes | 2.63 |
| 169 | 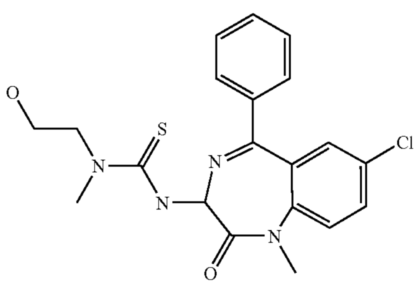 | 416.11 | Yes | 2.7 |
| 170 | 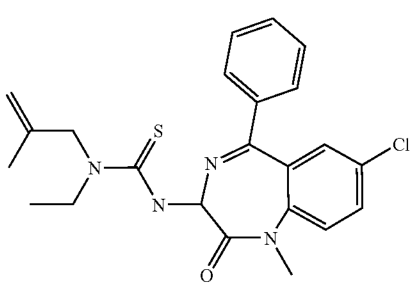 | 440.14 | Yes | 3.59 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 171 | 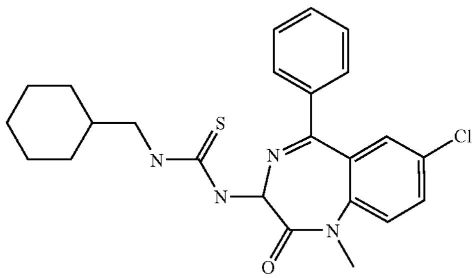 | 454.16 | No | |
| 172 | 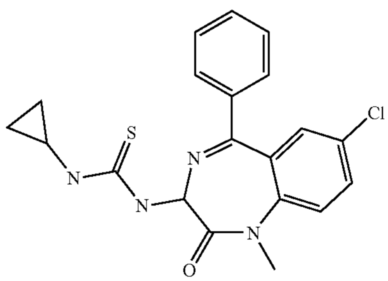 | 398.1 | No | |
| 173 | 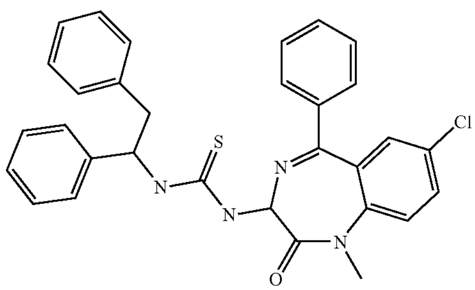 | 538.16 | Yes | 4.35 |
| 174 | 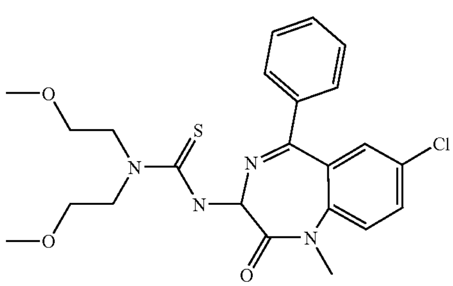 | 474.15 | Yes | 3.23 |
| 175 | 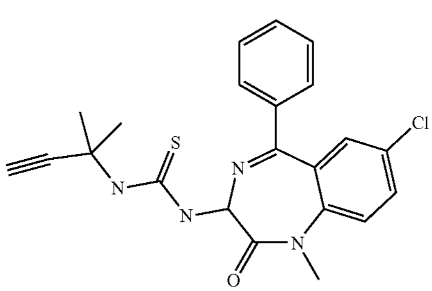 | 424.11 | Yes | 3.66 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 176 | 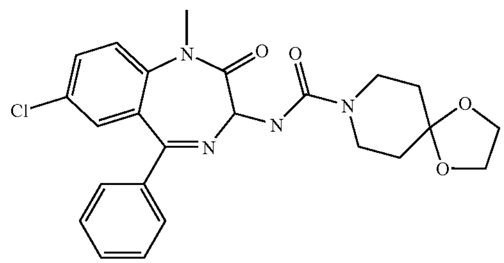 | 484.13 | Yes | 3.13 |
| 177 | 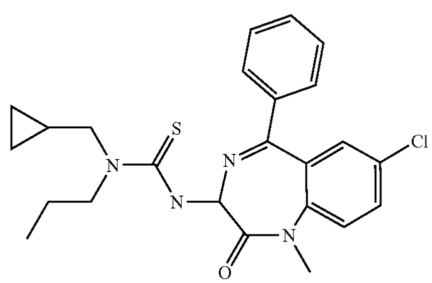 | 454.16 | Yes | 3.87 |
| 178 | 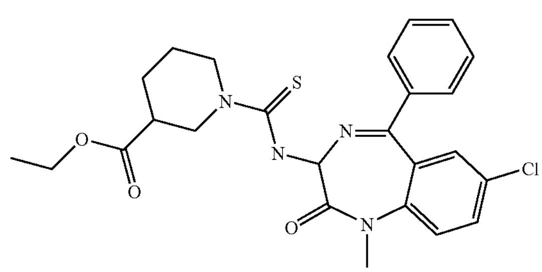 | 498.15 | Yes | 3.44 |
| 179 | 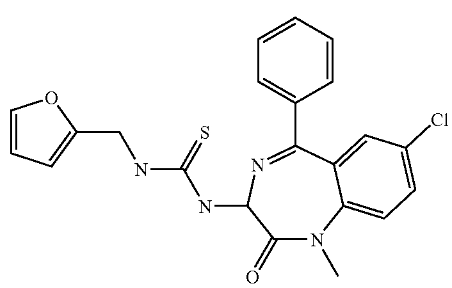 | 438.09 | Yes | 2.66, 3.16 |
| 180 | 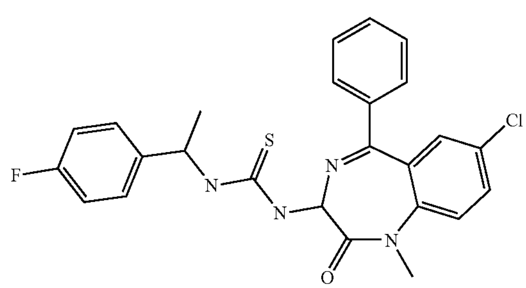 | 480.12 | Yes | 3.68 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 181 | 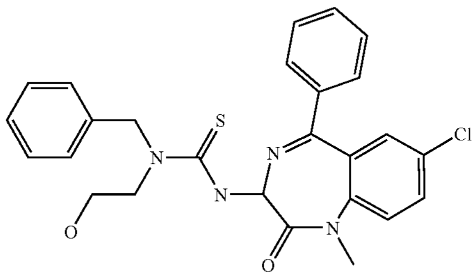 | 492.14 | Yes | 3.44 |
| 182 | 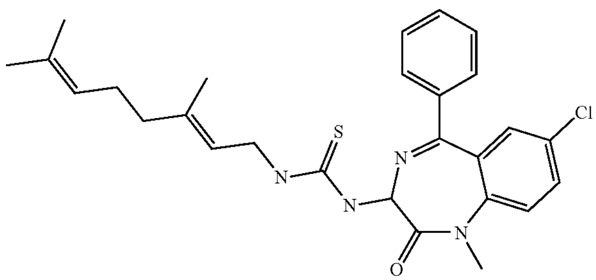 | 494.19 | Yes | 3.68, 4.04, 4.78 |
| 183 | 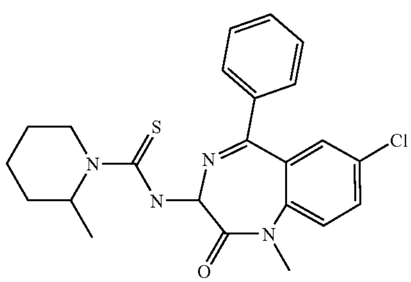 | 440.14 | Yes | 3.5 |
| 184 | 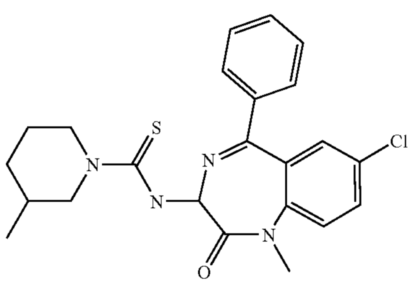 | 440.14 | Yes | 3.59 |
| 185 | 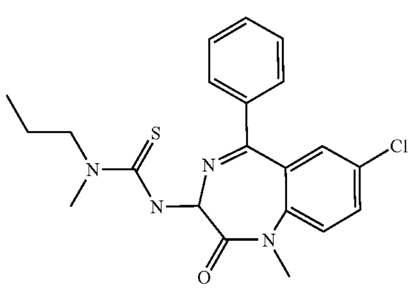 | 414.13 | No | |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 186 | 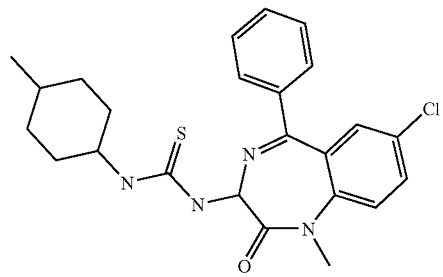 | 454.16 | No | |
| 187 | 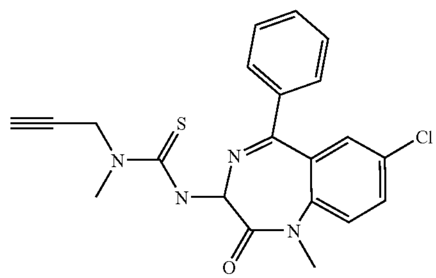 | 410.1 | Tentative | 2.81, 3.33 |
| 188 | 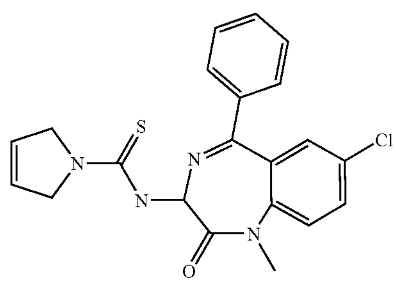 | 410.1 | Yes | 3.03, 6.5 |
| 189 | 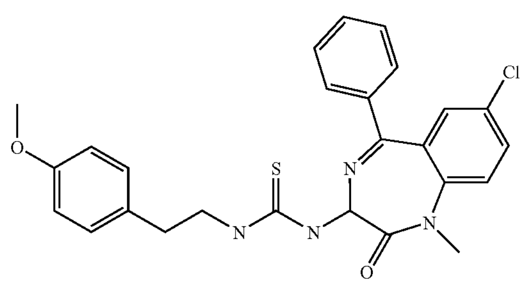 | 492.14 | Yes | 3.59 |
| 190 | 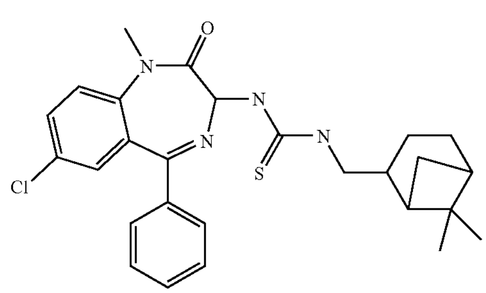 | 494.19 | Yes | 4.73 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 191 | 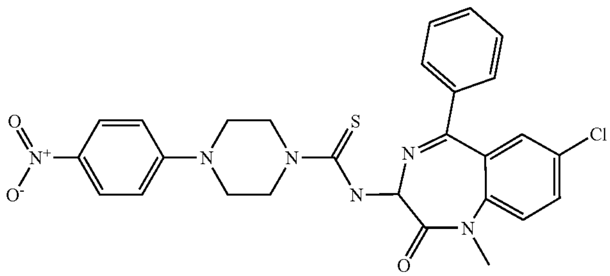 | 548.14 | Yes | 3.62 |
| 192 | 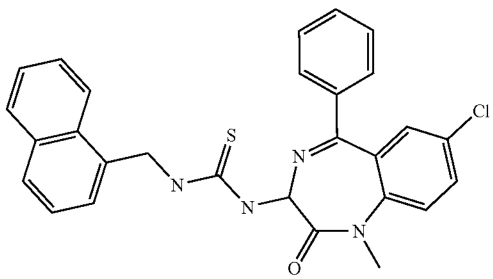 | 498.13 | Yes | 4.06 |
| 193 | 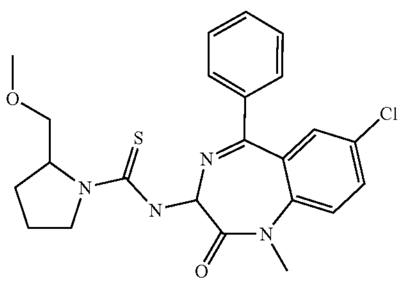 | 456.14 | Yes | 3.21 |
| 194 | 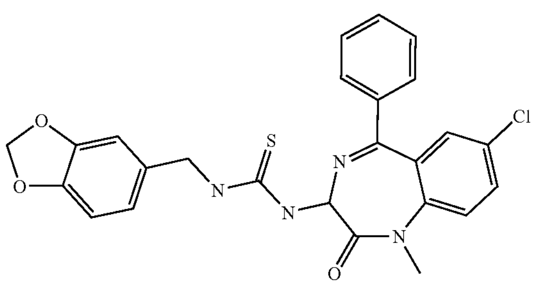 | 492.1 | Yes | 3.4 |
| 195 | 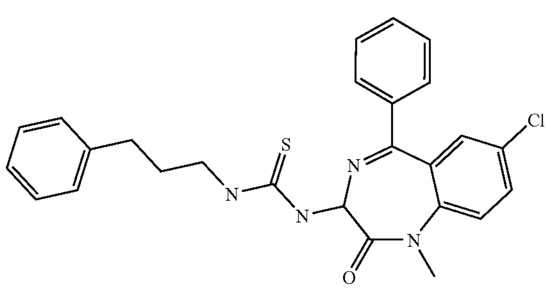 | 476.14 | Yes | 3.88 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 196 | 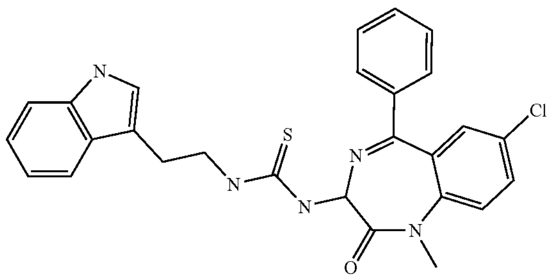 | 501.14 | Yes | 3.22, 3.43 |
| 197 | 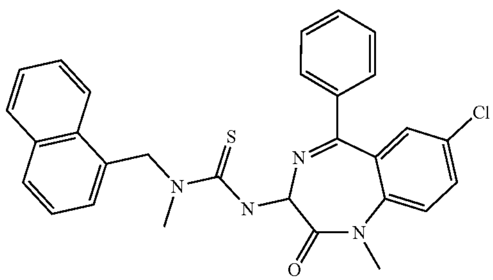 | 512.14 | Yes | 4.26 |
| 198 | 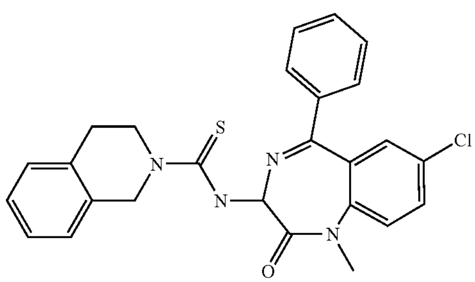 | 474.13 | Yes | 3.83 |
| 199 | 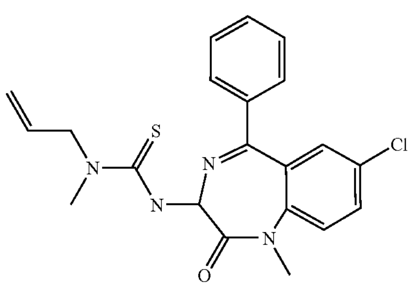 | 412.11 | Tentative | 3.12 |
| 200 | 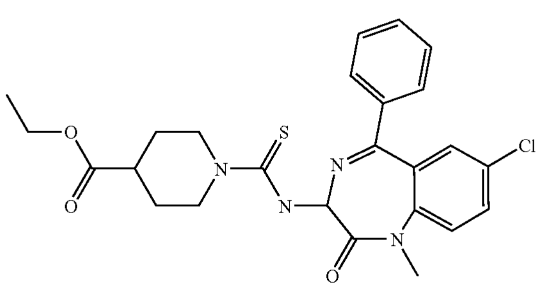 | 498.15 | Yes | 3.39 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 201 | 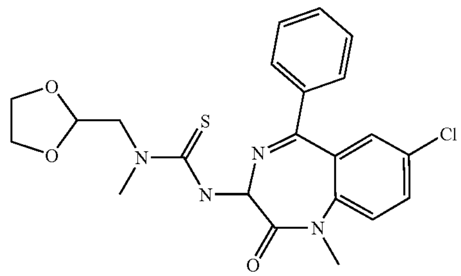 | 458.12 | Yes | 2.96 |
| 202 | 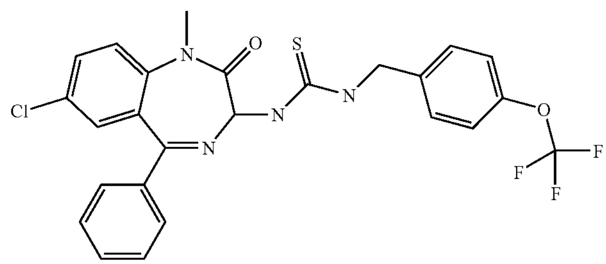 | 532.09 | Yes | 4.16 |
| 203 | 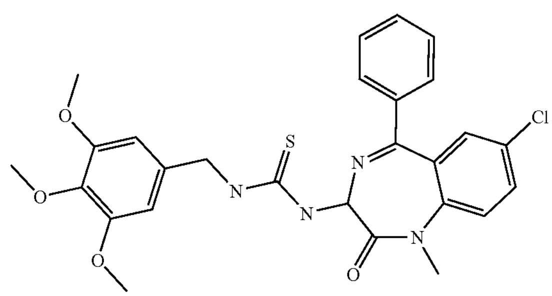 | 538.14 | Yes | 3.24 |
| 204 | 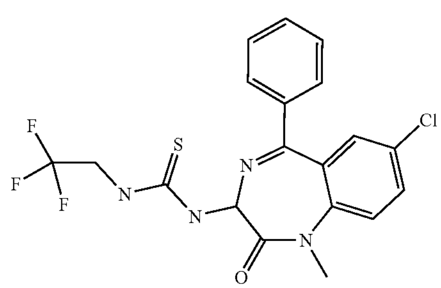 | 440.07 | No | |
| 205 | 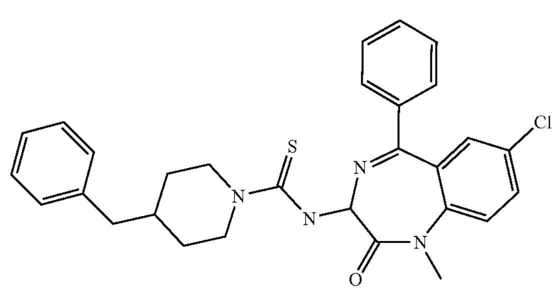 | 516.17 | Yes | 4.45 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 206 | 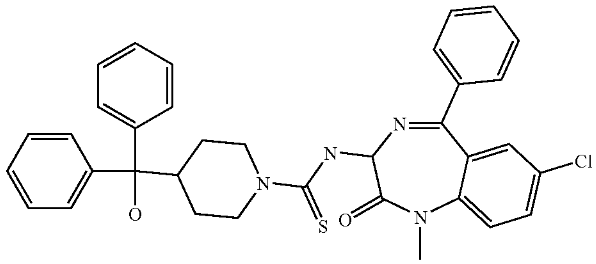 | 608.2 | Yes | 4.22 |
| 207 | 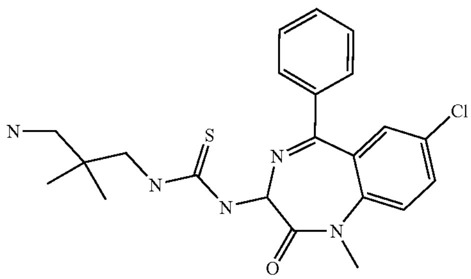 | 443.15 | Yes | 2.57 |
| 208 | 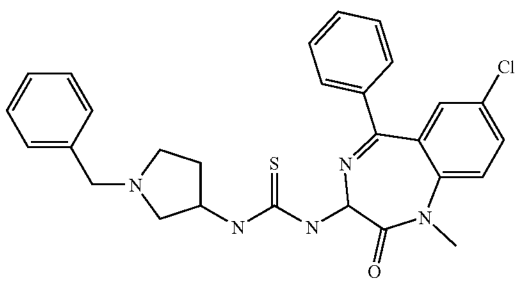 | 517.17 | Yes | 3.73 |
| 209 | 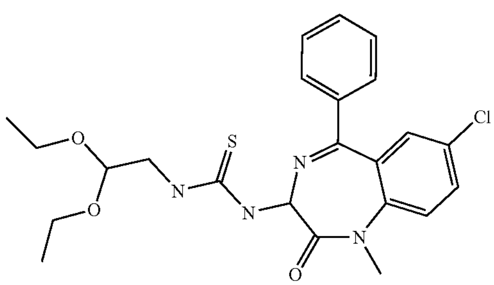 | 474.15 | Yes | 3.39 |
| 210 | 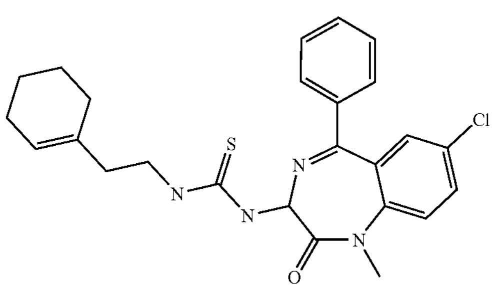 | 466.16 | Yes | 4.22 |

TABLE 1-continued
Spreadsheet of combinatorially prepared compounds with LCMS analysis of the reaction product.
| Compound # | Structure | Target Mass | Mass Found? | Rtn Time (MS) |
|---|---|---|---|---|
| 211 | 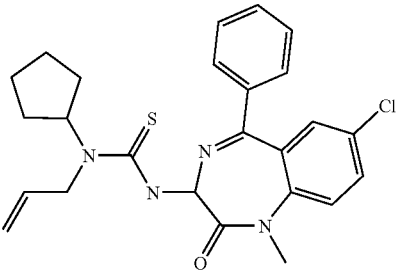 | 466.16 | Yes | 3.99 |
| 212 | 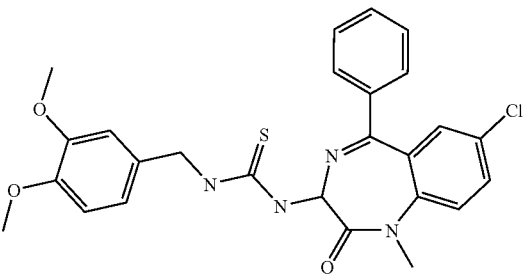 | 508.13 | Yes | 3.19 |
| 213 | 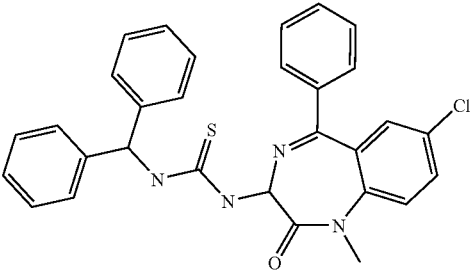 | 524.14 | Yes | 4.17 |
| 214 | 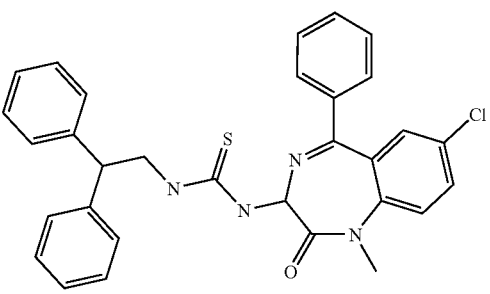 | 538.16 | Yes | 4.39 |
| 215 | 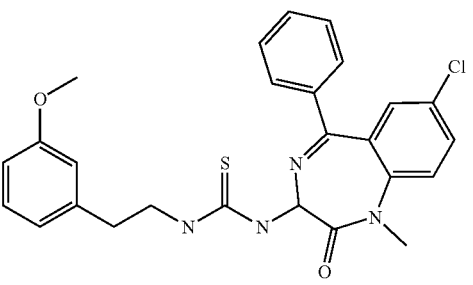 | 492.14 | Yes | 3.64 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 216 | 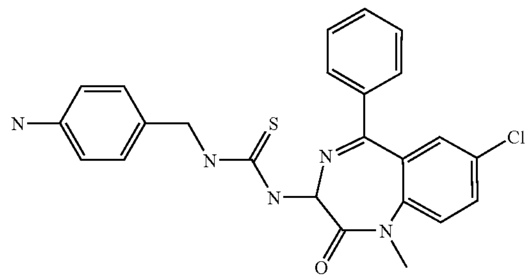 | 463.12 | Yes | 2.56, 2.82 |
| 217 | 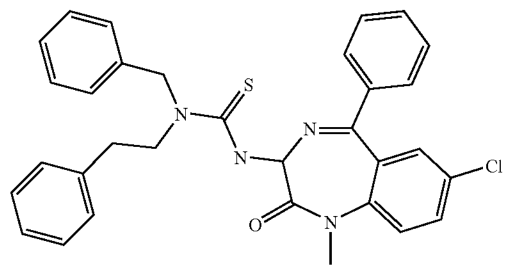 | 552.17 | Yes | 4.82 |
| 218 | 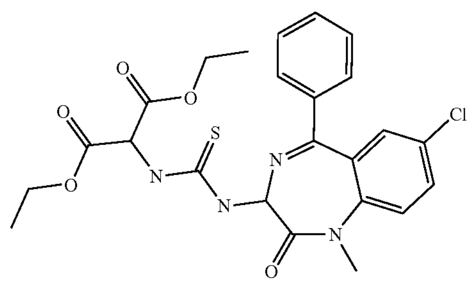 | 516.12 | Yes | 3.37 |
| 219 | 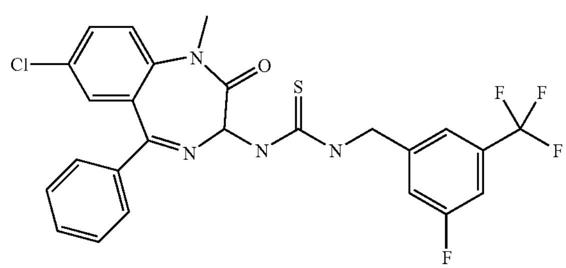 | 534.09 | Yes | 4.24 |
| 220 | 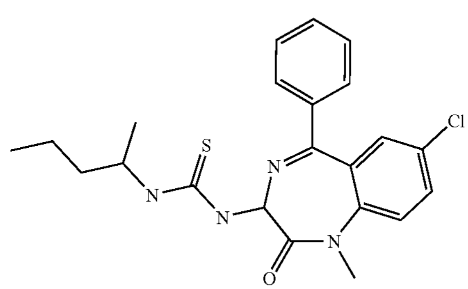 | 428.14 | Yes | 3.61 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 221 | 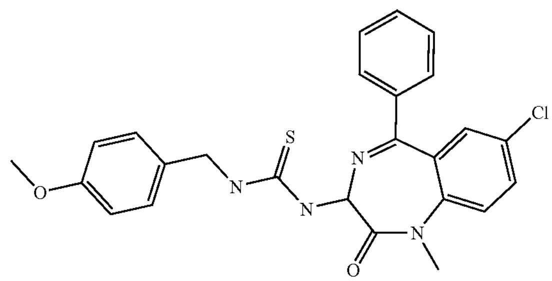 | 478.12 | Yes | 3.41 |
| 222 | 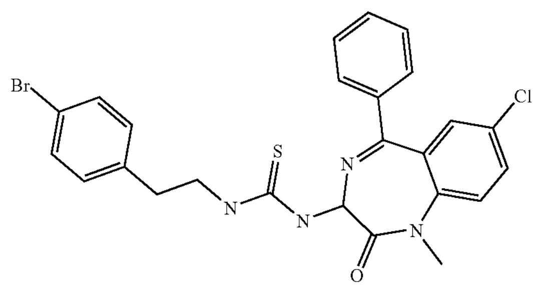 | 540.04 | Yes | 4.21 |
| 223 | 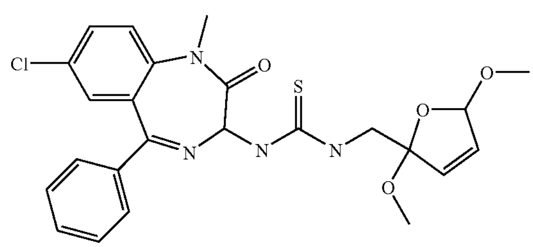 | 500.13 | Yes | 3.08 |
| 224 | 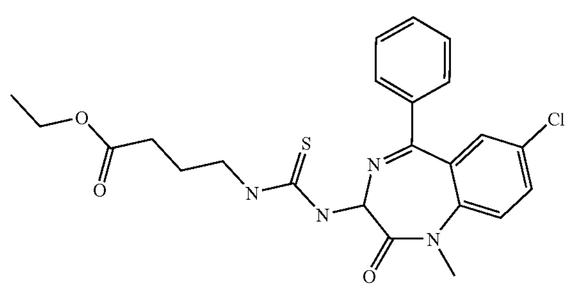 | 472.13 | Tentative | 3.13 |
| 225 | 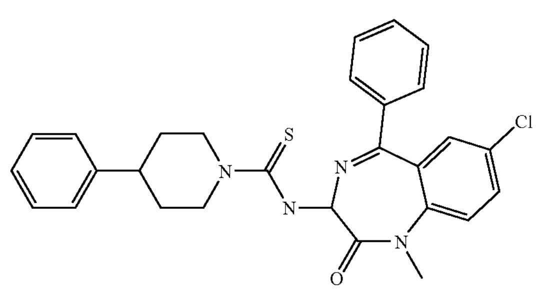 | 502.16 | No | |

TABLE 1-continued
Spreadsheet of combinatorially prepared compounds with LCMS analysis of the reaction product.
| Compound # | Structure | Target Mass | Mass Found? | Rtn Time (MS) |
|---|---|---|---|---|
| 226 | 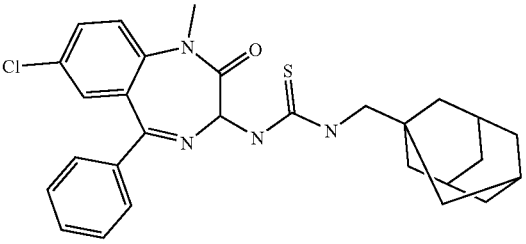 | 506.19 | Yes | 4.8 |
| 227 | 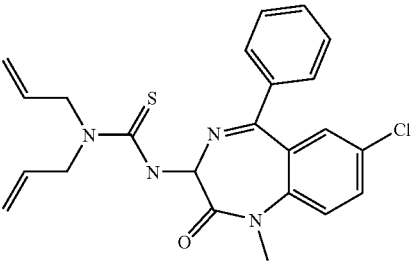 | 438.13 | Yes | 3.52 |
| 228 | 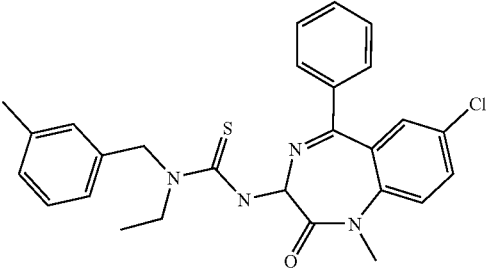 | 490.16 | Yes | 4.19 |
| 229 | 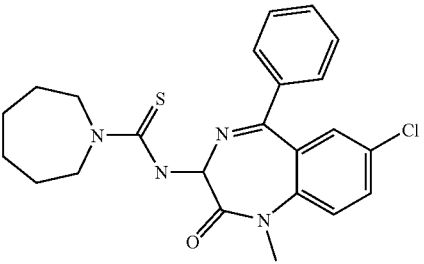 | 440.14 | Yes | 3.52 |
| 230 | 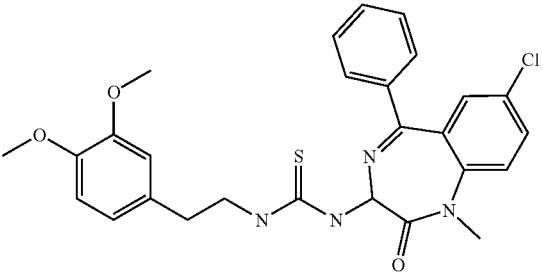 | 522.15 | Yes | 3.32 |

TABLE 1-continued
Spreadsheet of combinatorially prepared compounds with LCMS analysis of the reaction product.
| Compound # | Structure | Target Mass | Mass Found? | Rtn Time (MS) |
|---|---|---|---|---|
| 231 | 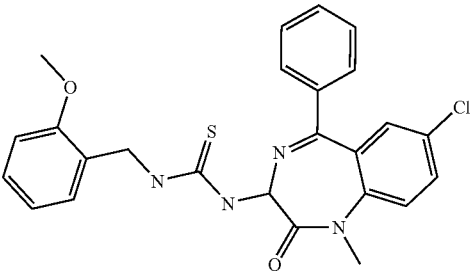 | 478.12 | Yes | 3.49 |
| 232 | 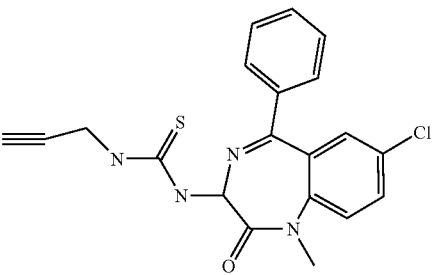 | 396.08 | No | |
| 233 | 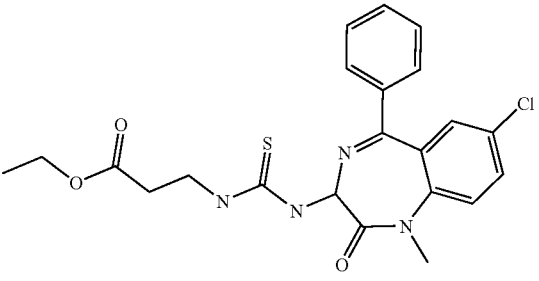 | 458.12 | Yes | 3.12 |
| 234 | 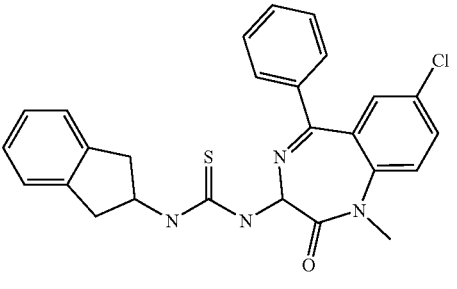 | 474.13 | No | |
| 235 | 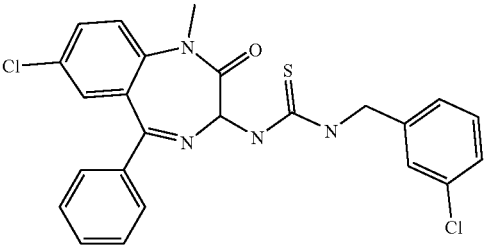 | 482.07 | Yes | 3.29, 3.86 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 236 | 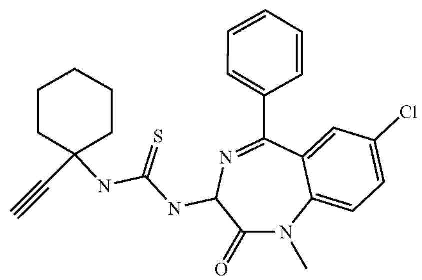 | 464.14 | Yes | 2.68, 4.77 |
| 237 | 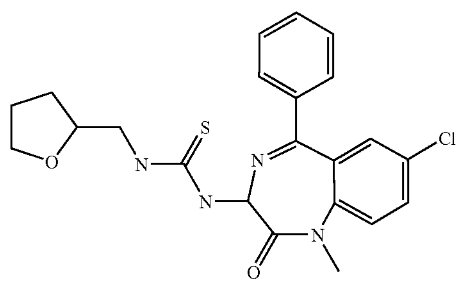 | 442.12 | Yes | 3.02 |
| 238 | 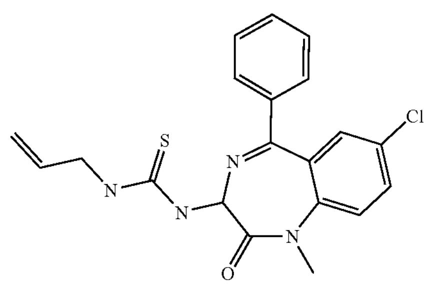 | 398.1 | No | |
| 239 | 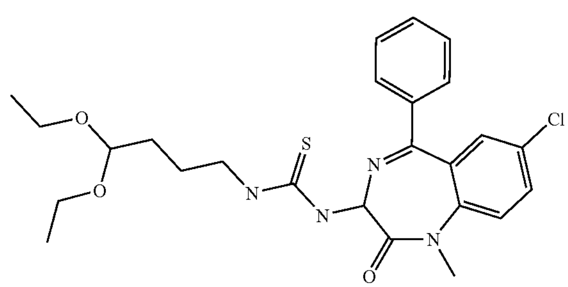 | 502.18 | Tentative | 4.31 |
| 240 | 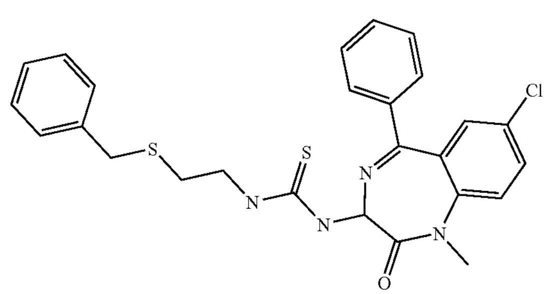 | 508.12 | Yes | 3.99 |

107                                                                                                 108

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 241 | 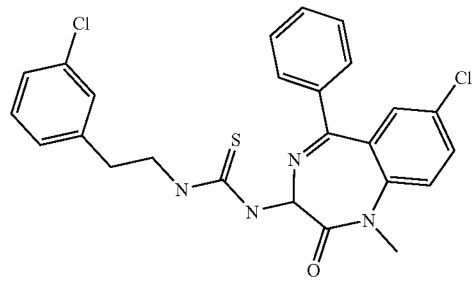 | 496.09 | Yes | 4.09 |
| 242 | 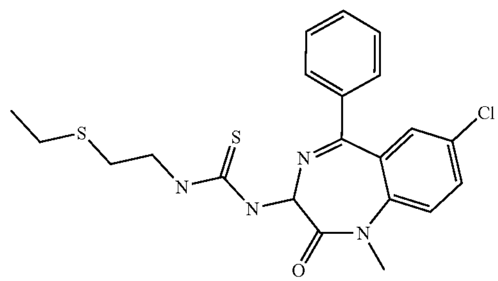 | 446.1 | Yes | 3.38 |
| 243 | 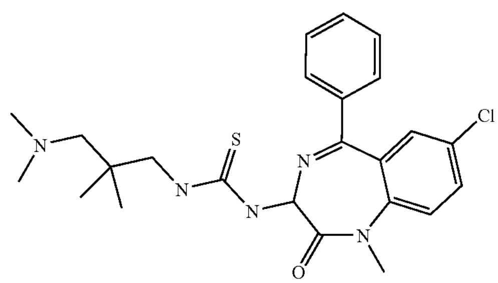 | 471.19 | Yes | 2.86 |
| 244 | 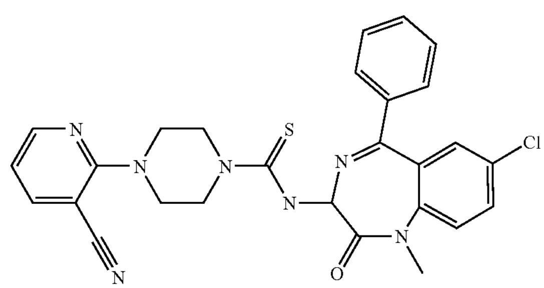 | 529.15 | Yes | 3.41 |
| 245 | 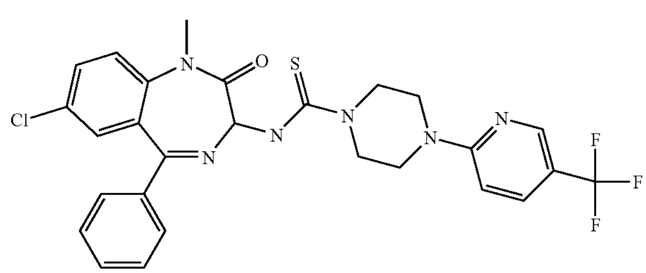 | 572.14 | Yes | 4.16 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 246 | 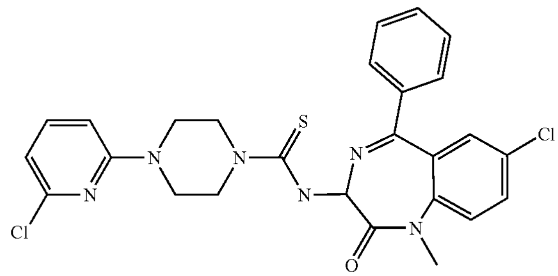 | 538.11 | Yes | 4 |
| 247 | 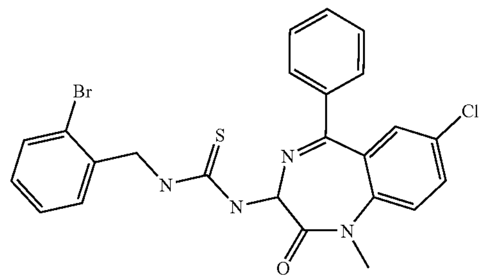 | 526.02 | No | |
| 248 | 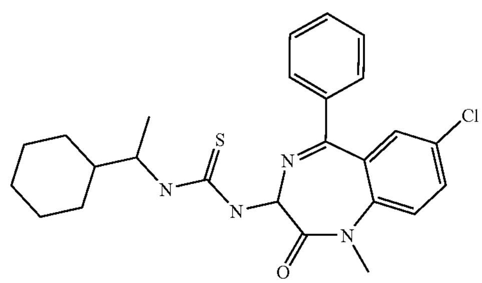 | 468.17 | No | |
| 249 | 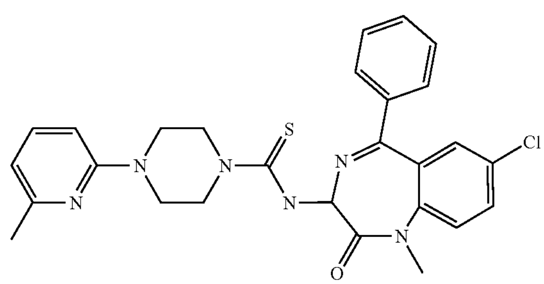 | 518.17 | Yes | 3.85 |
| 250 | 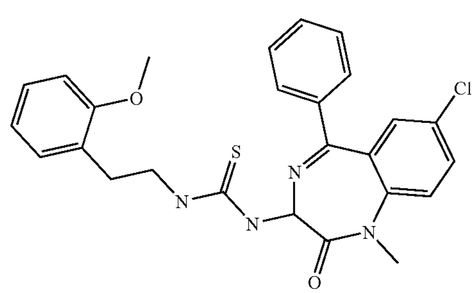 | 492.14 | Yes | 3.74 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 251 | 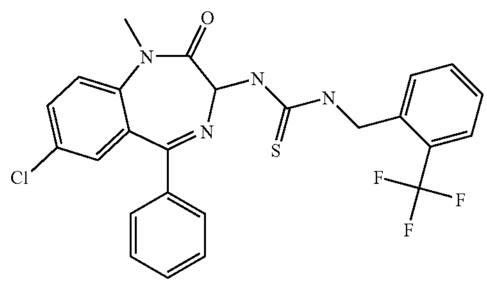 | 516.1 | Yes | 3.9 |
| 252 | 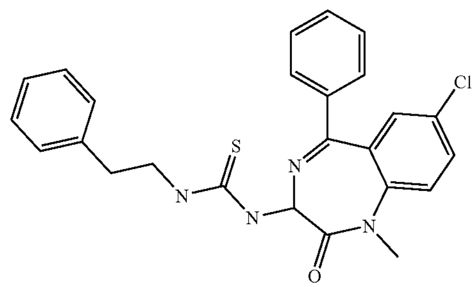 | 462.13 | Yes | 3.68 |
| 253 | 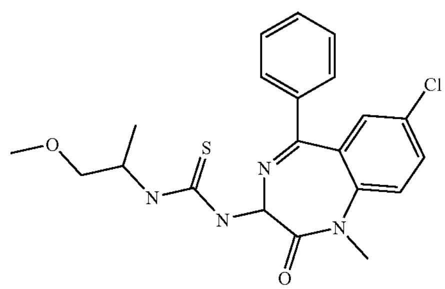 | 430.12 | Yes | 3.03 |
| 254 | 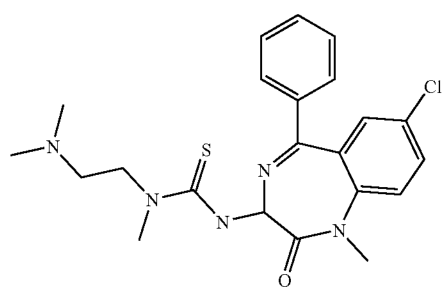 | 443.15 | Yes | 2.77 |
| 255 | 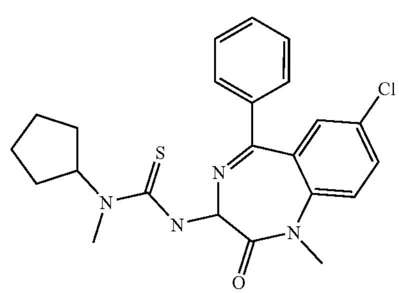 | 426.13 | Yes | 3.4 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 256 | 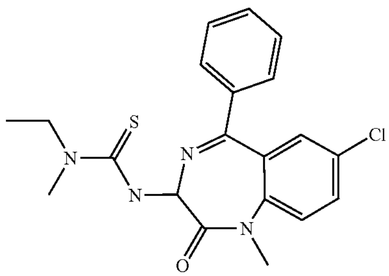 | 400.11 | No | |
| 257 | 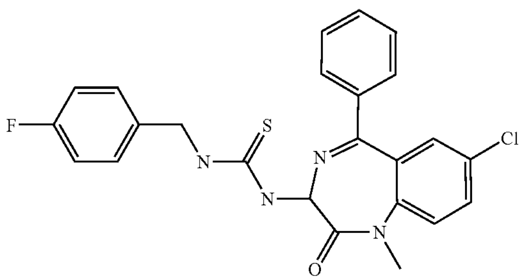 | 466.1 | Yes | 2.83, 3.54 |
| 258 | 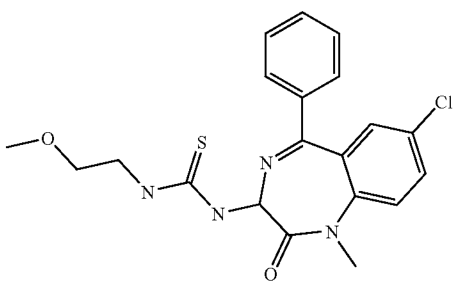 | 416.11 | Yes | 2.86 |
| 259 | 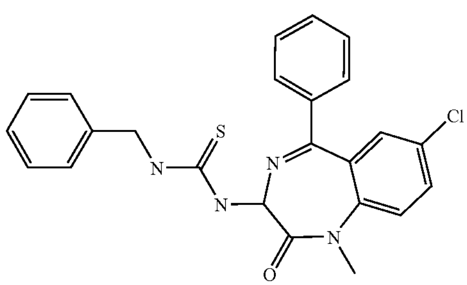 | 448.11 | Yes | 3.45 |
| 260 | 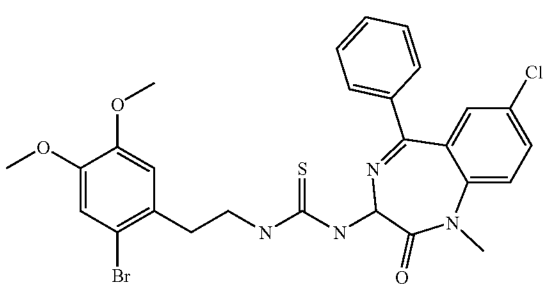 | 600.06 | Yes | 2.43, 3.84 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 261 | 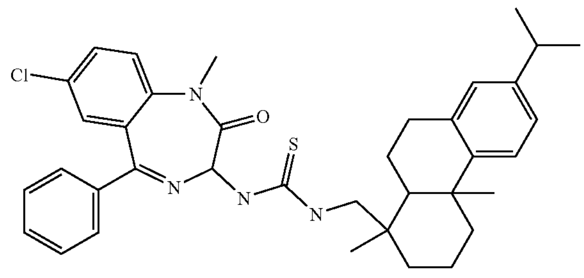 | 626.28 | Yes | 6.29 |
| 262 | 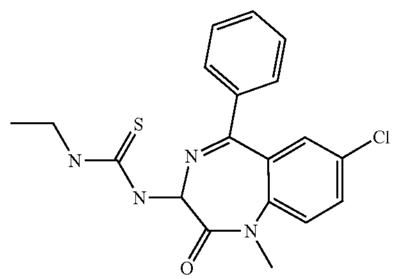 | 386.1 | No | |
| 263 | 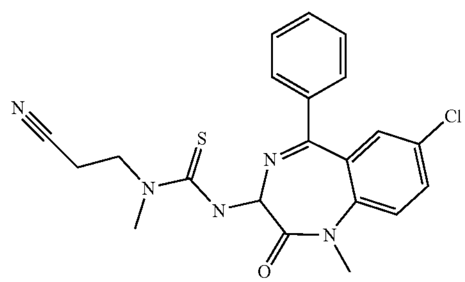 | 425.11 | Yes | 2.84 |
| 264 | 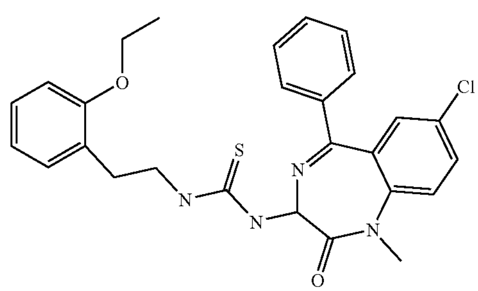 | 506.15 | Yes | 4.05 |
| 265 | 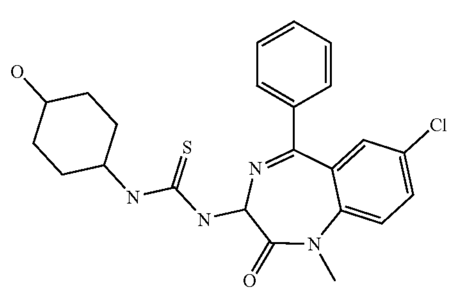 | 456.14 | Yes | 2.77 |

TABLE 1-continued
Spreadsheet of combinatorially prepared compounds with LCMS analysis of the reaction product.
| Compound # | Structure | Target Mass | Mass Found? | Rtn Time (MS) |
|---|---|---|---|---|
| 266 | 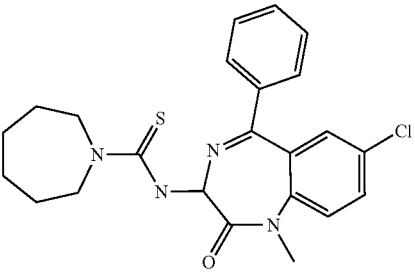 | 454.16 | Yes | 3.79 |
| 267 | 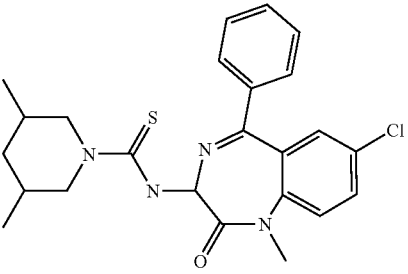 | 454.16 | Yes | 3.97 |
| 268 | 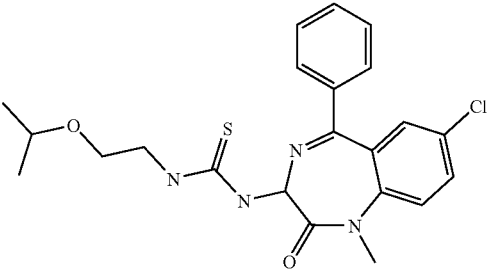 | 444.14 | Yes | 3.28 |
| 269 | 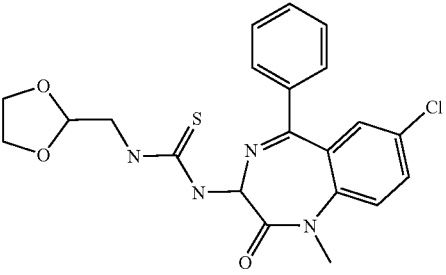 | 444.1 | Yes | 2.8 |
| 270 | 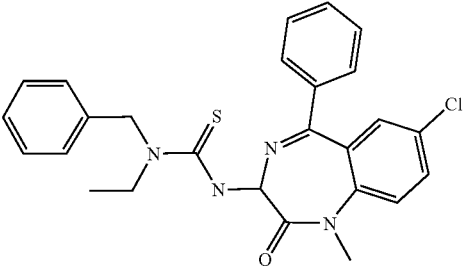 | 476.14 | Yes | 3.86 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 271 | 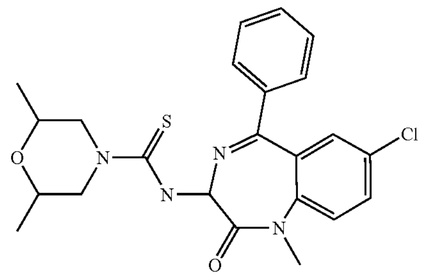 | 456.14 | Yes | 3.32 |
| 272 | 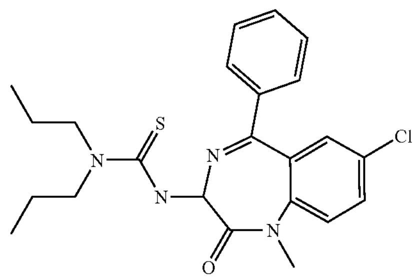 | 442.16 | Yes | 3.8 |
| 273 | 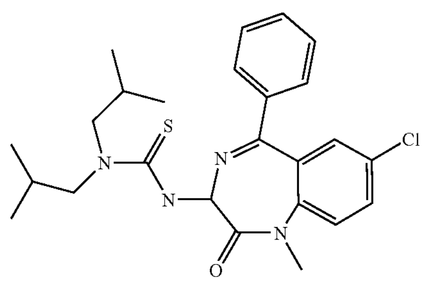 | 470.19 | Yes | 4.39 |
| 274 | 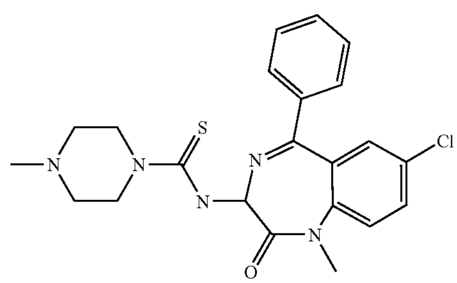 | 441.14 | Yes | 2.93 |
| 275 | 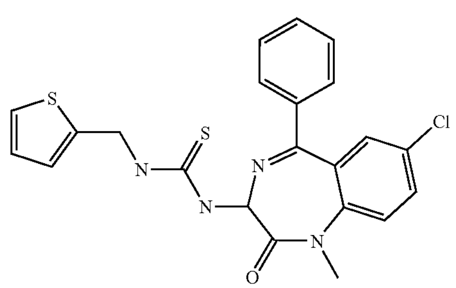 | 454.07 | Yes | 3.35 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 276 | 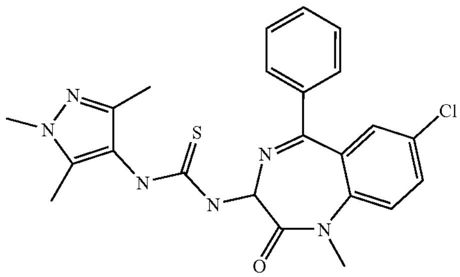 | 466.13 | Yes | 2.81 |
| 277 | 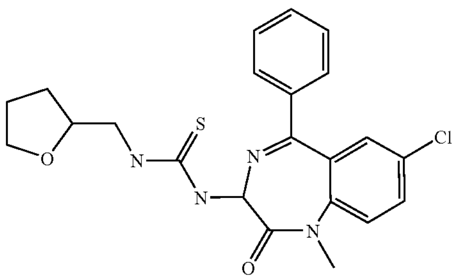 | 442.12 | Yes | 3.01 |
| 278 | 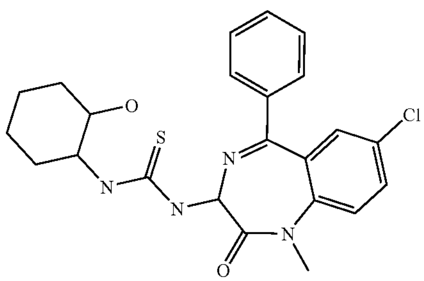 | 456.14 | Tentative | 3.13 |
| 279 | 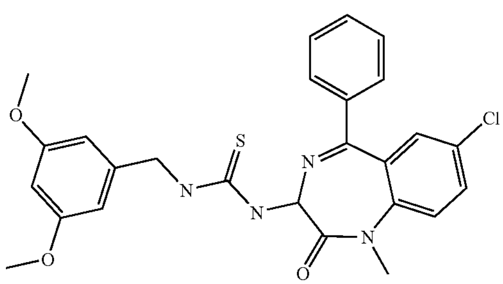 | 508.13 | Yes | 3.48 |
| 280 | 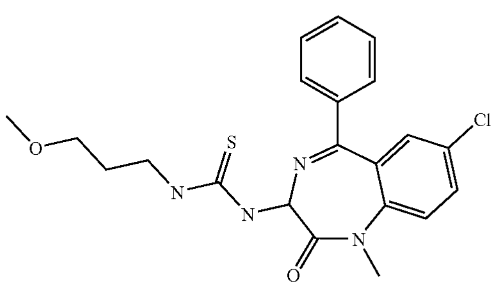 | 430.12 | Yes | 2.95 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 281 | 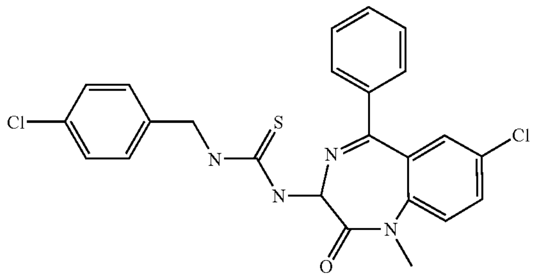 | 482.07 | Yes | 3.89 |
| 282 | 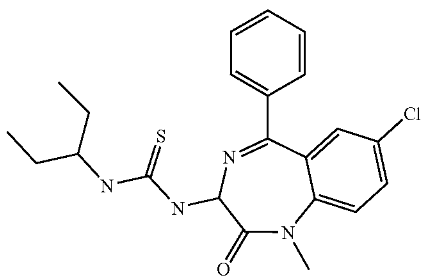 | 428.14 | Yes | 3.53 |
| 283 | 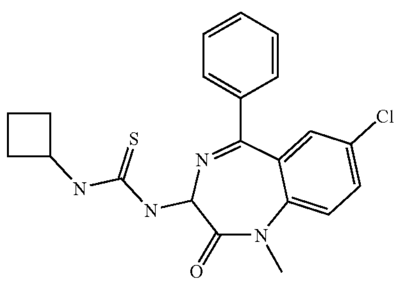 | 412.11 | Yes | 3.19 |
| 284 | 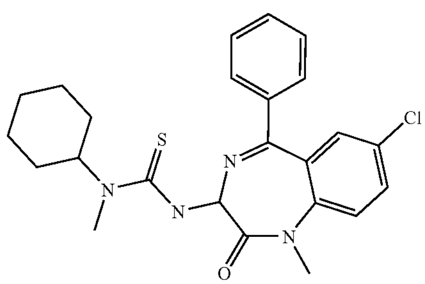 | 454.16 | Yes | 3.84 |
| 285 | 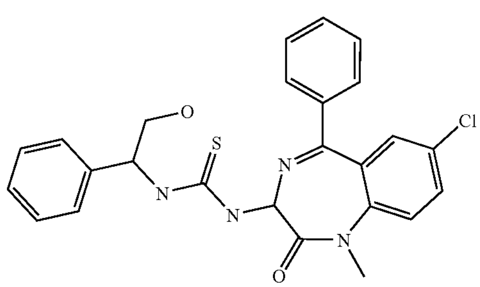 | 478.12 | Yes | 3.03, 3.16, 4.05 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 286 | 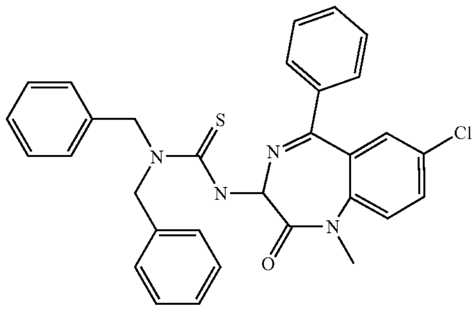 | 538.16 | Yes | 4.6 |
| 287 | 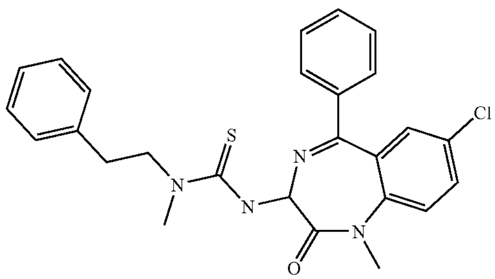 | 476.14 | Yes | 3.87 |
| 288 | 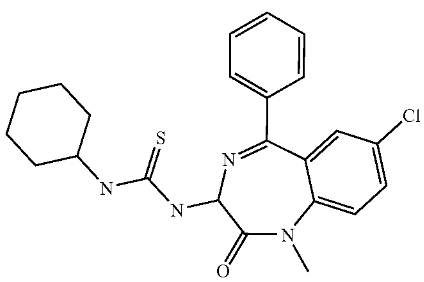 | 440.14 | Yes | 3.68 |
| 289 | 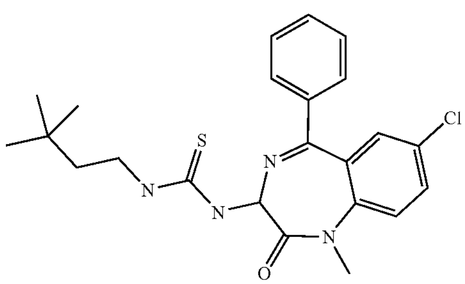 | 442.16 | Yes | 3.91 |
| 290 | 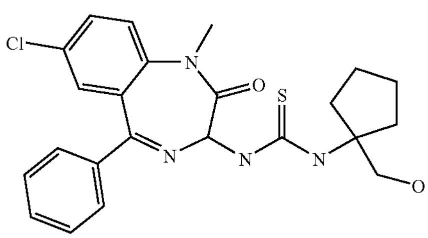 | 456.14 | Yes | 3.16 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 291 | 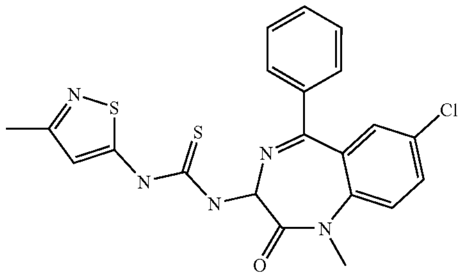 | 455.06 | No | |
| 292 | 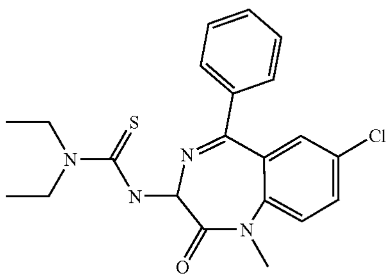 | 414.13 | Tentative | 3.12 |
| 293 | 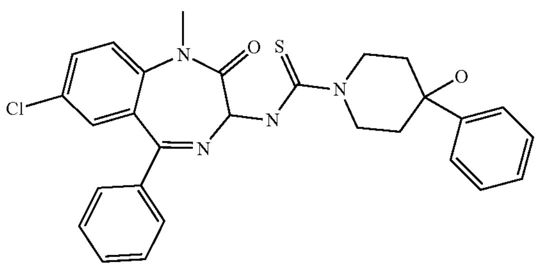 | 518.15 | Yes | 3.51 |
| 294 | 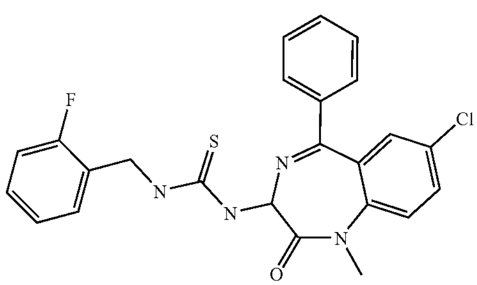 | 466.1 | Yes | 3.5 |
| 295 | 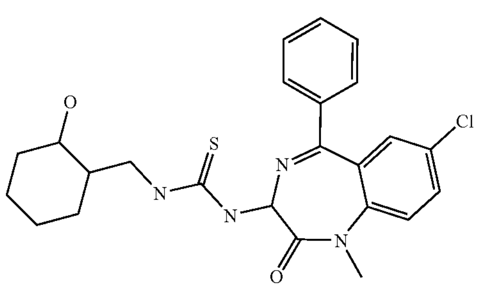 | 470.15 | No | |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 296 | 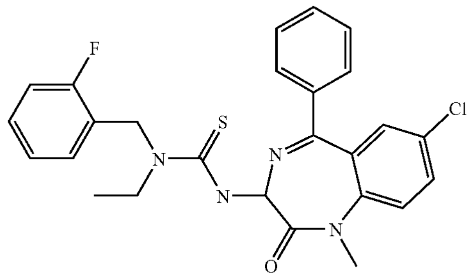 | 494.13 | Yes | 3.99 |
| 297 | 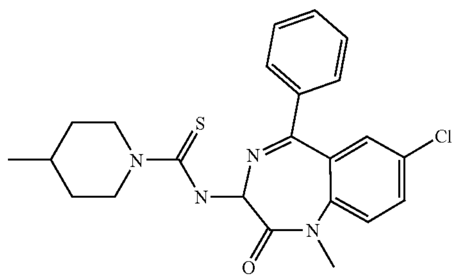 | 440.14 | Yes | 3.61 |
| 298 | 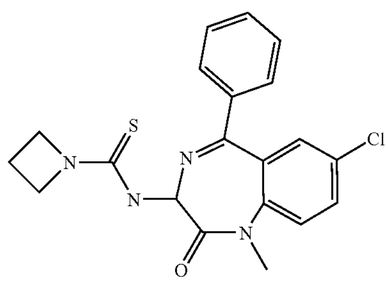 | 398.1 | No | |
| 299 | 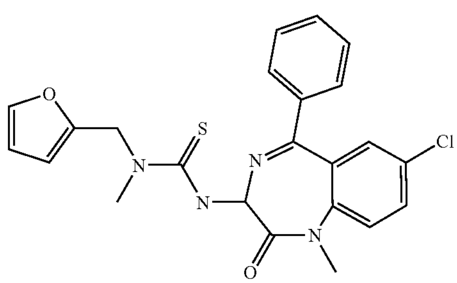 | 452.11 | No | |
| 300 | 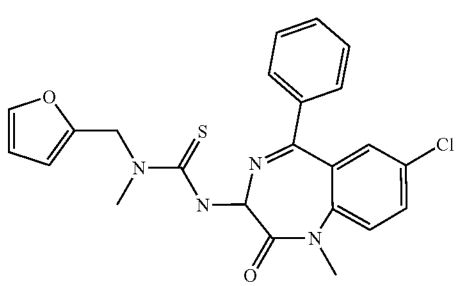 | 452.11 | No | |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 301 | 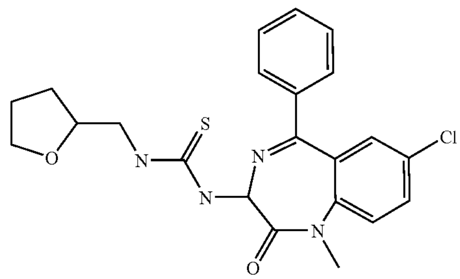 | 442.12 | Yes | 3.02 |
| 302 | 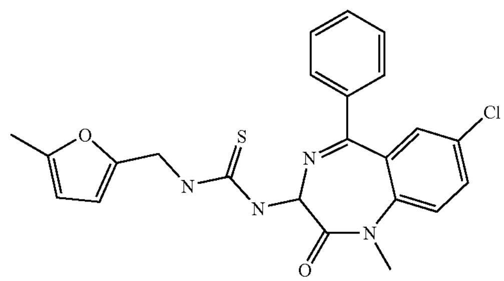 | 452.11 | Yes | 2.78, 3.41 |
| 303 | 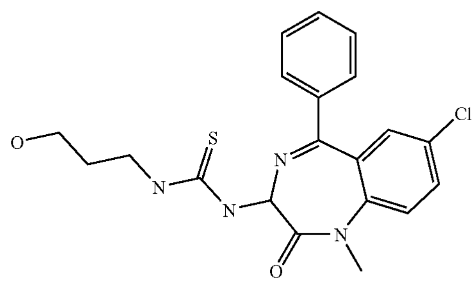 | 416.11 | Yes | 2.68 |
| 304 | 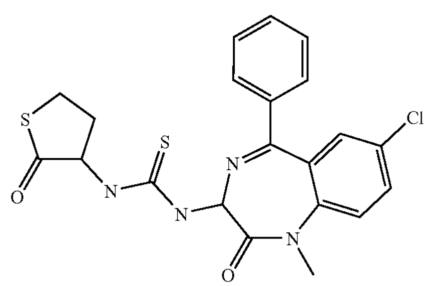 | 458.06 | No | |
| 305 | 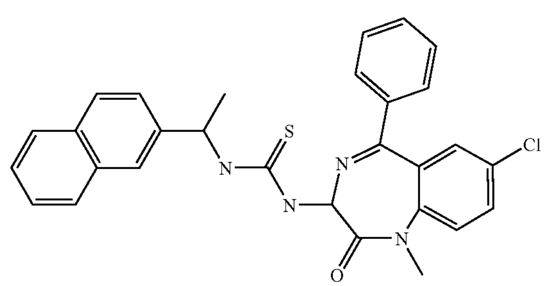 | 512.14 | Yes | 4.17 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 306 | 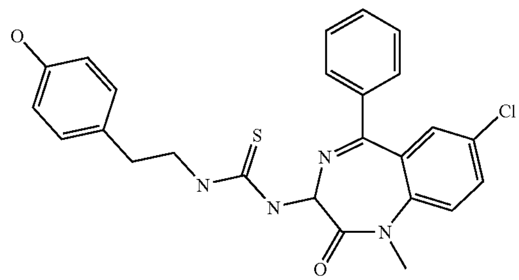 | 478.12 | Yes | 3.01 |
| 307 | 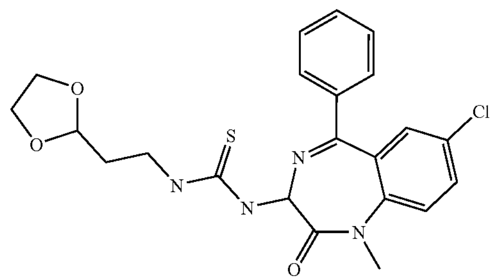 | 458.12 | Yes | 2.86 |
| 308 | 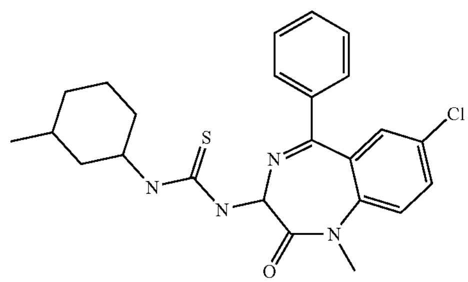 | 454.16 | Yes | 4.01 |
| 309 | 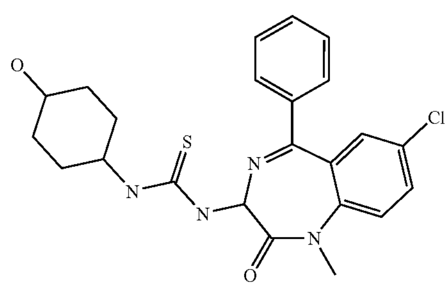 | 456.14 | Yes | 2.77 |
| 310 | 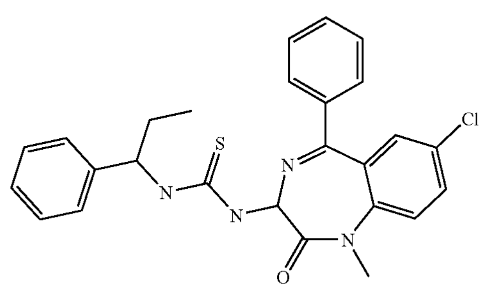 | 476.14 | Yes | 3.8 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 311 | 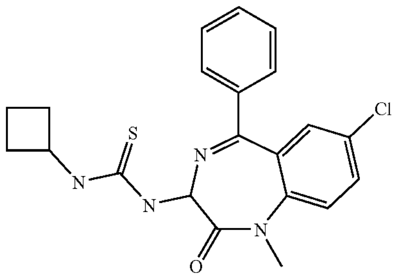 | 412.11 | Yes | 3.18, 6.2 |
| 312 | 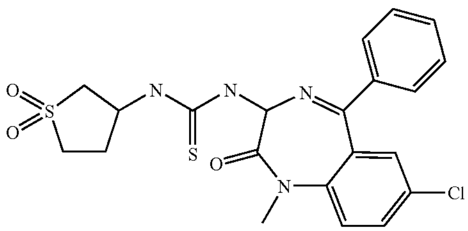 | 476.07 | Yes | 2.75 |
| 313 | 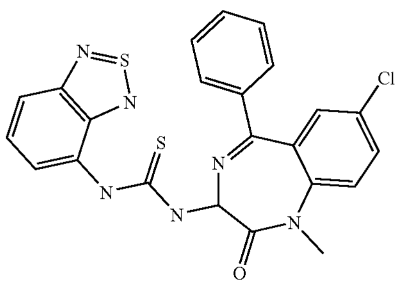 | 492.06 | Yes | 3.77 |
| 314 | 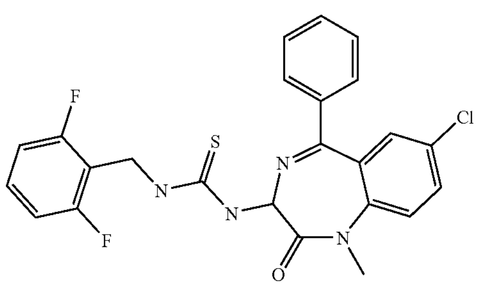 | 484.09 | Yes | 3.45 |
| 315 | 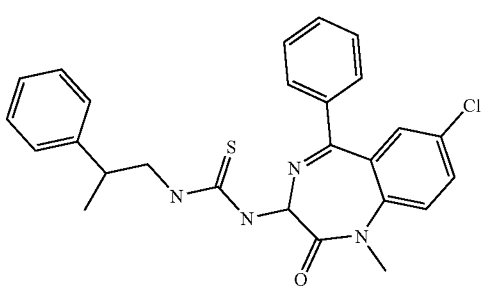 | 476.14 | Yes | 3.9 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 316 | 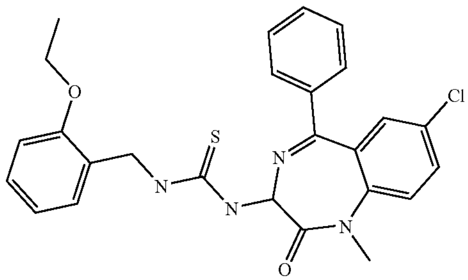 | 492.14 | Yes | 3.77 |
| 317 | 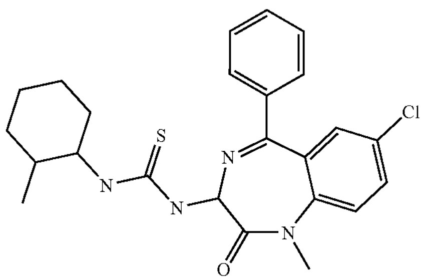 | 454.16 | Yes | 3.91 |
| 318 | 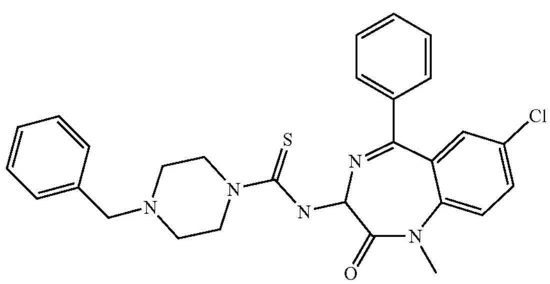 | 517.17 | No | |
| 319 | 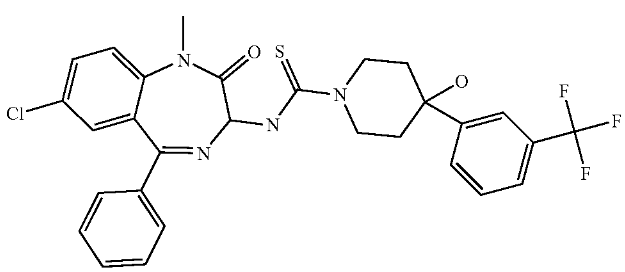 | 586.14 | Yes | 4 |
| 320 | 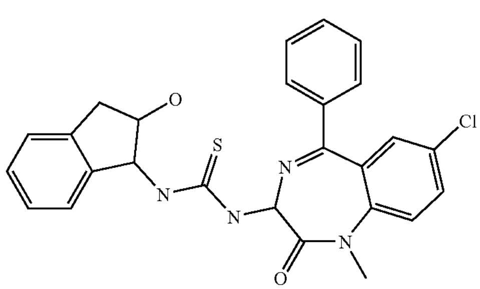 | 490.12 | Yes | 3.41, 3.63 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 321 | 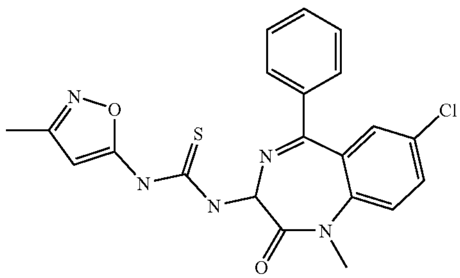 | 439.09 | Yes | 3.33 |
| 322 | 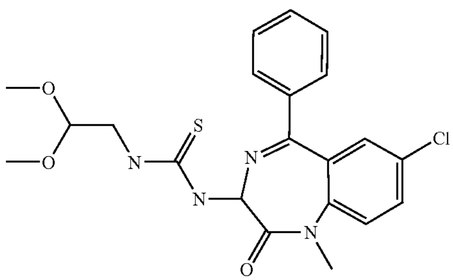 | 446.12 | Yes | 2.96 |
| 323 | 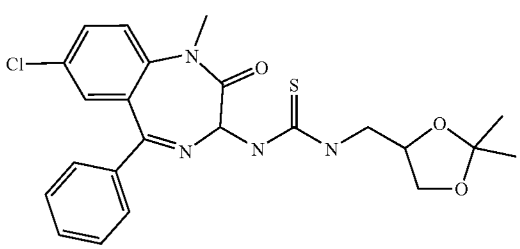 | 472.13 | Yes | 3.14 |
| 324 | 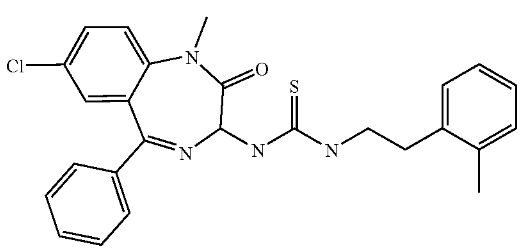 | 476.14 | Yes | 3.99 |
| 325 | 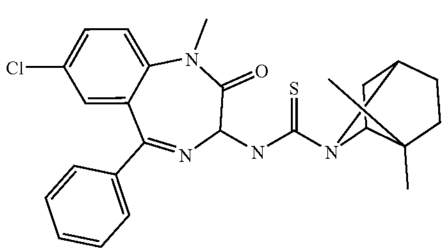 | 494.19 | No | |

TABLE 1-continued

Spreadsheet of combinatorially prepared compounds with LCMS analysis of the reaction product.

| Compound # | Structure | Target Mass | Mass Found? | Rtn Time (MS) |
| --- | --- | --- | --- | --- |
| 326 | 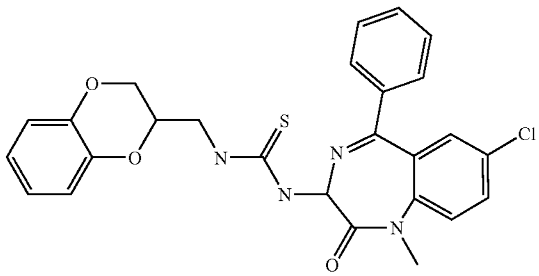 | 506.12 | Yes | 3.83 |
| 327 | 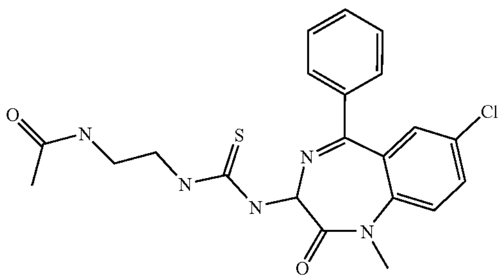 | 443.12 | Yes | 2.68 |
| 328 | 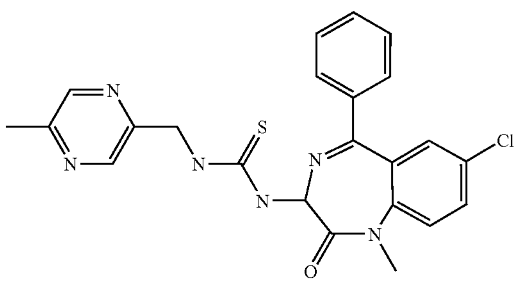 | 464.12 | Yes | 2.92 |
| 329 | 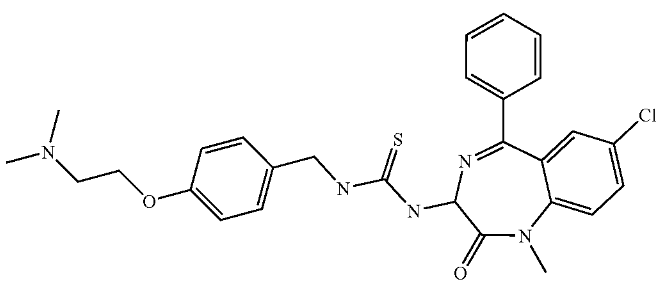 | 535.18 | Yes | 2.99 |
| 330 | 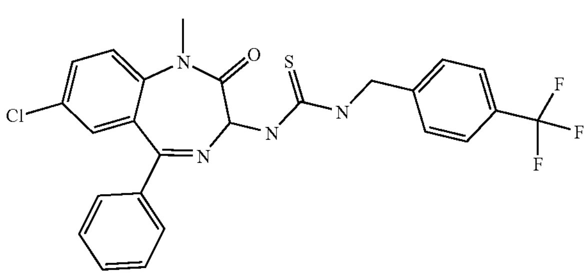 | 516.1 | Yes | 4.03 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 331 | 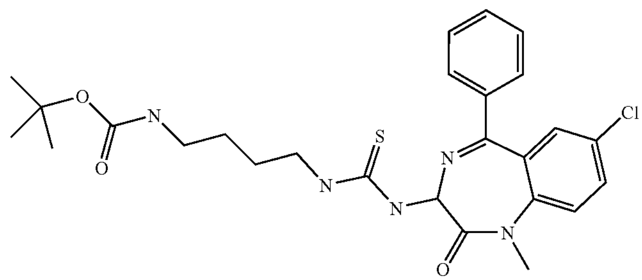 | 529.19 | Yes | 3.51 |
| 332 | 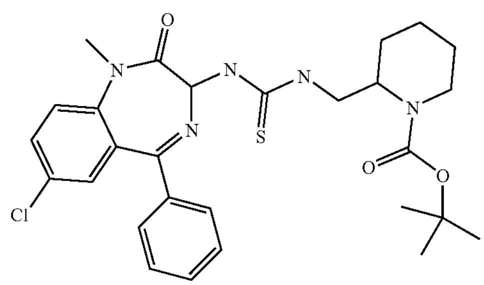 | 555.21 | Yes | 3.91, 4.15 |
| 333 | 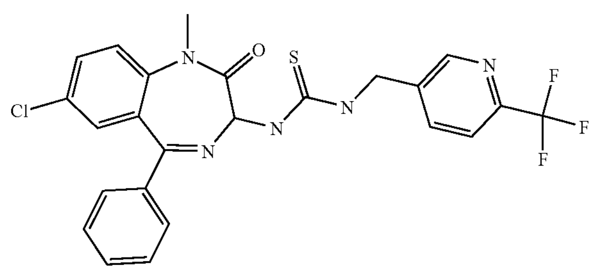 | 517.1 | Yes | 3.44 |
| 334 | 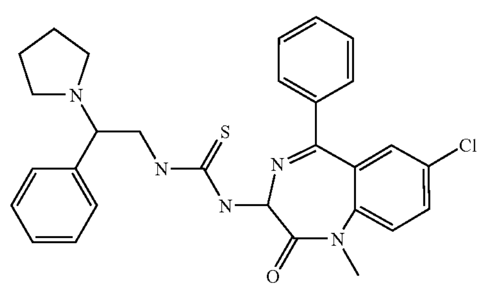 | 531.19 | Yes | 3.6, 3.76 |
| 335 | 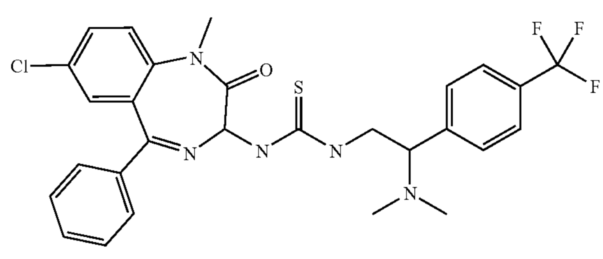 | 573.16 | Yes | 4.27 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 336 | 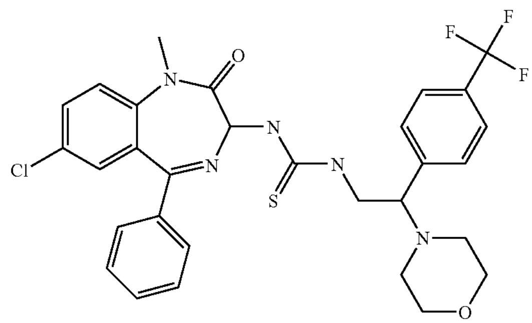 | 615.17 | Yes | 4.19 |
| 337 | 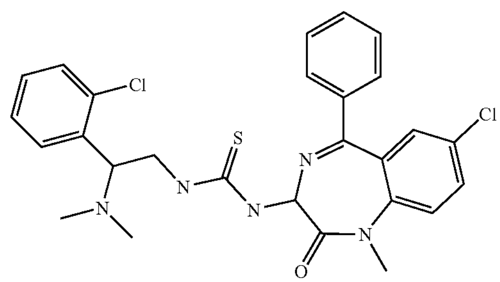 | 539.13 | Yes | 3.94 |
| 338 | 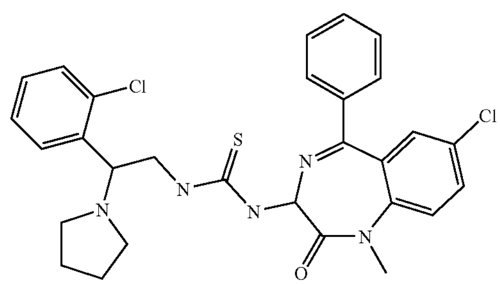 | 565.15 | Yes | 4.19, 4.36 |
| 339 | 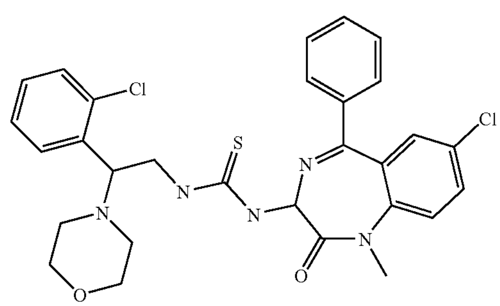 | 581.14 | Yes | 3.9 |
| 340 | 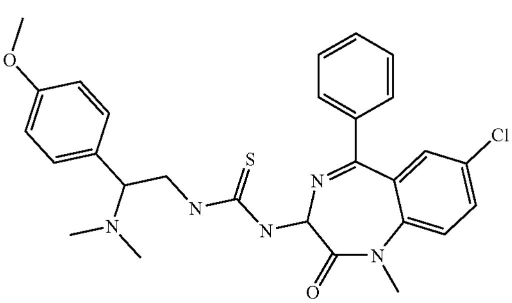 | 535.18 | Yes | 3.43 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 341 | 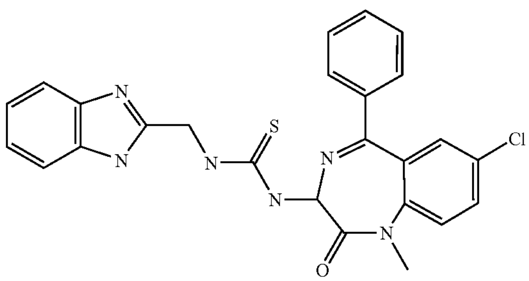 | 488.12 | No | |
| 342 | 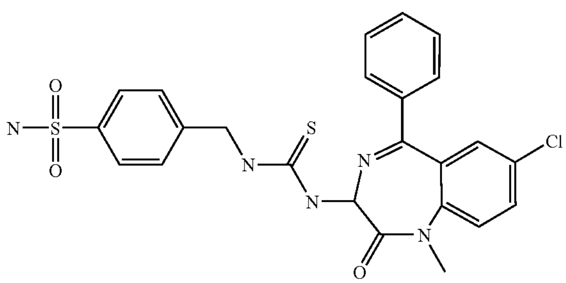 | 527.09 | Yes | 2.73 |
| 343 | 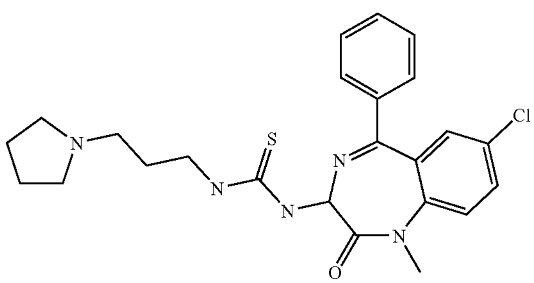 | 469.17 | Yes | 2.58 |
| 344 | 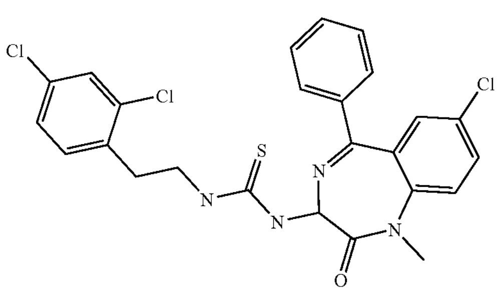 | 530.05 | Yes | 4.59 |
| 345 | 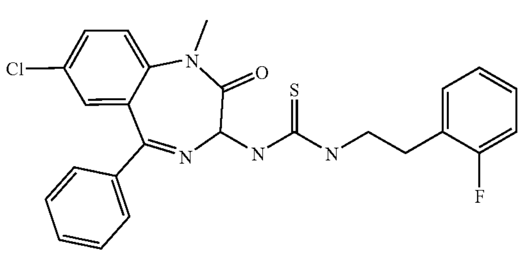 | 480.12 | Yes | 3.73 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 346 | 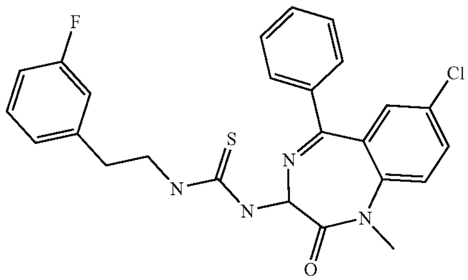 | 480.12 | Yes | 3.06, 3.76 |
| 347 | 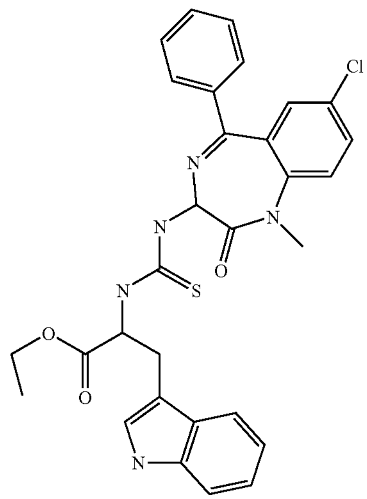 | 573.16 | Yes | 3.02 |
| 348 | 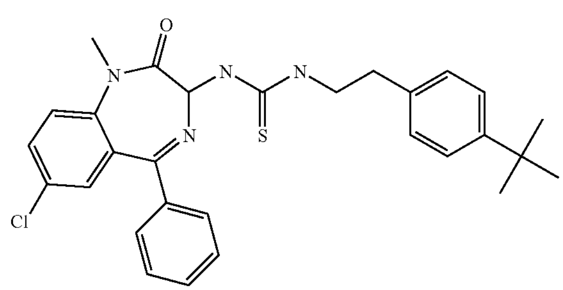 | 518.19 | Yes | 4.85 |
| 349 | 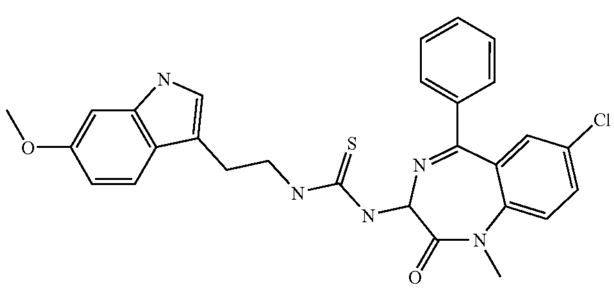 | 531.15 | Yes | 2.69, 3, 3.25, 3.36 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 350 | 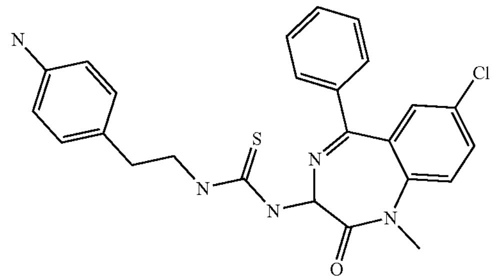 | 477.14 | Yes | 2.94 |
| 351 | 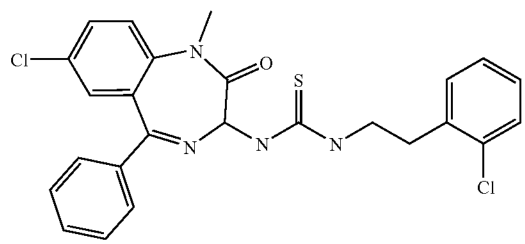 | 496.09 | Yes | 4.02 |
| 352 | 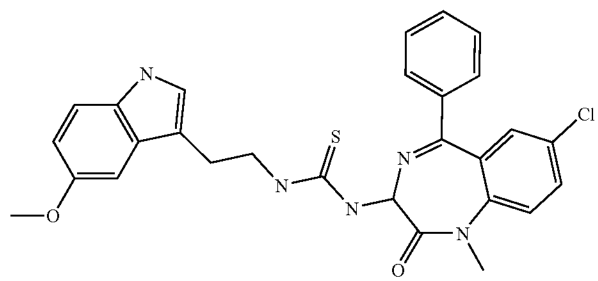 | 531.15 | Yes | 2.59, 3.2, 3.31 |
| 353 | 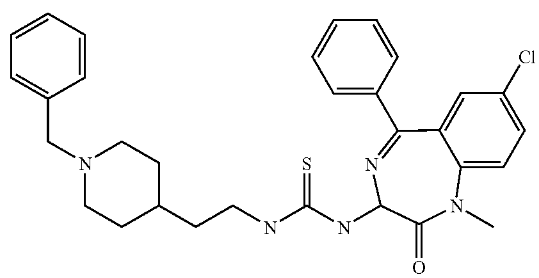 | 559.22 | Yes | 3.37 |
| 354 | 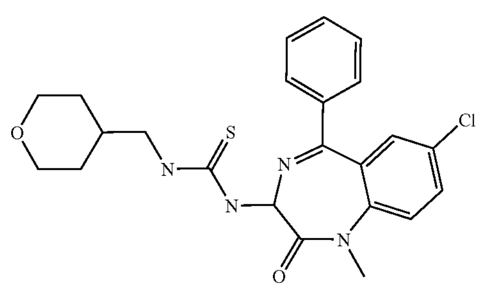 | 456.14 | Yes | 3.01 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 355 | 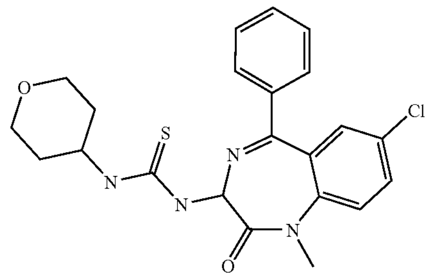 | 442.12 | Yes | 2.97 |
| 356 | 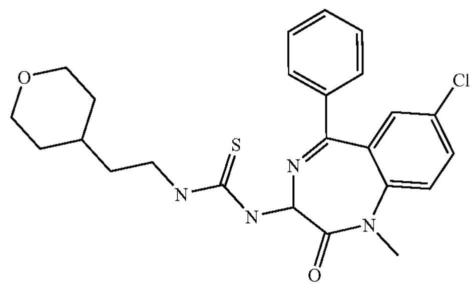 | 470.15 | Yes | 3.15 |
| 357 | 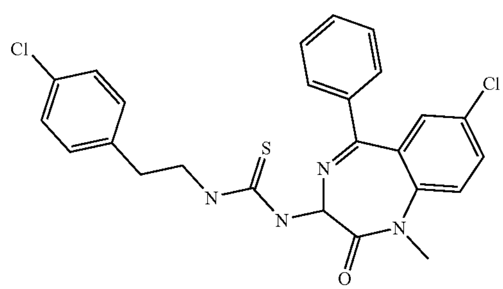 | 496.09 | Yes | 4.11 |
| 358 | 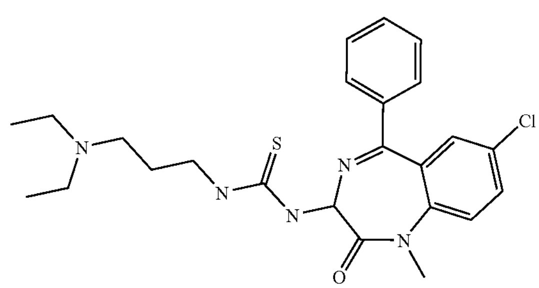 | 471.19 | Yes | 2.6 |
| 359 | 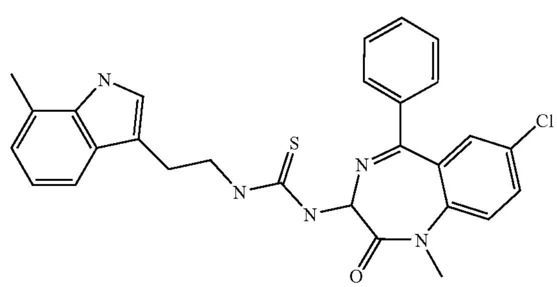 | 515.15 | Yes | 3.49, 3.69 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 360 | 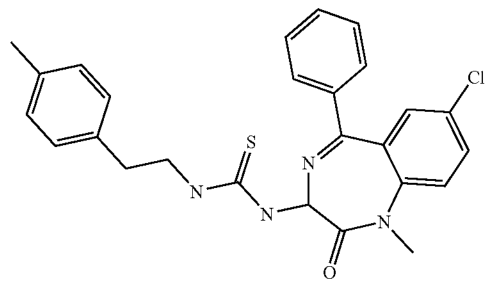 | 476.14 | Yes | 4.01 |
| 361 | 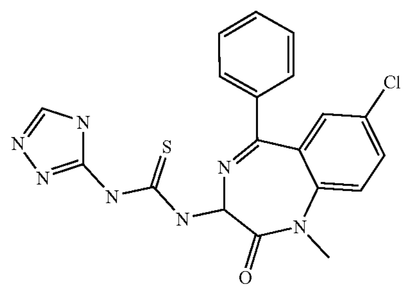 | 425.08 | Yes | 2.7 |
| 362 | 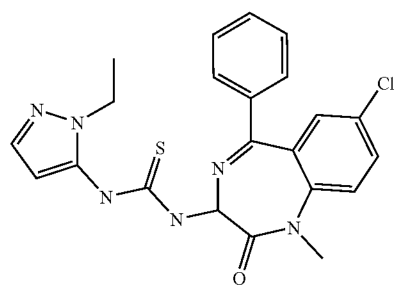 | 452.12 | Yes | 2.94 |
| 363 | 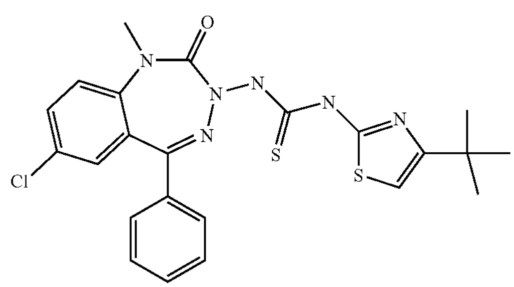 | 497.11 | Yes | 4.37 |
| 364 | 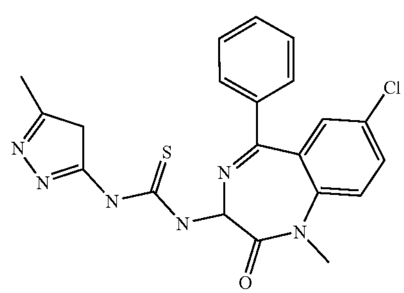 | 438.1 | Yes | 3.45 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 365 | 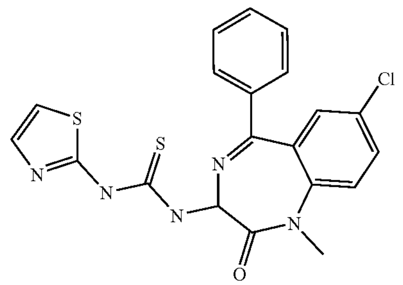 | 441.05 | Yes | 3.27 |
| 366 | 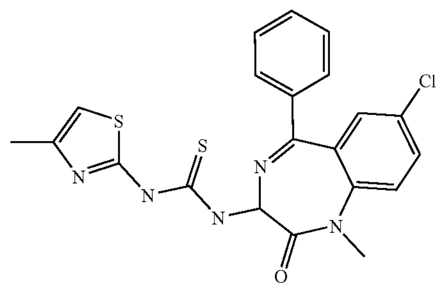 | 455.06 | Yes | 3.49 |
| 367 | 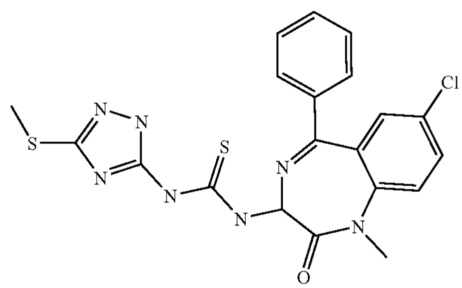 | 471.07 | No | |
| 368 | 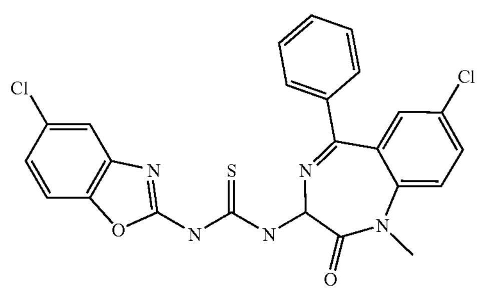 | 509.05 | No | |
| 369 | 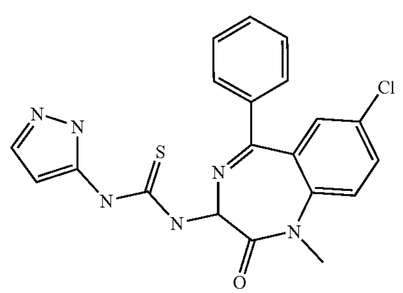 | 424.09 | Yes | 3.15 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 370 | 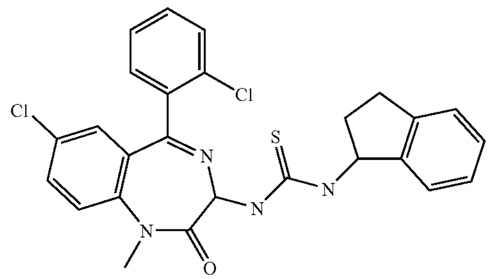 | 508.09 | No | |
| 371 | 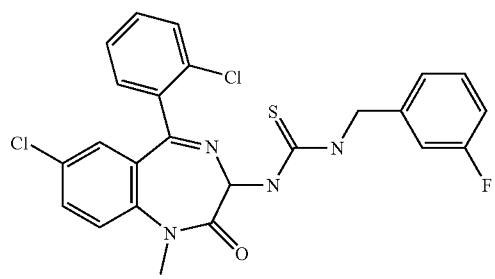 | 500.06 | Yes | 3.59 |
| 372 | 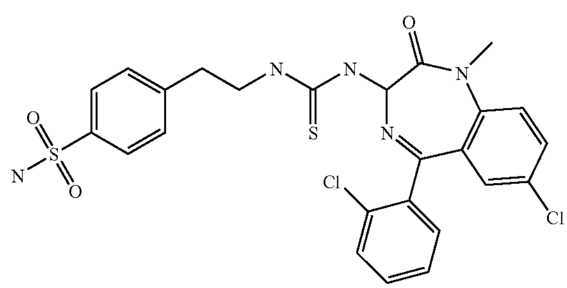 | 575.06 | Yes | 2.87 |
| 373 | 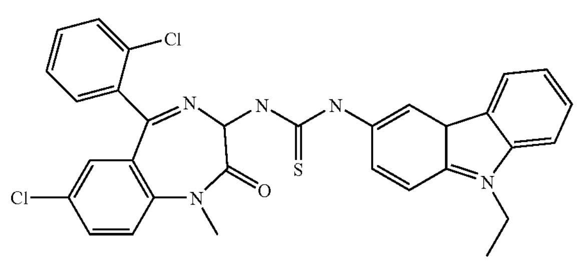 | 587.13 | No | |
| 374 | 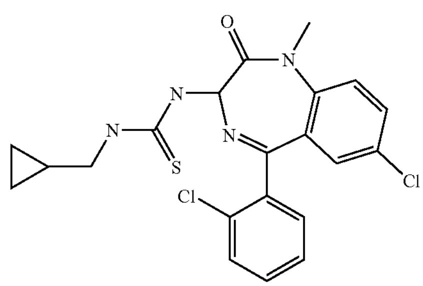 | 446.07 | No | |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 375 | 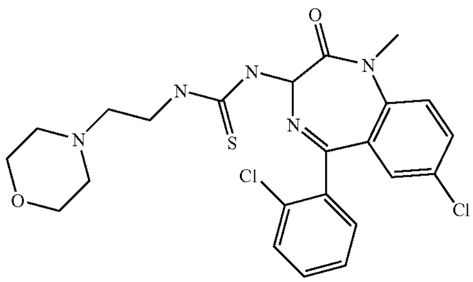 | 505.11 | Yes | 2.96 |
| 376 | 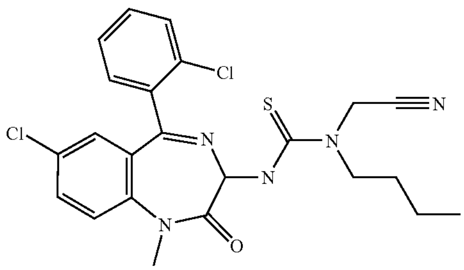 | 487.1 | Yes | 3.29, 4.02 |
| 377 | 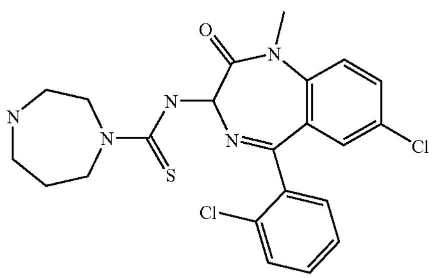 | 475.1 | Yes | 2.68 |
| 378 | 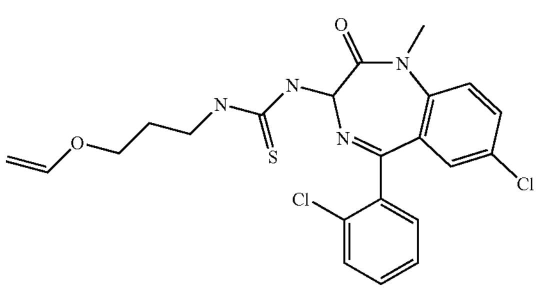 | 476.08 | No | |
| 379 | 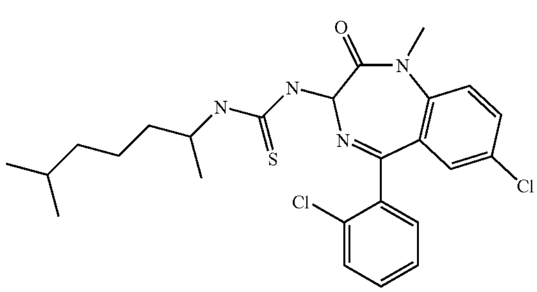 | 504.15 | Yes | 4.64 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 380 | 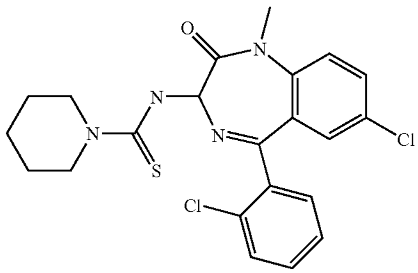 | 460.09 | Yes | 3.29 |
| 381 | 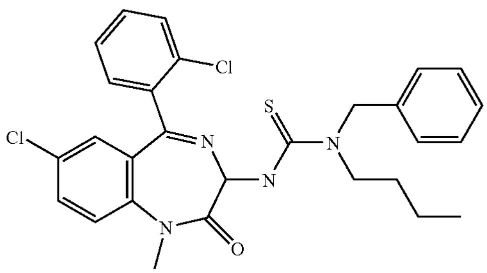 | 538.14 | Yes | 4.51 |
| 382 | 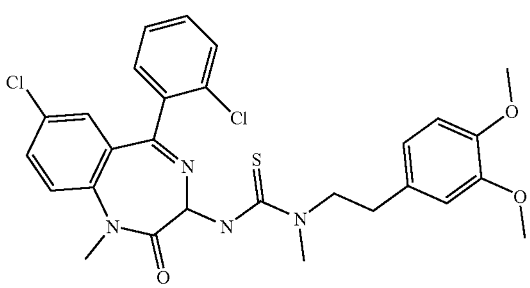 | 570.13 | Yes | 3.49 |
| 383 | 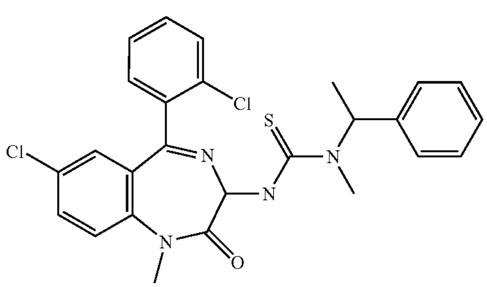 | 510.1 | Yes | 3.96 |
| 384 | 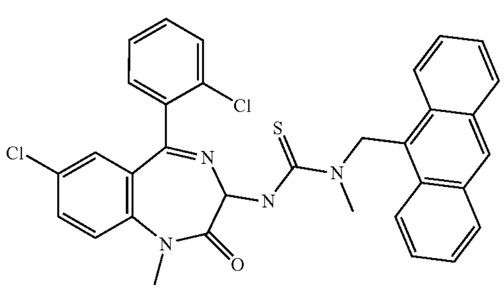 | 596.12 | Yes | |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 385 | 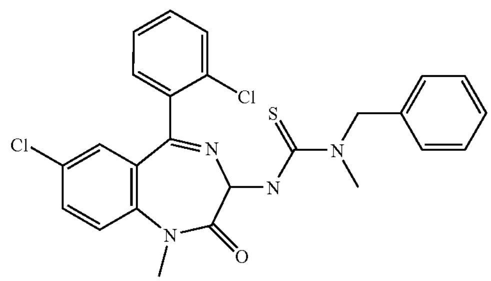 | 496.09 | Yes | 3.66 |
| 386 | 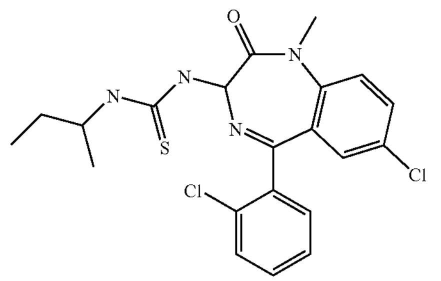 | 448.09 | No | |
| 387 | 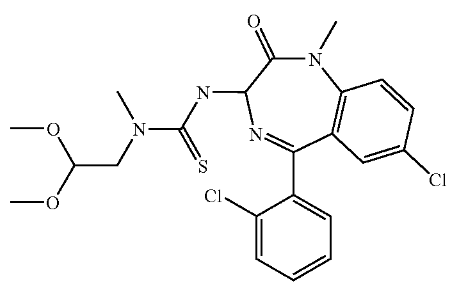 | 494.09 | Yes | 3.12 |
| 388 | 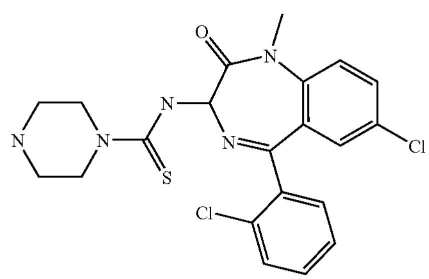 | 461.08 | Yes | 2.71 |
| 389 | 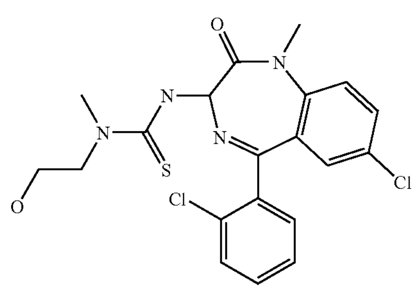 | 450.07 | Yes | 2.77 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 390 | 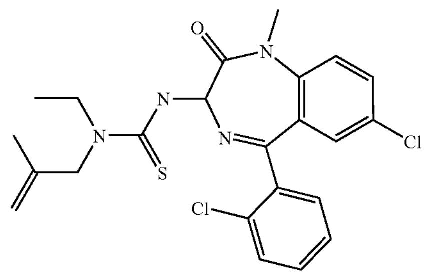 | 474.1 | Yes | 3.6 |
| 391 | 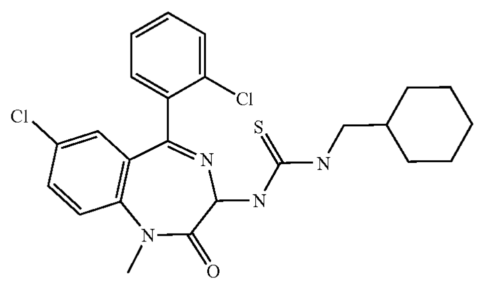 | 488.12 | No | |
| 392 | 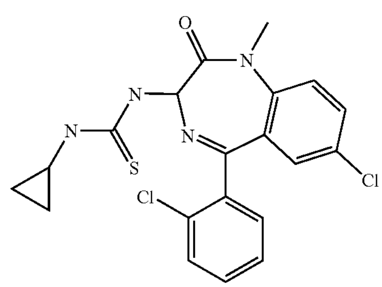 | 432.06 | No | |
| 393 | 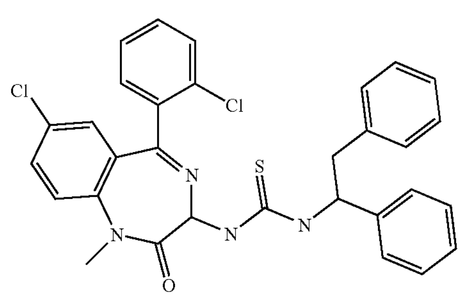 | 572.12 | Yes | 4.36 |
| 394 | 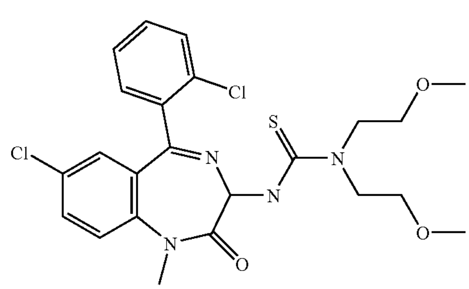 | 508.11 | Yes | 3.24 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 395 | 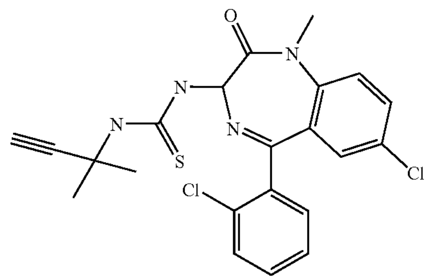 | 458.07 | Yes | 3.55 |
| 396 | 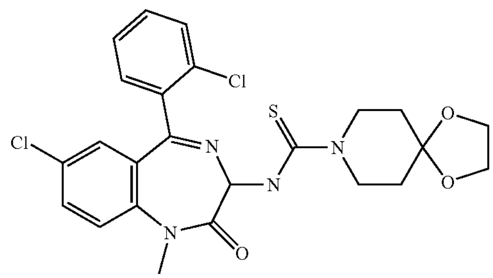 | 518.09 | Yes | 3.16 |
| 397 | 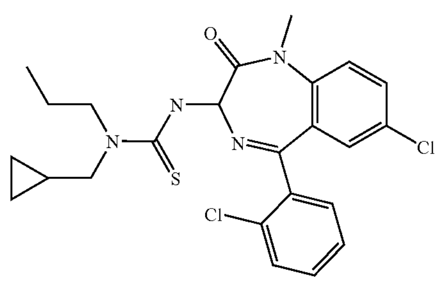 | 488.12 | Yes | 3.88 |
| 398 | 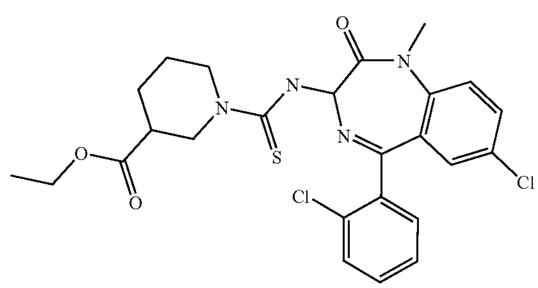 | 532.11 | Yes | 3.44 |
| 399 | 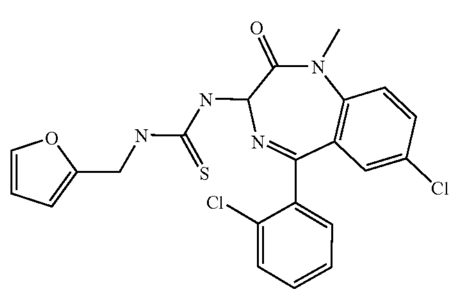 | 472.05 | Yes | 3.21 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 400 | | 514.08 | Yes | 3.72 |
| 401 | | 526.1 | Yes | 3.46 |
| 402 | | 528.15 | No | |
| 403 | | 474.1 | Yes | 3.51 |
| 404 | | 474.1 | Yes | 3.59 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 405 | 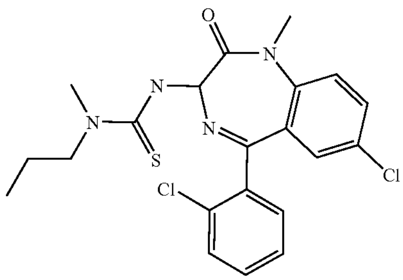 | 448.09 | No | |
| 406 | 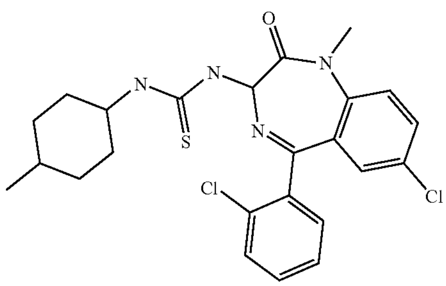 | 488.12 | No | |
| 407 | 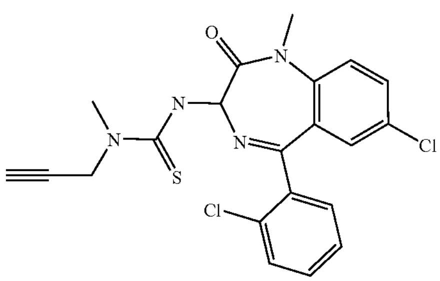 | 444.06 | Yes | 2.84, 3.26 |
| 408 | 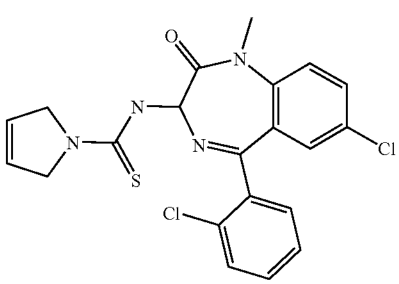 | 444.06 | Yes | 3.06 |
| 409 | 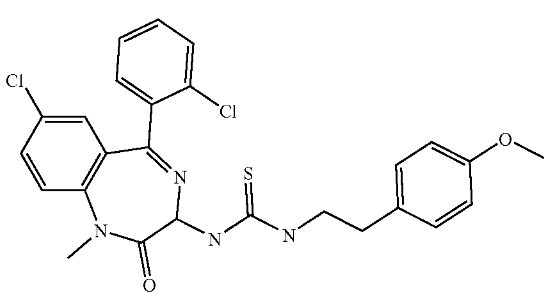 | 526.1 | Yes | 3.64 |

TABLE 1-continued

Spreadsheet of combinatorially prepared compounds with LCMS analysis of the reaction product.

| Compound # | Structure | Target Mass | Mass Found? | Rtn Time (MS) |
| --- | --- | --- | --- | --- |
| 410 | 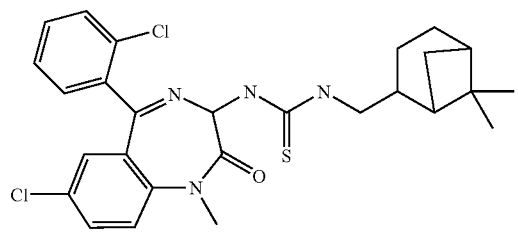 | 528.15 | Yes | 4.73 |
| 411 | 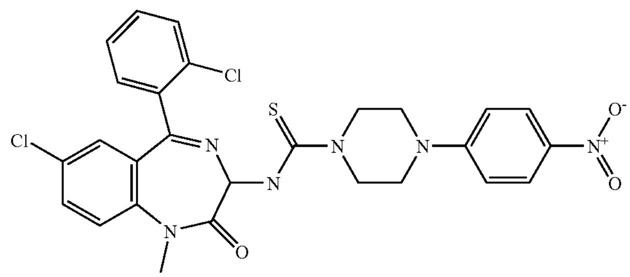 | 582.1 | Yes | 3.63 |
| 412 | 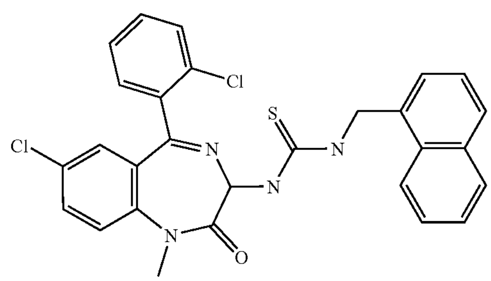 | 532.09 | Yes | 4.08 |
| 413 | 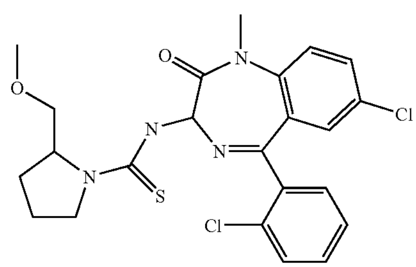 | 490.1 | Yes | 3.23 |
| 414 | 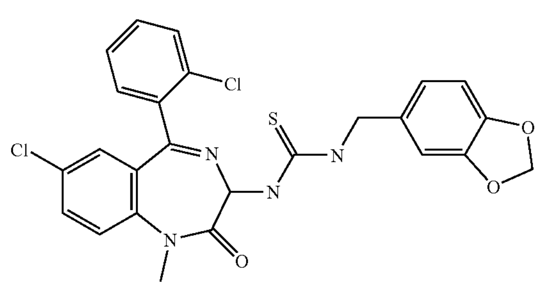 | 526.06 | Yes | 3.44 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 415 | 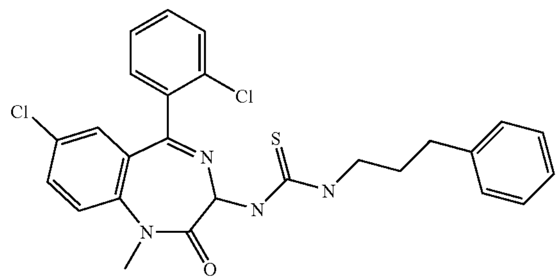 | 510.1 | Yes | 3.92 |
| 416 | 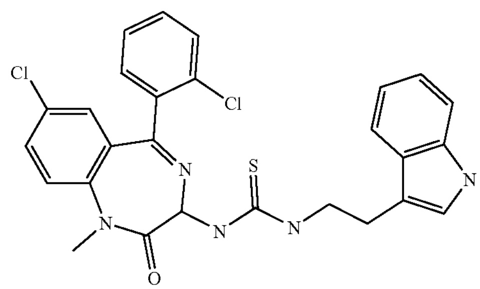 | 535.1 | Yes | 2.86, 3.28, 3.48 |
| 417 | 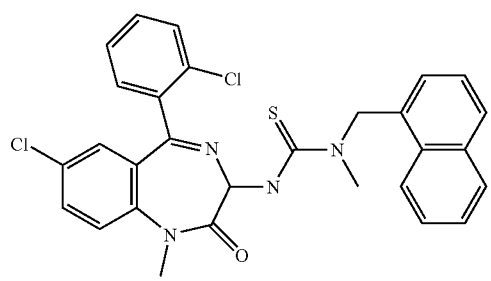 | 546.1 | Yes | 4.25 |
| 418 | 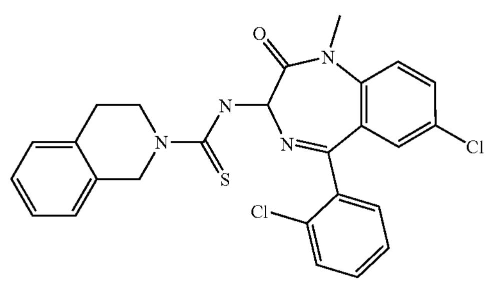 | 508.09 | Yes | 3.81 |
| 419 | 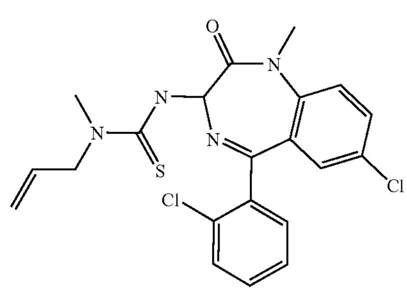 | 446.07 | Tentative | 3.1 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 420 | 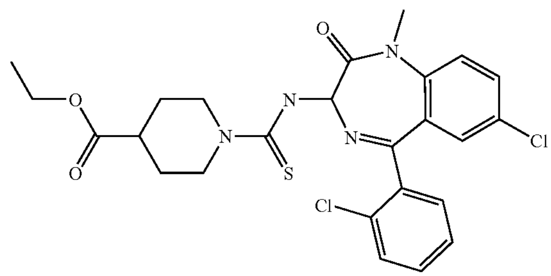 | 532.11 | Yes | 3.41 |
| 421 | 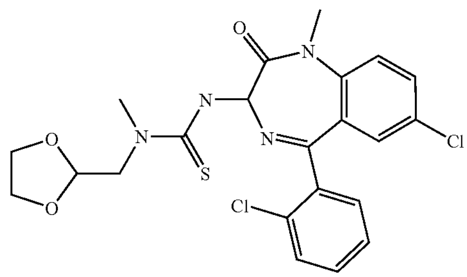 | 492.08 | Yes | 3.03 |
| 422 | 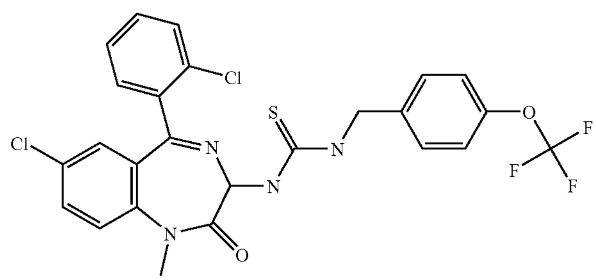 | 566.06 | Yes | 4.19 |
| 423 | 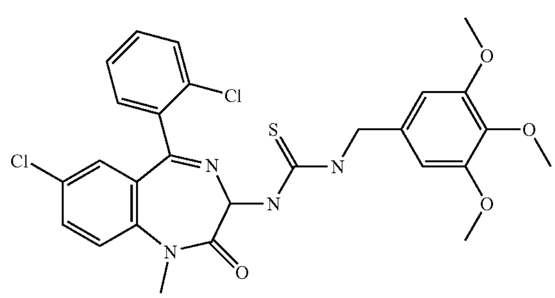 | 572.11 | Yes | 3.3 |
| 424 | 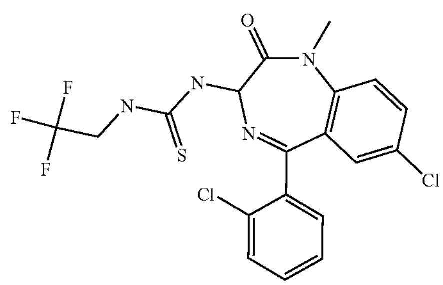 | 474.03 | No | |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 425 | 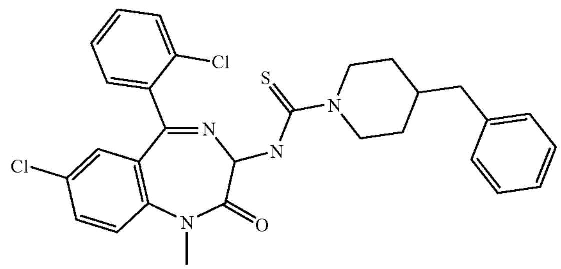 | 550.14 | Yes | 4.43 |
| 426 | 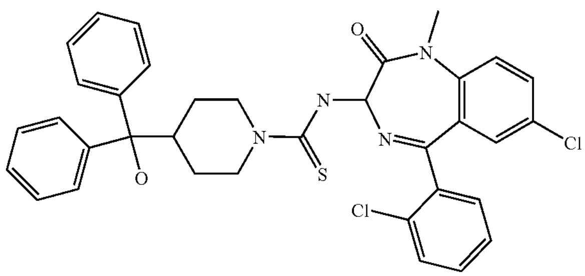 | 642.16 | Yes | 4.22 |
| 427 | 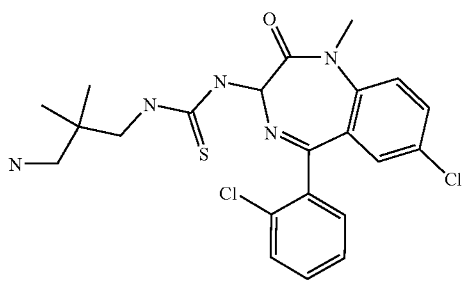 | 477.12 | Yes | 2.65 |
| 428 | 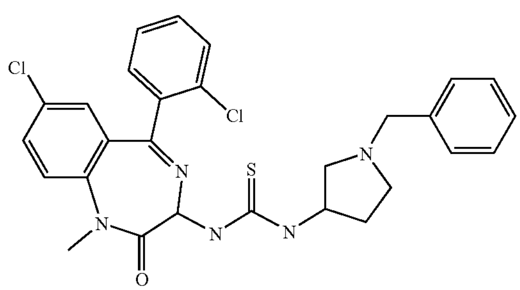 | 551.13 | Yes | 3.74 |
| 429 | 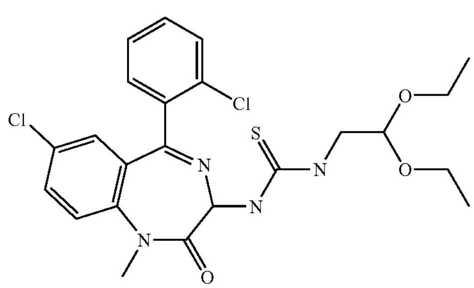 | 508.11 | Yes | 3.42 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 430 | 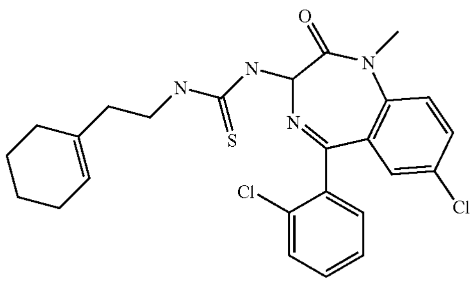 | 500.12 | Yes | 4.24 |
| 431 | 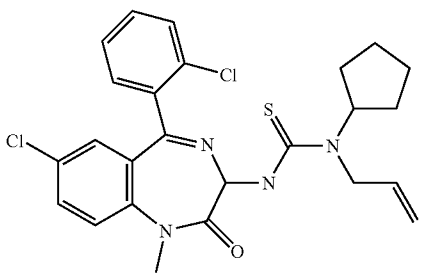 | 500.12 | Yes | 4 |
| 432 | 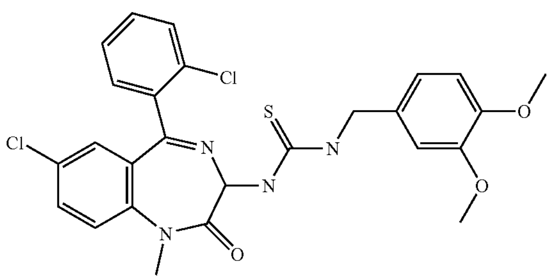 | 542.09 | Yes | 3.25 |
| 433 | 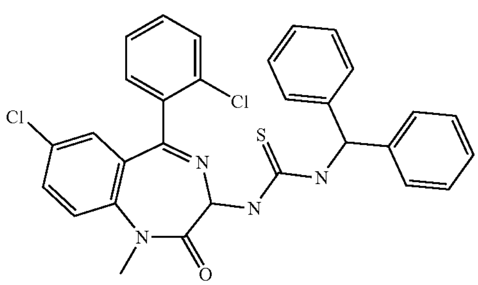 | 558.1 | Yes | 4.2 |
| 434 | 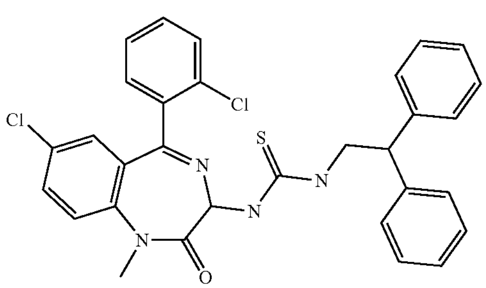 | 572.12 | Yes | 4.4 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 435 | 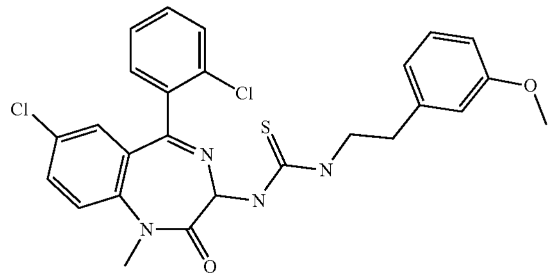 | 526.1 | Yes | 3.69 |
| 436 | 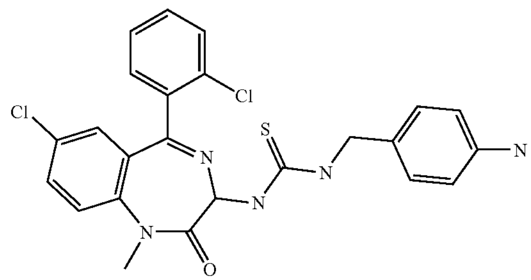 | 497.08 | Yes | 2.68 |
| 437 | 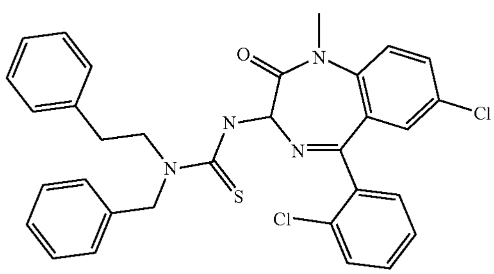 | 586.14 | Yes | 4.83 |
| 438 | 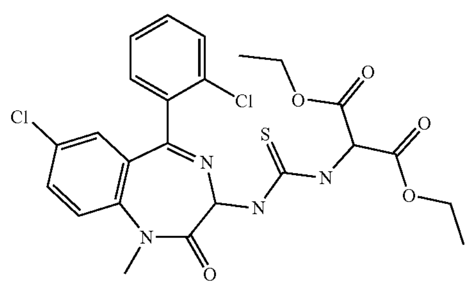 | 550.08 | Yes | 3.41 |
| 439 | 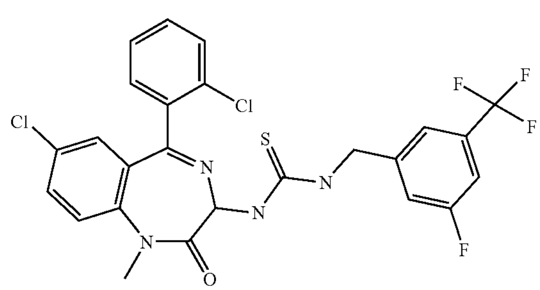 | 568.05 | Yes | 4.27 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 440 | 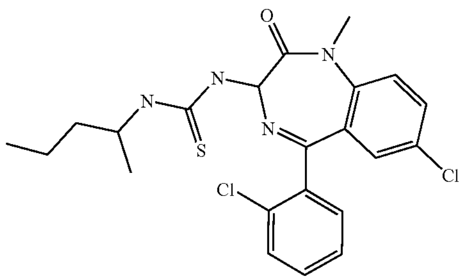 | 462.1 | Yes | 3.66 |
| 441 | 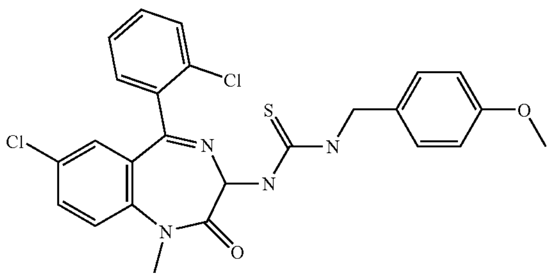 | 512.08 | Yes | 3.46 |
| 442 | 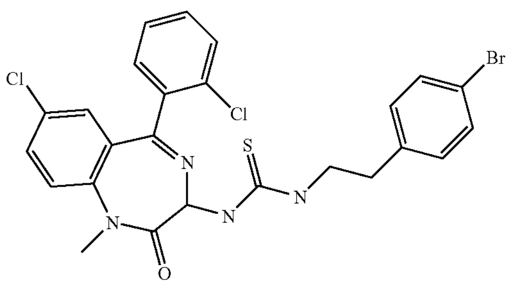 | 574 | Yes | 4.24 |
| 443 | 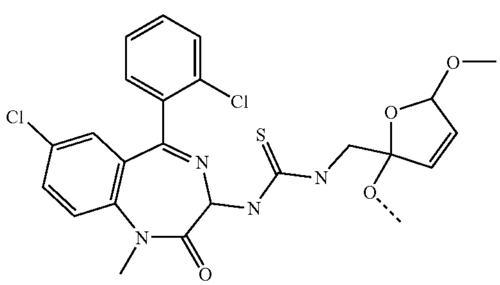 | 534.09 | Yes | 3.14 |
| 444 | 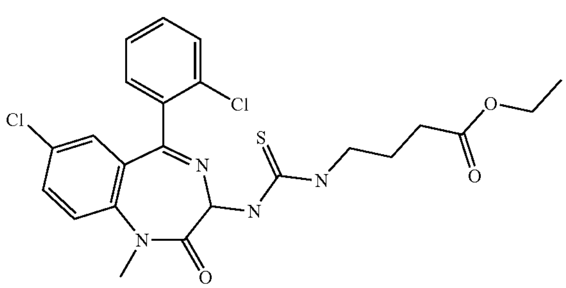 | 506.09 | Yes | 3.24 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 445 | 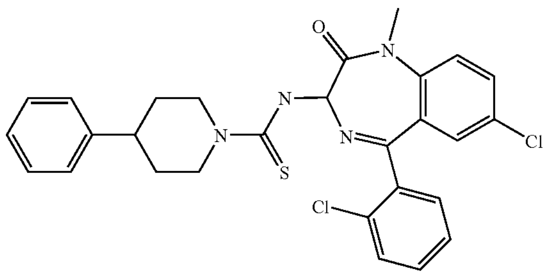 | 536.12 | No | |
| 446 | 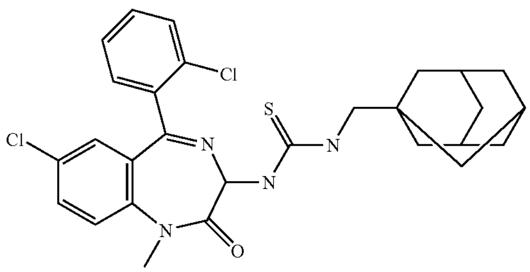 | 540.15 | Yes | 4.79 |
| 447 | 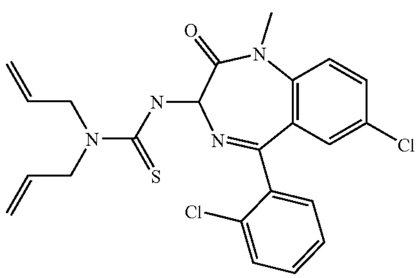 | 472.09 | Yes | 3.55 |
| 448 | 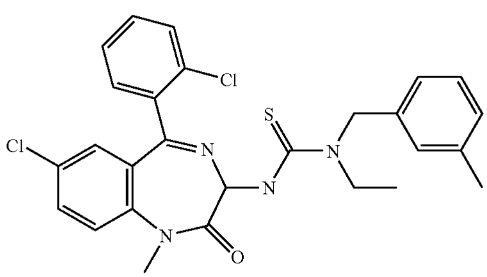 | 524.12 | Yes | 4.19 |
| 449 | 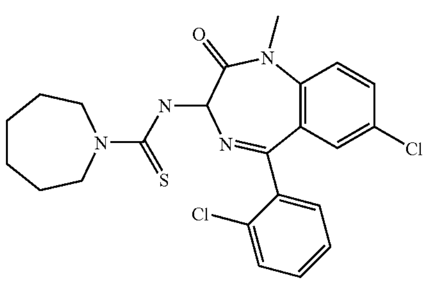 | 474.1 | Yes | 3.53 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 450 | 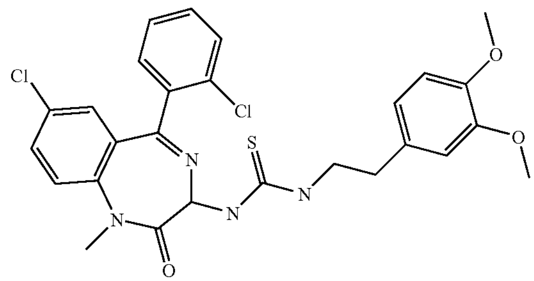 | 556.11 | Yes | 3.38 |
| 451 | 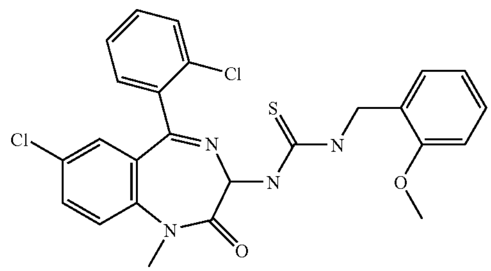 | 512.08 | Yes | 3.52 |
| 452 | 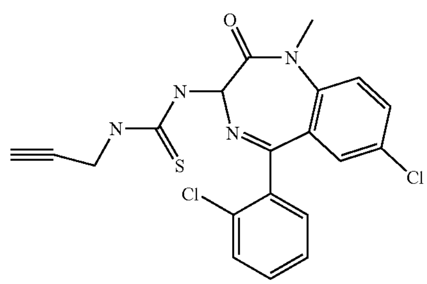 | 430.04 | Yes | 3.11, 6.48 |
| 453 | 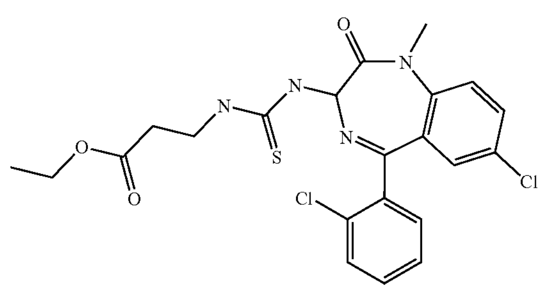 | 492.08 | Yes | 3.16 |
| 454 | 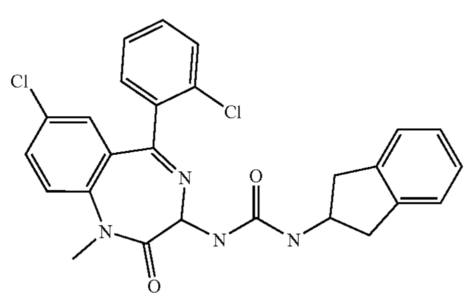 | 508.09 | Yes | 3.9 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 455 | 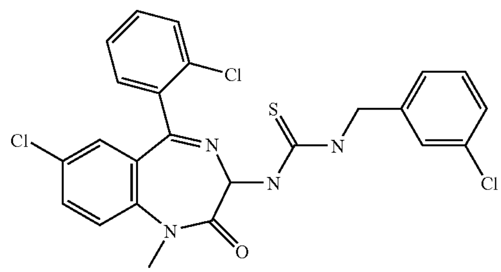 | 516.03 | Yes | 3.9 |
| 456 | 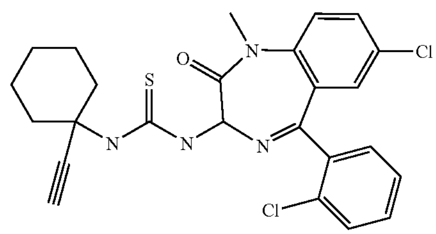 | 498.1 | Yes | 4.65, 6.23 |
| 457 | 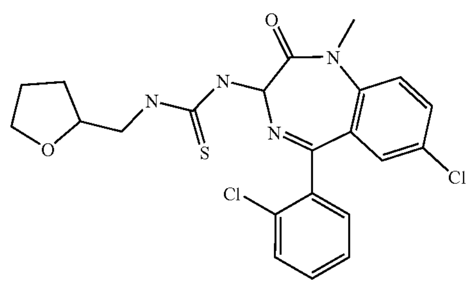 | 476.08 | Yes | 3.08 |
| 458 | 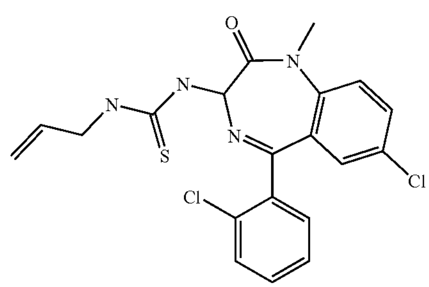 | 432.06 | No | |
| 459 | 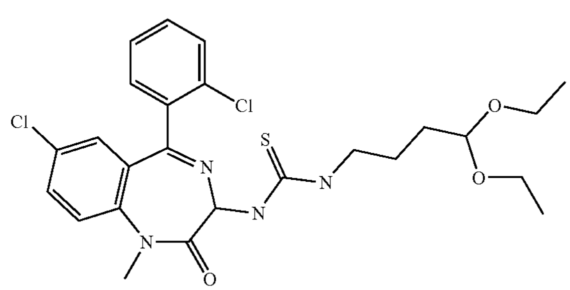 | 536.14 | No | |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 460 | 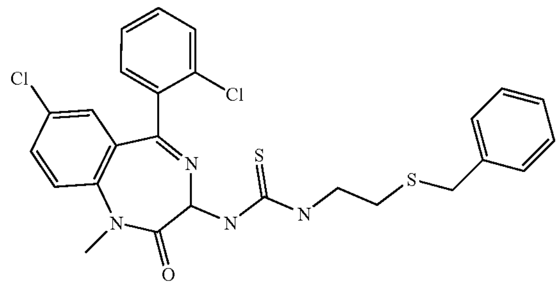 | 542.08 | Yes | 3.25, 4.03 |
| 461 | 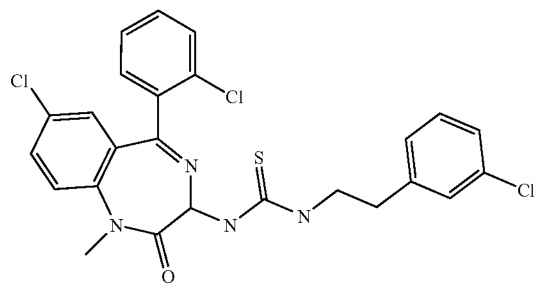 | 530.05 | Yes | 4.12 |
| 462 | 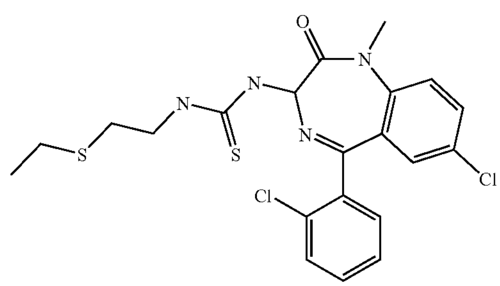 | 480.06 | Yes | 2.81, 3.43 |
| 463 | 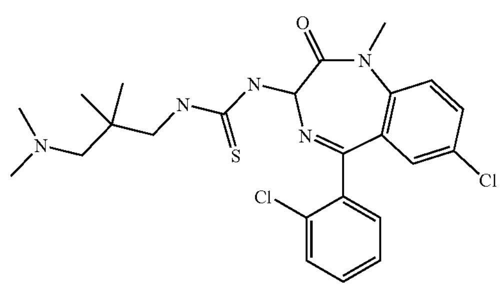 | 505.15 | Yes | 2.93 |
| 464 | 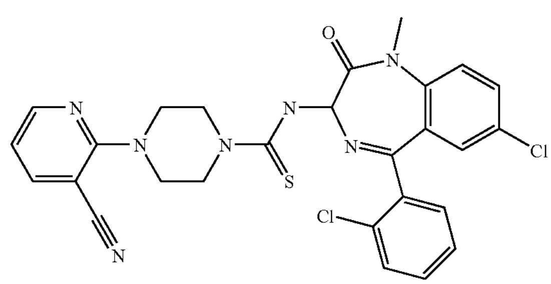 | 563.11 | Yes | 3.43 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 465 | 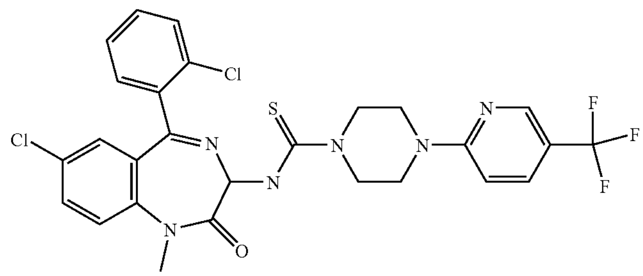 | 606.1 | Yes | 4.14 |
| 466 | 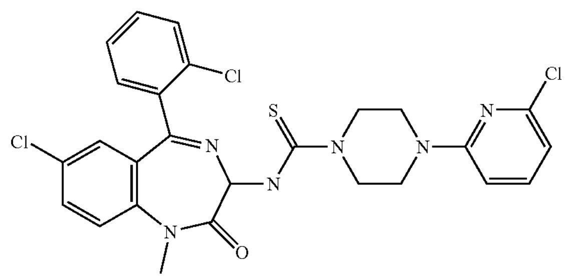 | 572.07 | Yes | 3.96 |
| 467 | 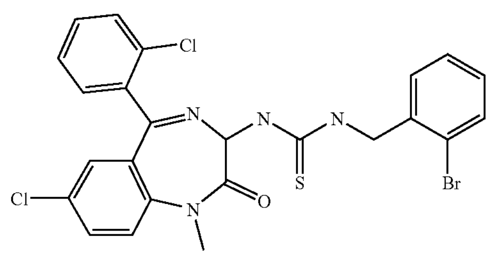 | 559.98 | Yes | 3.86 |
| 468 | 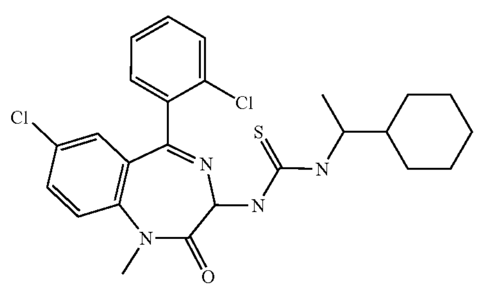 | 502.14 | No | |
| 469 | 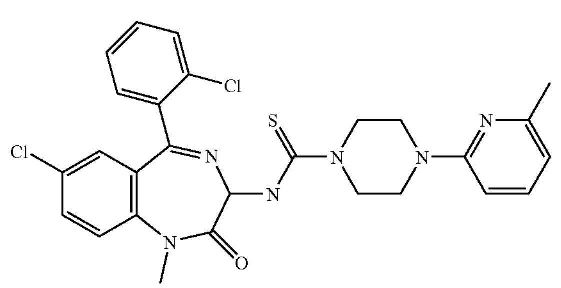 | 552.13 | Yes | 3.83 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 470 | 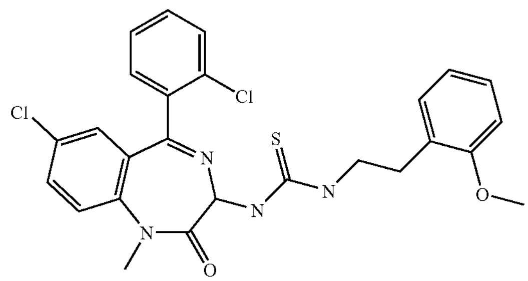 | 526.1 | Yes | 3.75 |
| 471 | 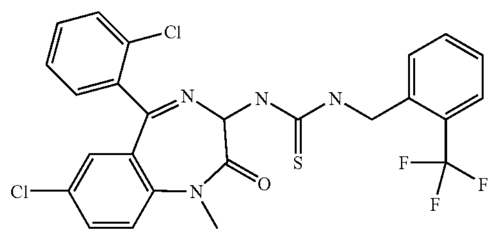 | 550.06 | Yes | 3.92 |
| 472 | 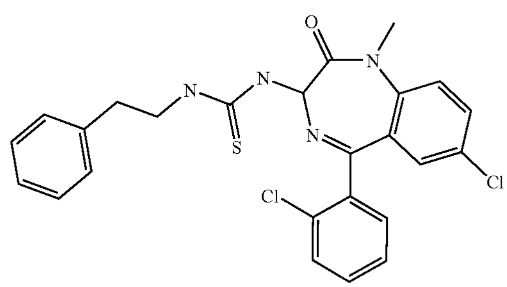 | 496.09 | Yes | 3.72 |
| 473 | 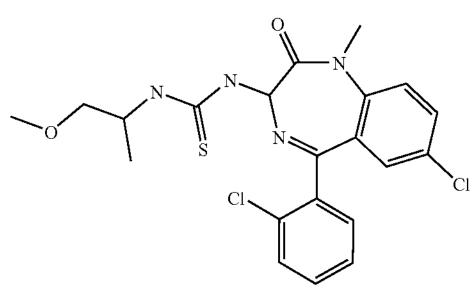 | 464.08 | Yes | 3.08 |
| 474 | 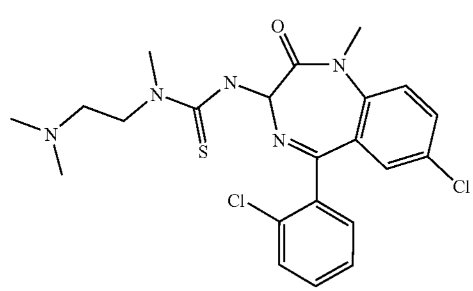 | 477.12 | Yes | 2.85 |

TABLE 1-continued
Spreadsheet of combinatorially prepared compounds with LCMS analysis of the reaction product.
| Compound # | Structure | Target Mass | Mass Found? | Rtn Time (MS) |
|---|---|---|---|---|
| 475 | 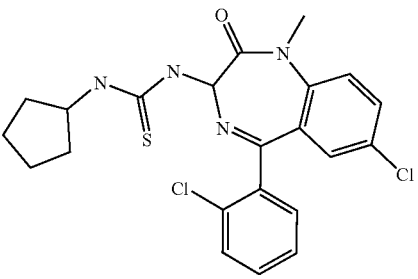 | 460.09 | Yes | 3.44 |
| 476 | 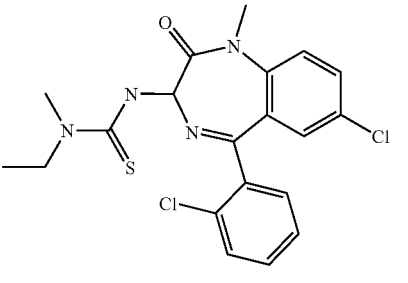 | 434.07 | No | |
| 477 | 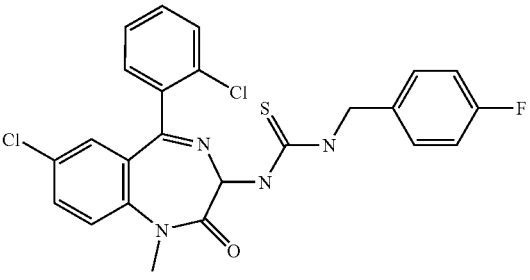 | 500.06 | Yes | 3.59 |
| 478 | 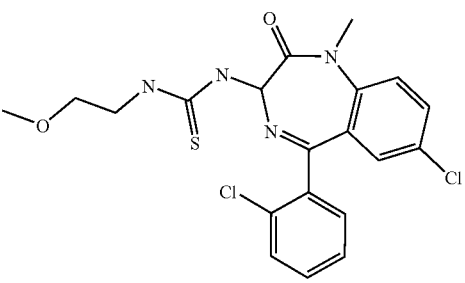 | 450.07 | Yes | 2.93 |
| 479 | 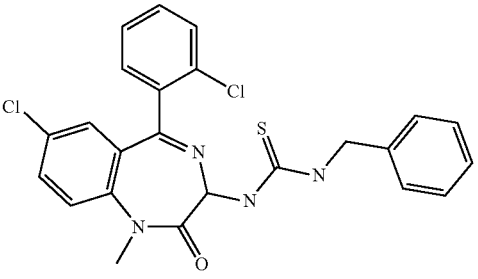 | 482.07 | Yes | 3.49 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 480 | 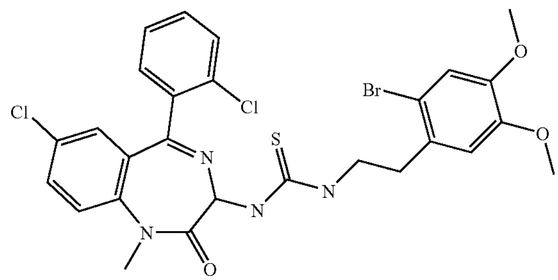 | 634.02 | Yes | 3.89 |
| 481 | 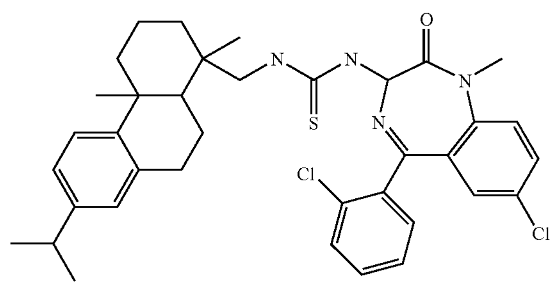 | 660.25 | No | |
| 482 | 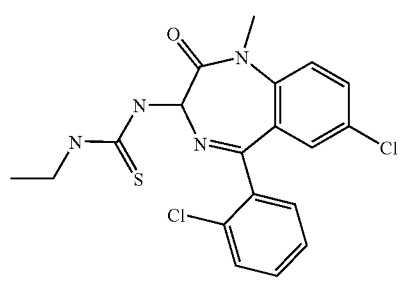 | 420.06 | No | |
| 483 | 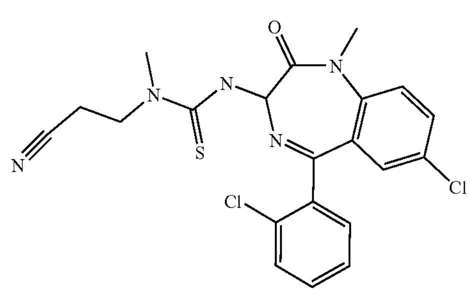 | 459.07 | Yes | 2.89 |
| 484 | 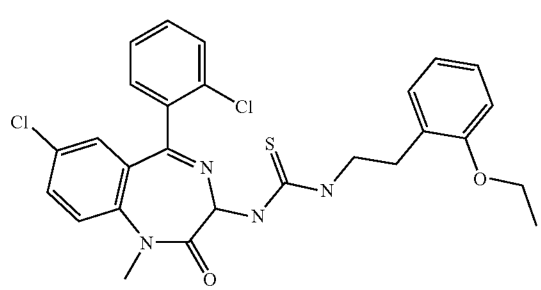 | 540.12 | Yes | 4.07 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 485 | 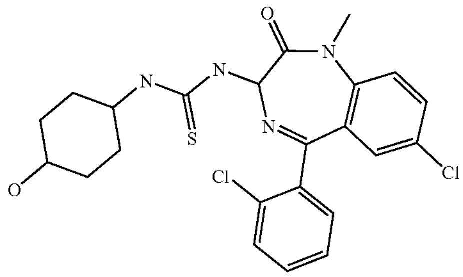 | 490.1 | Yes | 2.85 |
| 486 | 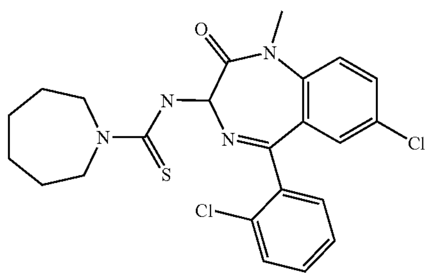 | 488.12 | Yes | 1.84, 3.8 |
| 487 | 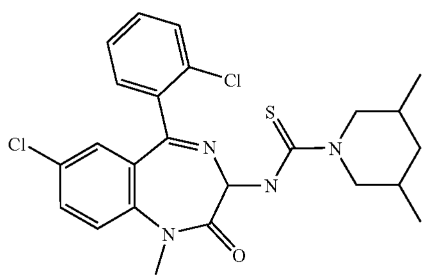 | 488.12 | Yes | 3.93 |
| 488 | 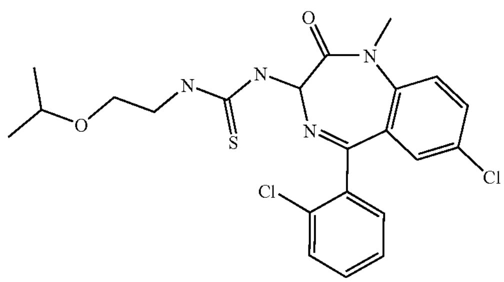 | 478.1 | Yes | 3.32 |
| 489 | 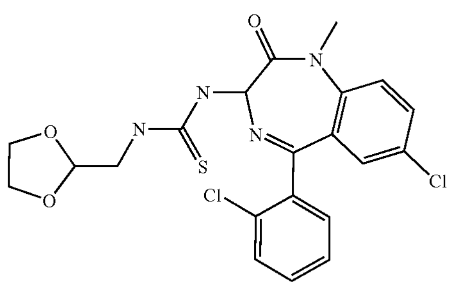 | 478.06 | Yes | 2.87 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 490 | 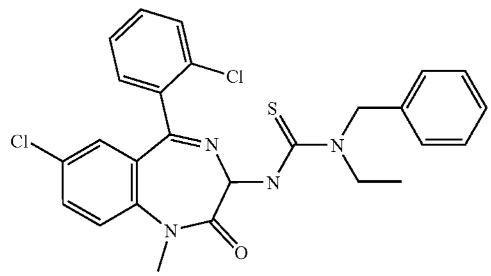 | 510.1 | Yes | 3.87 |
| 491 | 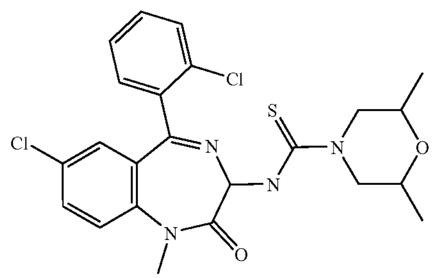 | 490.1 | Yes | 3.3 |
| 492 | 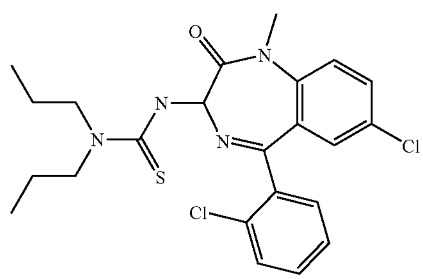 | 476.12 | Yes | 3.81 |
| 493 | 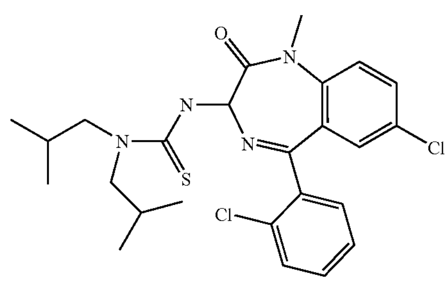 | 504.15 | Yes | 4.39 |
| 494 | 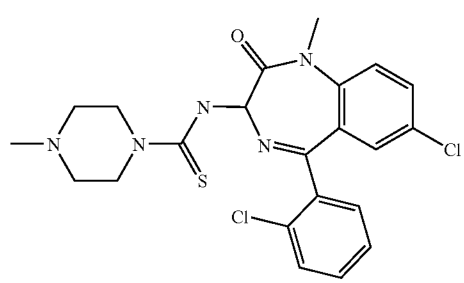 | 475.1 | Yes | 2.99 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 495 | 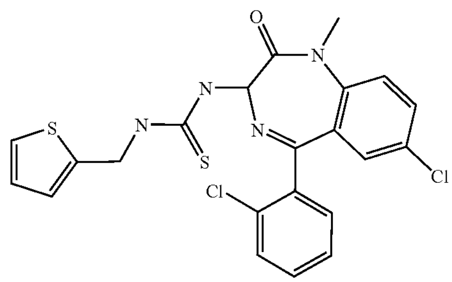 | 488.03 | Yes | 3.37 |
| 496 | 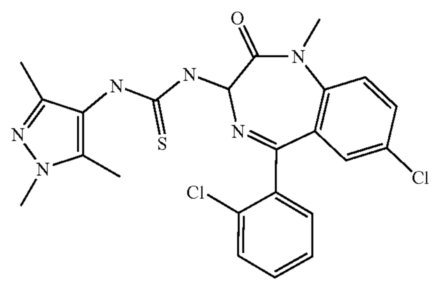 | 500.1 | Yes | 2.88 |
| 497 | 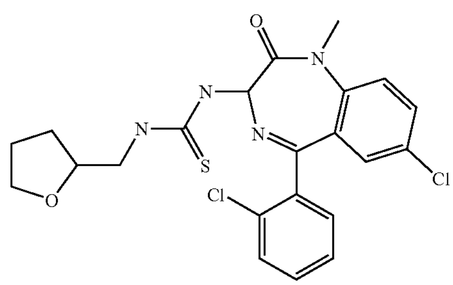 | 476.08 | Yes | 3.08 |
| 498 | 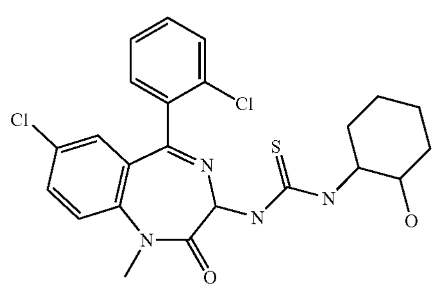 | 490.1 | No | |
| 499 | 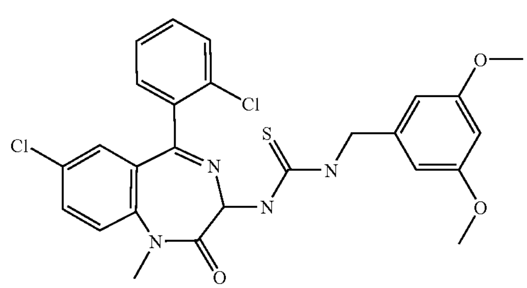 | 542.09 | Yes | 3.53 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 500 | 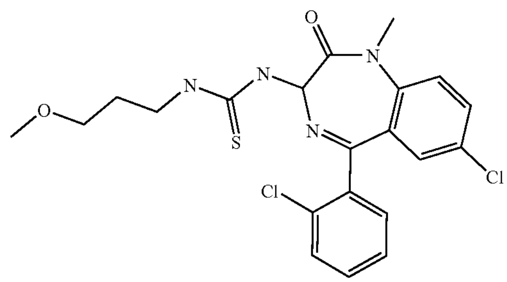 | 464.08 | Yes | 3 |
| 501 | 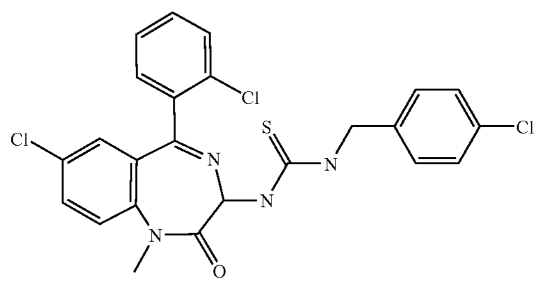 | 516.03 | Yes | 3.92 |
| 502 | 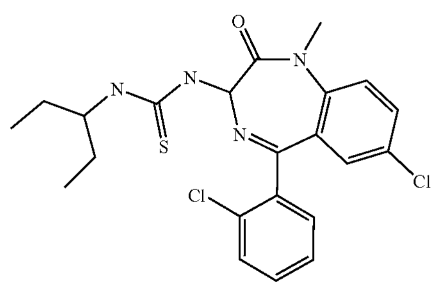 | 462.1 | Yes | 3.58 |
| 503 | 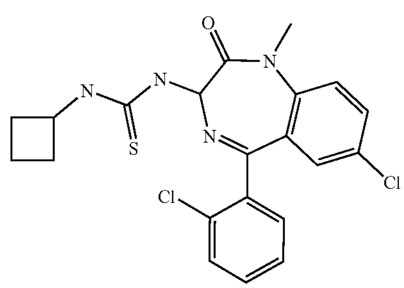 | 446.07 | Yes | 3.24 |
| 504 | 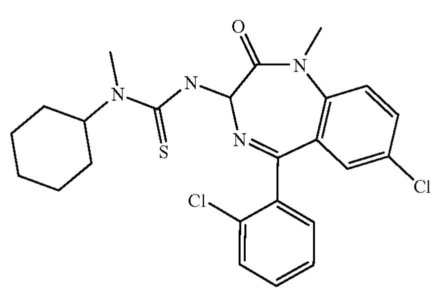 | 488.12 | Yes | 3.86 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 505 | 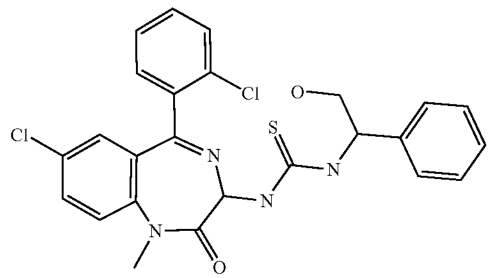 | 512.08 | Yes | 3.16 |
| 506 | 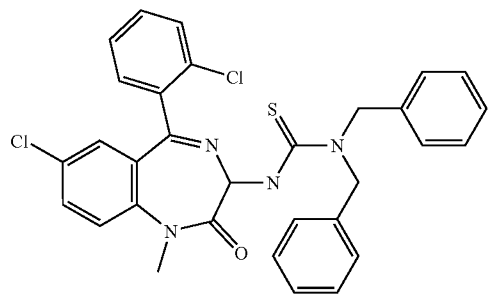 | 572.12 | Yes | 4.56 |
| 507 | 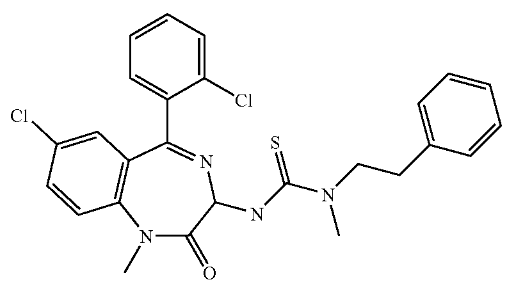 | 510.1 | Yes | 3.89 |
| 508 | 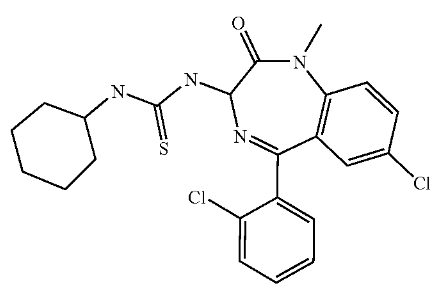 | 474.1 | Yes | 3.7 |
| 509 | 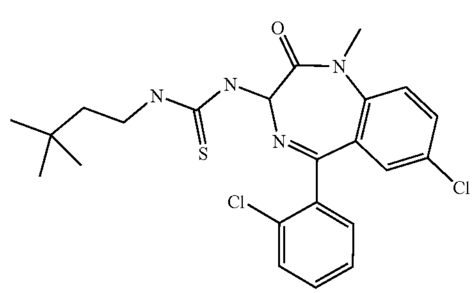 | 476.12 | Yes | 3.94 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 510 | 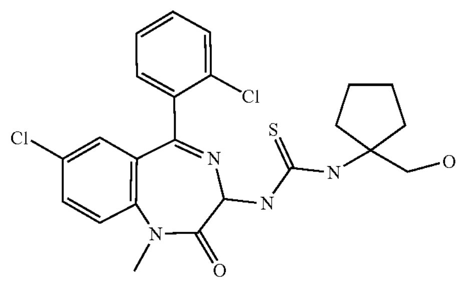 | 490.1 | Yes | 3.21 |
| 511 | 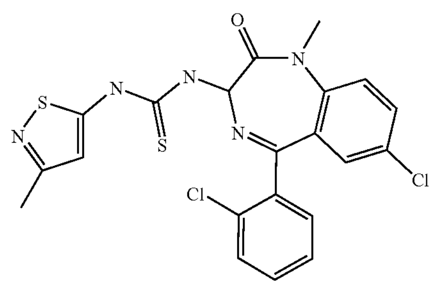 | 489.03 | No | |
| 512 | 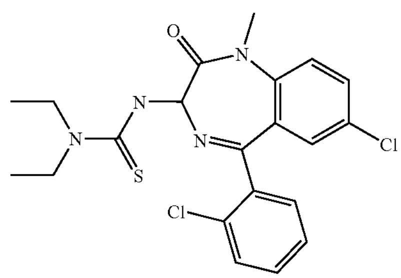 | 448.09 | Tentative | 2.76 |
| 513 | 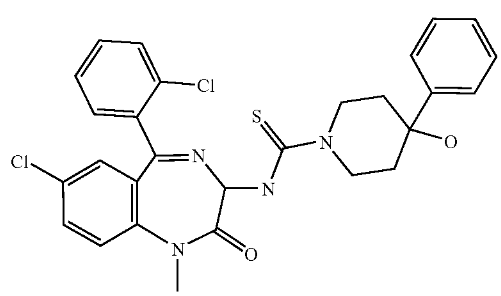 | 552.12 | Yes | 3.53 |
| 514 | 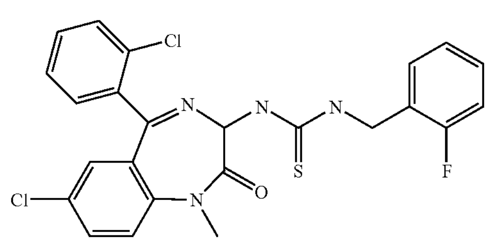 | 500.06 | Yes | 3.54 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 515 | 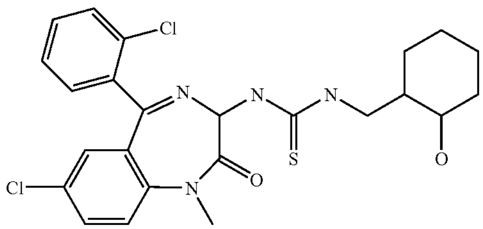 | 504.12 | Yes | 3.34 |
| 516 | 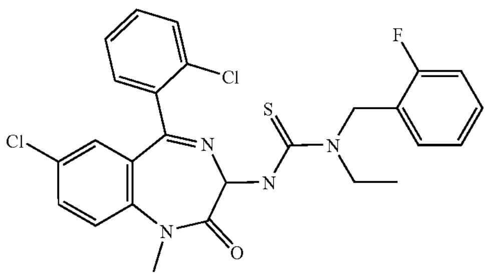 | 528.1 | Yes | 3.98 |
| 517 | 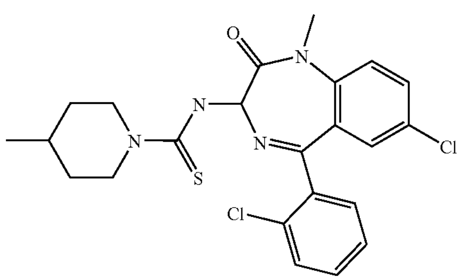 | 474.1 | Yes | 3.61 |
| 518 | 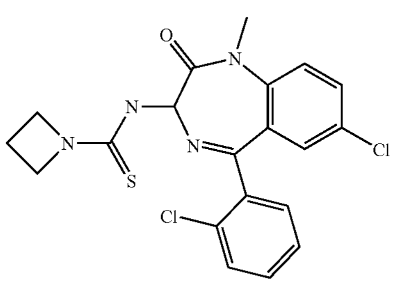 | 432.06 | No | |
| 519 | 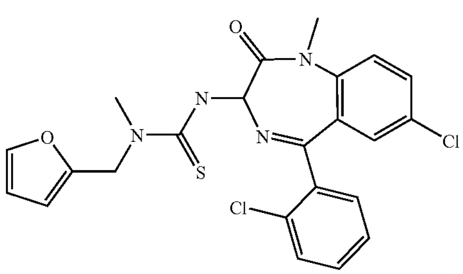 | 486.07 | No | |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 520 | 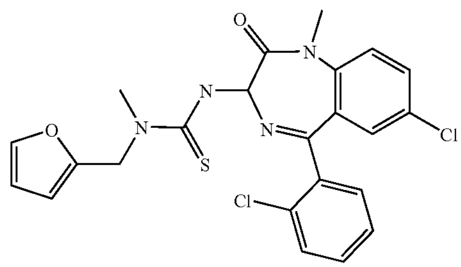 | 486.07 | No | |
| 521 | 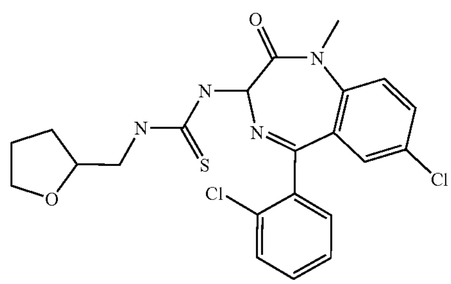 | 476.08 | Yes | 3.07 |
| 522 | 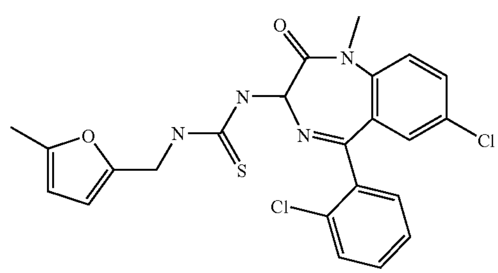 | 486.07 | Yes | 3.46 |
| 523 | 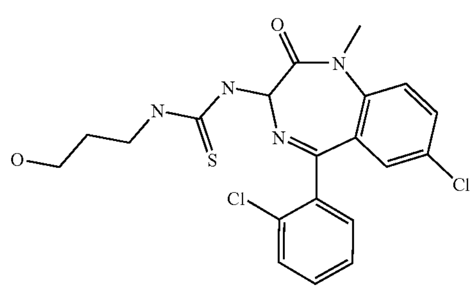 | 450.07 | Yes | 2.75 |
| 524 | 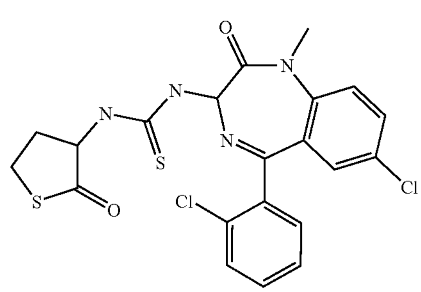 | 492.02 | Tentative | 6.5 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 525 | 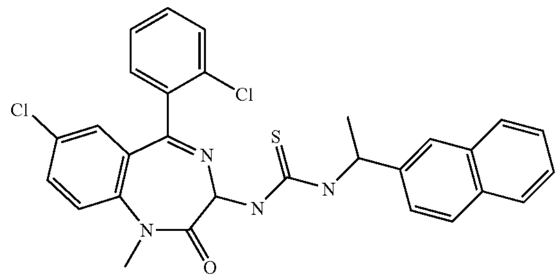 | 546.1 | Yes | 4.2 |
| 526 | 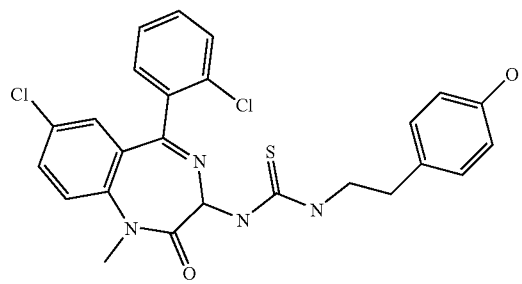 | 512.08 | Yes | 3.08 |
| 527 | 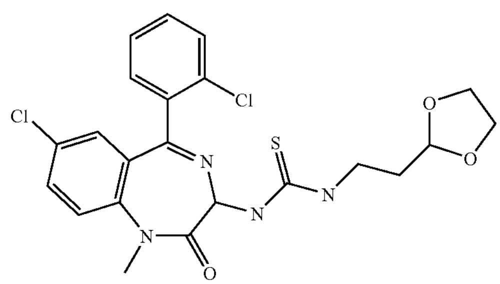 | 492.08 | Yes | 2.93 |
| 528 | 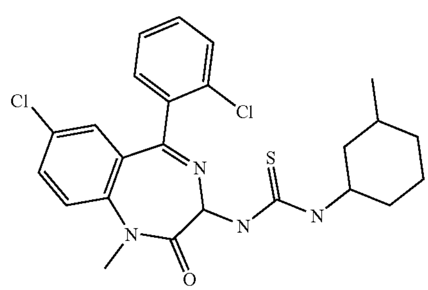 | 488.12 | Yes | 4.04 |
| 529 | 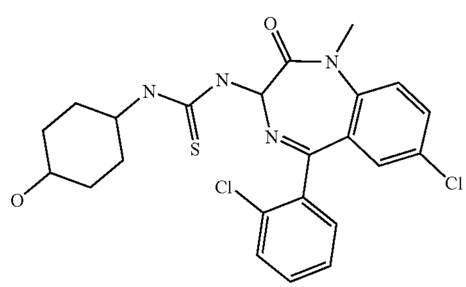 | 490.1 | Yes | 2.85 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 530 | 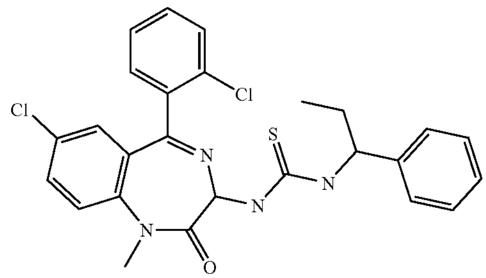 | 510.1 | Yes | 3.84 |
| 531 | 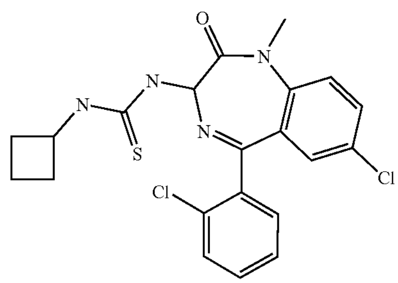 | 446.07 | Yes | 3.3 |
| 532 | 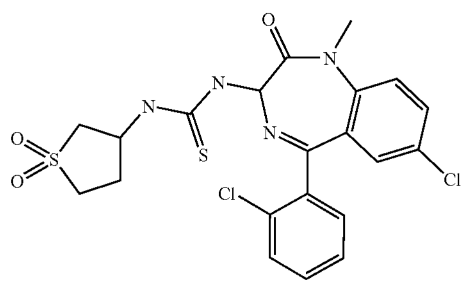 | 510.04 | Yes | 2.82 |
| 533 | 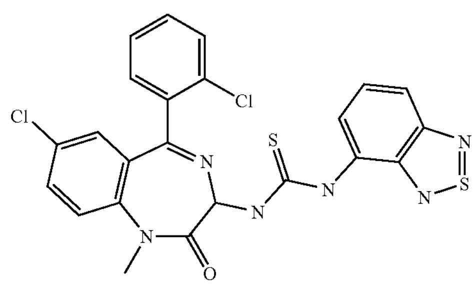 | 526.02 | Yes | 3.76 |
| 534 | 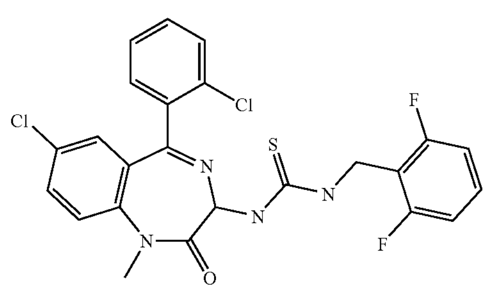 | 518.05 | Yes | 3.47 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 535 | 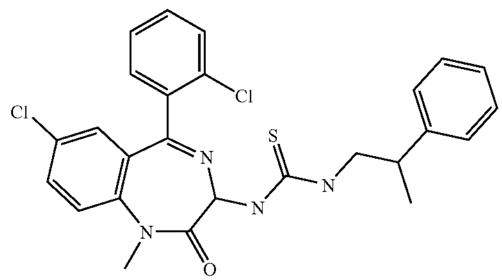 | 510.1 | Yes | 3.91 |
| 536 | 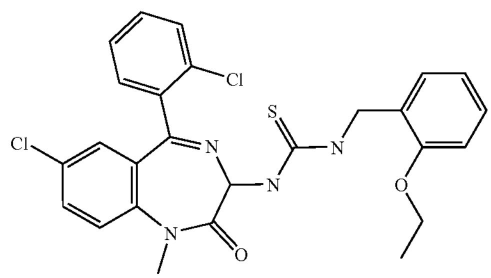 | 526.1 | Yes | 3.8 |
| 537 | 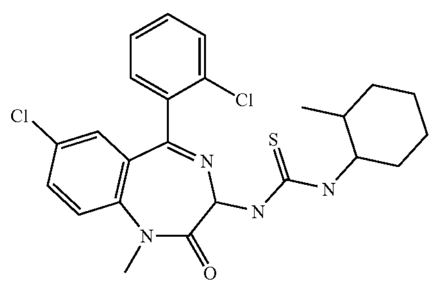 | 488.12 | Yes | 3.93 |
| 538 | 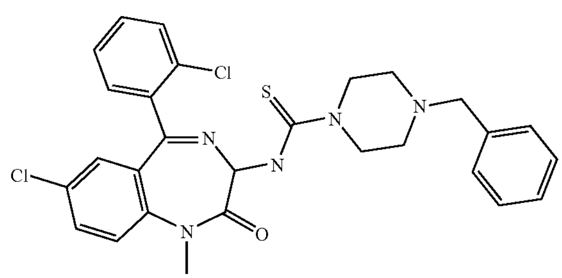 | 551.13 | No | |
| 539 | 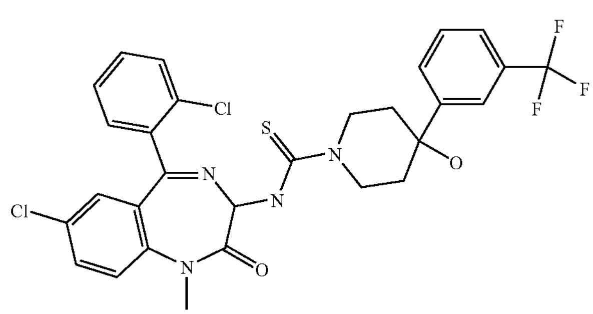 | 620.1 | Yes | 4.03 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 540 | 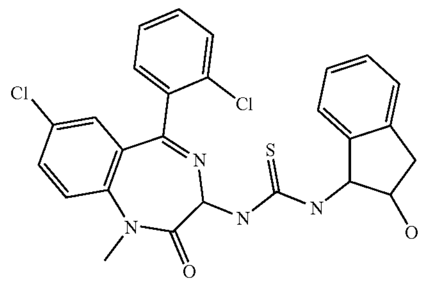 | 524.08 | Yes | 3.57 |
| 541 | 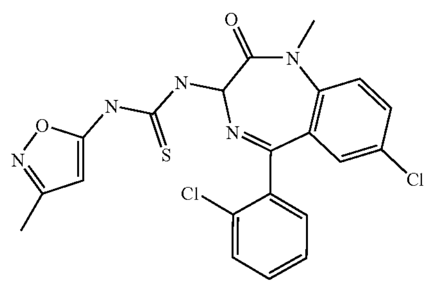 | 473.05 | Yes | 2.79, 3.36 |
| 542 | 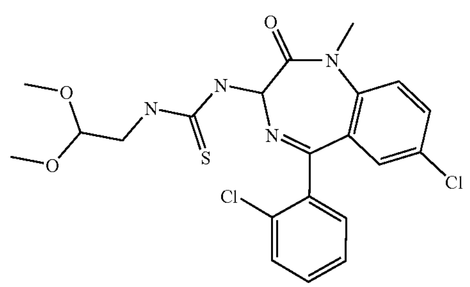 | 480.08 | Yes | 3.02 |
| 543 | 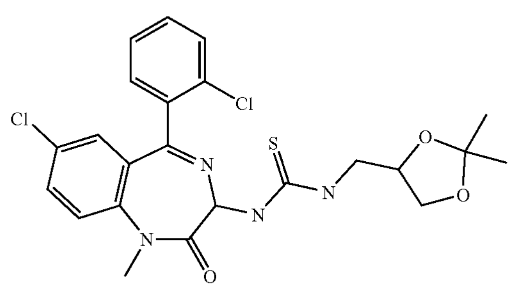 | 506.09 | Yes | 3.19 |
| 544 | 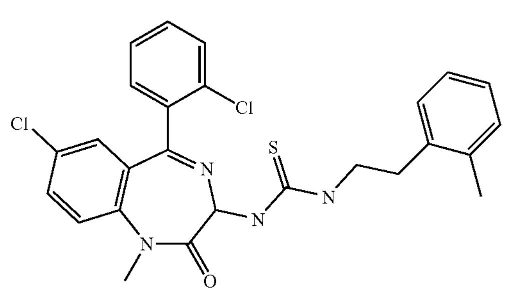 | 510.1 | Yes | 4.02 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 545 | 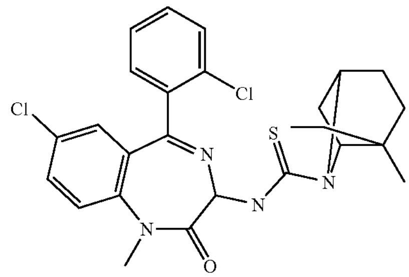 | 528.15 | No | |
| 546 | 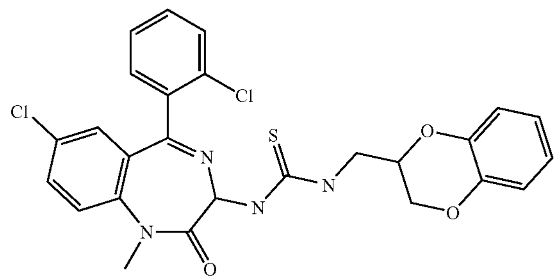 | 540.08 | Yes | 3.86 |
| 547 | 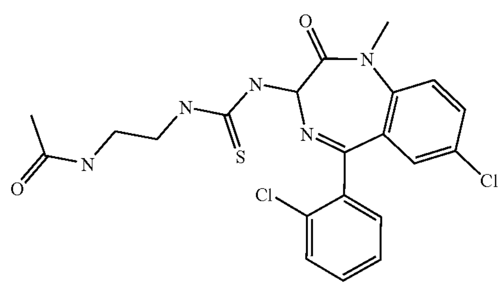 | 477.08 | Yes | 2.76 |
| 548 | 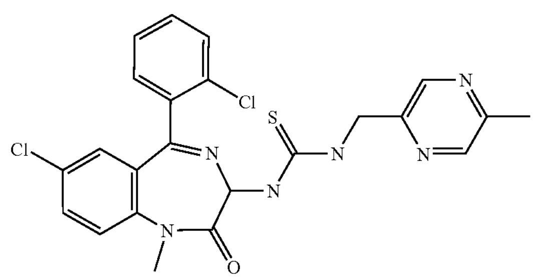 | 498.08 | Yes | 2.97 |
| 549 | 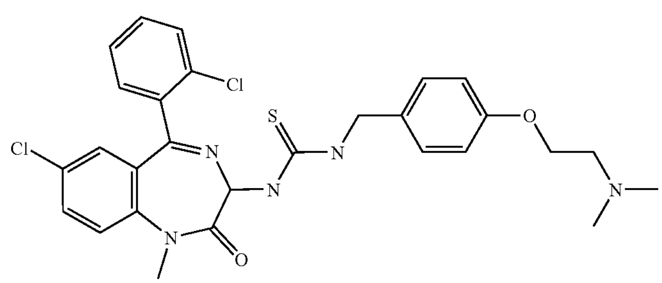 | 569.14 | Yes | 3.06 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 550 | | 550.06 | Yes | 4.06 |
| 551 | | 563.15 | Yes | 3.57 |
| 552 | | 589.17 | Yes | 3.89, 4.18 |
| 553 | | 551.06 | Yes | 3.49 |
| 554 | | 565.15 | Yes | 3.68 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 555 | 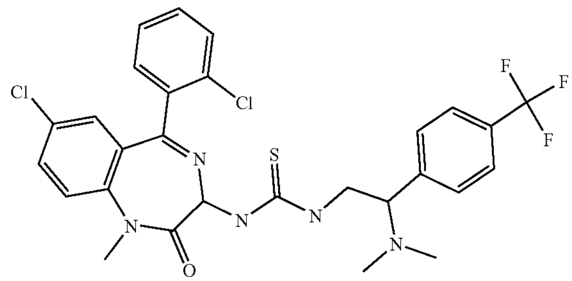 | 607.12 | Yes | 4.24 |
| 556 | 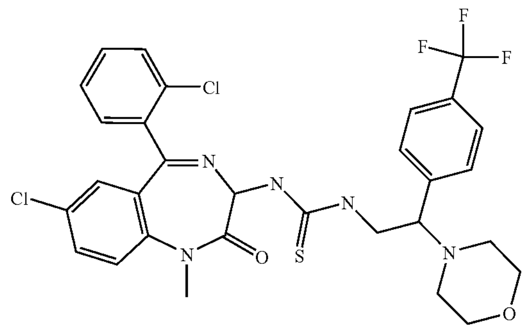 | 649.13 | Yes | 4.2 |
| 557 | 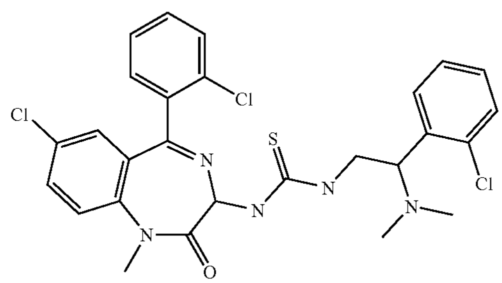 | 573.09 | Yes | 3.92 |
| 558 | 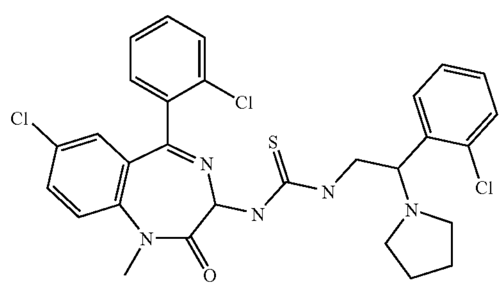 | 599.11 | Yes | 4.3 |
| 559 | 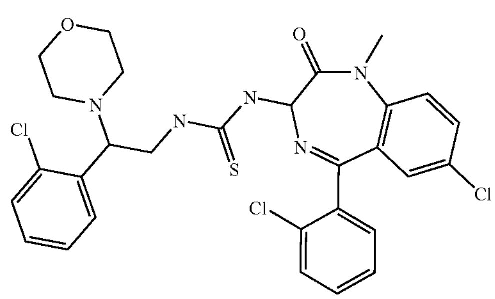 | 615.1 | Yes | 3.93 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 560 | 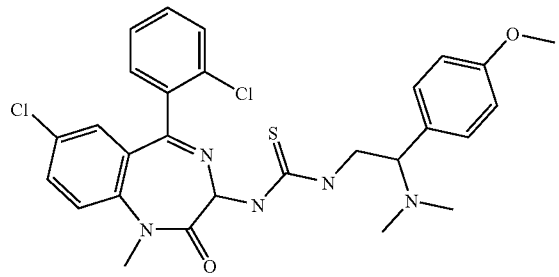 | 569.14 | Yes | 3.46 |
| 561 | 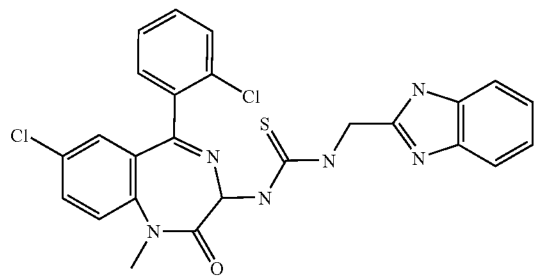 | 522.08 | Yes | 3.32 |
| 562 | 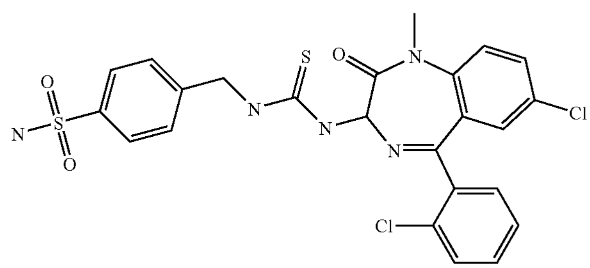 | 561.05 | Yes | 2.79 |
| 563 | 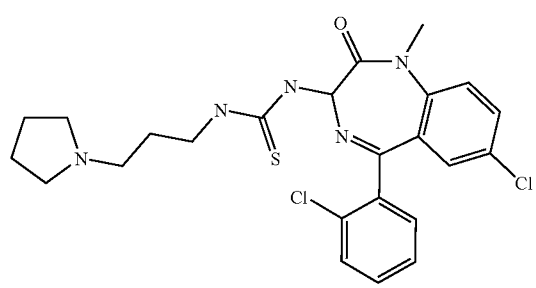 | 503.13 | Tentative | 2.68 |
| 564 | 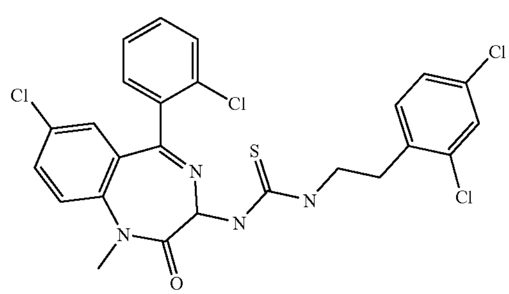 | 564.01 | Yes | 4.61 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 565 | 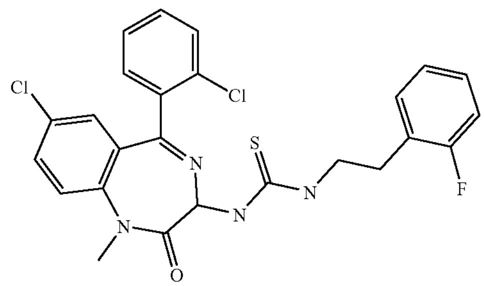 | 514.08 | Yes | 3.75 |
| 566 | 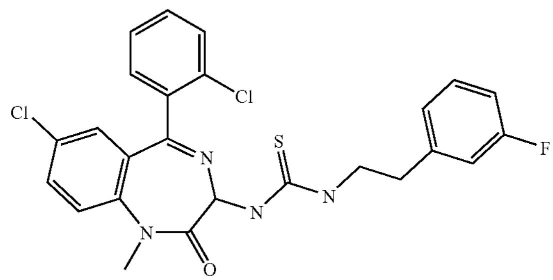 | 514.08 | Yes | 3.8 |
| 567 | 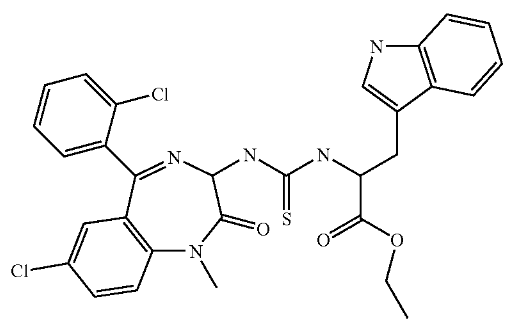 | 607.12 | Yes | 3.86 |
| 568 | 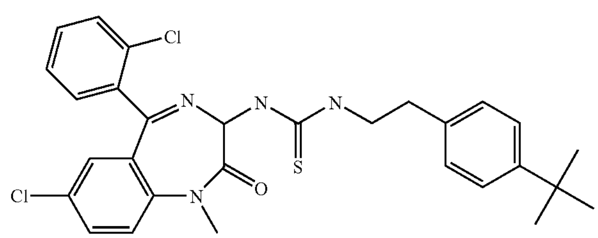 | 552.15 | Yes | 4.85 |
| 569 | 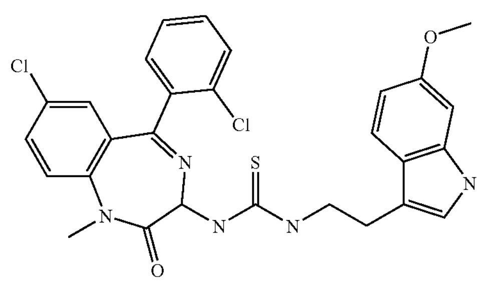 | 565.11 | Yes | 3.41 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 570 | 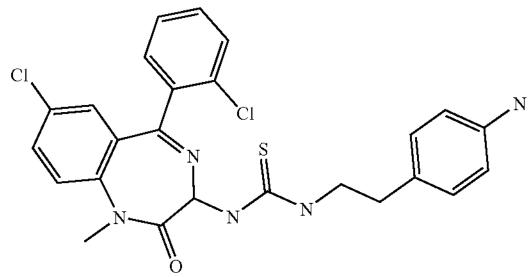 | 511.1 | Yes | 3 |
| 571 | 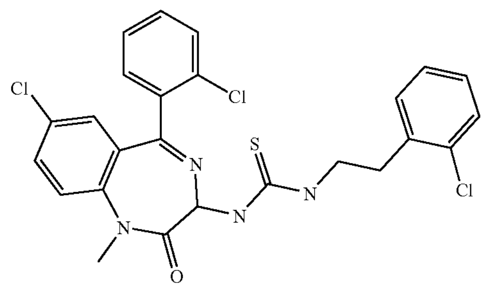 | 530.05 | Yes | 4.03 |
| 572 | 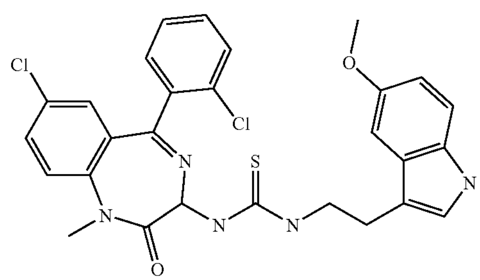 | 565.11 | Yes | 3.36 |
| 573 | 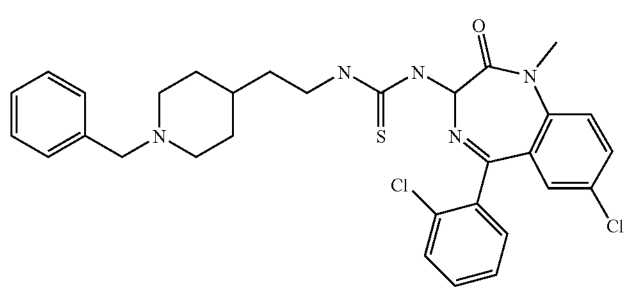 | 593.18 | Yes | 3.43 |
| 574 | 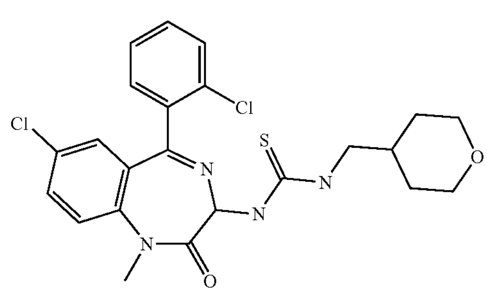 | 490.1 | Yes | 3.08 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 575 | 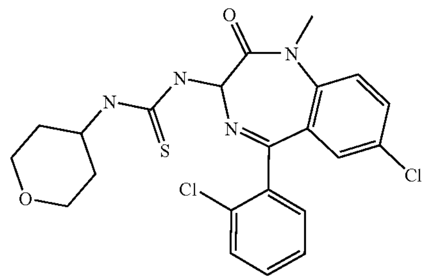 | 476.08 | Yes | 3.03 |
| 576 | 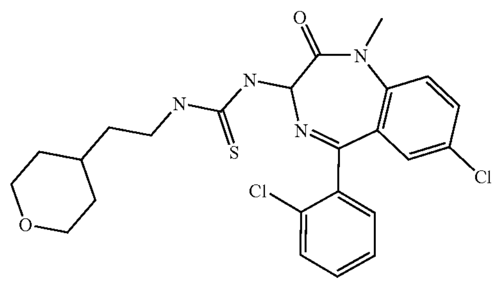 | 504.12 | Yes | 3.21 |
| 577 | 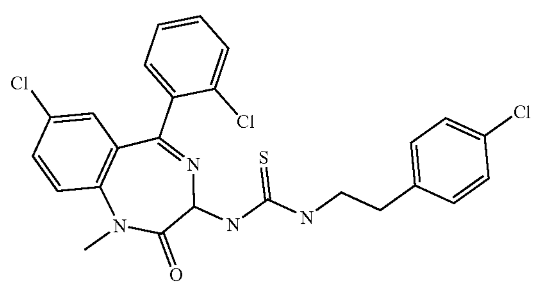 | 530.05 | Yes | 4.14 |
| 578 | 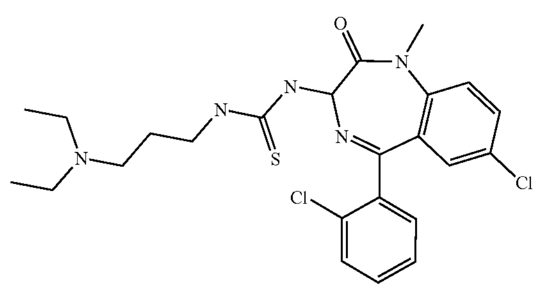 | 505.15 | Yes | 2.69 |
| 579 | 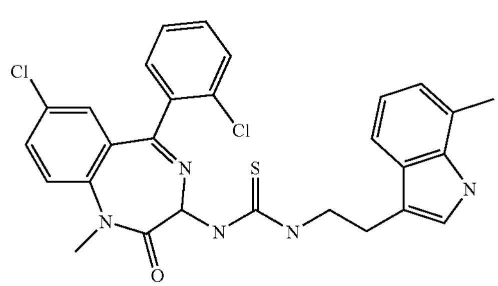 | 549.12 | Yes | 3.54, 3.74 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 580 | 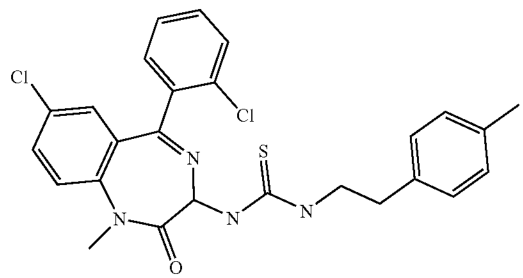 | 510.1 | Yes | 4.03 |
| 581 | 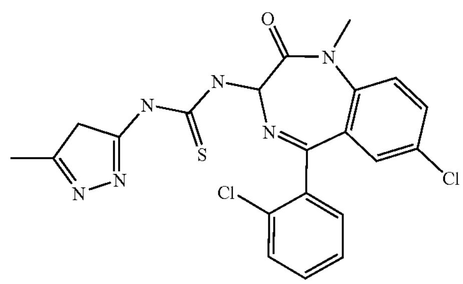 | 472.06 | Yes | 2.87 |
| 582 | 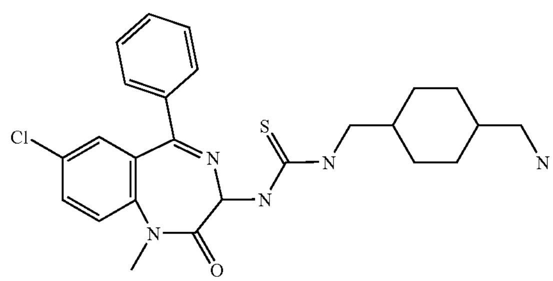 | 483.19 | Yes | 2.57 |
| 583 | 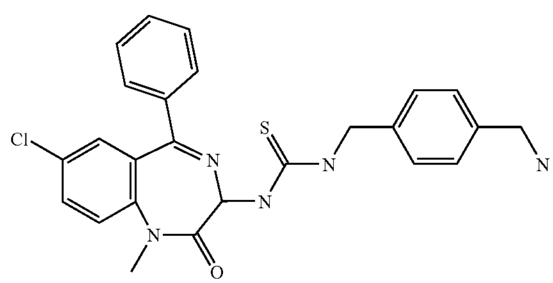 | 477.1 | Yes | 2.38, 2.62 |
| 584 | 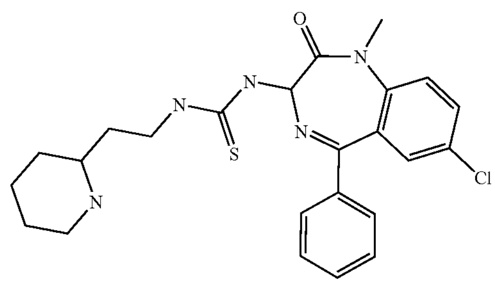 | 469.2 | Yes | 2.63, 5.03 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 585 | 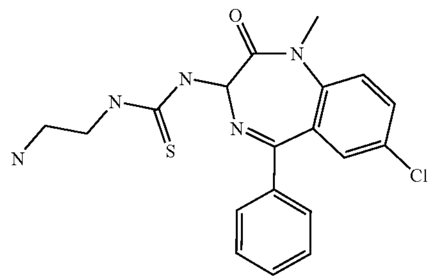 | 401.11 | Yes | 2.45 |
| 586 | 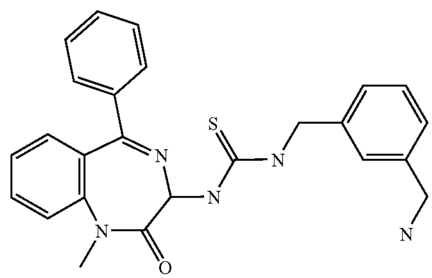 | 477.1 | Yes | 2.67, 3.16 |
| 587 | 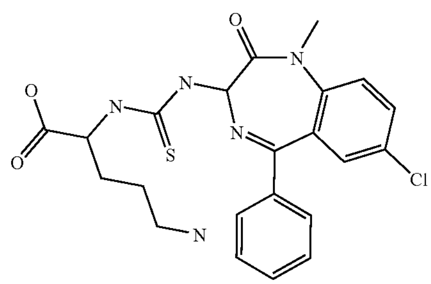 | 473.13 | No | |
| 588 | 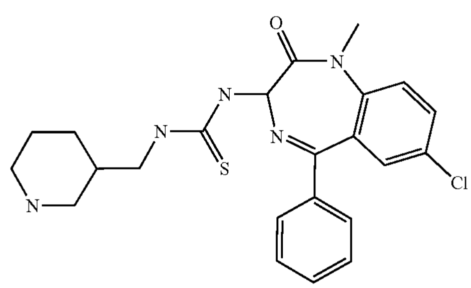 | 455.2 | Yes | 2.56, 3.84 |
| 589 | 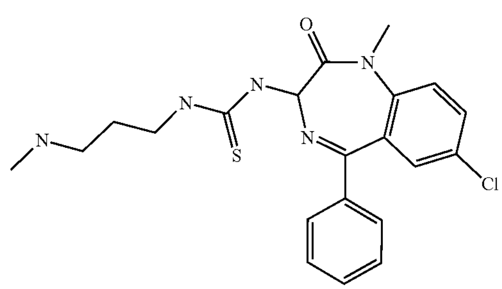 | 429.14 | Yes | 2.48 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 590 | 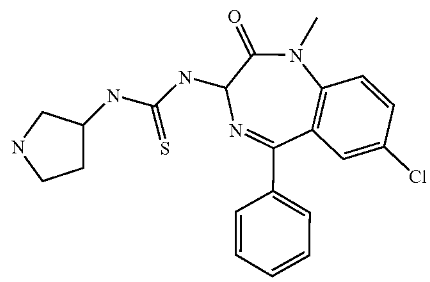 | 427.12 | Yes | 2.49 |
| 591 | 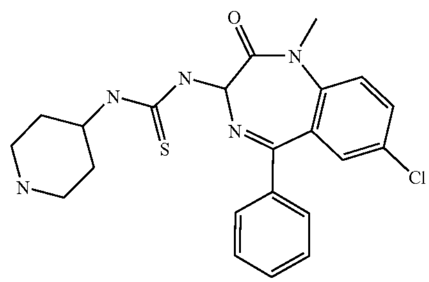 | 441.14 | Yes | 2.5 |
| 592 | 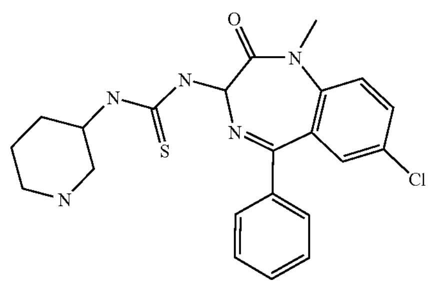 | 441.1 | Yes | 2.48, 2.92 |
| 593 | 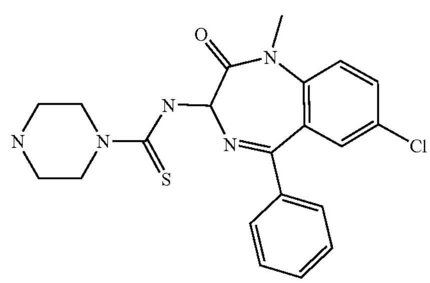 | 427.12 | Yes | 2.62 |
| 594 | 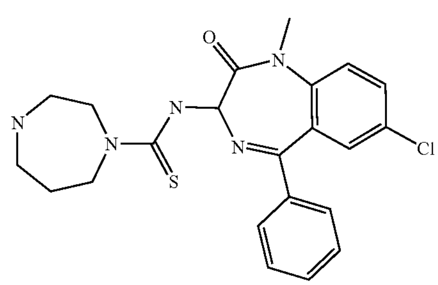 | 441.14 | Yes | 2.58 |

TABLE 1-continued
Spreadsheet of combinatorially prepared compounds with LCMS analysis of the reaction product.
| Compound # | Structure | Target Mass | Mass Found? | Rtn Time (MS) |
|---|---|---|---|---|
| 595 | 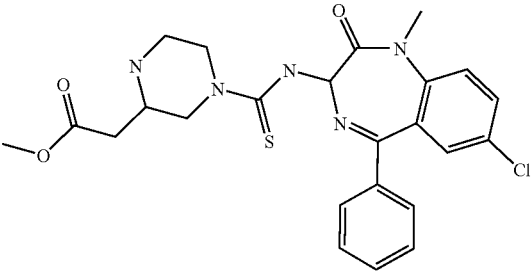 | 499.1 | Yes | 2.81, 3.84 |
| 596 | 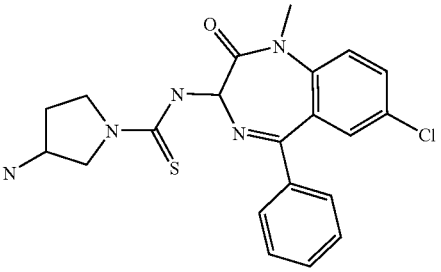 | 427.12 | Yes | 2.53 |
| 597 | 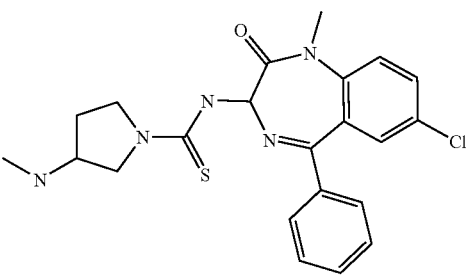 | 441.14 | Yes | 2.59 |
| 598 | 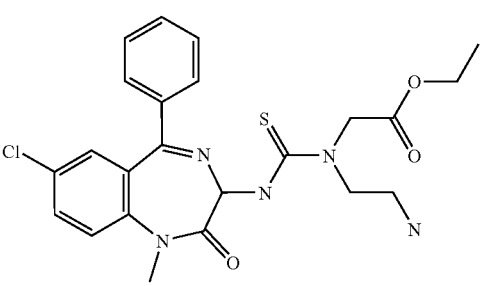 | 487.14 | No | |
| 599 | 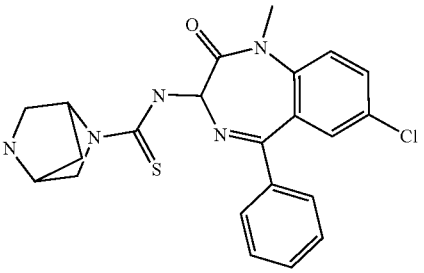 | 439.12 | Yes | 2.56 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 600 | 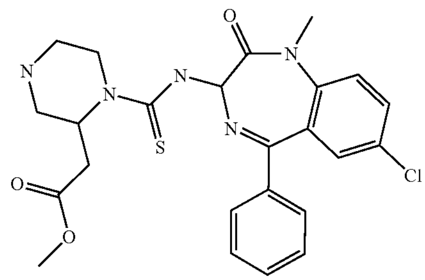 | 499.14 | Yes | 2.81 |
| 601 | 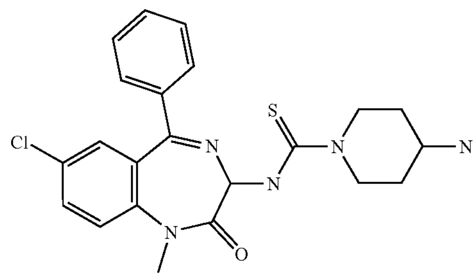 | 441.14 | Yes | 2.53 |
| 602 | 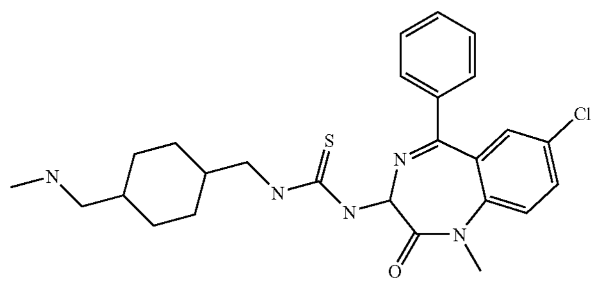 | 497.2 | No | |
| 603 | 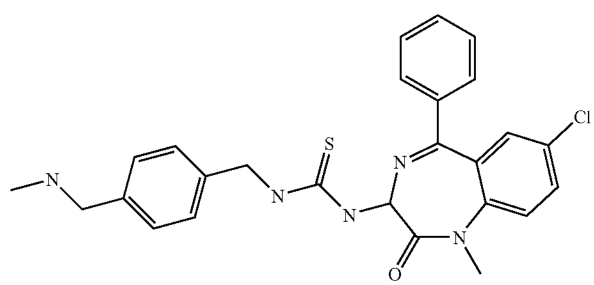 | 491.15 | Tentative | 2.87 |
| 604 | 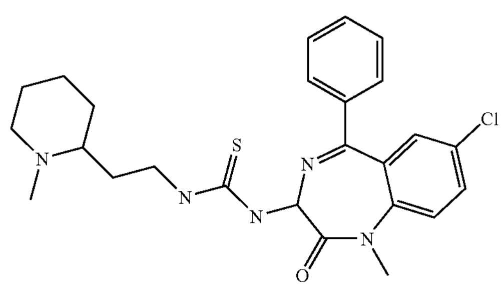 | 483.19 | Tentative | 2.63 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 605 | 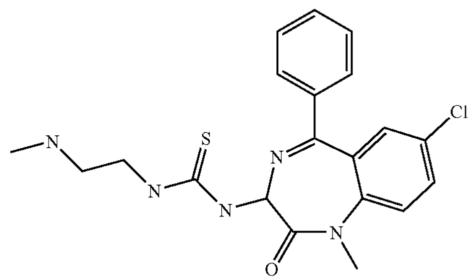 | 415.1 | Yes | 2.49, 3.01 |
| 606 | 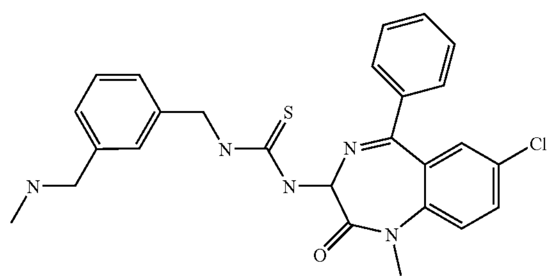 | 491.15 | No | |
| 607 | 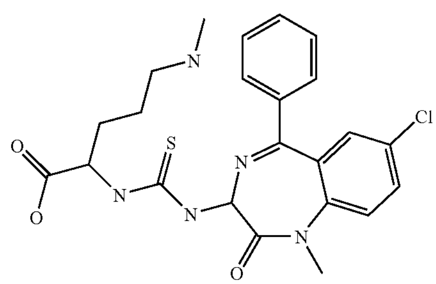 | 487.14 | No | |
| 608 | 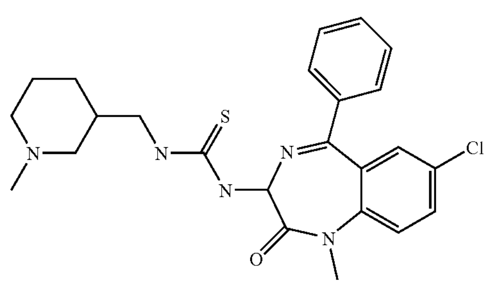 | 469.17 | Yes | 2.64 |
| 609 | 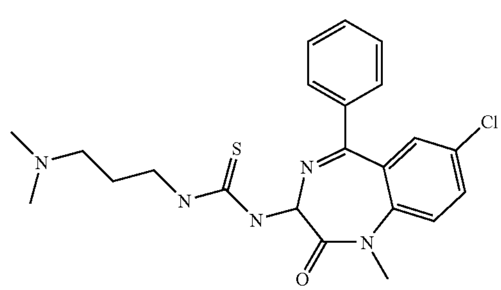 | 443.15 | Yes | |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 610 | 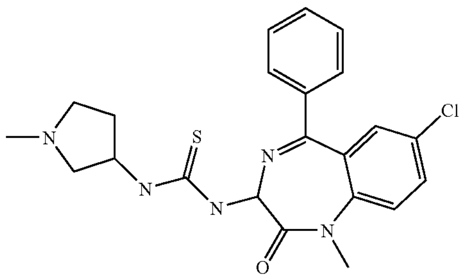 | 441.14 | Yes | 2.76 |
| 611 | 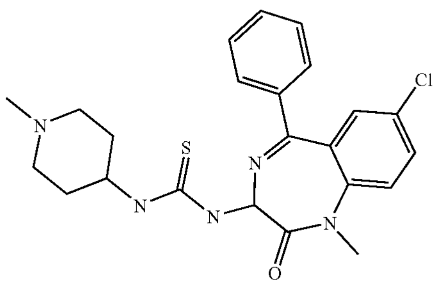 | 455.15 | Yes | 2.68 |
| 612 | 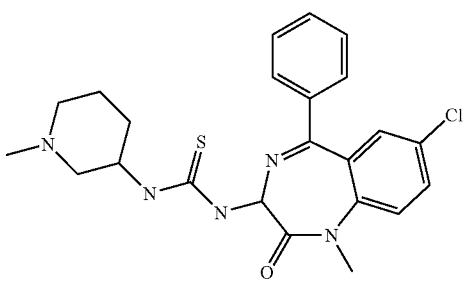 | 455.15 | Yes | 2.76 |
| 613 | 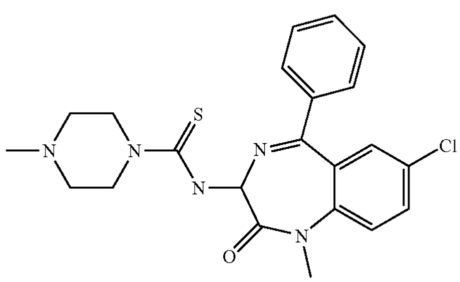 | 441.14 | Yes | 2.93 |
| 614 | 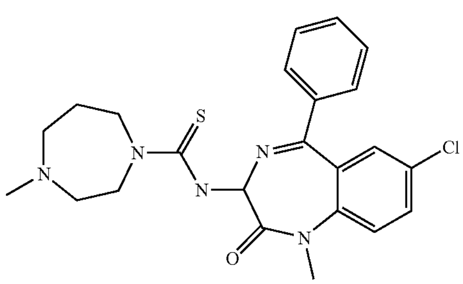 | 455.15 | Yes | 2.8 |

TABLE 1-continued

Spreadsheet of combinatorially prepared compounds with LCMS analysis of the reaction product.

| Compound # | Structure | Target Mass | Mass Found? | Rtn Time (MS) |
| --- | --- | --- | --- | --- |
| 615 | 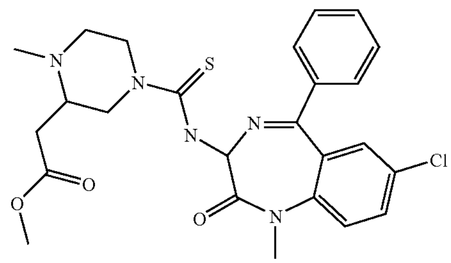 | 513.16 | Yes | 3.13 |
| 616 | 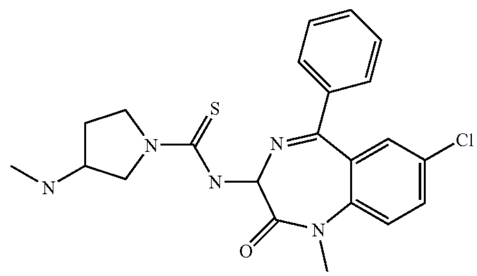 | 441.14 | Tentative | 2.9 |
| 617 | 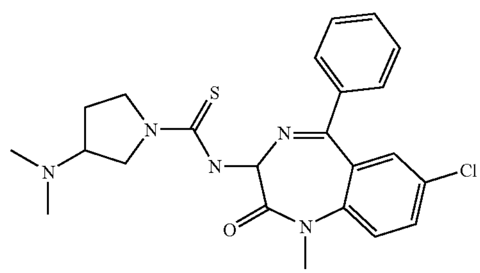 | 455.15 | Yes | 2.9 |
| 618 | 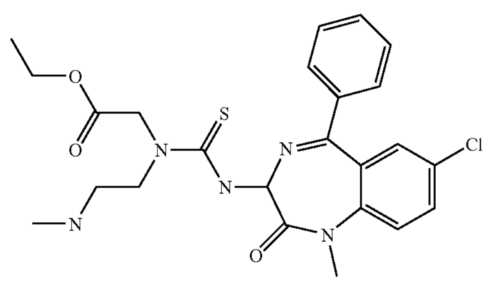 | 501.16 | No | |
| 619 | 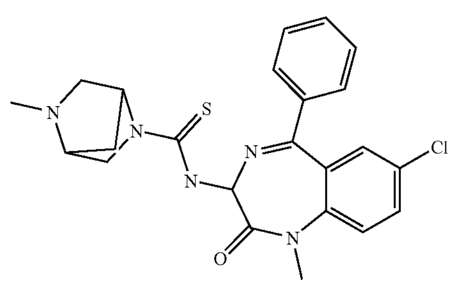 | 453.14 | Yes | 2.73 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 620 | 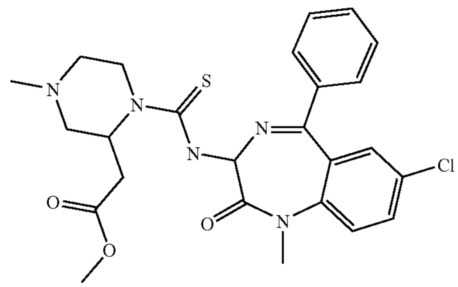 | 513.16 | Yes | 3.13 |
| 621 | 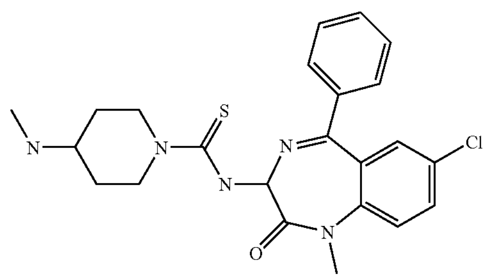 | 455.15 | No | |
| 622 | 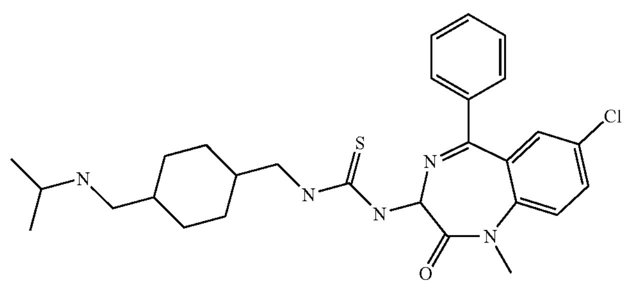 | 525.23 | Yes | 3.15 |
| 623 | 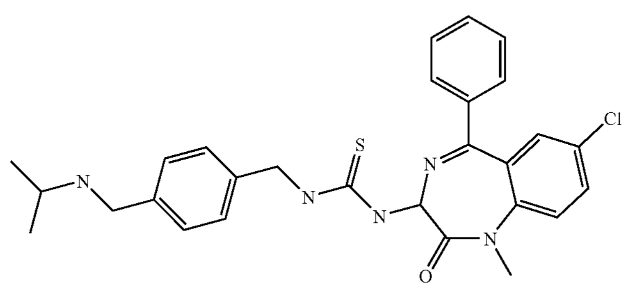 | 519.19 | Yes | 2.72 |
| 624 | 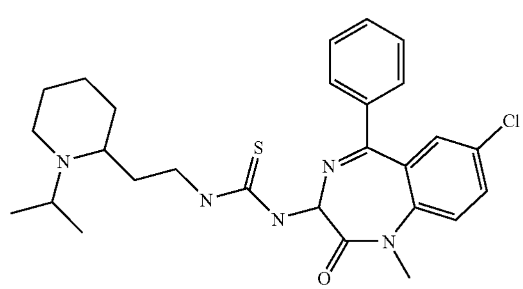 | 511.22 | Yes | 3.19 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 625 | 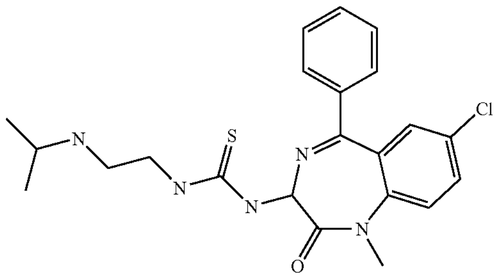 | 443.15 | Yes | 2.64 |
| 626 | 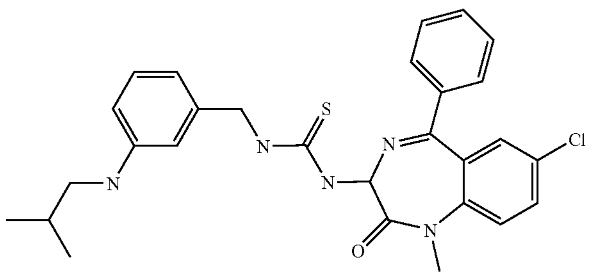 | 519.19 | Tentative | |
| 627 | 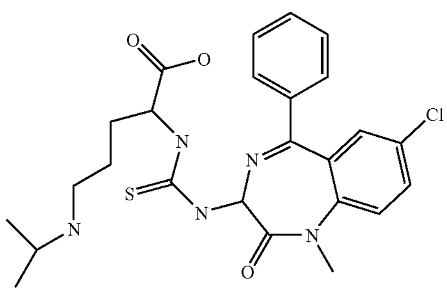 | 515.18 | Tentative | 3.73 |
| 628 | 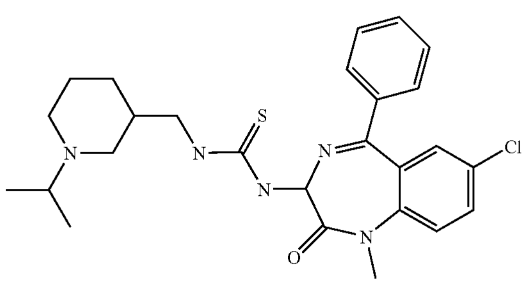 | 497.2 | Yes | 2.66, 2.88 |
| 629 | 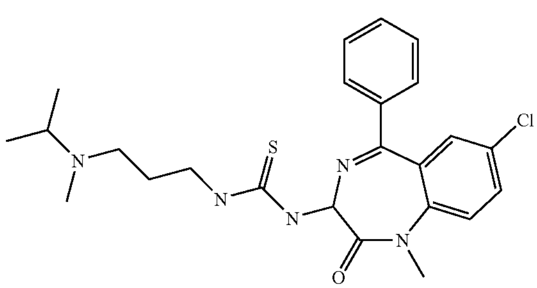 | 471.19 | Yes | 2.76 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 630 | 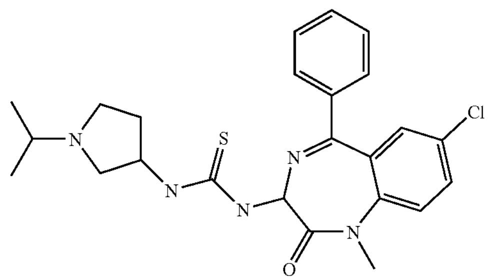 | 469.17 | Yes | 2.76 |
| 631 | 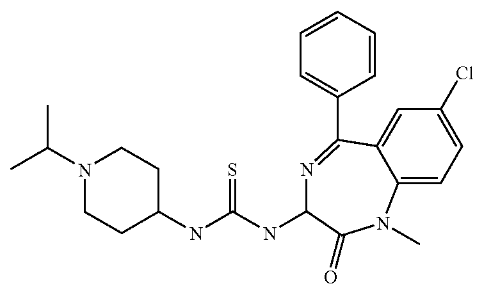 | 483.19 | Yes | 2.68 |
| 632 | 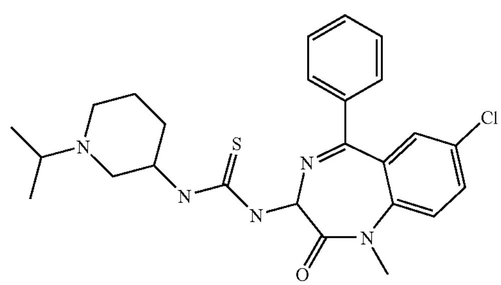 | 483.19 | Yes | 2.78 |
| 633 | 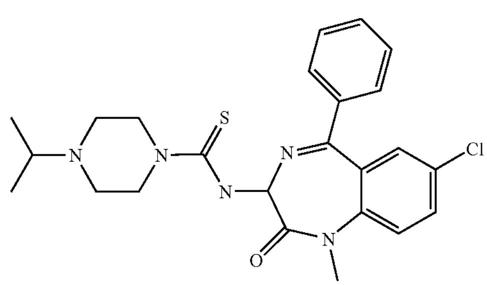 | 469.2 | Yes | 2.51, 3.27 |
| 634 | 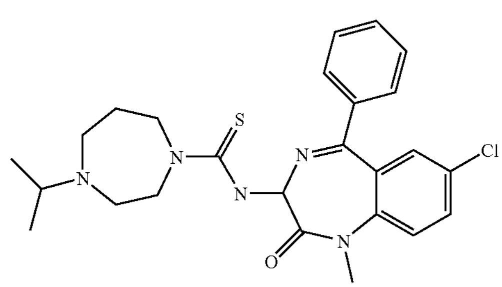 | 483.2 | Yes | 2.54, 2.91 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 635 | 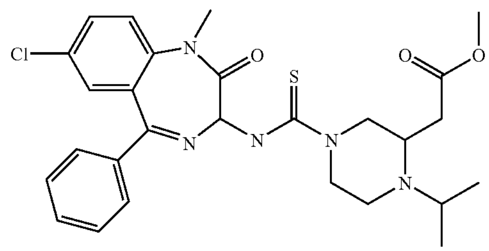 | 541.19 | Yes | 3.79 |
| 636 | 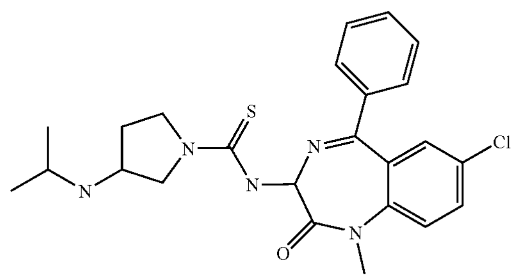 | 469.2 | Yes | 2.76, 3.1 |
| 637 | 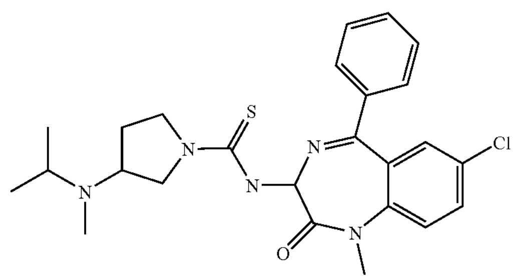 | 483.2 | Yes | 2.5, 3.09 |
| 638 | 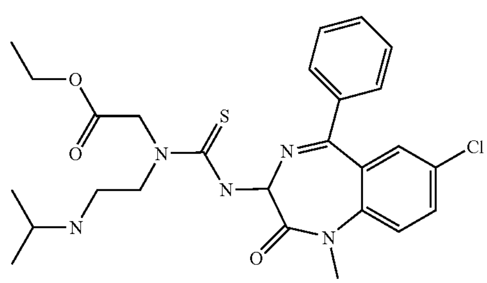 | 529.19 | No | |
| 639 | 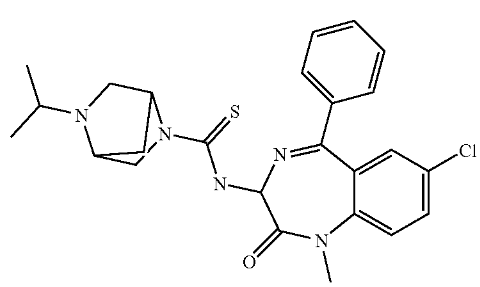 | 481.2 | Yes | 2.5, 2.97 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 640 | | 541.2 | Yes | 3.79, 4.07 |
| 641 | | 483.2 | Tentative | 2.4, 2.98 |
| 642 | | 524.21 | Yes | 2.82 |
| 643 | | 518.17 | Yes | 2.64 |
| 644 | | 510.2 | Tentative | 2.9 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 645 | 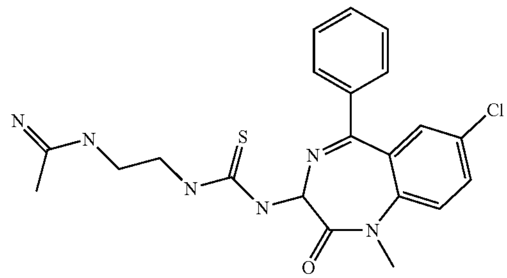 | 442.13 | Yes | 2.48 |
| 646 | 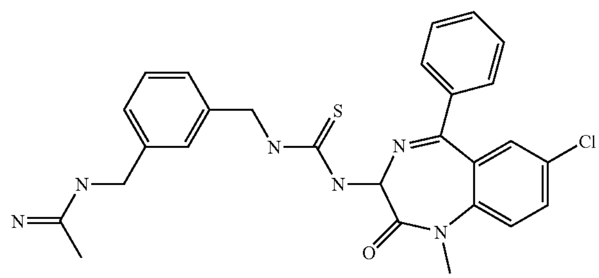 | 518.17 | Yes | 2.68 |
| 647 | 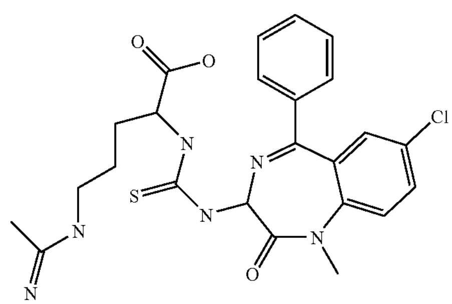 | 514.16 | No | |
| 648 | 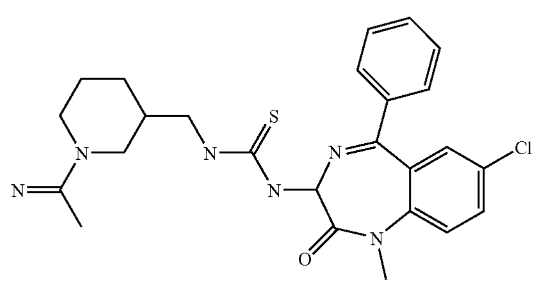 | 496.18 | Yes | 2.6 |
| 649 | 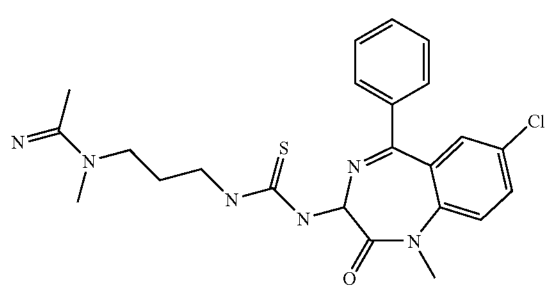 | 470.17 | Yes | 2.52 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 650 | 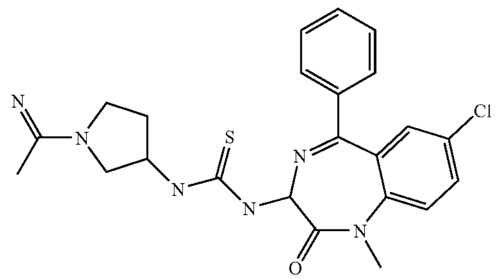 | 468.2 | Yes | 2.24, 2.53 |
| 651 | 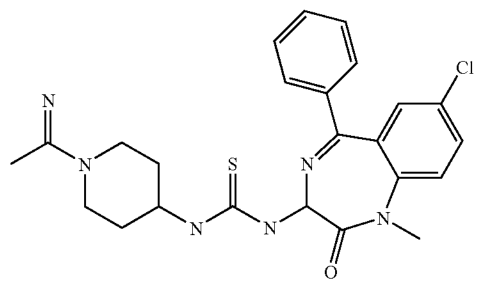 | 482.2 | Yes | 2.15, 2.52 |
| 652 | 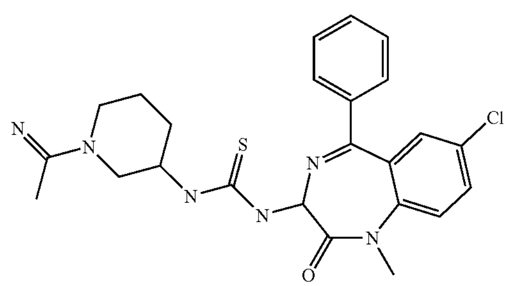 | 482.17 | Yes | 2.65 |
| 653 | 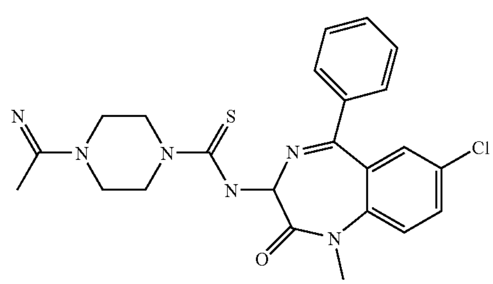 | 468.15 | Yes | 2.52 |
| 654 | 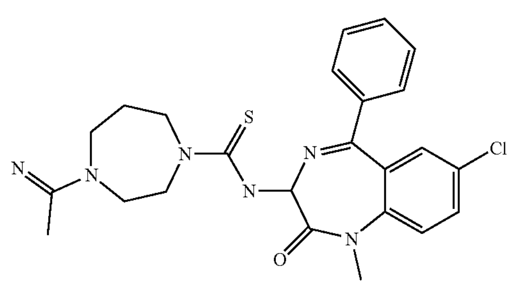 | 482.17 | Yes | 2.55 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 655 | 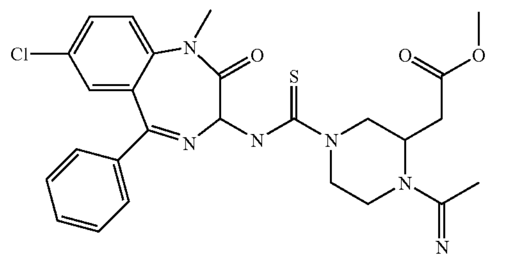 | 540.17 | Yes | 2.66 |
| 656 | 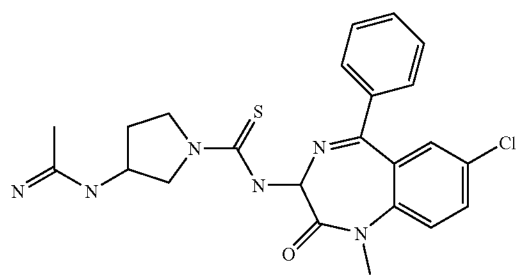 | 468.15 | Yes | 2.52 |
| 657 | 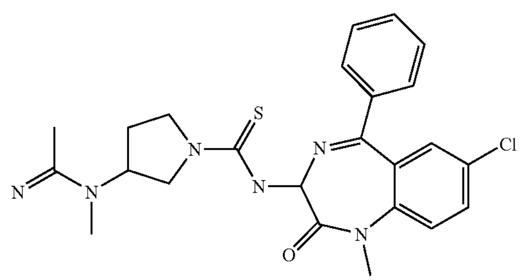 | 482.17 | Yes | 2.52 |
| 658 | 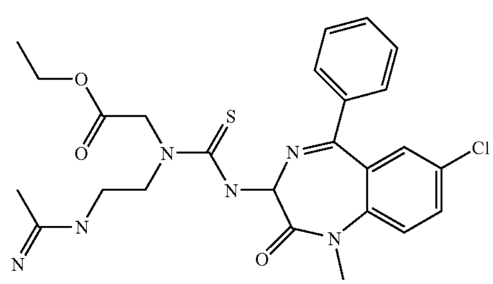 | 528.17 | No | |
| 659 | 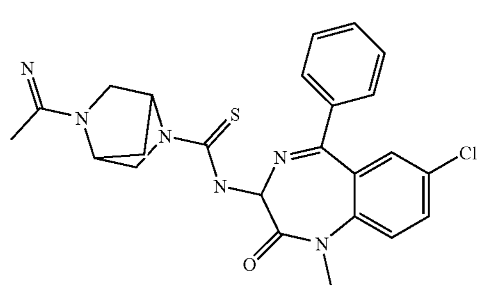 | 480.15 | Yes | 2.51 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 660 | 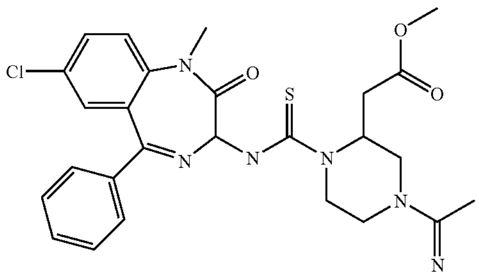 | 540.17 | Yes | |
| 661 | 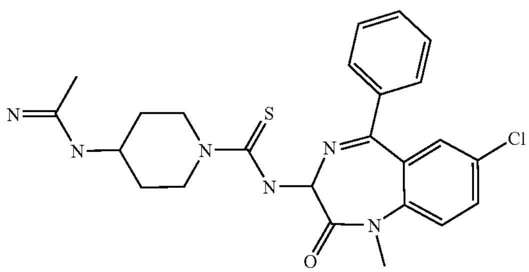 | 482.17 | Yes | 2.58 |
| 662 | 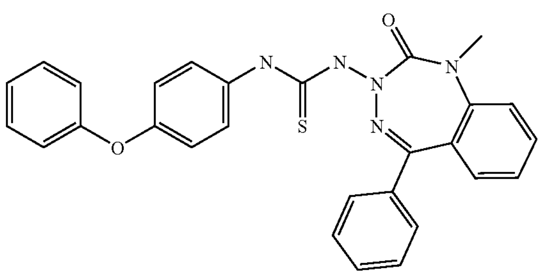 | 492.16 | Yes | 3.63 |
| 663 | 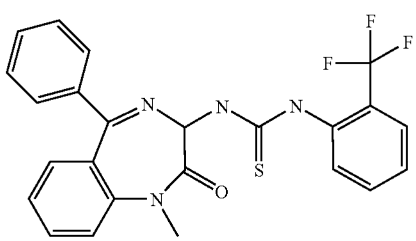 | 468.12 | Yes | 2.99 |
| 664 | 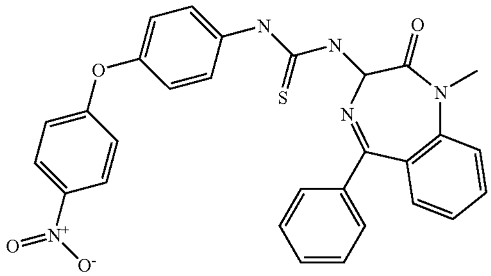 | 537.15 | Yes | 3.64 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 665 | 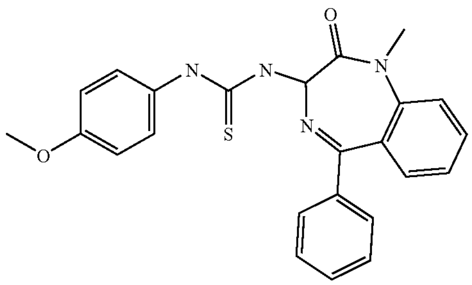 | 430.15 | Yes | 2.78 |
| 666 | 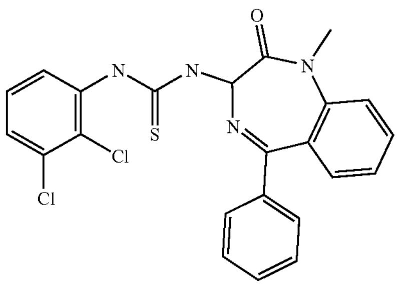 | 468.06 | Tentative | 3.33 |
| 667 | 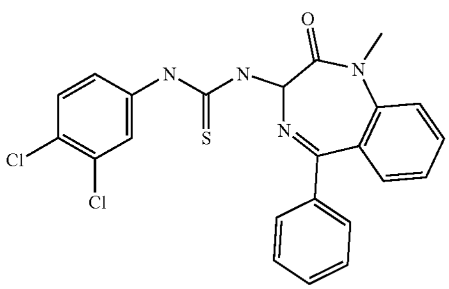 | 468.06 | Yes | 3.76 |
| 668 | 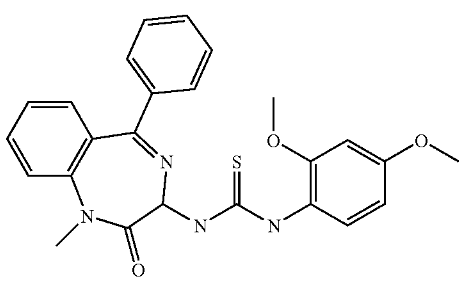 | 460.16 | Yes | 2.76 |
| 669 | 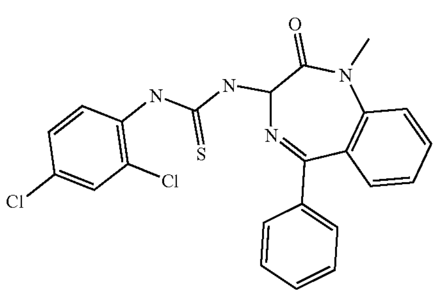 | 468.06 | Yes | |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 670 | | 430.15 | No | |
| 671 | | 428.17 | Yes | 3.08 |
| 672 | | 445.12 | Yes | 3.03 |
| 673 | | 478.05 | No | |
| 674 | | 425.13 | Yes | 2.89 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 675 | 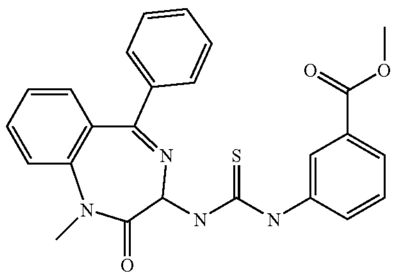 | 458.14 | No | |
| 676 | 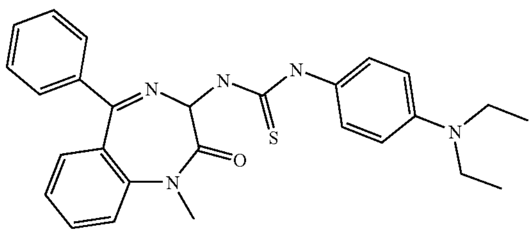 | 471.21 | Yes | 3.41 |
| 677 | 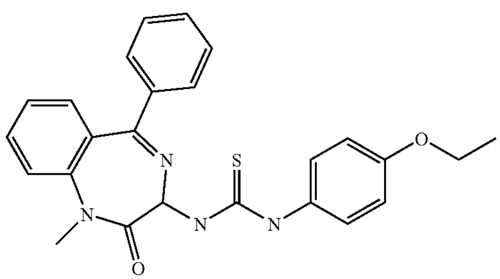 | 444.16 | Yes | 3.01 |
| 678 | 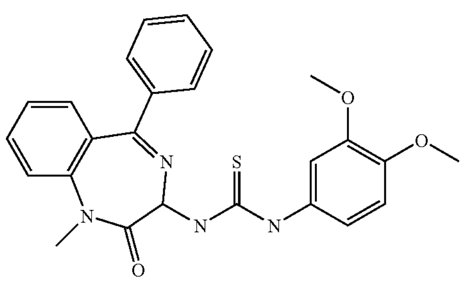 | 460.16 | Yes | 2.68 |
| 679 | 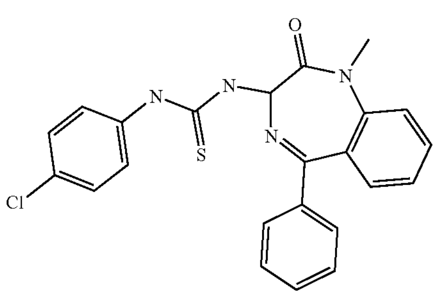 | 434.1 | Tentative | 3.32 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 680 | 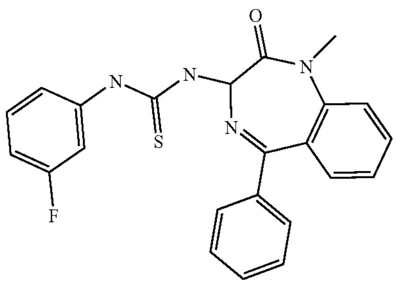 | 418.13 | Yes | 3.01 |
| 681 | 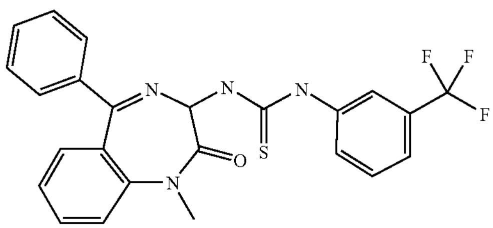 | 468.12 | Yes | 3.44 |
| 682 | 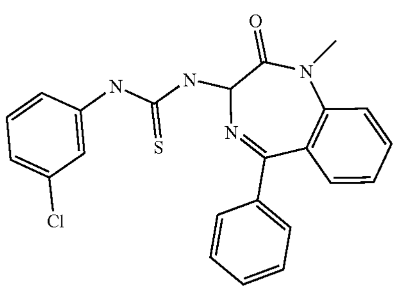 | 434.1 | Yes | 3.21, 6.45 |
| 683 | 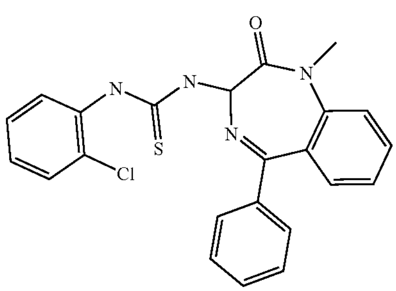 | 434.1 | Yes | 2.93, 6.48 |
| 684 | 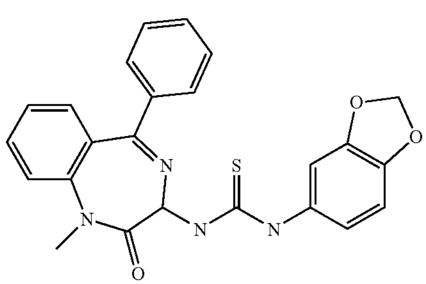 | 444.13 | Yes | 2.73 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 685 | 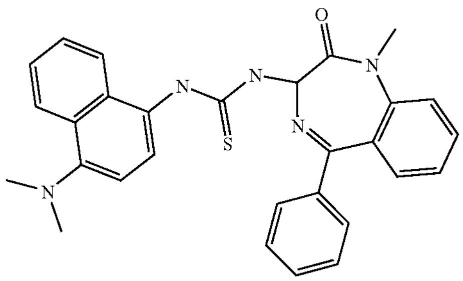 | 493.19 | Yes | 3.31 |
| 686 | 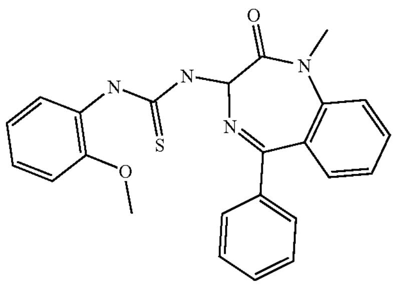 | 430.15 | Yes | 2.79 |
| 687 | 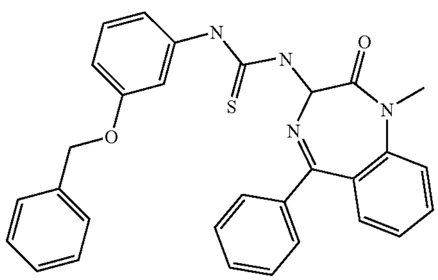 | 506.18 | Yes | 3.7 |
| 688 | 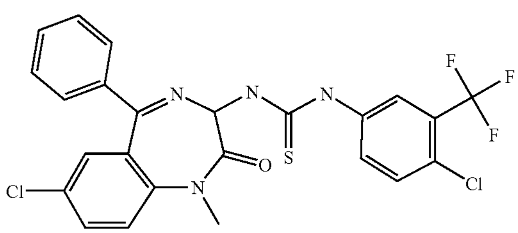 | 536.05 | Yes | 4.46 |
| 689 | 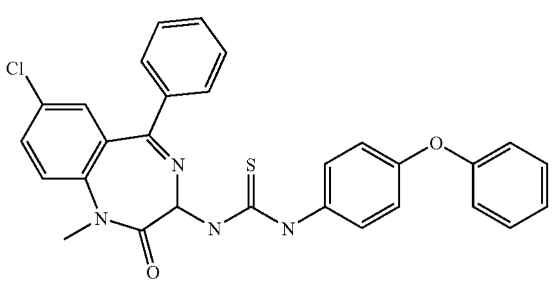 | 526.1 | Yes | 2.53, 4.15 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 690 | 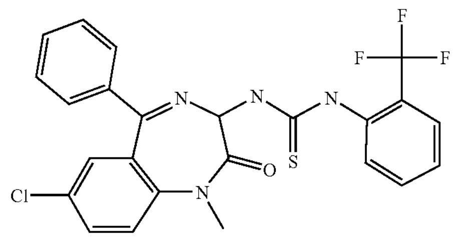 | 502.08 | Yes | 3.39 |
| 691 | 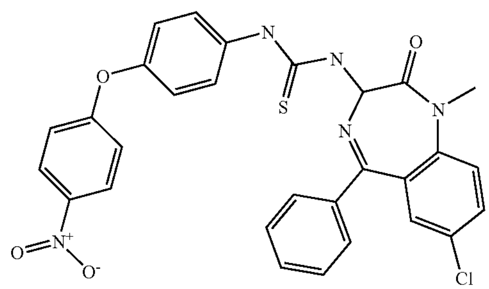 | 571.11 | No | |
| 692 | 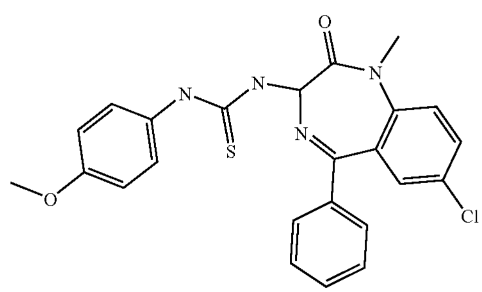 | 464.11 | Yes | 3.16 |
| 693 | 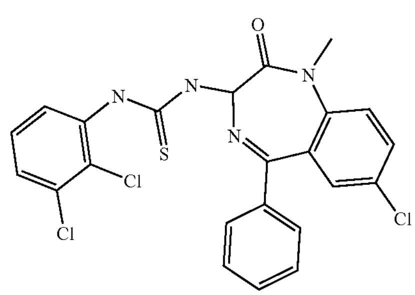 | 502.02 | Yes | 3.81 |
| 694 | 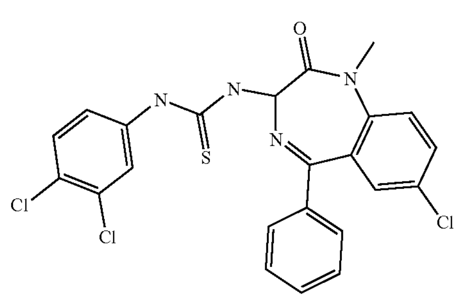 | 502.02 | Yes | |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 695 | 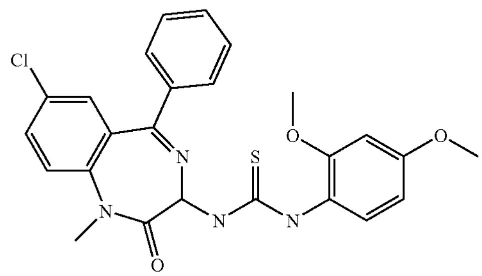 | 494.1 | Yes | 3.14, 3.45 |
| 696 | 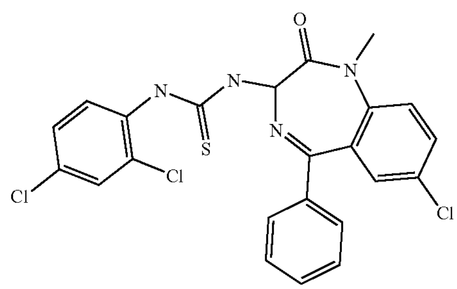 | 502.02 | No | |
| 697 | 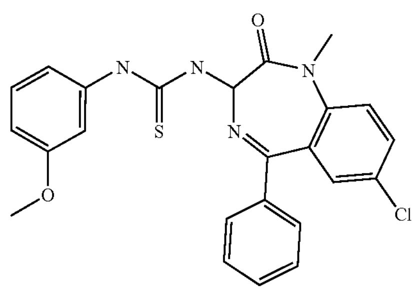 | 464.11 | Yes | 3.34 |
| 698 | 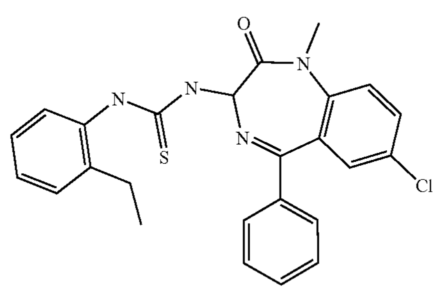 | 462.13 | Yes | 3.49 |
| 699 | 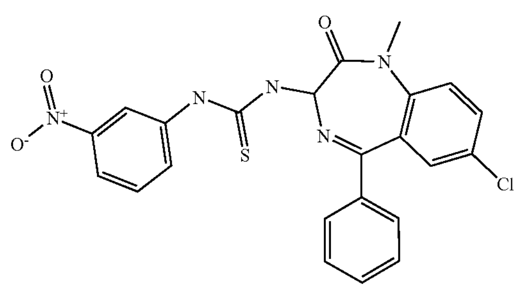 | 479.08 | No | |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 700 | 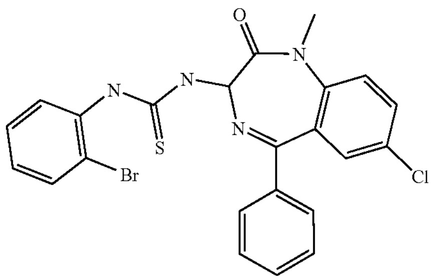 | 512.01 | Yes | 3.36 |
| 701 | 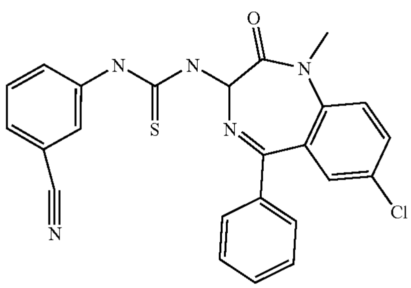 | 459.09 | Yes | 3.27 |
| 702 | 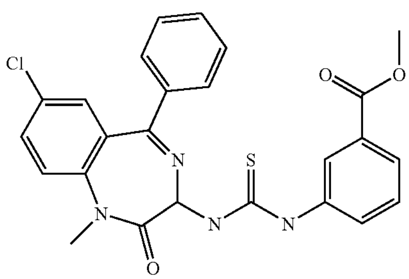 | 492.1 | Yes | 3.37, 6.53 |
| 703 | 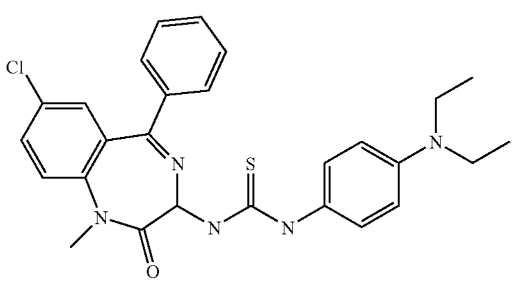 | 505.17 | Yes | 3.86 |
| 704 | 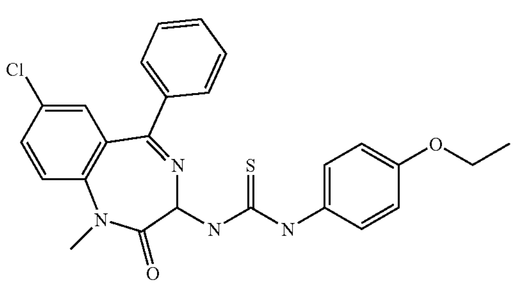 | 478.12 | Yes | 3.46 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 705 | 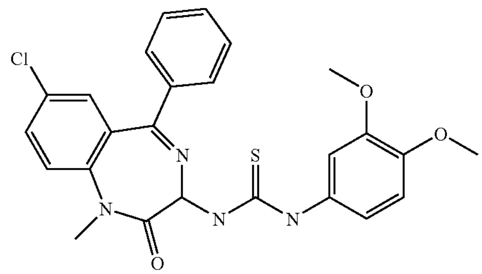 | 494.12 | Yes | 2.99 |
| 706 | 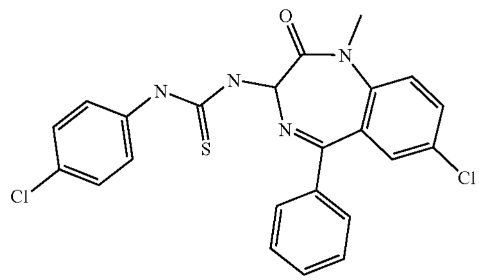 | 468.06 | Yes | 3.76 |
| 707 | 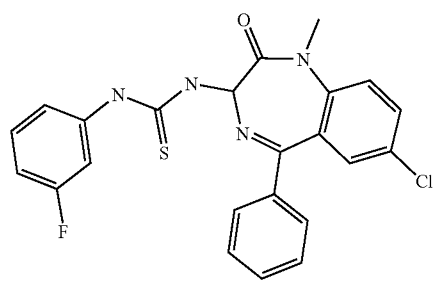 | 452.09 | Yes | 3.45 |
| 708 | 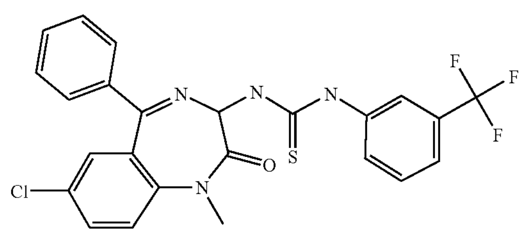 | 502.08 | Yes | 3.92 |
| 709 | 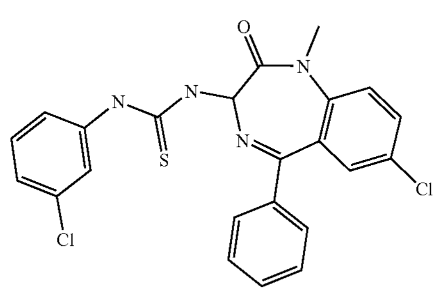 | 468.06 | Yes | 3.74 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 710 | 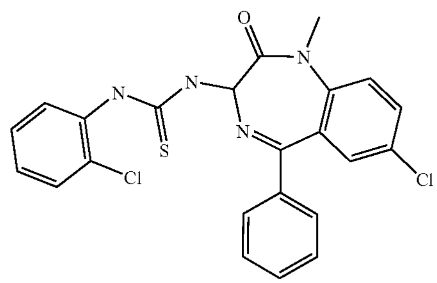 | 468.06 | Yes | 3.34 |
| 711 | 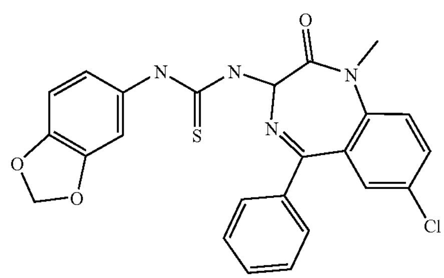 | 478.1 | Yes | 3.12, 3.49 |
| 712 | 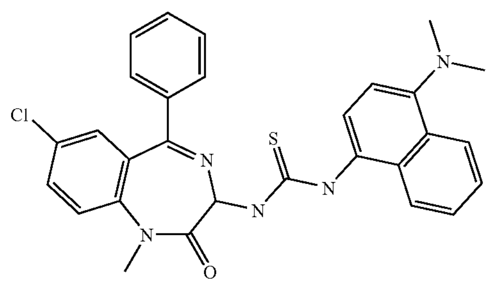 | 527.2 | Yes | 3.76, 4.81 |
| 713 | 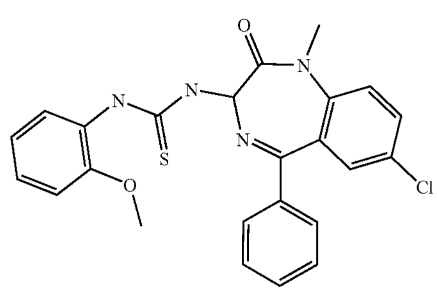 | 464.1 | Yes | 3.19, 3.53 |
| 714 | 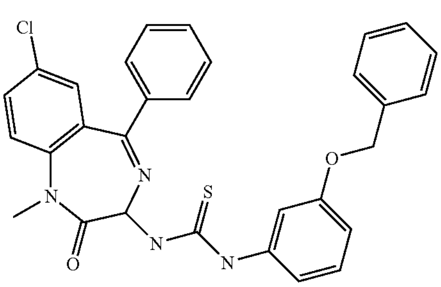 | 540.1 (blank) | Tentative | 6.4 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 715 | 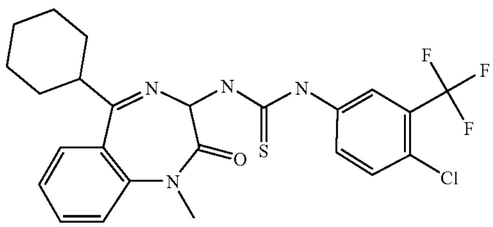 | 508.13 | Yes | 4.35, 6.57 |
| 716 | 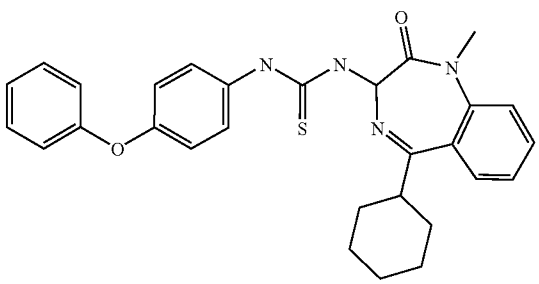 | 498.21 | Yes | 4.18 |
| 717 | 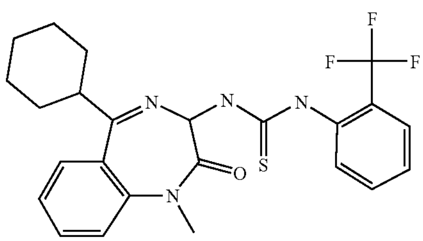 | 474.17 | Yes | 3.4 |
| 718 | 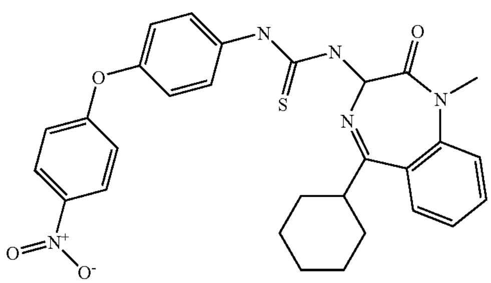 | 543.19 | Yes | 2.52, 4.19 |
| 719 | 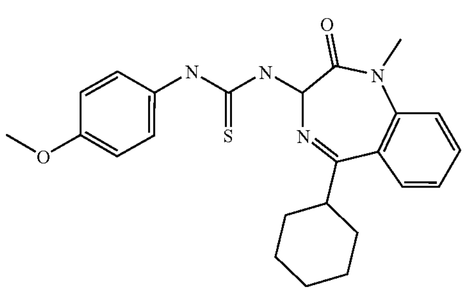 | 436.19 | Yes | 2.7, 3.18 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 720 | 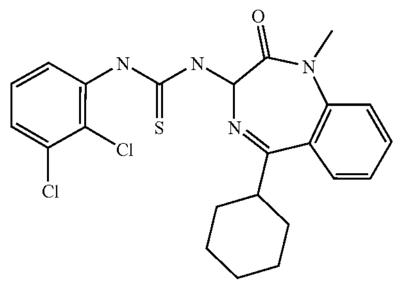 | 474.1 | Yes | 3.76 |
| 721 | 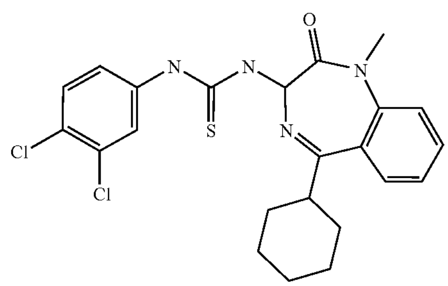 | 474.1 | Yes | 4.21 |
| 722 | 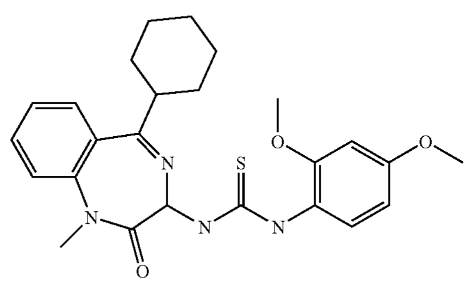 | 466.2 | Yes | 3.2 |
| 723 | 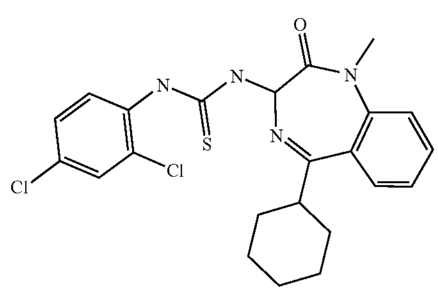 | 474.1 | Yes | 3.96 |
| 724 | 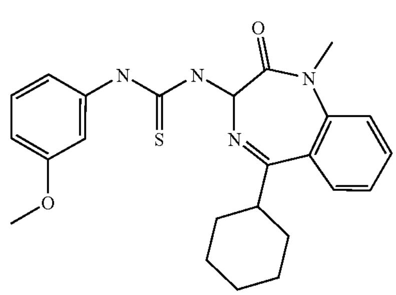 | 436.19 | Yes | 3.4 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 725 | 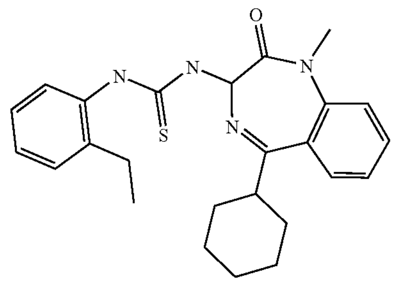 | 434.21 | Yes | 3.57 |
| 726 | 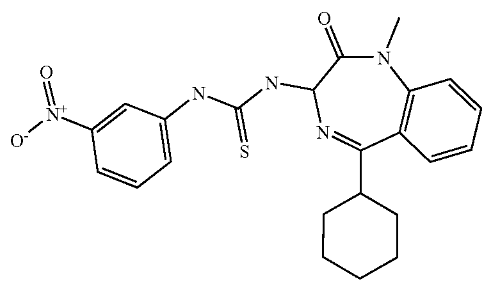 | 451.17 | Yes | 3.45 |
| 727 | 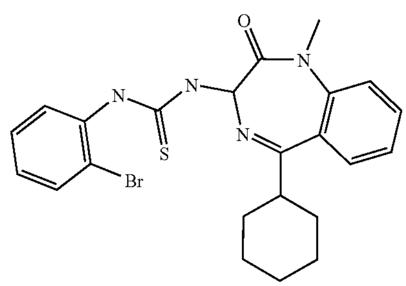 | 484.09 | Yes | 3.37 |
| 728 | 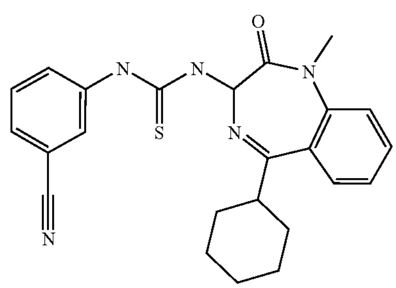 | 431.18 | Yes | 3.23 |
| 729 | 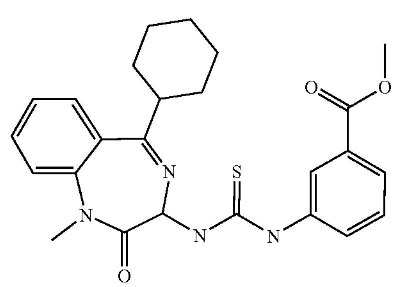 | 464.19 | Yes | 3.34 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 730 | 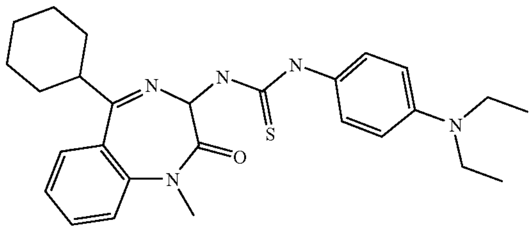 | 477.26 | Yes | 3.98 |
| 731 | 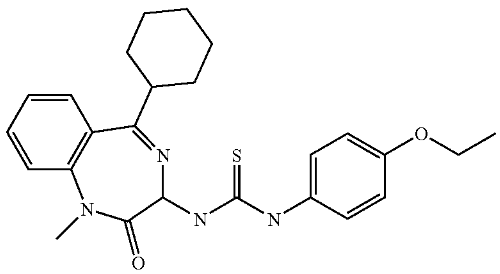 | 450.21 | Yes | 3.48 |
| 732 | 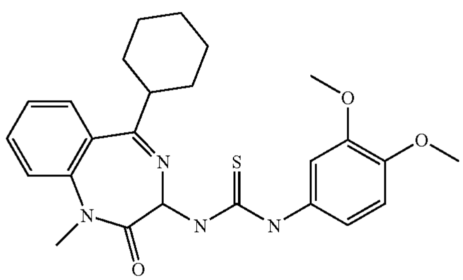 | 466.2 | Yes | 3.04 |
| 733 | 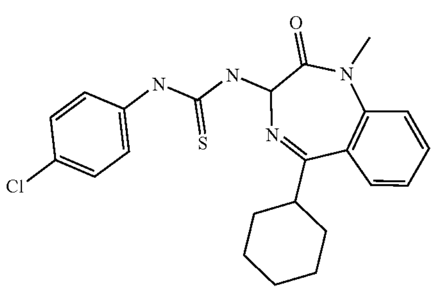 | 440.14 | Yes | 3.72 |
| 734 | 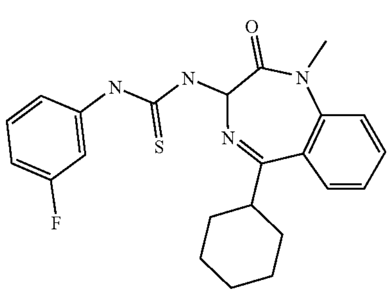 | 424.17 | Yes | 3.41 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 735 | 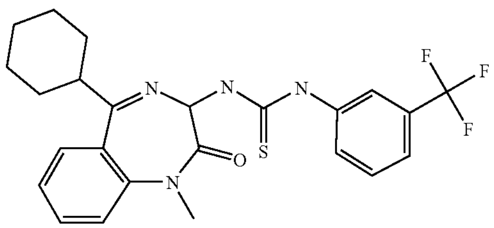 | 474.17 | Yes | 3.87 |
| 736 | 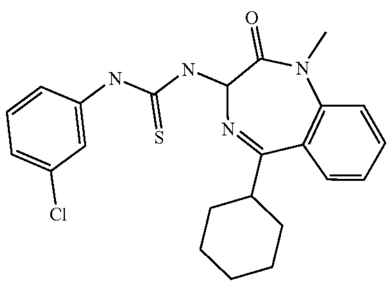 | 440.14 | Yes | 3.7 |
| 737 | 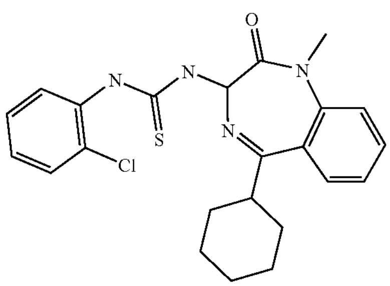 | 440.14 | Yes | 3.35 |
| 738 | 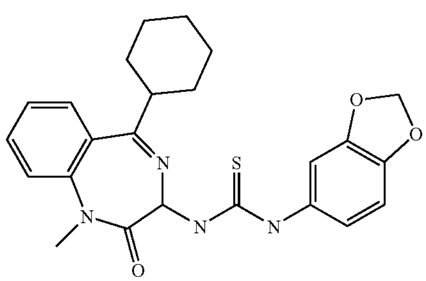 | 450.17 | Yes | 3.09 |
| 739 | 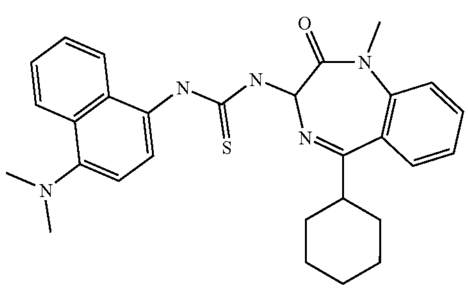 | 499.24 | Yes | 3.87 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 740 | 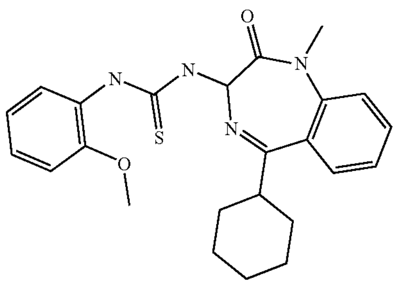 | 436.19 | Yes | 3.18 |
| 741 | 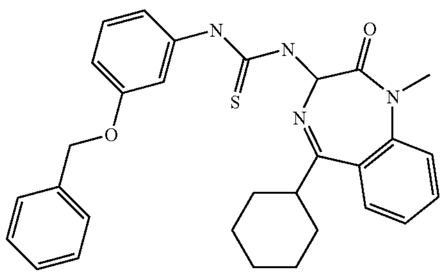 | 512.22 | No | |
| 742 | 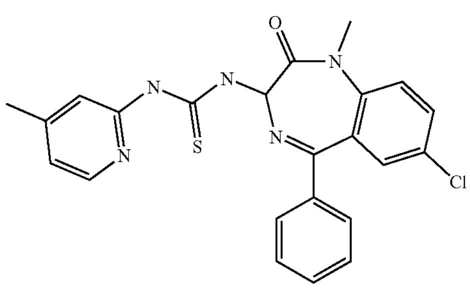 | 449.11 | No | |
| 743 | 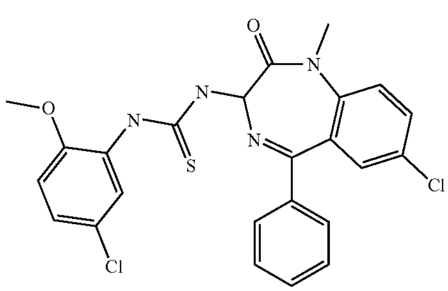 | 498.07 | Yes | 3.74 |
| 744 | 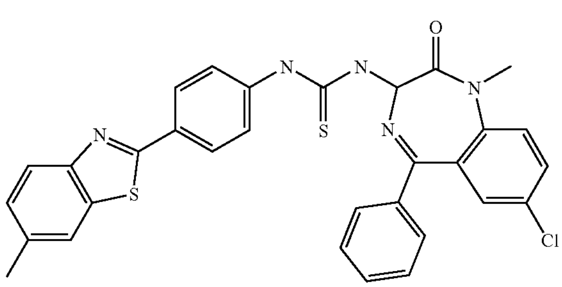 | 581.11 | No | |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 745 | 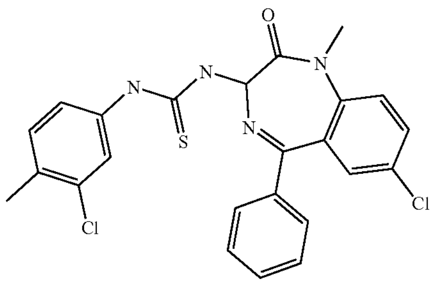 | 482.07 | Yes | 4 |
| 746 | 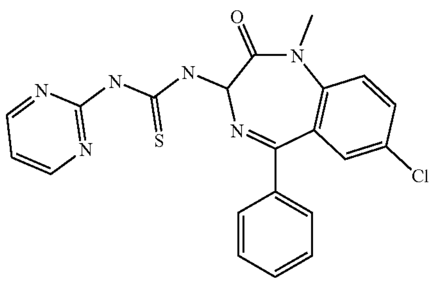 | 436.09 | Yes | 2.98 |
| 747 | 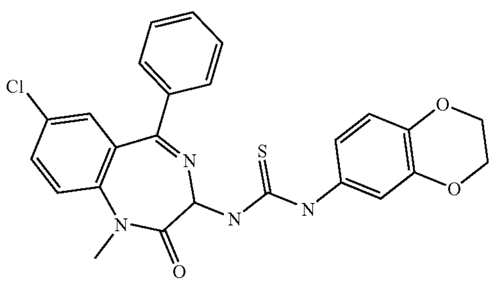 | 492.1 | Yes | 3.1 |
| 748 | 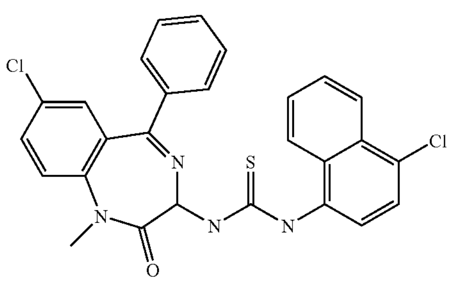 | 518.07 | Yes | |
| 749 | 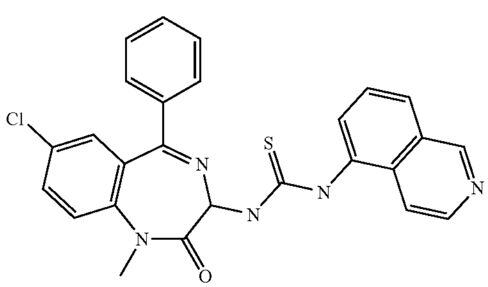 | 485.11 | Yes | 3.02 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 750 | 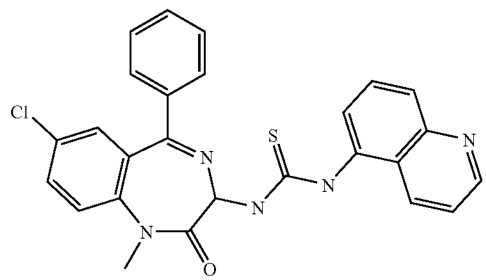 | 485.11 | Yes | 3.63 |
| 751 | 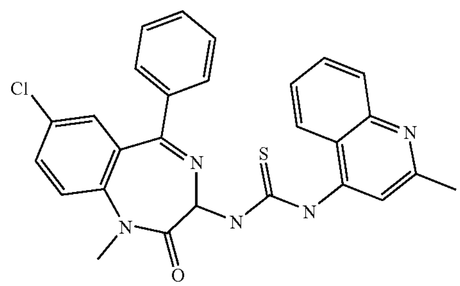 | 499.12 | Yes | 3.42 |
| 752 | 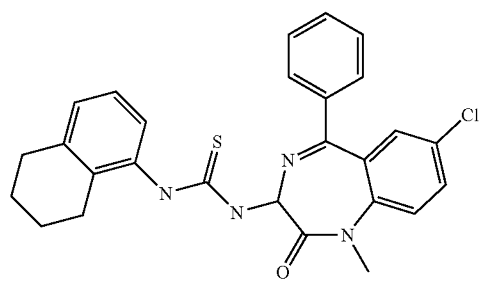 | 488.14 | Yes | 3.86 |
| 753 | 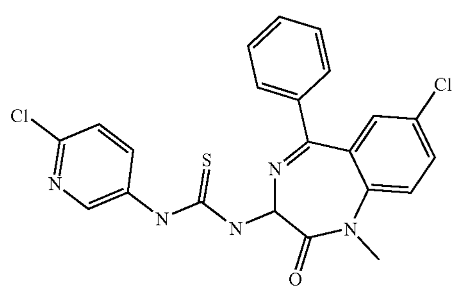 | 469.05 | Yes | 3.4 |
| 754 | 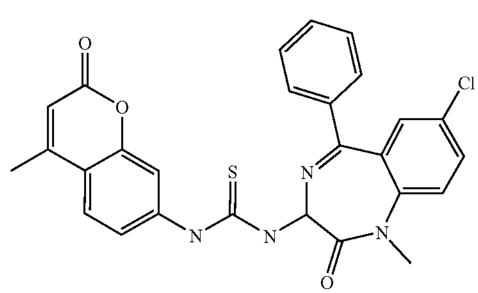 | 516.1 | No | |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 755 | 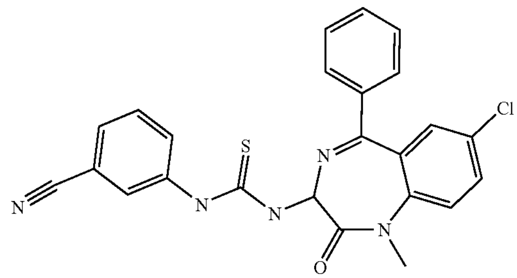 | 459.09 | Yes | 3.27 |
| 756 | 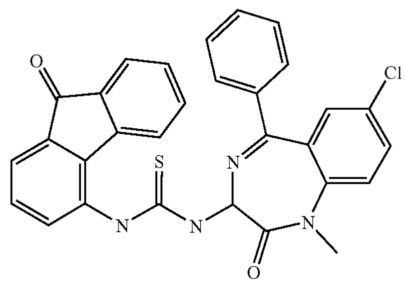 | 536.11 | Yes | 3.51 |
| 757 | 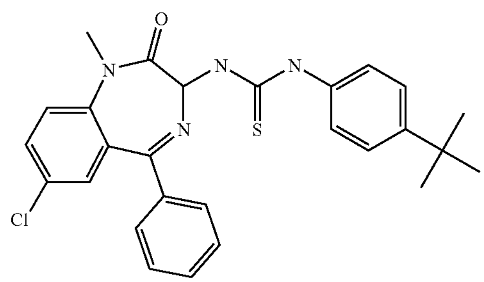 | 490.16 | Yes | 4.28 |
| 758 | 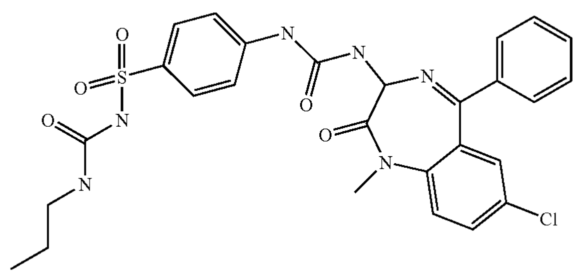 | 612.14 | Yes | 2.89 |
| 759 | 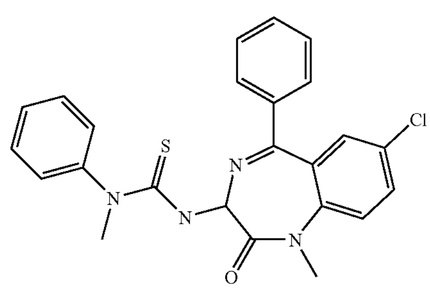 | 448.11 | Yes | 3.44 |

TABLE 1-continued
Spreadsheet of combinatorially prepared compounds with LCMS analysis of the reaction product.
| Compound # | Structure | Target Mass | Mass Found? | Rtn Time (MS) |
|---|---|---|---|---|
| 760 | 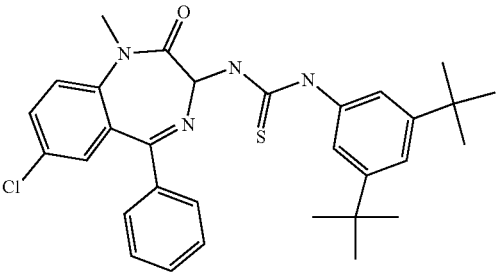 | 546.22 | Tentative | 6.44 |
| 761 | 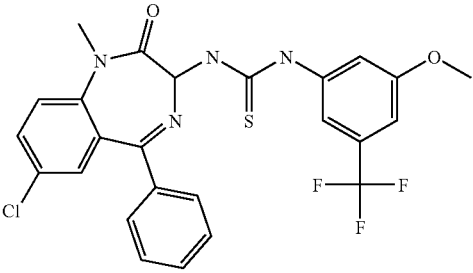 | 532.09 | Yes | 4.11 |
| 762 | 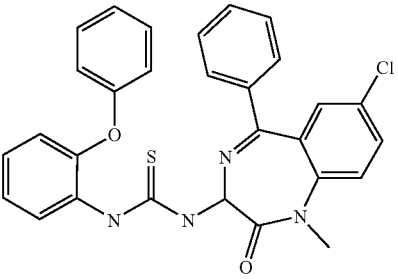 | 526.12 | No | |
| 763 | 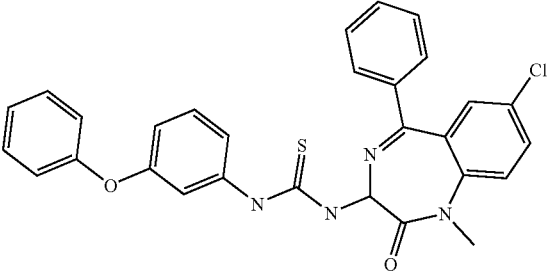 | 526.12 | Yes | 4.19 |
| 764 | 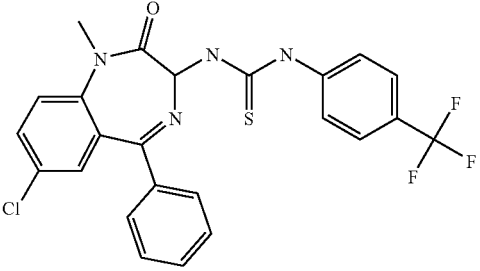 | 502.08 | Yes | 4.11 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 765 | 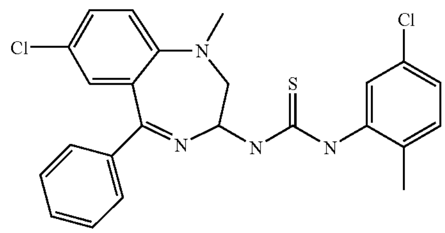 | 482.07 | Yes | 3.67 |
| 766 | 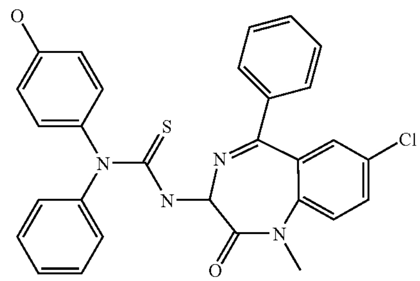 | 526.12 | Yes | 3.31 |
| 767 | 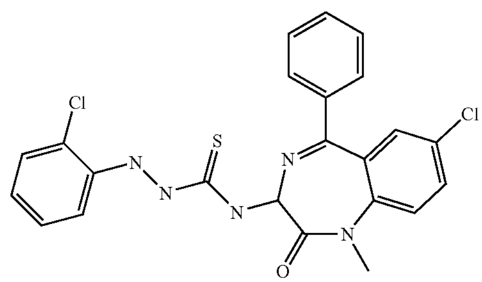 | 483.07 | Yes | 3.44 |
| 768 | 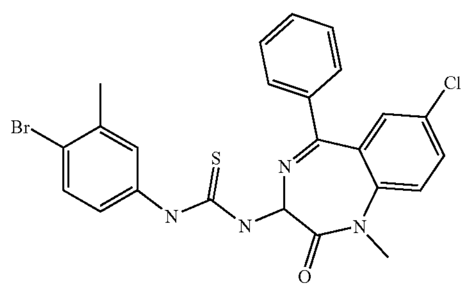 | 526.02 | Yes | 4.15 |
| 769 | 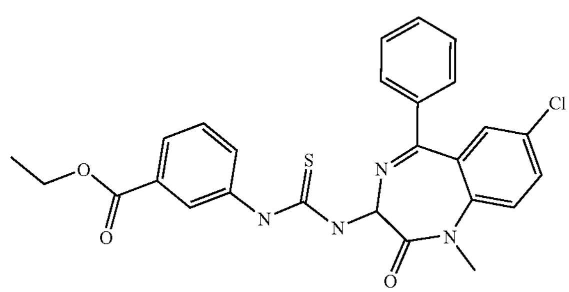 | 506.12 | No | |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 770 | 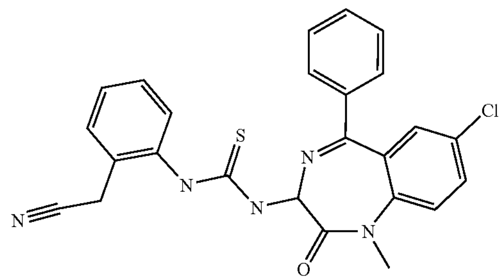 | 473.11 | No | |
| 771 | 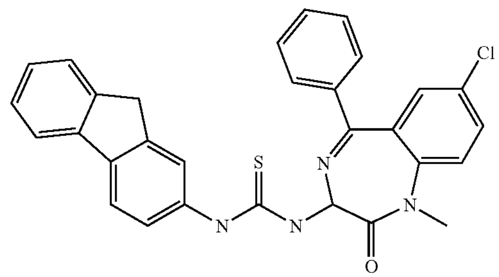 | 522.13 | Yes | 3.06 |
| 772 | 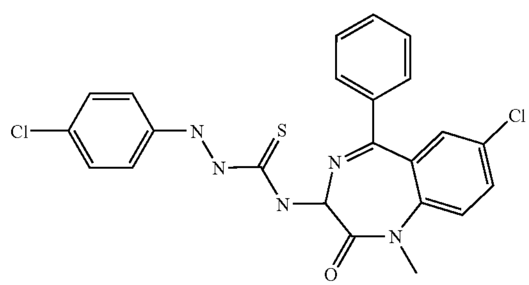 | 483.07 | No | |
| 773 | 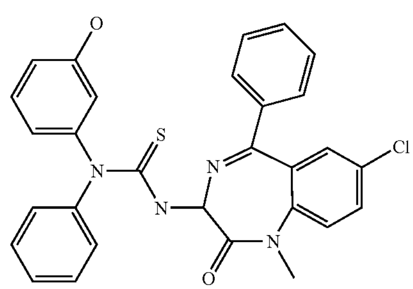 | 526.12 | Yes | 3.37 |
| 774 | 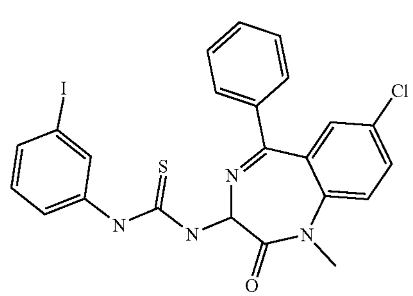 | 559.99 | Yes | 3.93 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 775 | 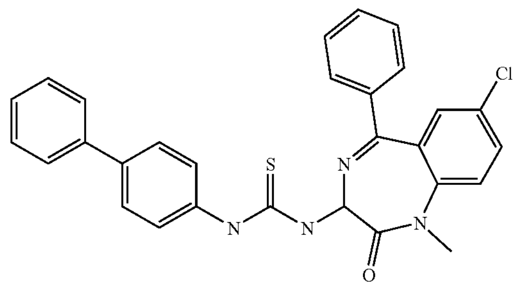 | 510.13 | Yes | 4.2 |
| 776 | 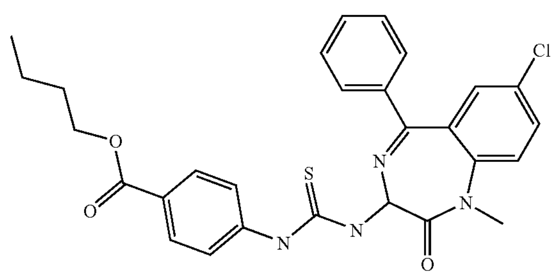 | 534.15 | Yes | 4.55 |
| 777 | 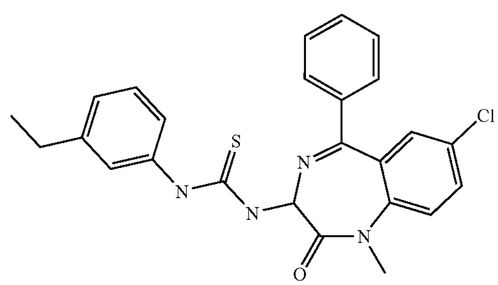 | 462.13 | Yes | |
| 778 | 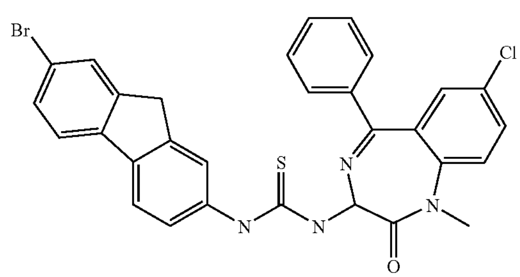 | 600.04 | No | |
| 779 | 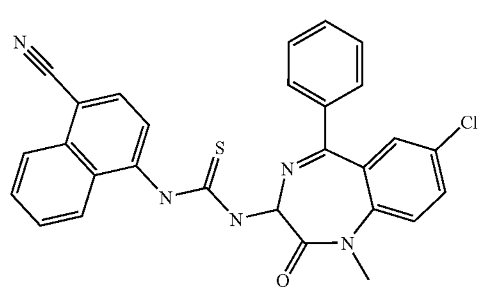 | 509.11 | Yes | 3.57 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 780 | 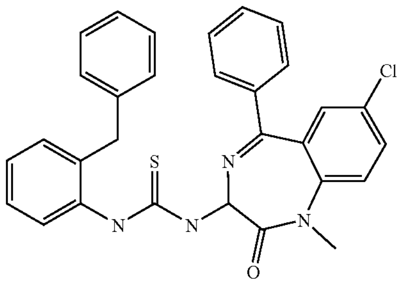 | 524.14 | Yes | 3.92 |
| 781 | 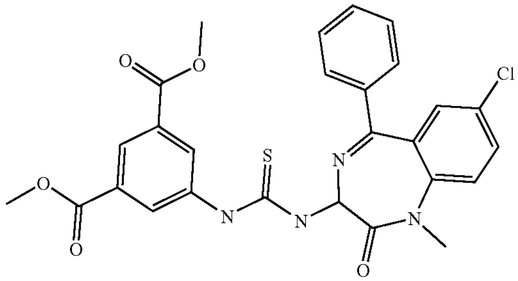 | 550.11 | Yes | 3.55 |
| 782 | 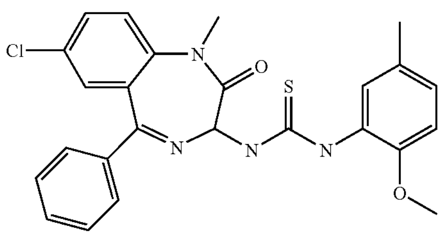 | 478.12 | No | |
| 783 | 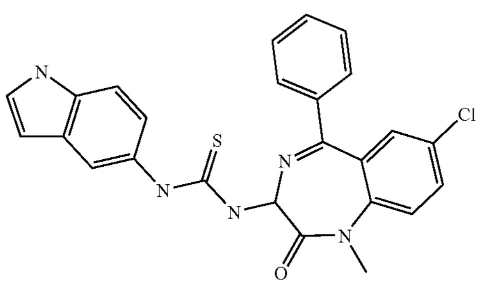 | 473.11 | Tentative | 2.93 |
| 784 | 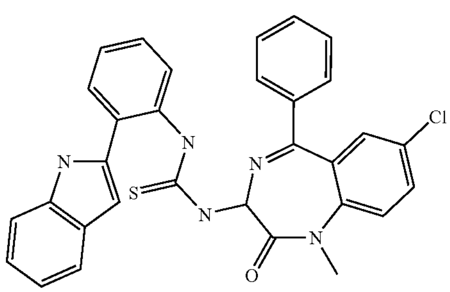 | 549.14 | Yes | 3.87 |

TABLE 1-continued
Spreadsheet of combinatorially prepared compounds with LCMS analysis of the reaction product.
| Compound # | Structure | Target Mass | Mass Found? | Rtn Time (MS) |
|---|---|---|---|---|
| 785 | 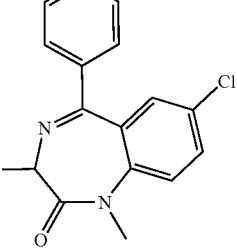 | 550.11 | Yes | 3.57 |
| 786 | 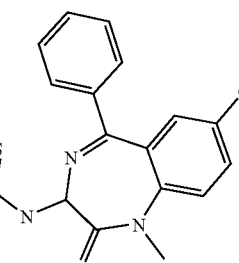 | 514.12 | Yes | |
| 787 | 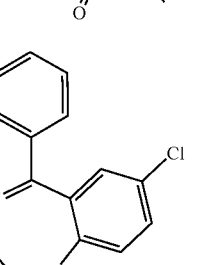 | 434.1 | Yes | 3.21, 6.52 |
| 788 | 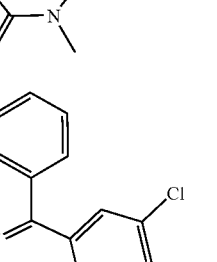 | 452.09 | Yes | 3.45 |
| 789 | 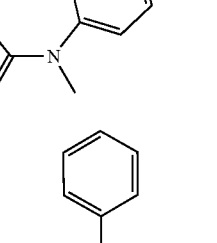 | 464.11 | Yes | 3.27, 3.62 |

TABLE 1-continued
Spreadsheet of combinatorially prepared compounds with LCMS analysis of the reaction product.
| Compound # | Structure | Target Mass | Mass Found? | Rtn Time (MS) |
|---|---|---|---|---|
| 790 | 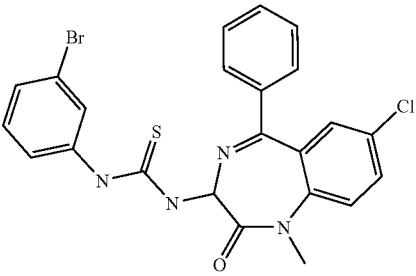 | 512.01 | Yes | 3.82 |
| 791 | 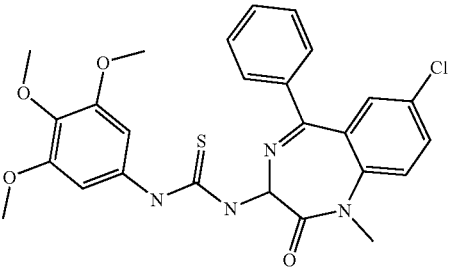 | 524.13 | Yes | 3.11, 3.58 |
| 792 | 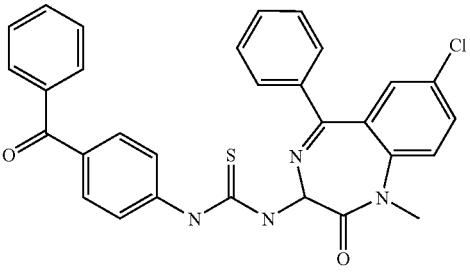 | 538.12 | Yes | 4.05 |
| 793 | 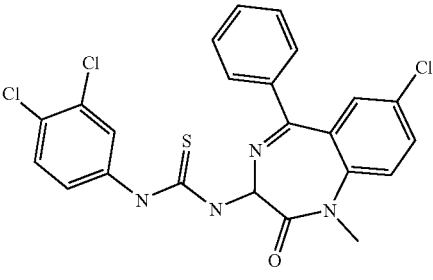 | 502.02 | Yes | 4.3 |
| 794 | 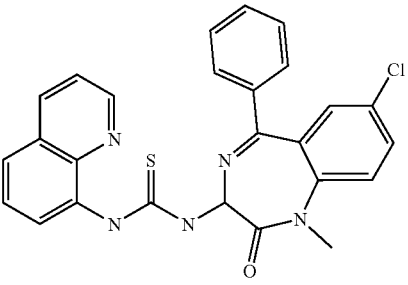 | 485.11 | Yes | 3.62 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 795 | | 466.1 | Yes | 3.43 |
| 796 | | 460.11 | Yes | 3.66 |
| 797 | | 504.01 | Yes | 6.43 |
| 798 | | 502.02 | Yes | 4.55 |
| 799 | | 493.05 | Yes | 3.41 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 800 | 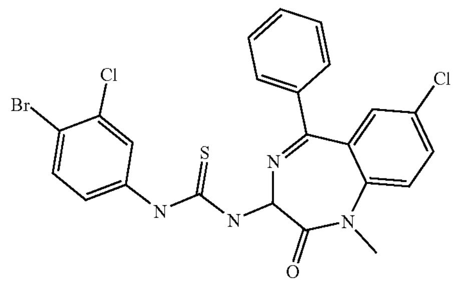 | 545.97 | Yes | 4.41 |
| 801 | 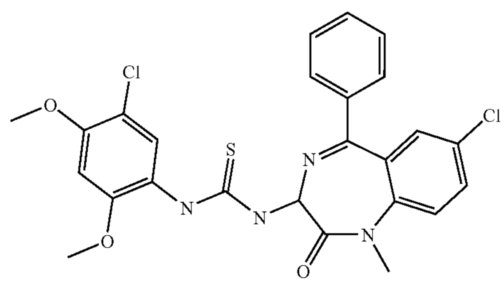 | 528.08 | Yes | 3.39 |
| 802 | 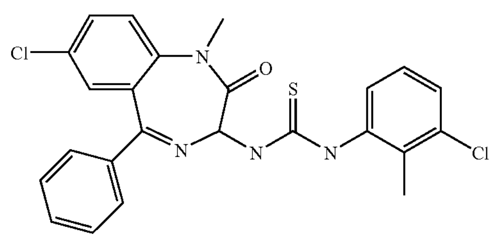 | 482.07 | Yes | 3.44, 3.71 |
| 803 | 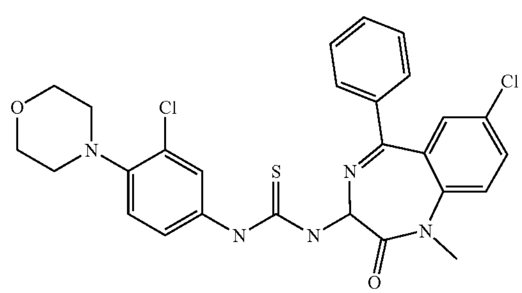 | 553.11 | Yes | 3.65 |
| 804 | 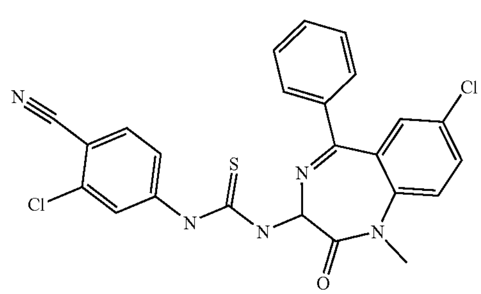 | 493.05 | Yes | 3.9 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 805 | 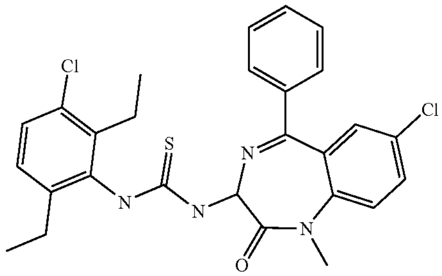 | 524.12 | Yes | 4.35, 6.49 |
| 806 | 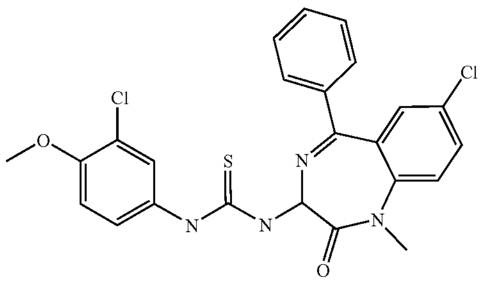 | 498.07 | Yes | 3.42 |
| 807 | 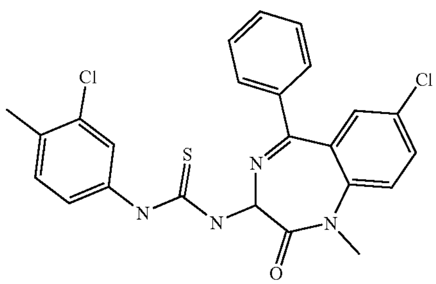 | 482.07 | Yes | 3.99 |
| 808 | 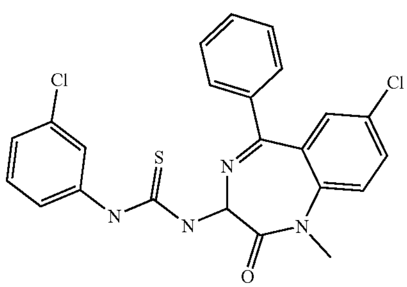 | 468.06 | Yes | 3.74 |
| 809 | 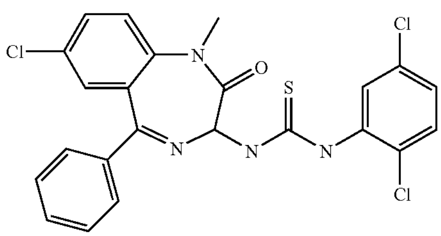 | 502.02 | Yes | 3.92 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 810 | 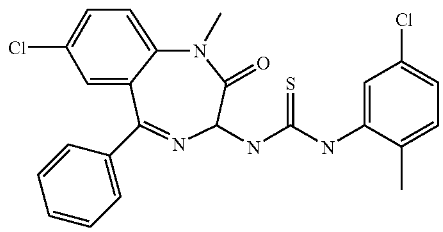 | 482.07 | Yes | 3.68 |
| 811 | 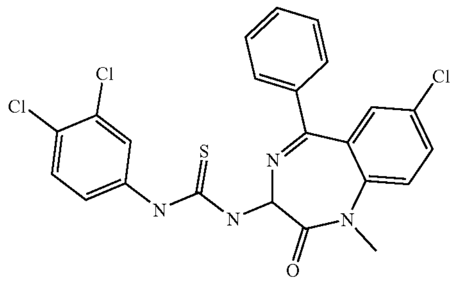 | 502.02 | Yes | 4.32 |
| 812 | 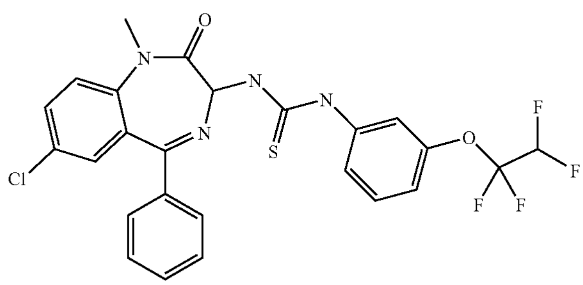 | 550.09 | No | |
| 813 | 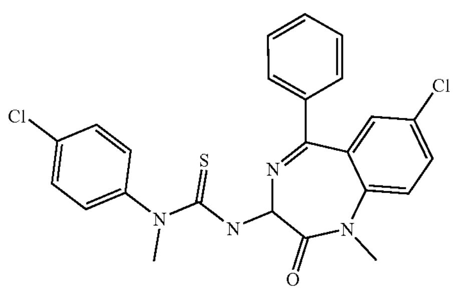 | 482.07 | Yes | 3.84 |
| 814 | 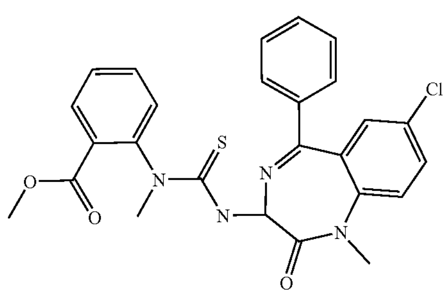 | 506.12 | Yes | 3.25 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 815 | 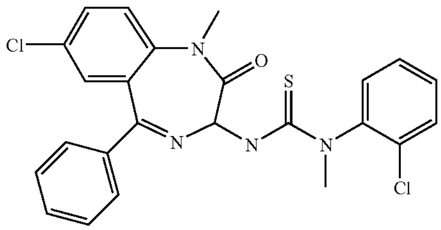 | 482.07 | Yes | 3.62 |
| 816 | 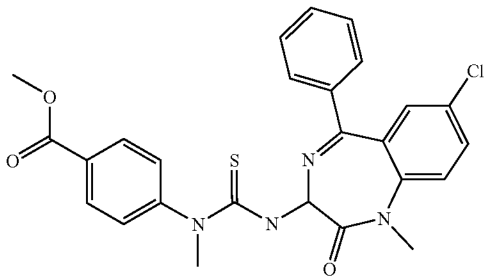 | 506.12 | Yes | 3.57, 4.02 |
| 817 | 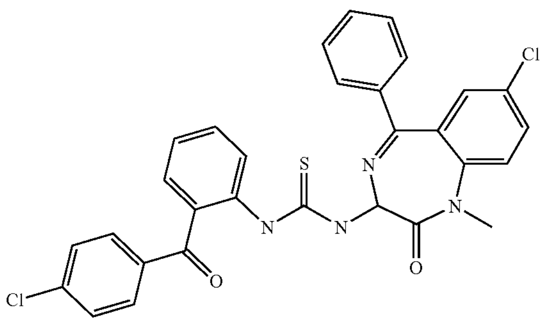 | 572.08 | Yes | 4.36 |
| 818 | 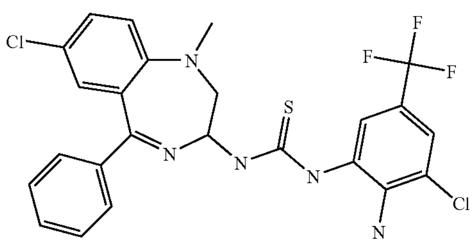 | 551.06 | Yes | 3.92 |
| 819 | 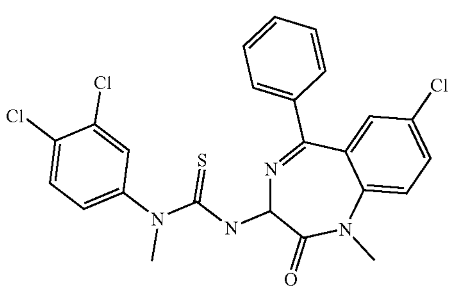 | 516.03 | Yes | |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 820 | 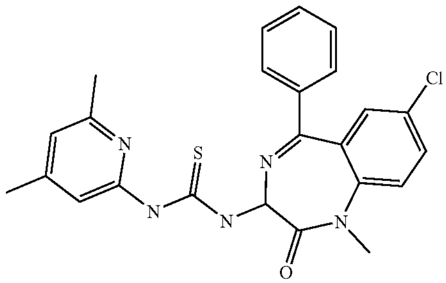 | 463.12 | Yes | 3.69 |
| 821 | 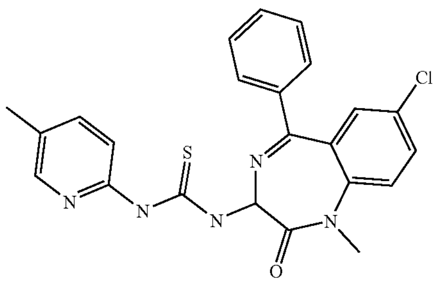 | 449.11 | Yes | 3.39 |
| 822 | 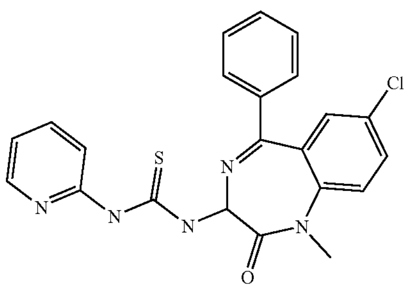 | 435.09 | Yes | 3.14 |
| 823 | 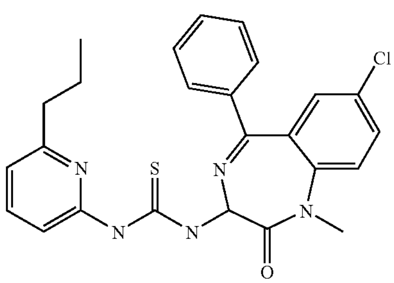 | 477.14 | Yes | 4.18 |
| 824 | 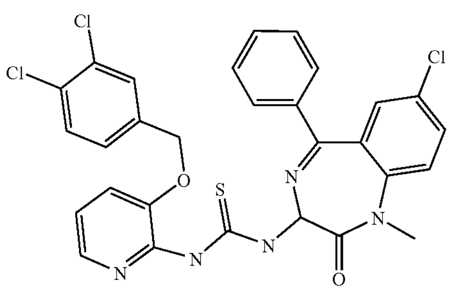 | 609.06 | Tentative | 3.91 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 825 | 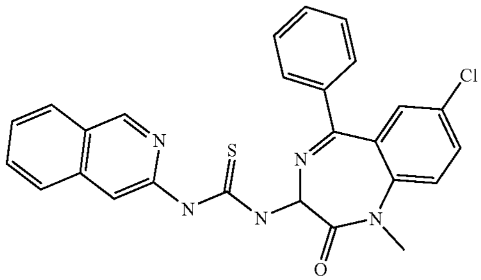 | 485.11 | Yes | 3.69 |
| 826 | 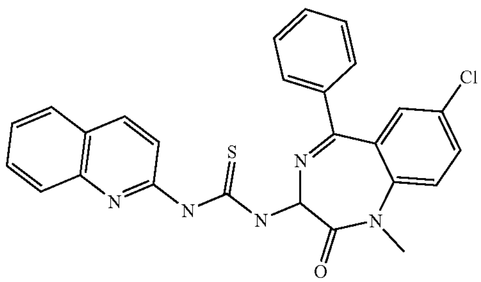 | 485.11 | Yes | 3.82 |
| 827 | 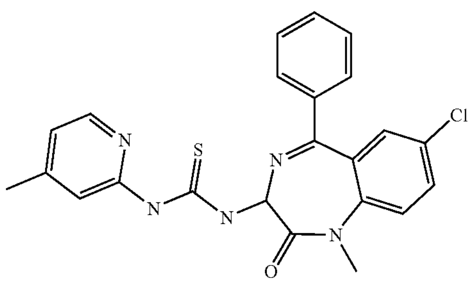 | 449.11 | Yes | 3.37 |
| 828 | 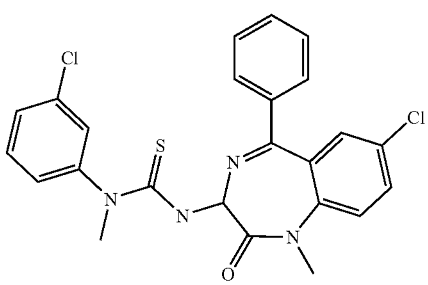 | 482.07 | Yes | 3.86 |
| 829 | 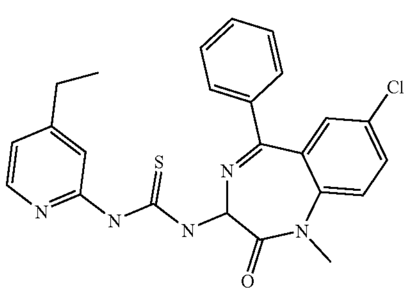 | 463.12 | Yes | 3.64 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 830 | 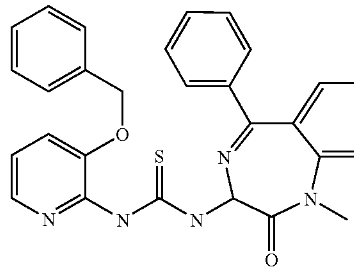 | 541.13 | No | |
| 831 | 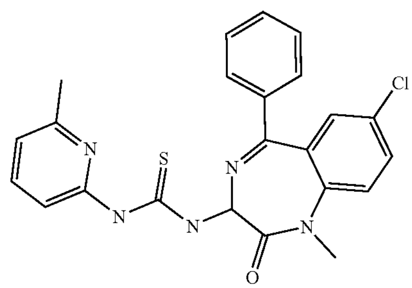 | 449.11 | Yes | 3.4 |
| 832 | 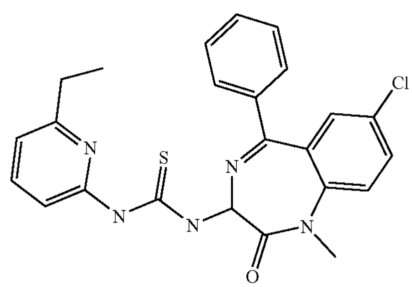 | 463.12 | Yes | 3.81 |
| 833 | 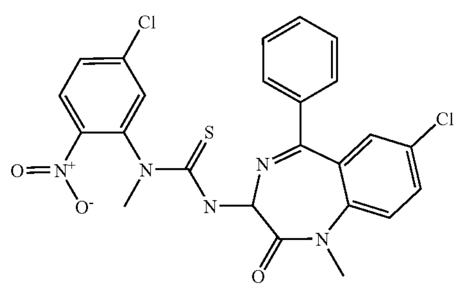 | 527.06 | No | |
| 834 | 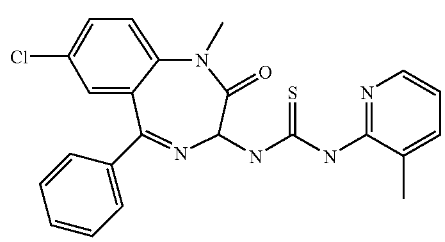 | 449.11 | Yes | 3.45 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 835 | 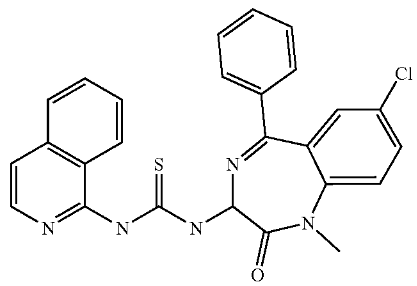 | 485.11 | No | |
| 836 | 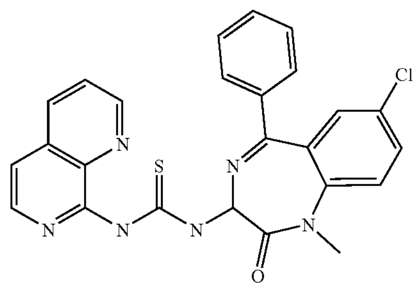 | 486.1 | No | |
| 837 | 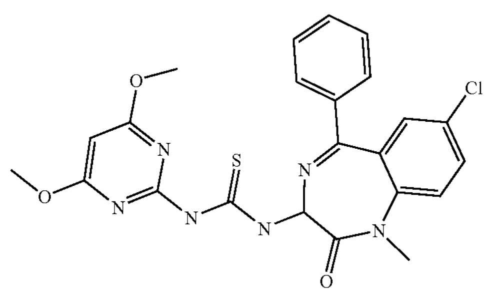 | 496.11 | No | |
| 838 | 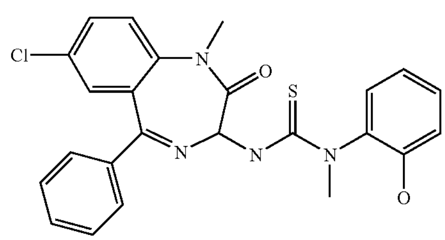 | 464.11 | Yes | 3.15 |
| 839 | 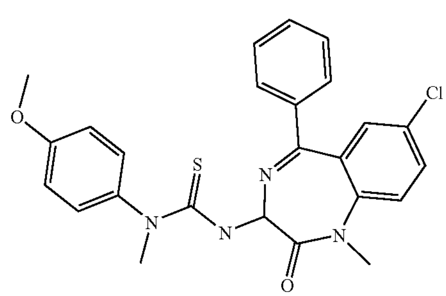 | 478.12 | Yes | 2.76, 3.53, 3.93 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 840 | 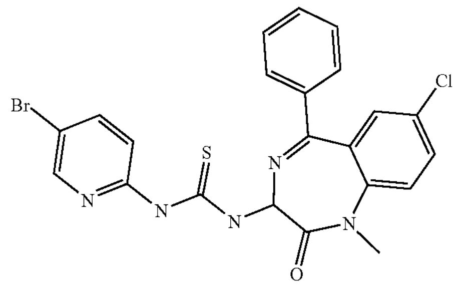 | 513 | Yes | 3.75 |
| 841 | 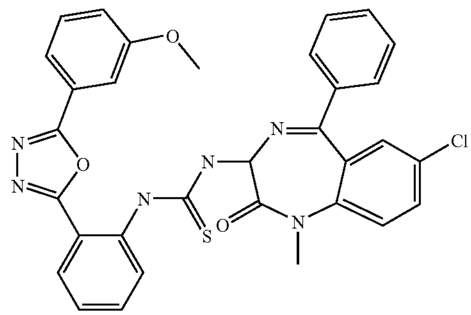 | 608.14 | Yes | 3.96 |
| 842 | 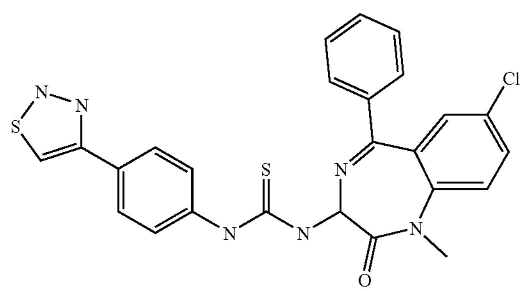 | 518.08 | Yes | 3.29 |
| 843 | 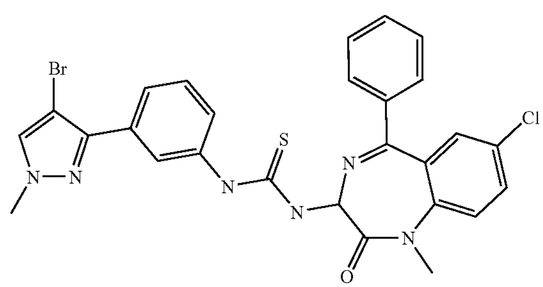 | 592.04 | Yes | 3.8 |
| 844 | 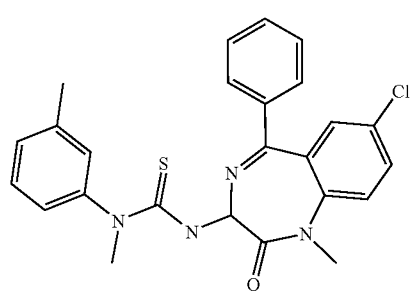 | 462.13 | Yes | 3.76, 4.37 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 845 | 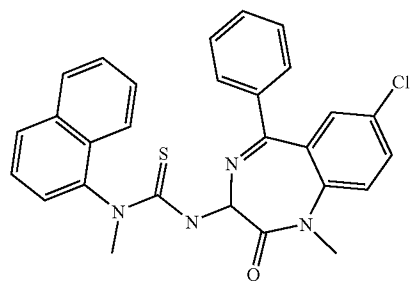 | 498.13 | Yes | 3.99, 4.74 |
| 846 | 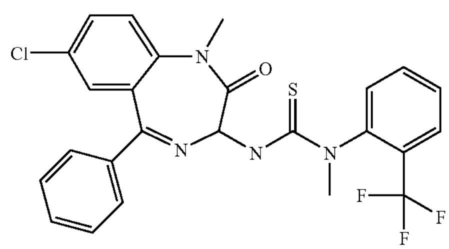 | 516.1 | No | |
| 847 | 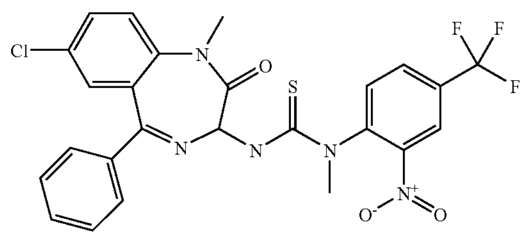 | 561.08 | No | |
| 848 | 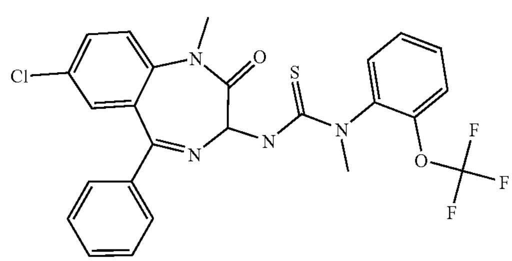 | 532.09 | Tentative | 3.92 |
| 849 | 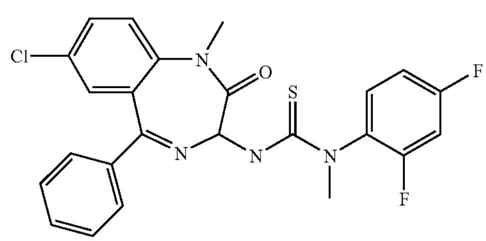 | 484.09 | Yes | 3.56 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 850 | 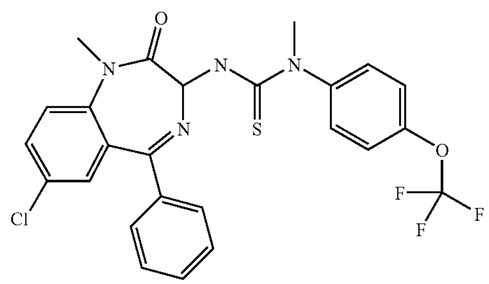 | 532.09 | No | |
| 851 | 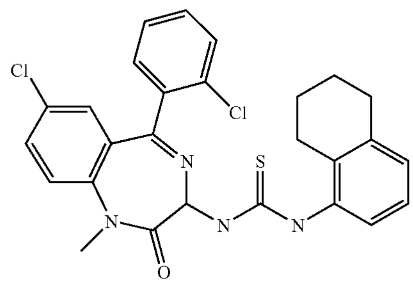 | 522.1 | No | |
| 852 | 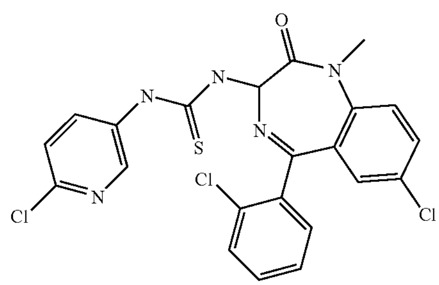 | 503.01 | Yes | 3.44 |
| 853 | 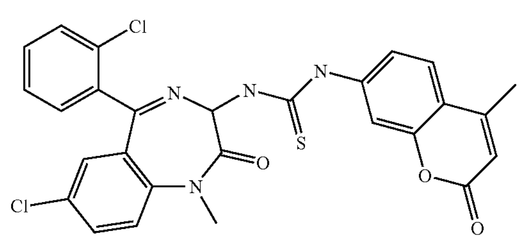 | 550.06 | No | |
| 854 | 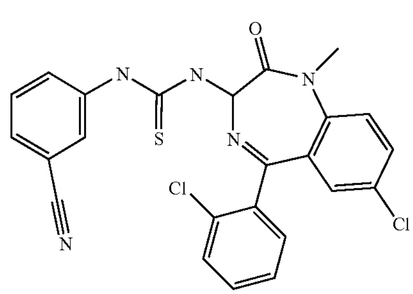 | 493.055 | Yes | 3.3 |

TABLE 1-continued
Spreadsheet of combinatorially prepared compounds with LCMS analysis of the reaction product.
| Compound # | Structure | Target Mass | Mass Found? | Rtn Time (MS) |
|---|---|---|---|---|
| 855 | 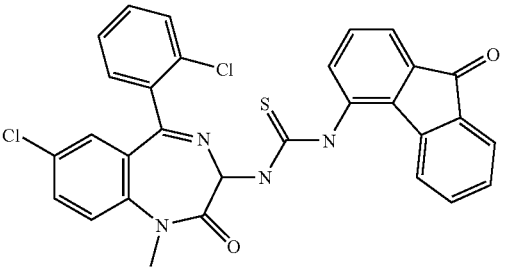 | 570.07 | No | |
| 856 | 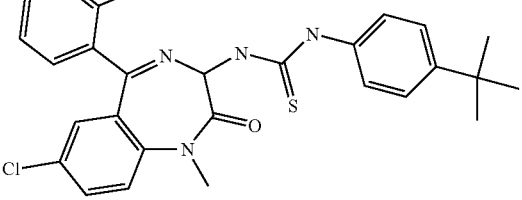 | 524.12 | Yes | 4.3 |
| 857 | 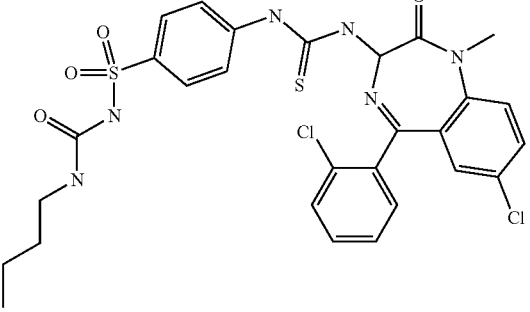 | 646.1 | Yes | 2.96 |
| 858 | 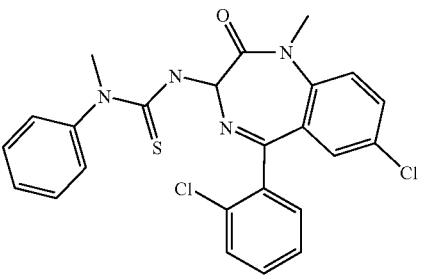 | 482.07 | Yes | 3.47 |
| 859 | 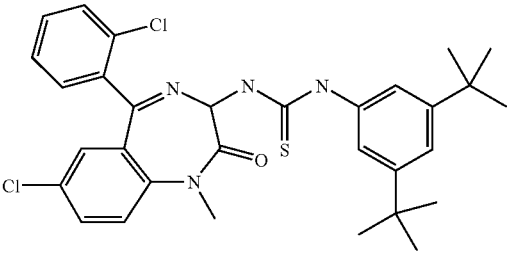 | 580.18 | Yes | 5.17 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 860 | 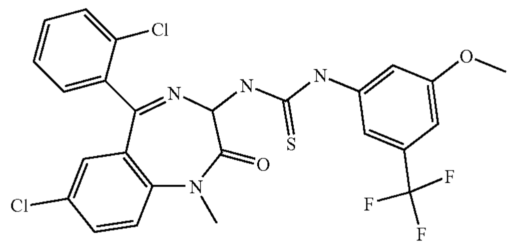 | 566.06 | Yes | |
| 861 | 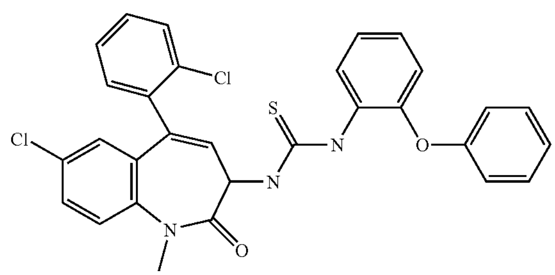 | 560.08 | No | |
| 862 | 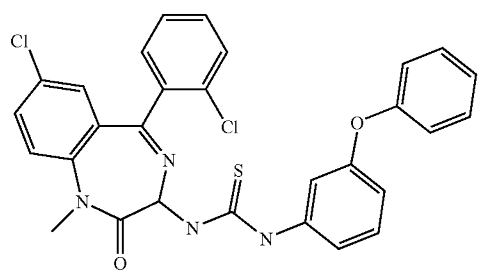 | 560.08 | Yes | |
| 863 | 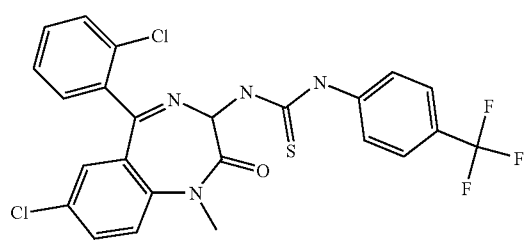 | 536.05 | Yes | 4.12 |
| 864 | 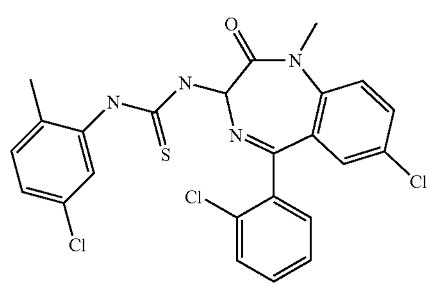 | 516.03 | Tentative | 3.67 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 865 | 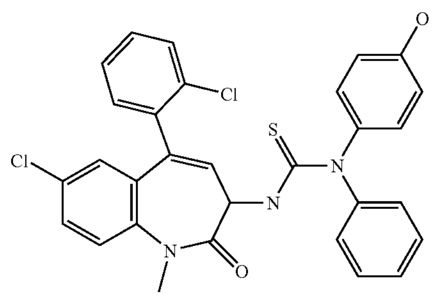 | 560.08 | Yes | 3.33 |
| 866 | 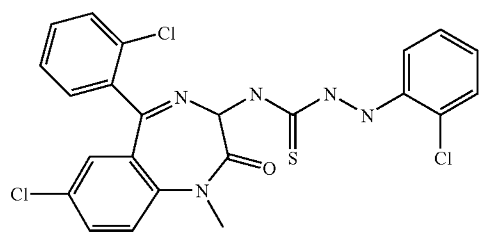 | 517.03 | Yes | 3.38, 3.96 |
| 867 | 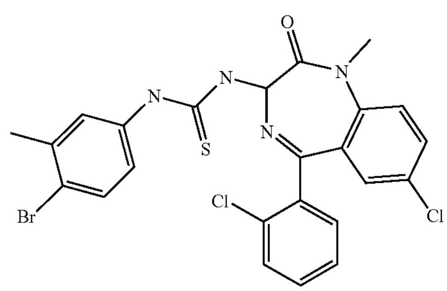 | 559.98 | Tentative | 4.16 |
| 868 | 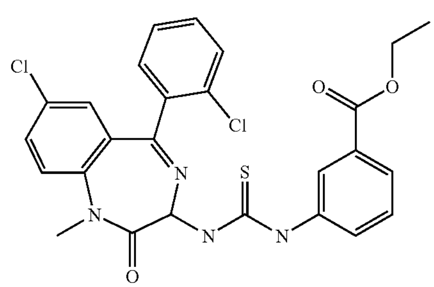 | 540.08 | No | |
| 869 | 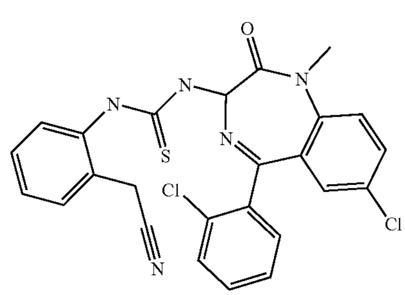 | 507.07 | No | |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 870 | 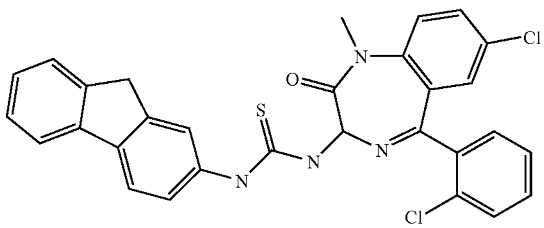 | 556.09 | Yes | 4.26 |
| 871 | 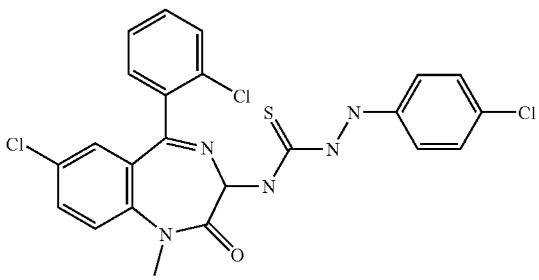 | 517.03 | No | |
| 872 | 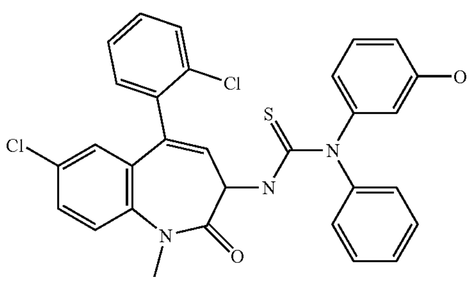 | 560.08 | Yes | 3.39 |
| 873 | 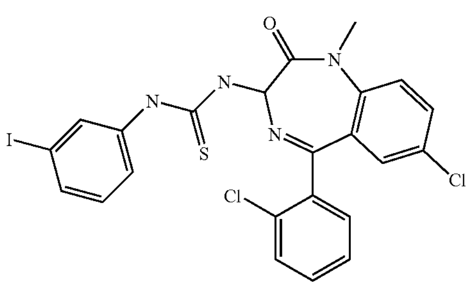 | 593.95 | No | |
| 874 | 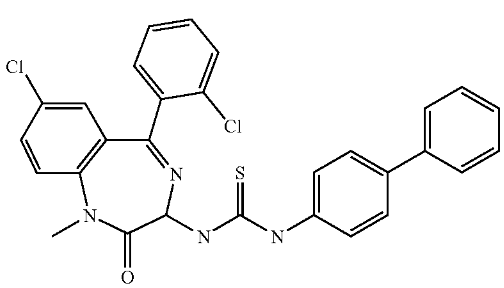 | 544.09 | Yes | 4.21 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 875 | 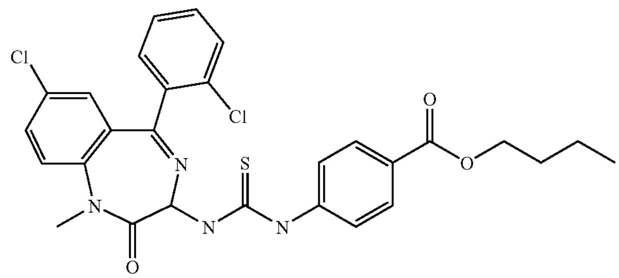 | 568.11 | Yes | 4.55 |
| 876 | 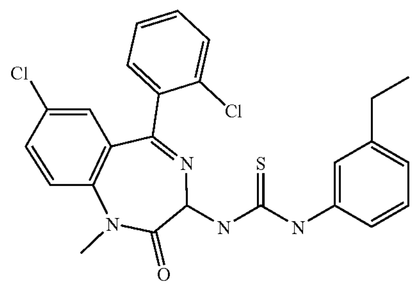 | 496.09 | No | |
| 877 | 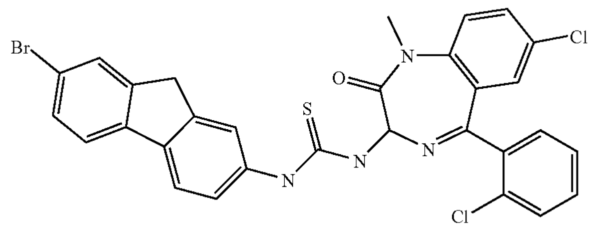 | 634 | No | |
| 878 | 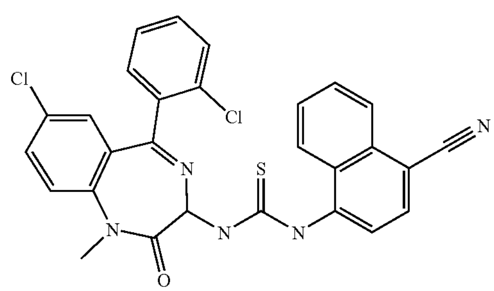 | 543.07 | Yes | 3.59 |
| 879 | 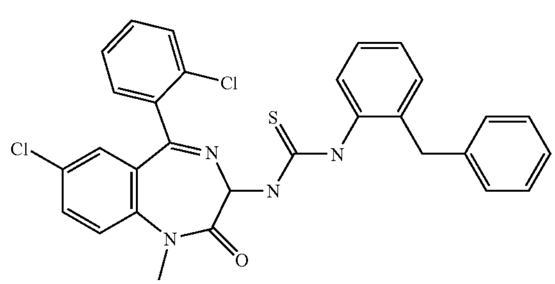 | 558.1 | Yes | 3.94 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 880 | 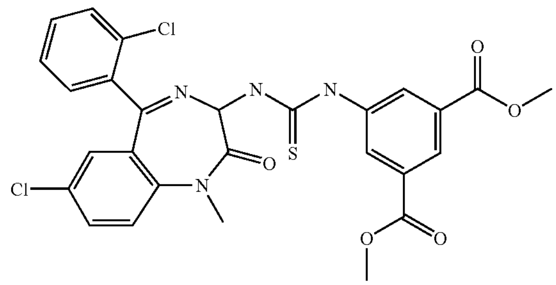 | 584.07 | Yes | 3.57 |
| 881 | 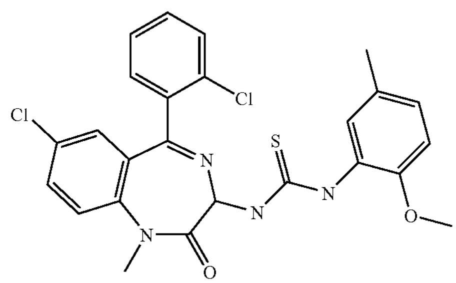 | 512.08 | No | |
| 882 | 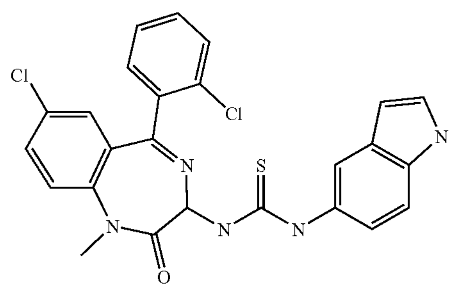 | 507.07 | Yes | 3.01 |
| 883 | 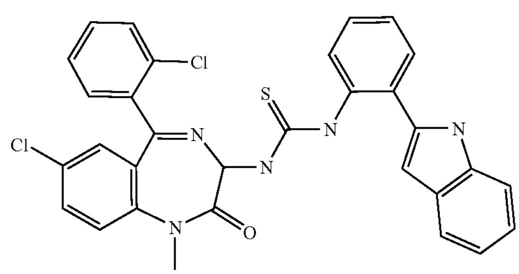 | 583.1 | Yes | 3.93 |
| 884 | 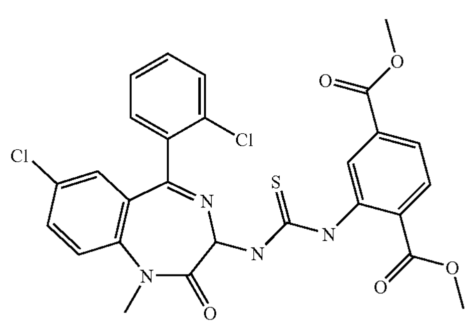 | 584.07 | Yes | 3.5 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 885 | 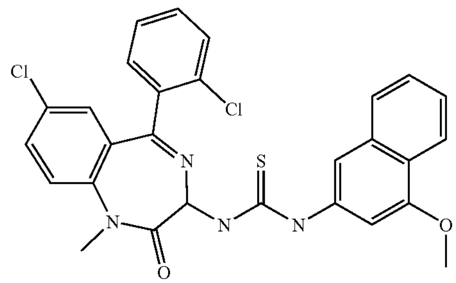 | 548.08 | Tentative | 4.47 |
| 886 | 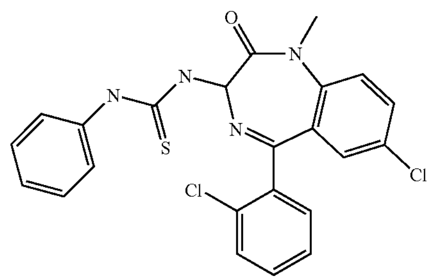 | 468.06 | Yes | 3.24 |
| 887 | 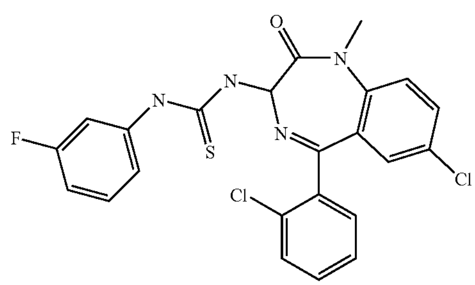 | 486.05 | Yes | 3.48 |
| 888 | 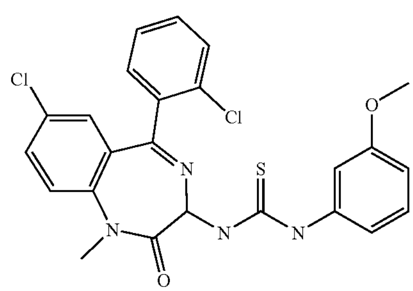 | 498.07 | Yes | 3.29 |
| 889 | 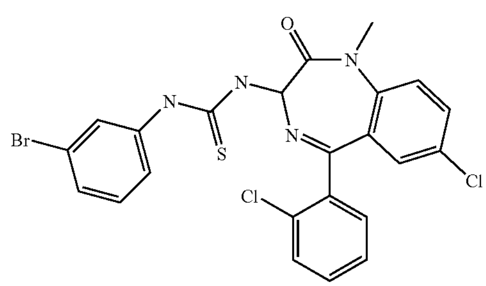 | 545.97 | No | |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 890 | 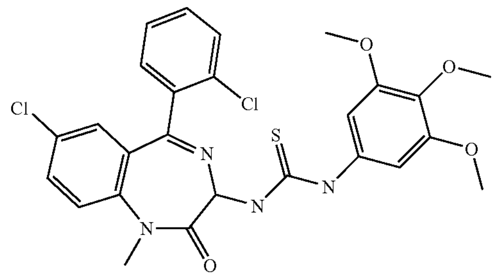 | 558.09 | Yes | 2.02, 3.17, 3.48 |
| 891 | 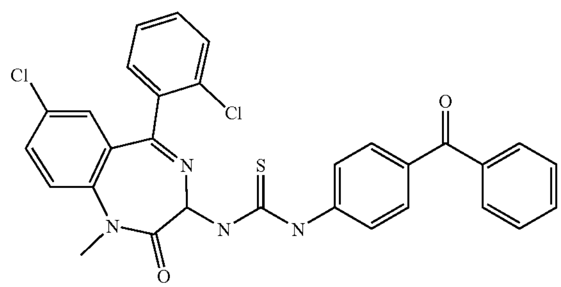 | 572.08 | Yes | 4.07 |
| 892 | 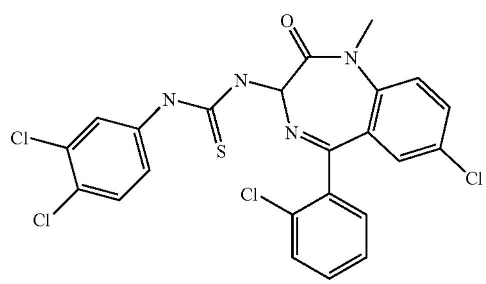 | 535.98 | Yes | 4.31 |
| 893 | 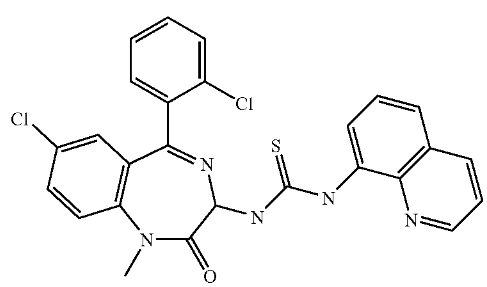 | 519.07 | Yes | 3.61 |
| 894 | 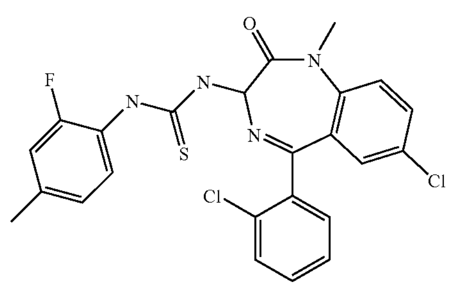 | 500.06 | Yes | 3.46 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 895 | 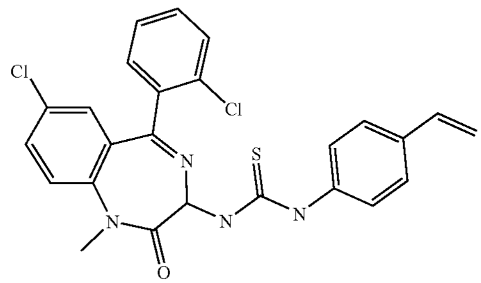 | 494.07 | Yes | 3.69 |
| 896 | 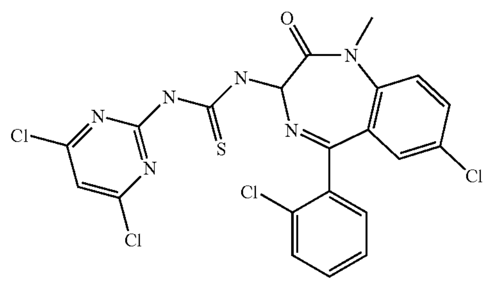 | 537.97 | No | |
| 897 | 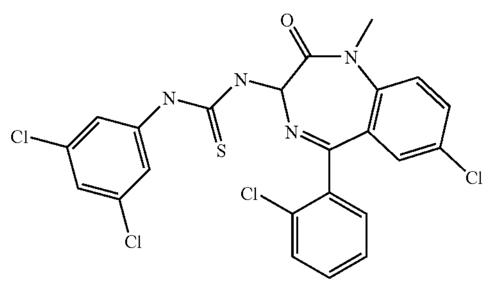 | 535.98 | No | |
| 898 | 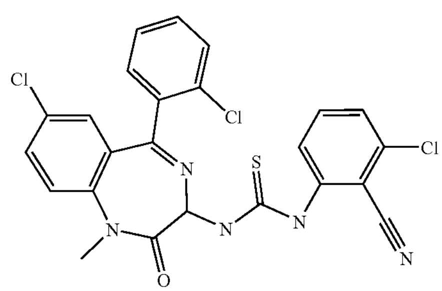 | 527.01 | Yes | 3.44 |
| 899 | 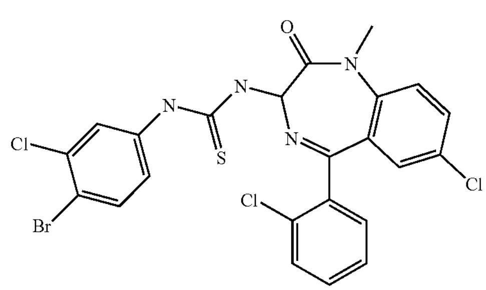 | 579.93 | Tentative | 4.41 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 900 | 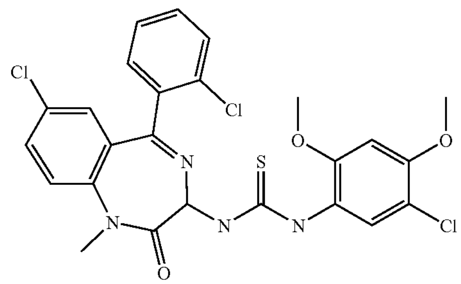 | 562.04 | Yes | 3.41 |
| 901 | 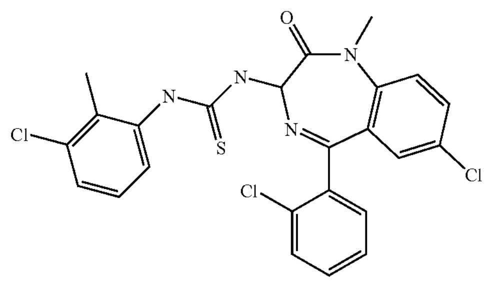 | 516.03 | Tentative | 3.71 |
| 902 | 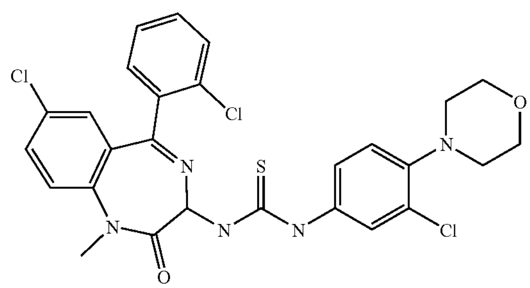 | 587.07 | Yes | 3.68 |
| 903 | 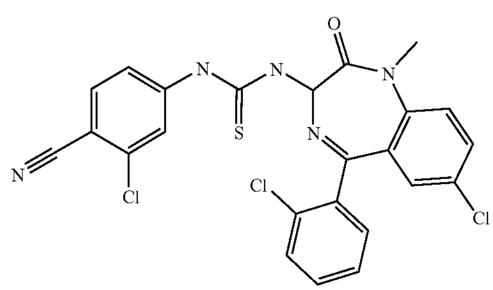 | 527.01 | Yes | 3.9 |
| 904 | 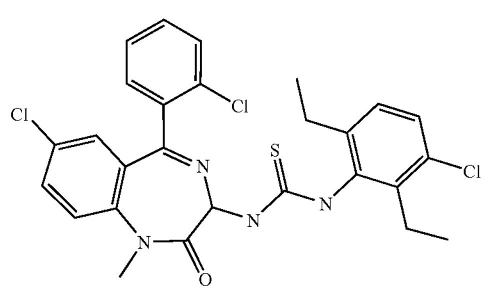 | 558.08 | Yes | 4.37 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 905 | 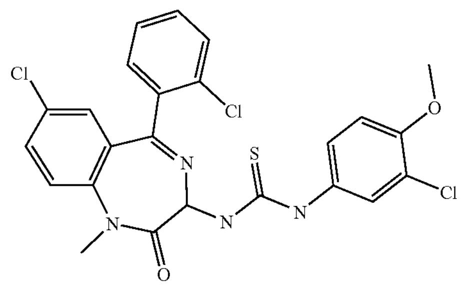 | 532.03 | Yes | 3.46 |
| 906 | 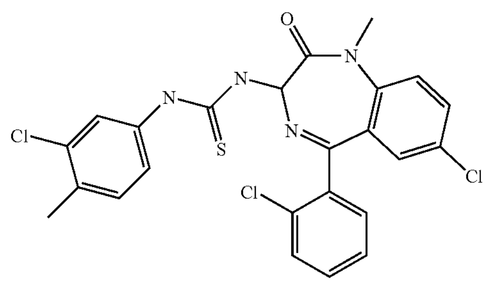 | 516.03 | Tentative | 3.99 |
| 907 | 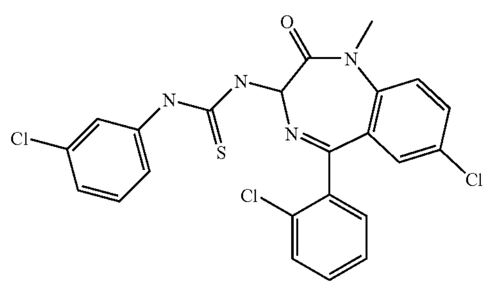 | 502.02 | Yes | 3.76 |
| 908 | 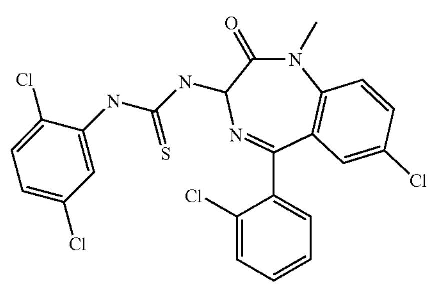 | 535.98 | Yes | 3.93 |
| 909 | 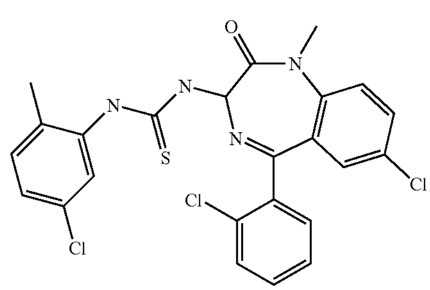 | 516.03 | Tentative | 3.68 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 910 | 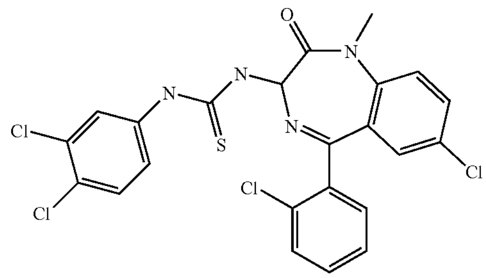 | 535.98 | Yes | |
| 911 | 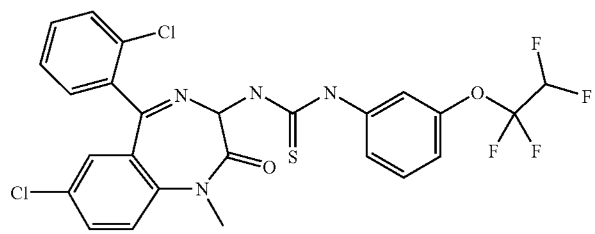 | 584.05 | No | |
| 912 | 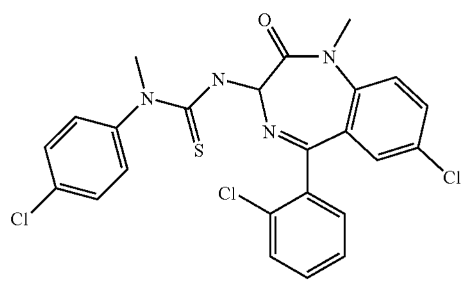 | 516.03 | Yes | 3.84 |
| 913 | 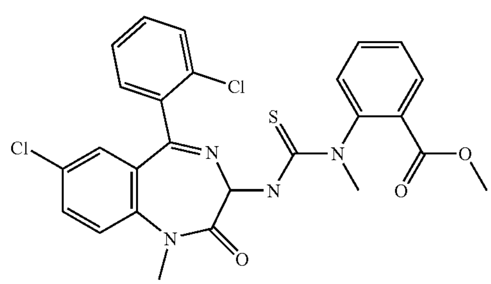 | 540.08 | Yes | 3.29 |
| 914 | 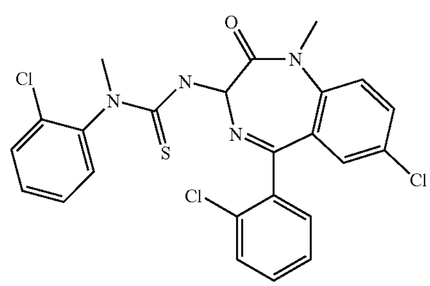 | 516.03 | Yes | 3.64 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 915 | 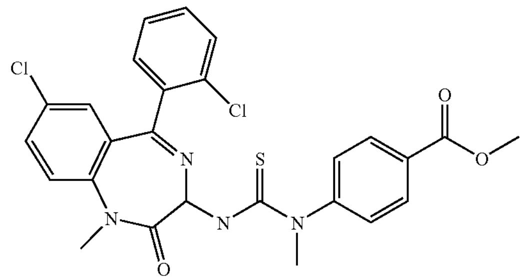 | 540.08 | Yes | 3.58 |
| 916 | 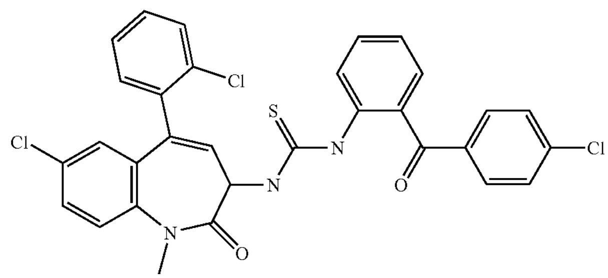 | 606.05 | Yes | 4.4 |
| 917 | 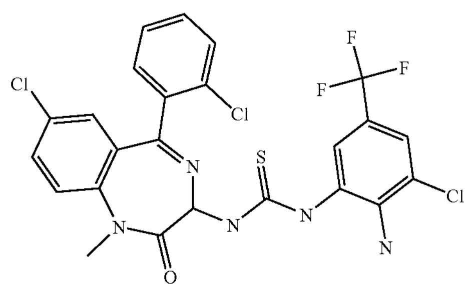 | 585.02 | Yes | 3.92 |
| 918 | 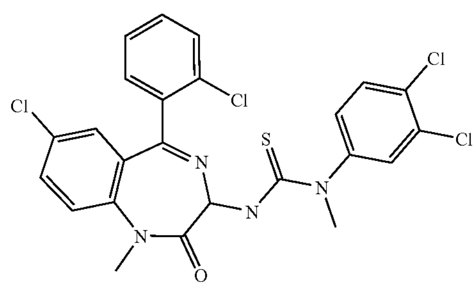 | 550 | Yes | 4.25 |
| 919 | 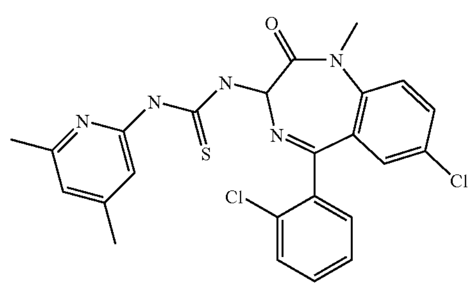 | 497.08 | Yes | 3.67 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 920 | 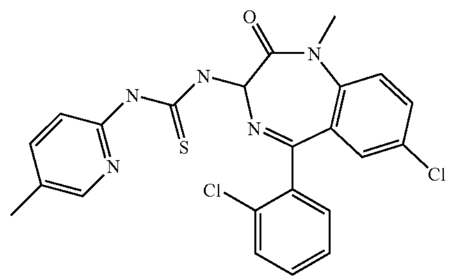 | 483.07 | Yes | 3.36 |
| 921 | 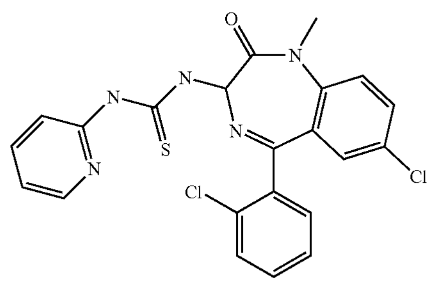 | 469.05 | Yes | 3.14 |
| 922 | 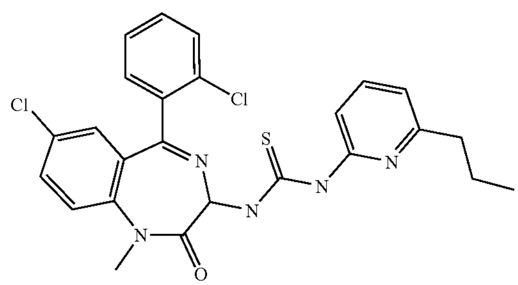 | 511.1 | Yes | 4.05 |
| 923 | 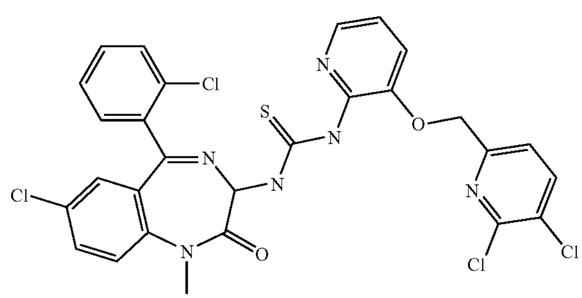 | 643.02 | No | |
| 924 | 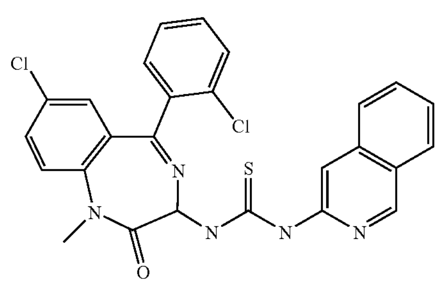 | 519.07 | Yes | 3.65 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 925 | 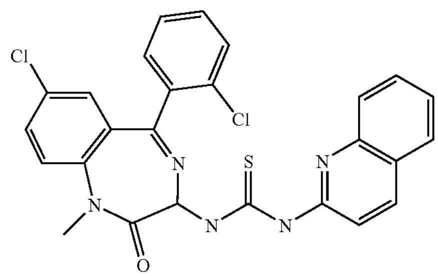 | 519.07 | Yes | 3.83 |
| 926 | 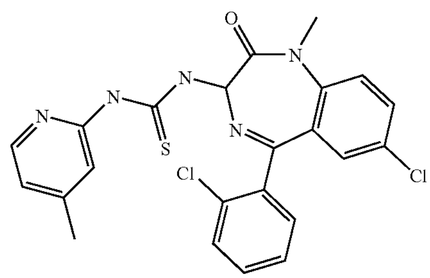 | 483.07 | Yes | 3.35 |
| 927 | 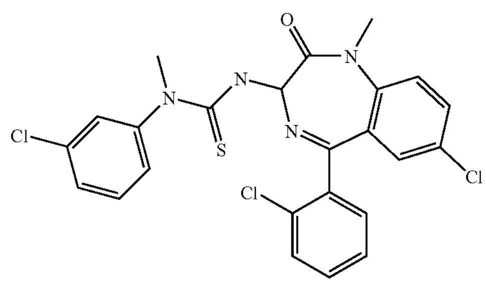 | 516.03 | Yes | 3.85 |
| 928 | 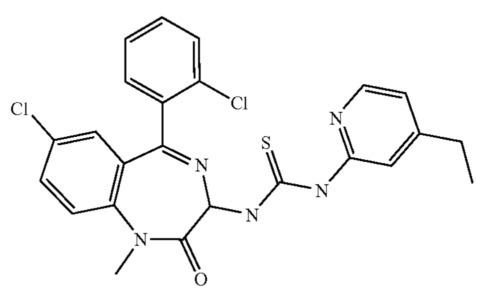 | 497.08 | Yes | 3.59 |
| 929 | 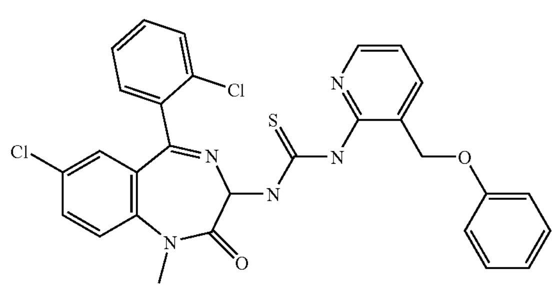 | 575.09 | No | |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 930 | 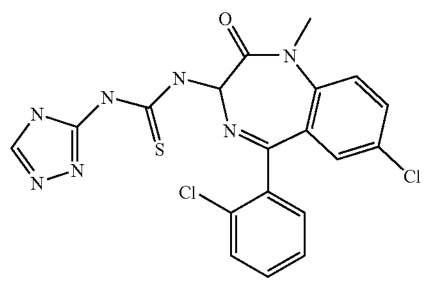 | 459.04 | Yes | 3.11 |
| 931 | 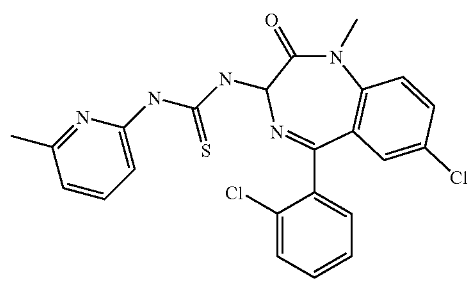 | 483.07 | Yes | 3.4 |
| 932 | 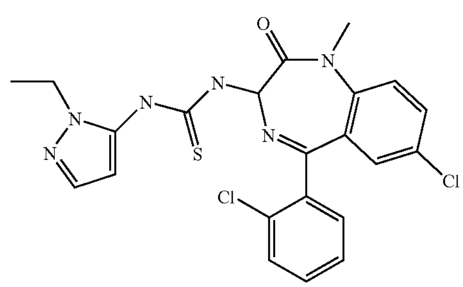 | 486.08 | Yes | 2.99 |
| 933 | 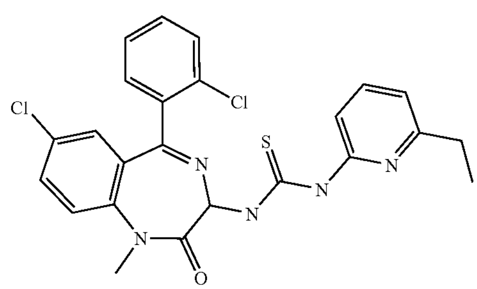 | 497.08 | Yes | 3.71 |
| 934 | 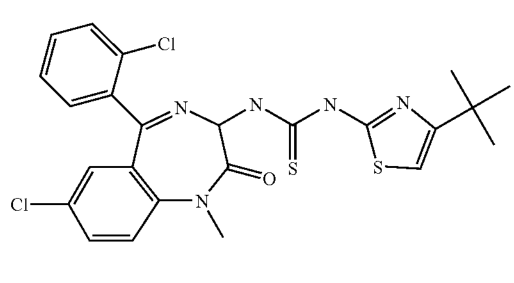 | 531.07 | Yes | 4.27 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 935 | 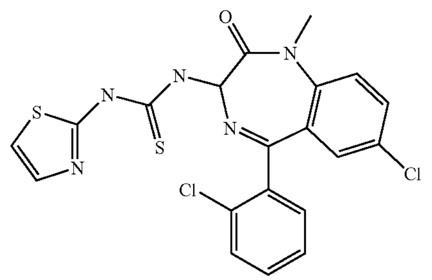 | 475.01 | Yes | 3.28 |
| 936 | 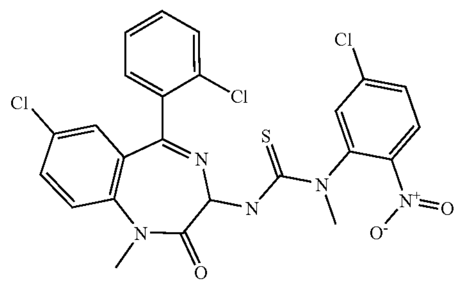 | 561.02 | No | |
| 937 | 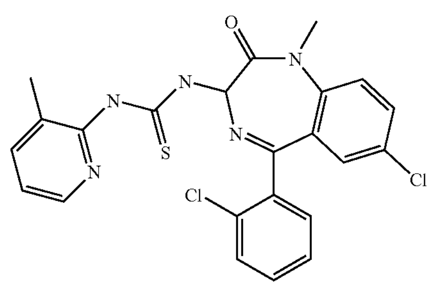 | 483.07 | Yes | 3.42 |
| 938 | 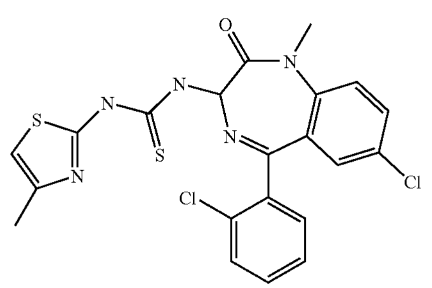 | 489.03 | Yes | 3.47 |
| 939 | 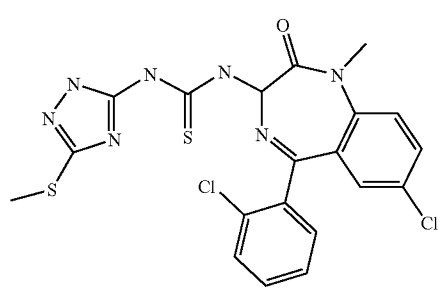 | 505.03 | Yes | |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 940 | 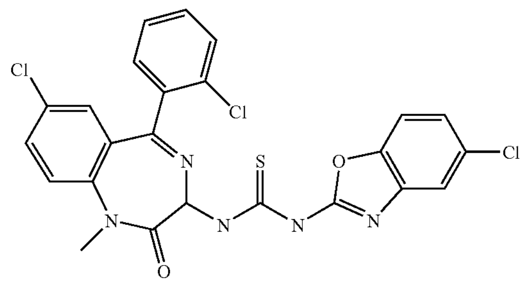 | 543.01 | No | |
| 941 | 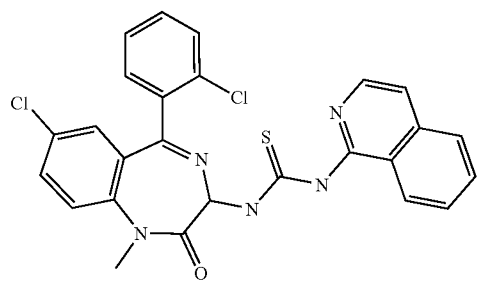 | 519.07 | Yes | 3.87 |
| 942 | 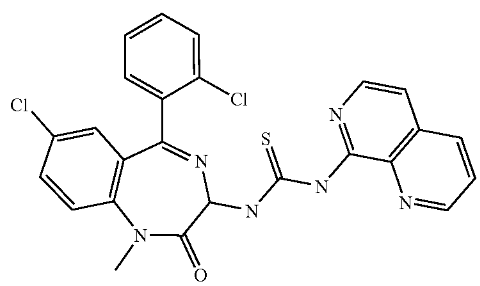 | 520.06 | No | |
| 943 | 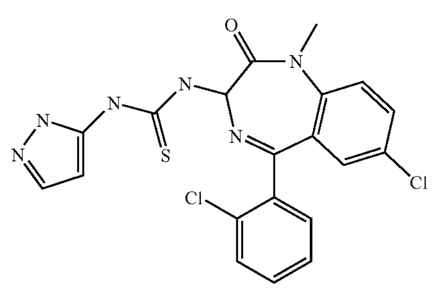 | 458.05 | Yes | 2.78 |
| 944 | 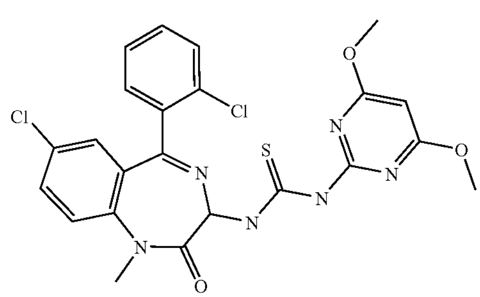 | 530.07 | No | |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 945 | 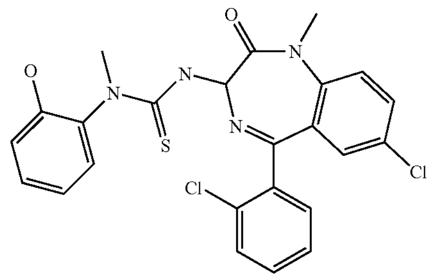 | 498.07 | Yes | 3.2 |
| 946 | 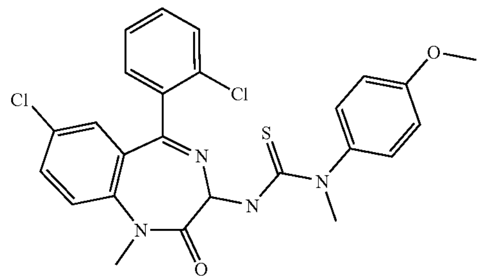 | 512.08 | Yes | 3.55 |
| 947 | 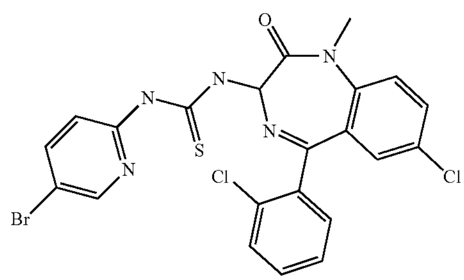 | 546.96 | Yes | 3.69 |
| 948 | 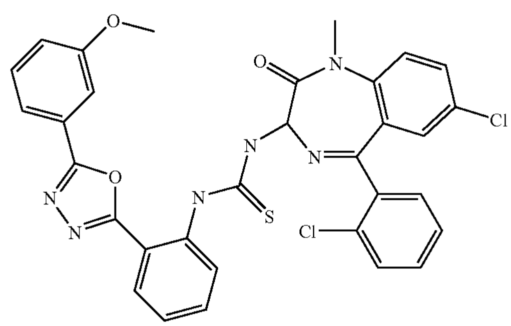 | 642.1 | Yes | 3.98 |
| 949 | 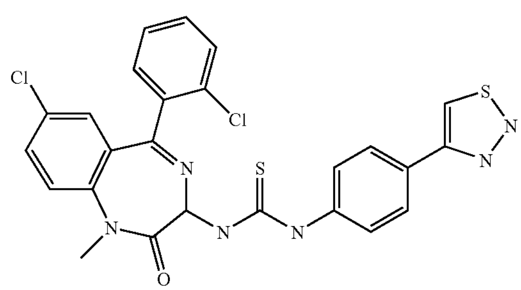 | 552.04 | Yes | 3.34 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 950 | 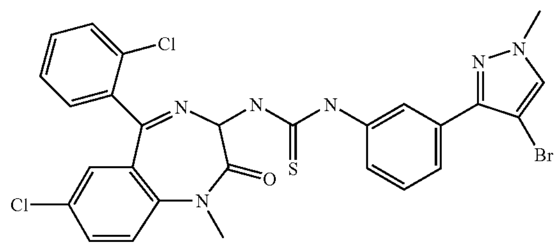 | 626.01 | Yes | 3.79 |
| 951 | 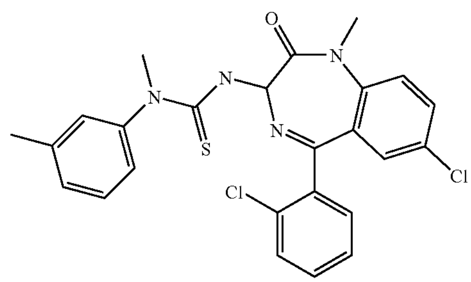 | 496.09 | Yes | 3.77, 4.2 |
| 952 | 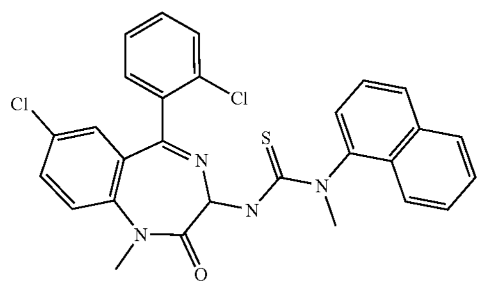 | 532.09 | Yes | 4, 4.52 |
| 953 | 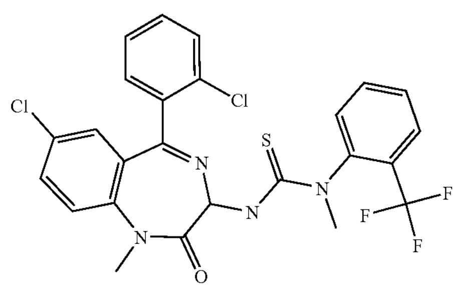 | 550.06 | Yes | 3.74 |
| 954 | 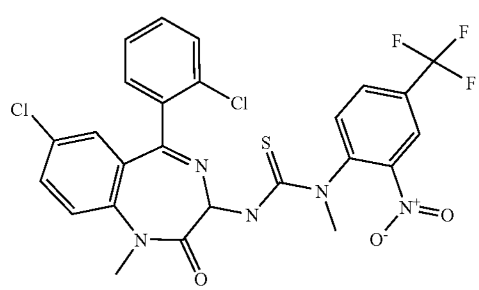 | 595.05 | No | |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 955 | 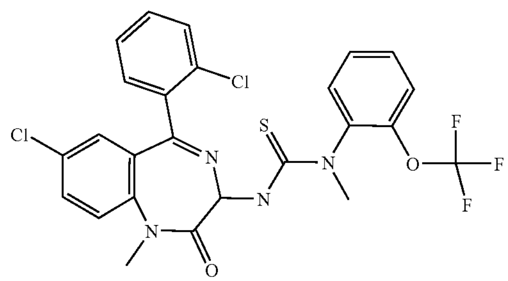 | 566.06 | Yes | 3.91 |
| 956 | 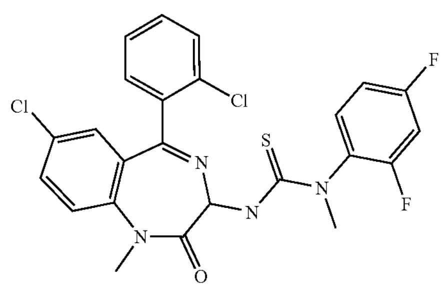 | 518.05 | Yes | 3.59 |
| 957 | 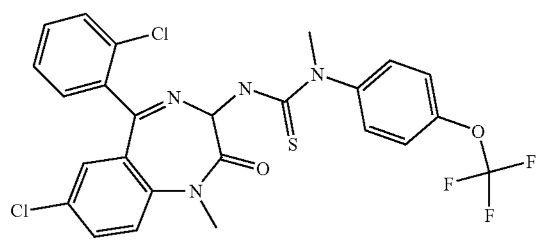 | 566.06 | No | |
| 958 | 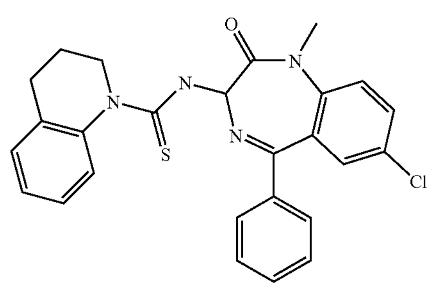 | 474.13 | Yes | 4 |
| 959 | 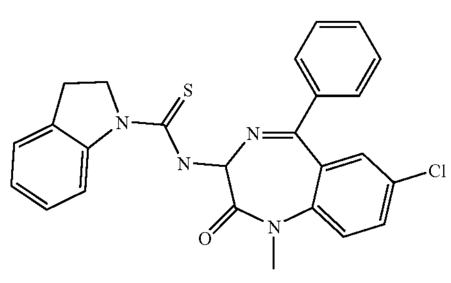 | 460.11 | Yes | 3.9 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 960 | 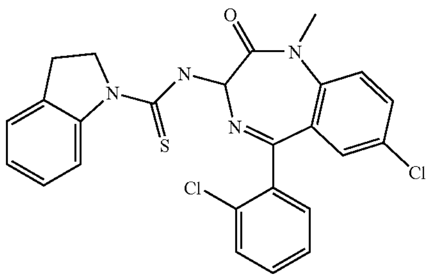 | 494.07 | Yes | 3.9 |
| 961 | 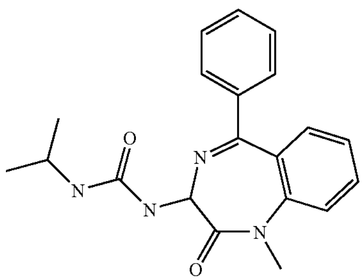 | 350.17 | Tentative | 2.46 |
| 962 | 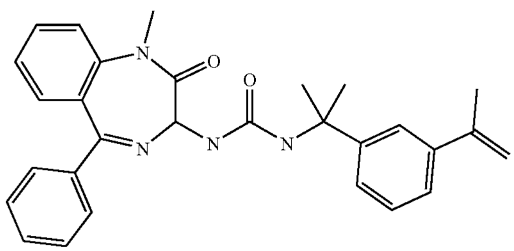 | 466.2 | Yes | 3.55, 6.41 |
| 963 | 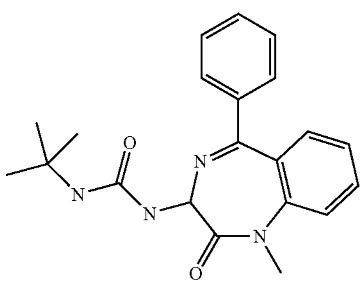 | 364.19 | Tentative | 2.68 |
| 964 | 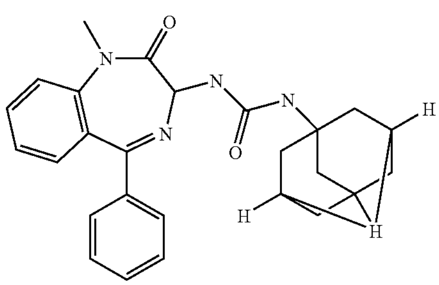 | 442.24 | Yes | 3.55 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 965 | 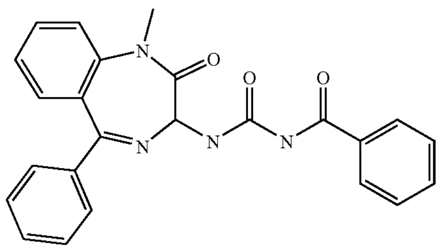 | 412.15 | Tentative | 2.78 |
| 966 | 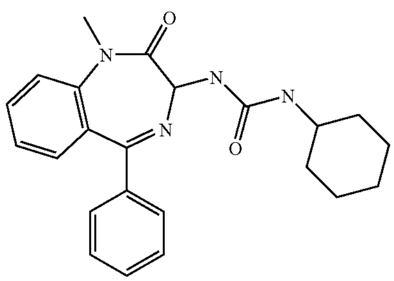 | 390.21 | Tentative | 2.86 |
| 967 | 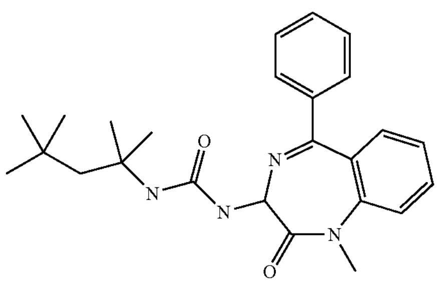 | 420.25 | Tentative | 3.55 |
| 968 | 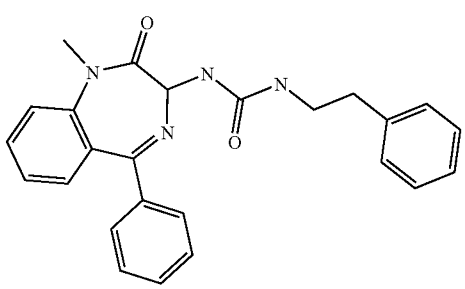 | 412.19 | Tentative | 2.88 |
| 969 | 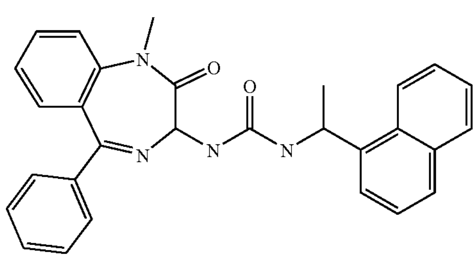 | 462.21 | Yes | 3.21 |

TABLE 1-continued
Spreadsheet of combinatorially prepared compounds with LCMS analysis of the reaction product.
| Compound # | Structure | Target Mass | Mass Found? | Rtn Time (MS) |
|---|---|---|---|---|
| 970 | 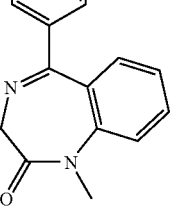 | 378.21 | Tentative | 2.91 |
| 971 | 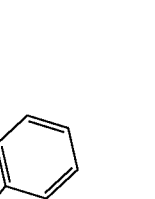 | 424.03 | No | |
| 972 | 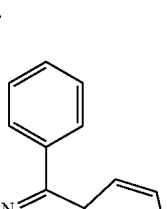 | 394.16 | Tentative | 2.4 |
| 973 | 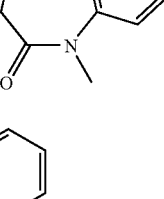 | 422.2 | Tentative | 2.63 |
| 974 | 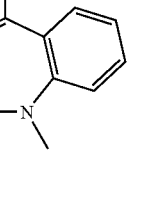 | 472.2 | Yes | 2.15, 3.38 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 975 | 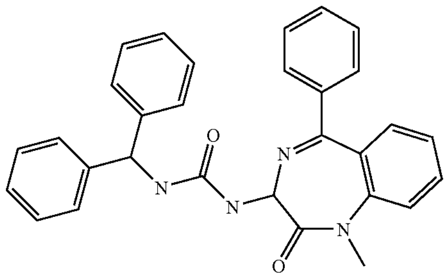 | 474.21 | Yes | 3.23 |
| 976 | 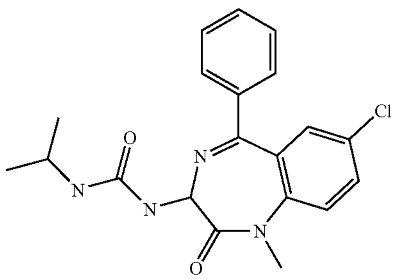 | 384.1 | Tentative | 2.75, 3.26 |
| 977 | 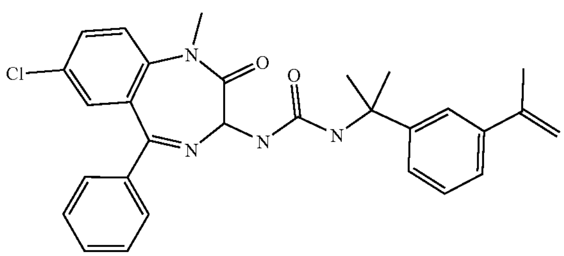 | 500.2 | Yes | 3.64, 4.02 |
| 978 | 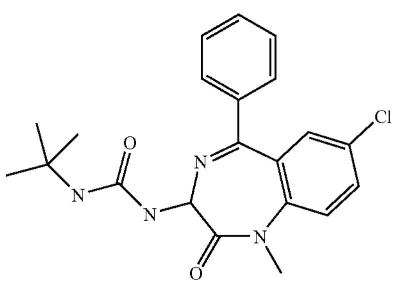 | 398.2 | Tentative | 3.02, 3.66 |
| 979 | 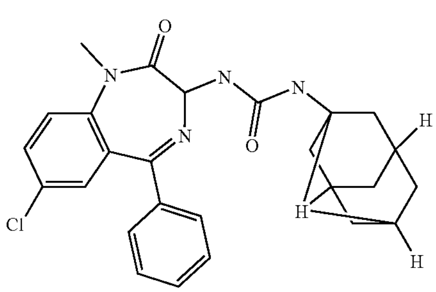 | 476.2 | Yes | 4.06 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 980 | 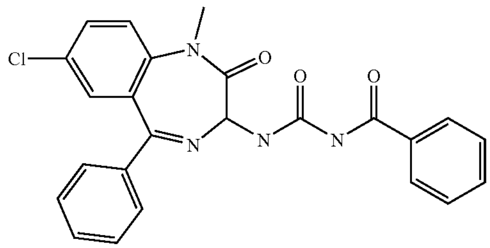 | 446.11 | Yes | 3.11 |
| 981 | 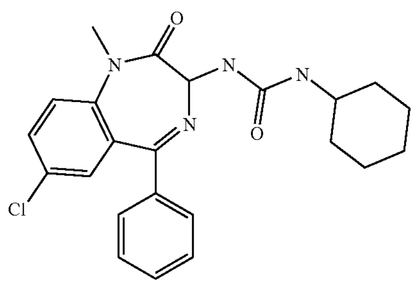 | 424.2 | Tentative | 3.23, 3.88 |
| 982 | 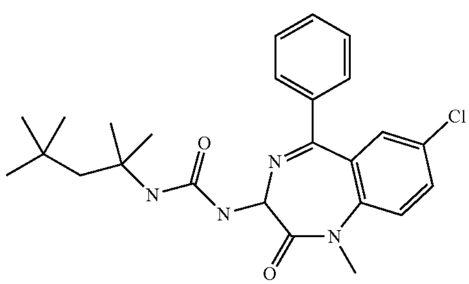 | 454.2 | Yes | 4.06, 4.8 |
| 983 | 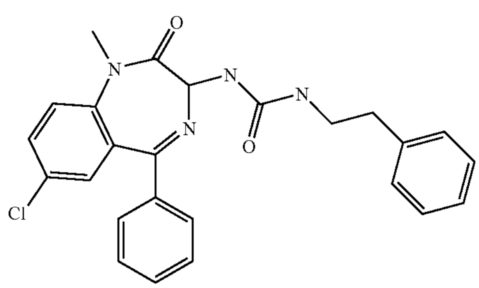 | 446.2 | Yes | 3.22, 3.85 |
| 984 | 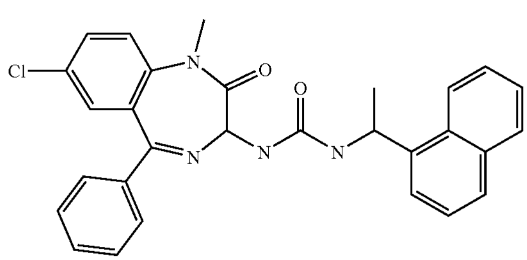 | 496.2 | Yes | 3.6, 3.71 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 985 | 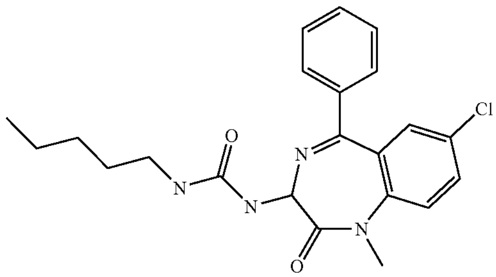 | 412.2 | Tentative | 3.28, 3.93 |
| 986 | 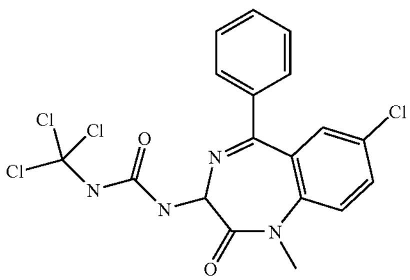 | 457.99 | No | |
| 987 | 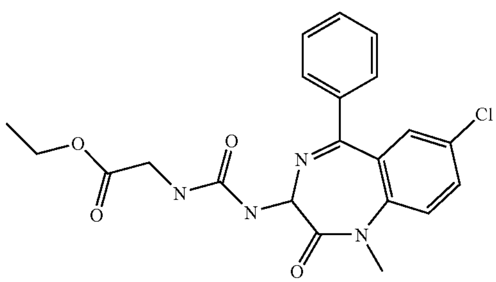 | 428.1 | Yes | 2.68, 3.08 |
| 988 | 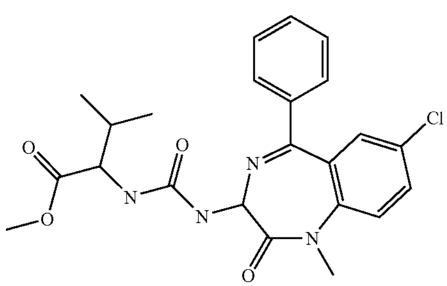 | 456.2 | Yes | 2.89, 3.34, 3.73 |
| 989 | 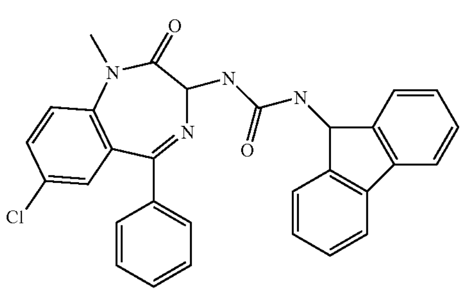 | 506.15 | Yes | 3.84 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 990 | 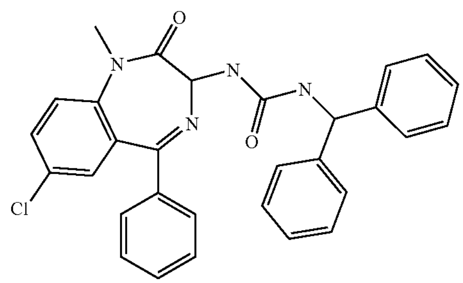 | 508.17 | Yes | 3.65 |
| 991 | 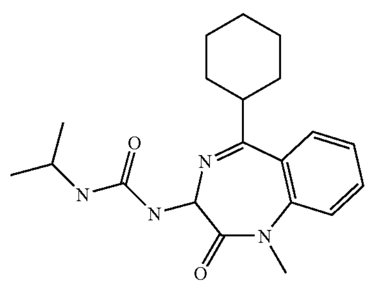 | 356.22 | Tentative | 2.81 |
| 992 | 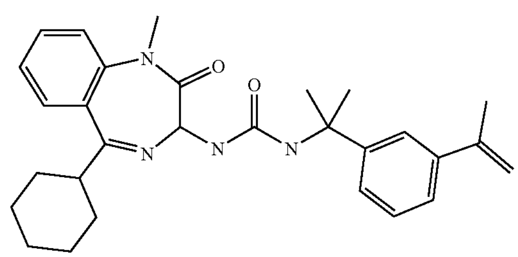 | 472.28 | Yes | 4.11, 6.46 |
| 993 | 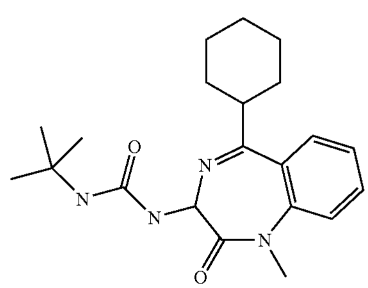 | 370.24 | Tentative | 3.05 |
| 994 | 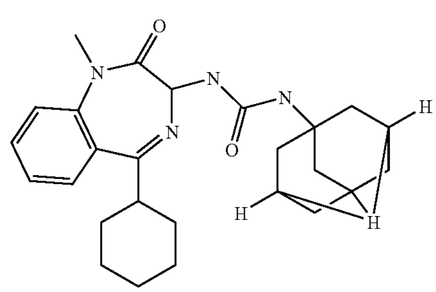 | 448.28 | Yes | 4.07 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 995 | 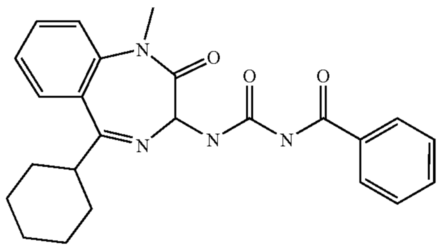 | 418.2 | Tentative | 3.22 |
| 996 | 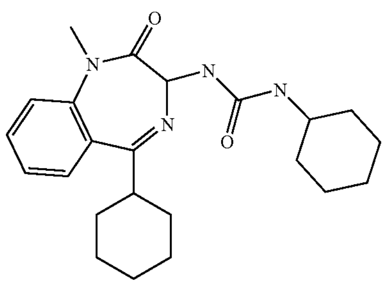 | 396.25 | Tentative | 3.29 |
| 997 | 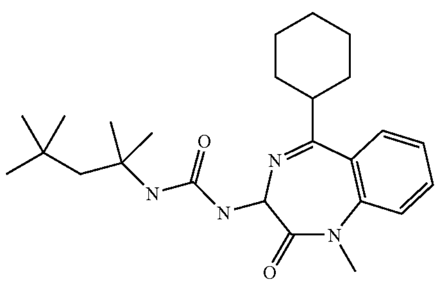 | 426.3 | Yes | 4.09 |
| 998 | 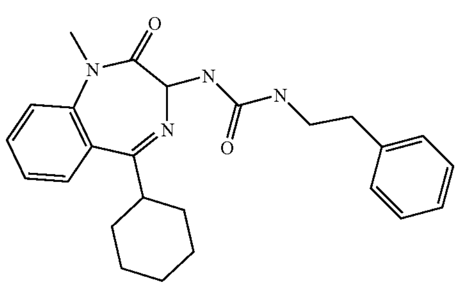 | 418.24 | Yes | 3.29 |
| 999 | 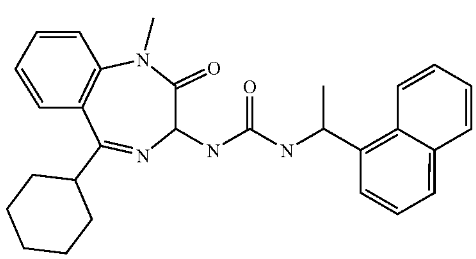 | 468.25 | Yes | 3.67 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 1000 | 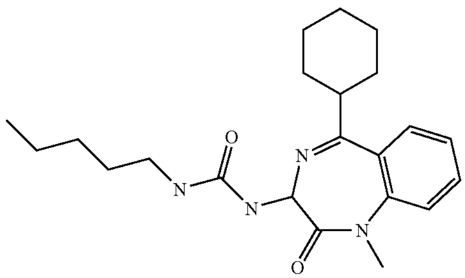 | 384.25 | Tentative | 3.35 |
| 1001 | 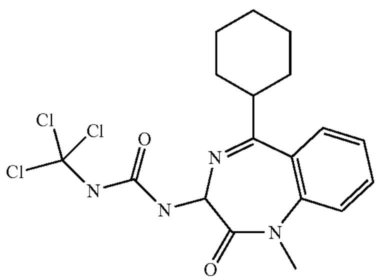 | 430.07 | No | |
| 1002 | 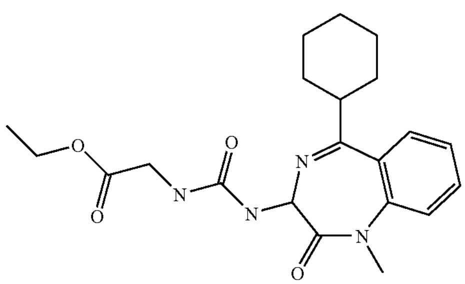 | 400.21 | Yes | 2.72 |
| 1003 | 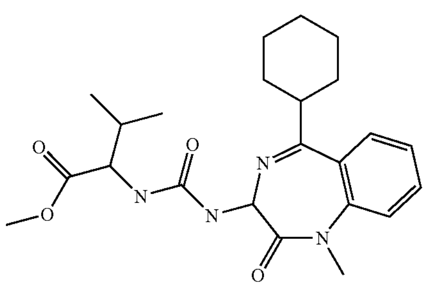 | 428.24 | Tentative | 3.08 |
| 1004 | 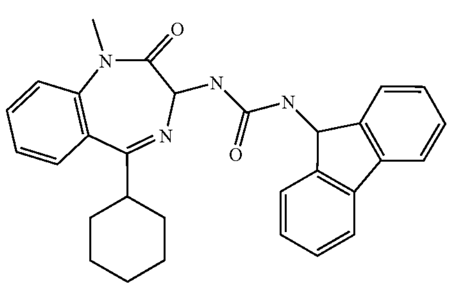 | 478.24 | Yes | 3.85 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 1005 | 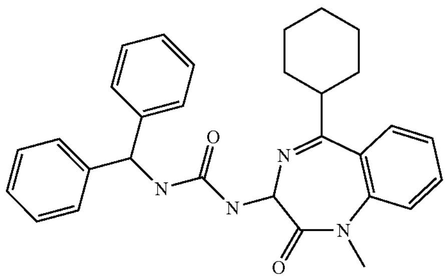 | 480.25 | Yes | 2.7, 3.73 |
| 1006 | 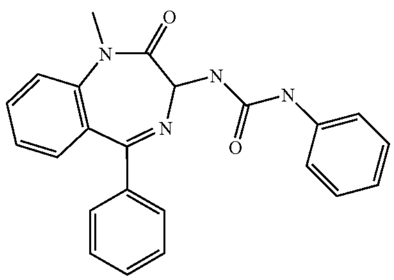 | 384.16 | Tentative | 2.74 |
| 1007 | 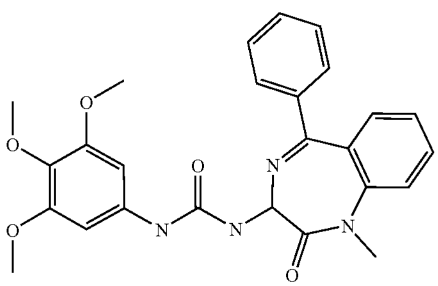 | 474.19 | Yes | 2.7 |
| 1008 | 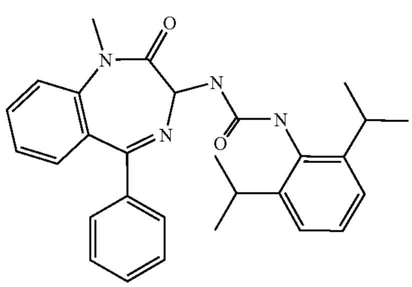 | 468.25 | Yes | 3.73 |
| 1009 | 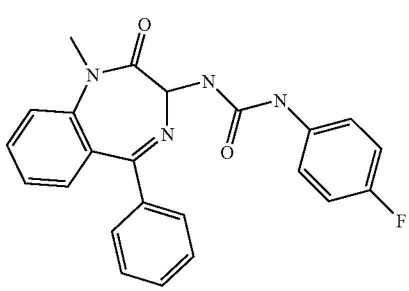 | 402.15 | Yes | 2.81 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 1010 | 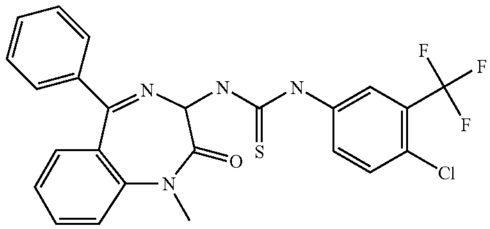 | 502.01 | Yes | 3.06, 3.9 |
| 1011 | 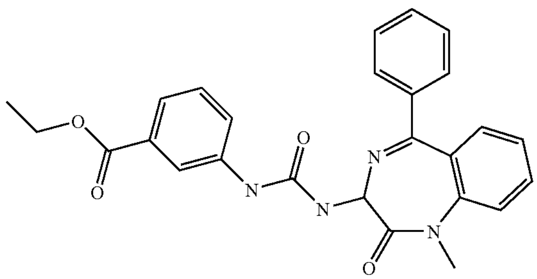 | 456.2 | Yes | 2.15, 3.05 |
| 1012 | 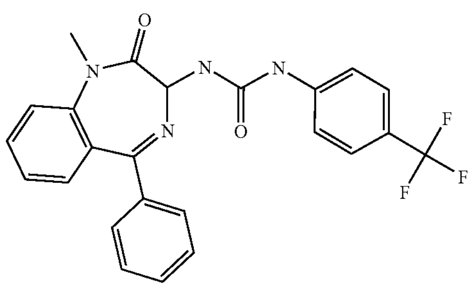 | 452.15 | Yes | 3.32 |
| 1013 | 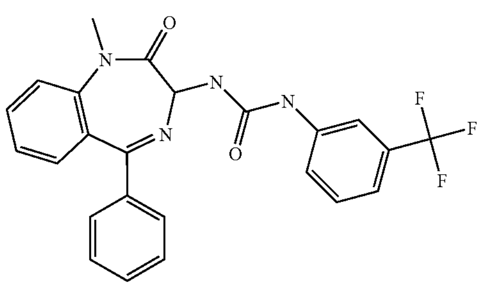 | 452.15 | No | |
| 1014 | 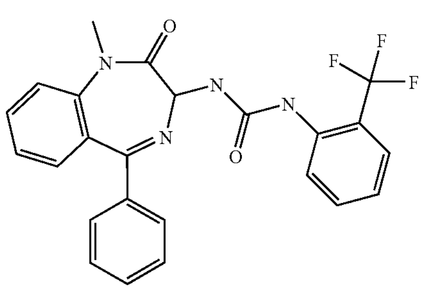 | 452.15 | Yes | 2.96 |

US 7,375,101 B2

417                                                                                                          418

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 1015 | 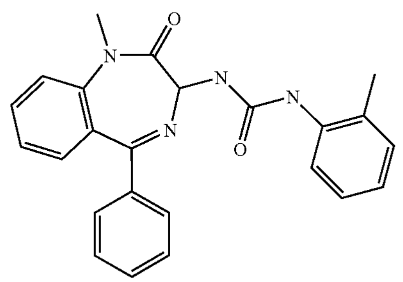 | 398.17 | Tentative | 2.8 |
| 1016 | 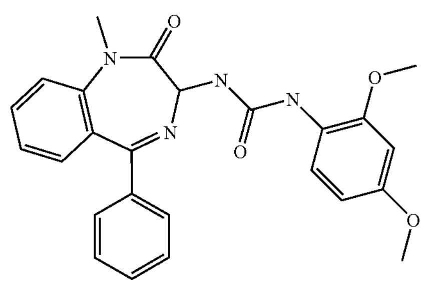 | 444.18 | Yes | 2.76 |
| 1017 | 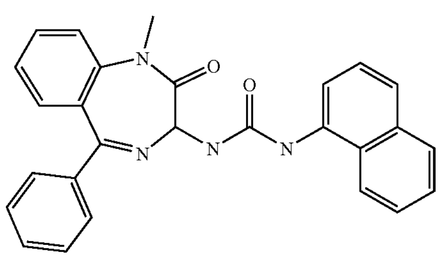 | 434.17 | Tentative | 3.03 |
| 1018 | 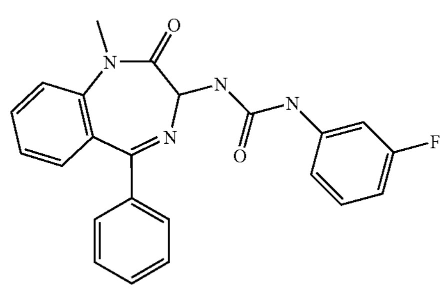 | 402.15 | Tentative | 2.9 |
| 1019 | 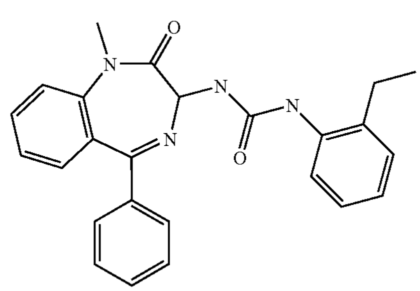 | 412.19 | Yes | 2.97 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 1020 | 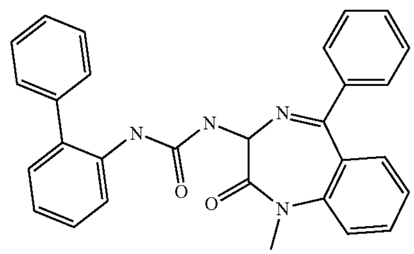 | 460.19 | Yes | 3.3 |
| 1021 | 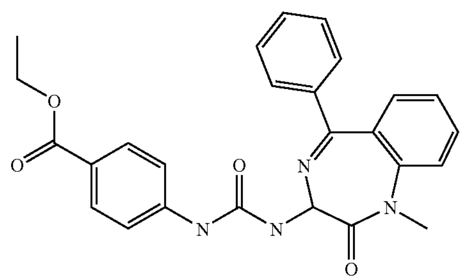 | 456.18 | Yes | 3.1 |
| 1022 | 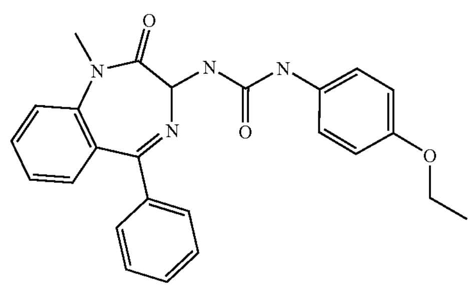 | 428.18 | Tentative | 2.88 |
| 1023 | 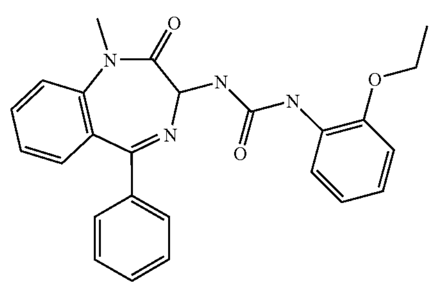 | 428.18 | Yes | 3.01 |
| 1024 | 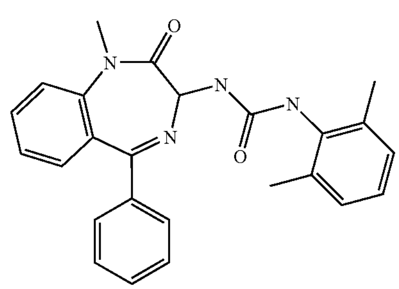 | 412.19 | Tentative | 2.86 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 1025 | 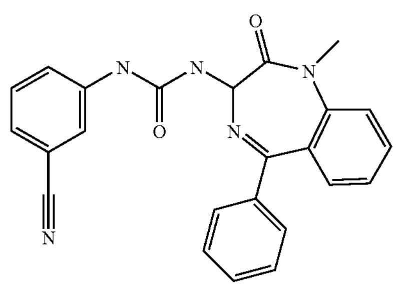 | 409.15 | Yes | 2.74 |
| 1026 | 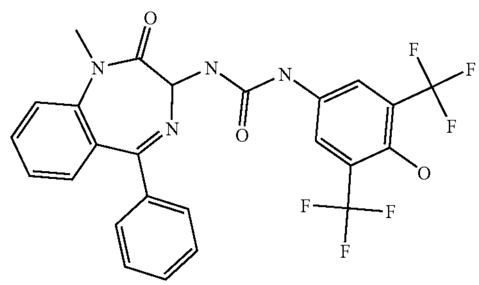 | 520.13 | No | |
| 1027 | 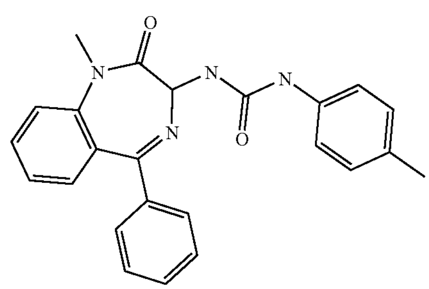 | 398.17 | Tentative | 2.93 |
| 1028 | 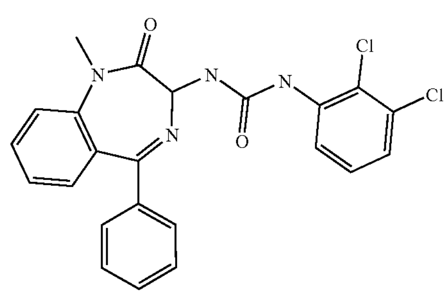 | 452.08 | Yes | 3.36 |
| 1029 | 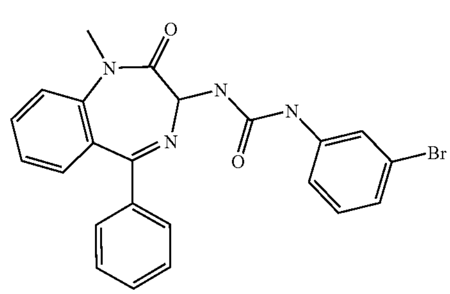 | 462.07 | Yes | 3.2 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 1030 | 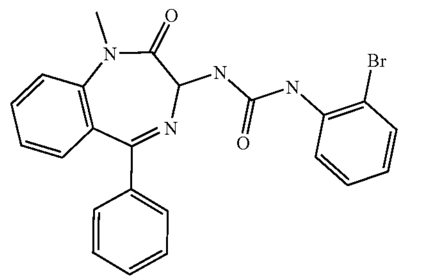 | 462.07 | Yes | 3.02 |
| 1031 | 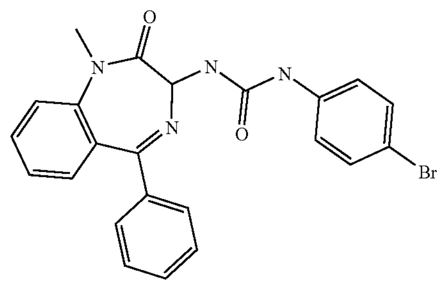 | 462.07 | Tentative | 3.21 |
| 1032 | 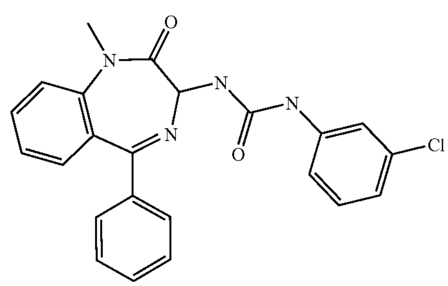 | 418.12 | Yes | |
| 1033 | 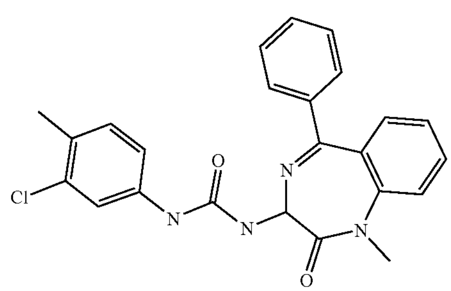 | 432.1 | Yes | 3.36, 6.43 |
| 1034 | 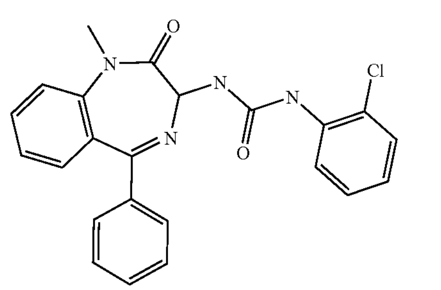 | 418.12 | No | |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 1035 | 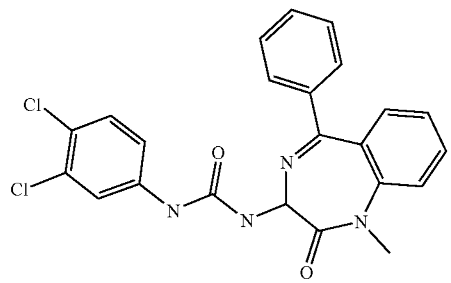 | 452.08 | Yes | 3.53 |
| 1036 | 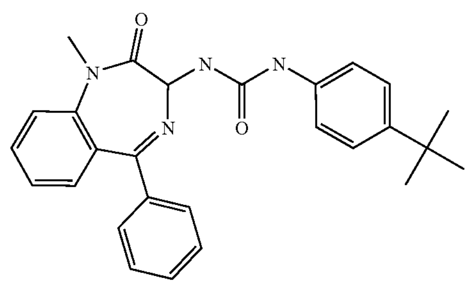 | 440.22 | Yes | 3.66 |
| 1037 | 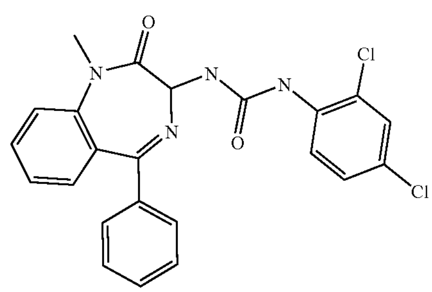 | 452.08 | Yes | |
| 1038 | 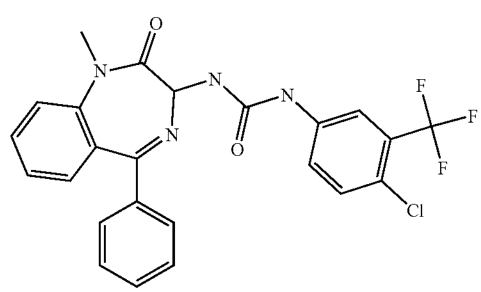 | 486.11 | No | |
| 1039 | 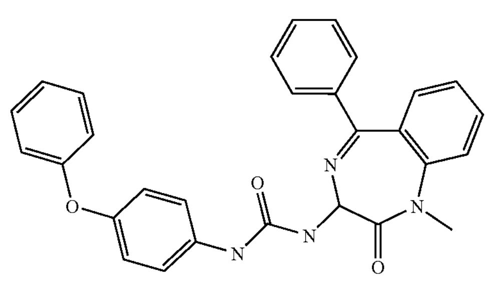 | 476.2 | Yes | 3.21, 3.49, 6.51 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 1040 | 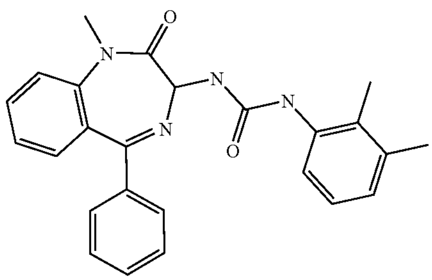 | 412.19 | Tentative | 2.95 |
| 1041 | 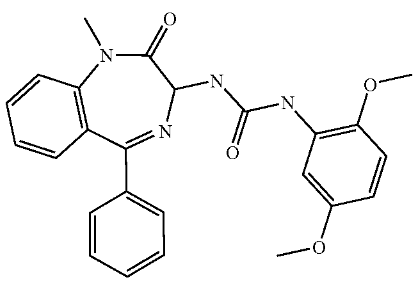 | 444.18 | Yes | 2.84 |
| 1042 | 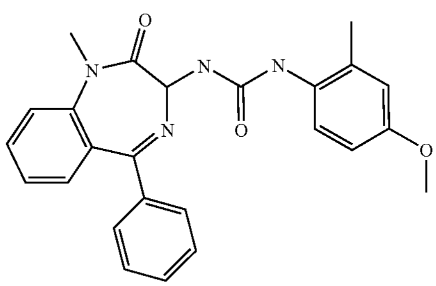 | 428.18 | Tentative | 2.74 |
| 1043 | 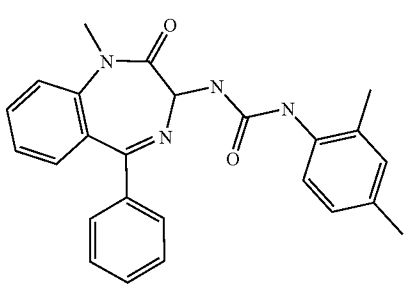 | 412.19 | No | |
| 1044 | 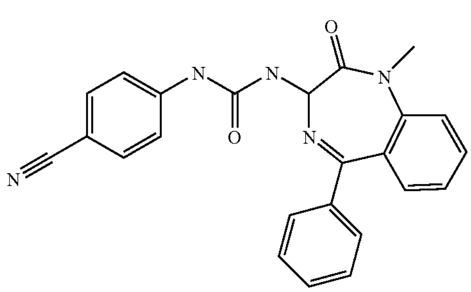 | 409.2 | Yes | 2.75, 3.22 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 1045 | 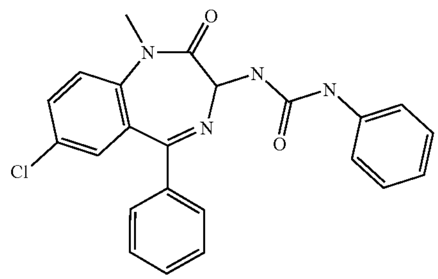 | 418.1 | Tentative | 3.1, 3.5 |
| 1046 | 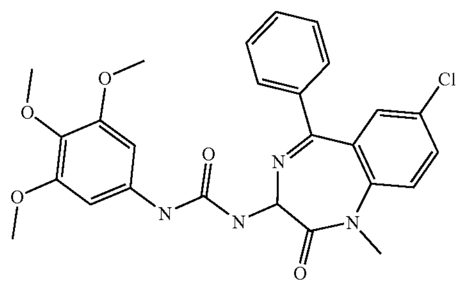 | 508.2 | Yes | 3.01, 3.39 |
| 1047 | 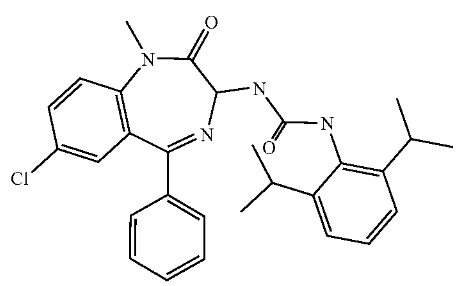 | 502.2 | Yes | 4.18, 4.67 |
| 1048 | 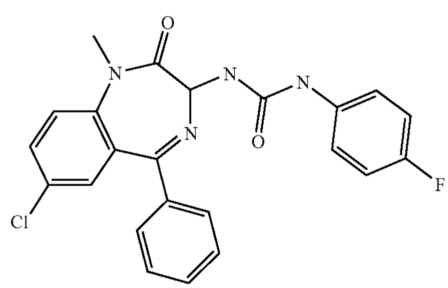 | 436.1 | Yes | 3.18, 3.61 |
| 1049 | 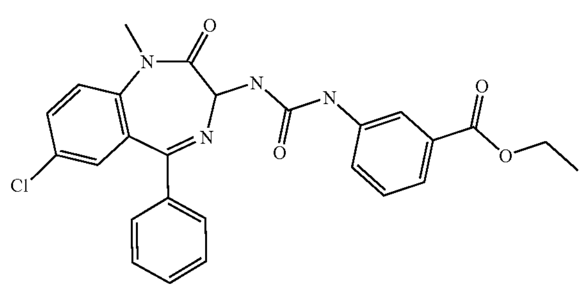 | 490.1 | Yes | 3.48, 3.99 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 1050 | 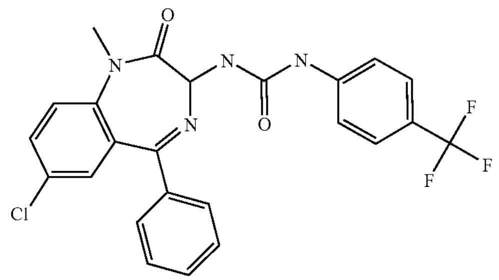 | 486.11 | Yes | 3.79 |
| 1051 | 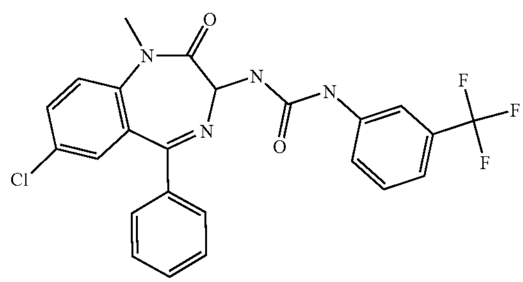 | 486.1 | Yes | 2.79, 3.73, 4.25 |
| 1052 | 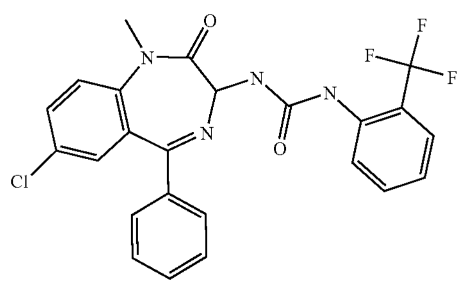 | 486.11 | Yes | 3.33 |
| 1053 | 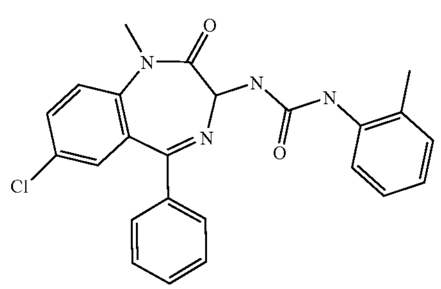 | 432.1 | Tentative | 3.16, 3.62 |
| 1054 | 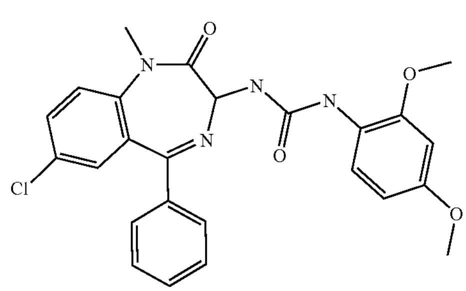 | 478.14 | Yes | 3.09 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 1055 | 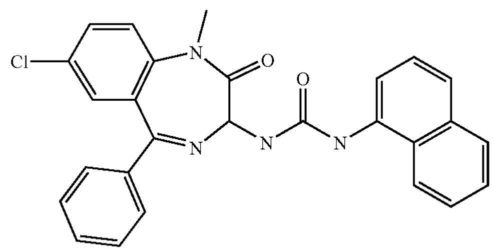 | 468.14 | Yes | 3.42 |
| 1056 | 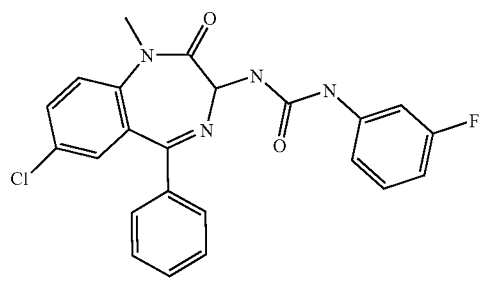 | 436.1 | Yes | 3.27, 3.73 |
| 1057 | 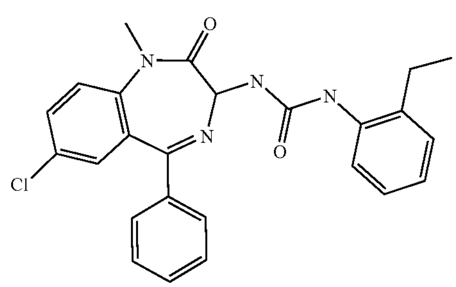 | 446.2 | Yes | 3.36, 3.87 |
| 1058 | 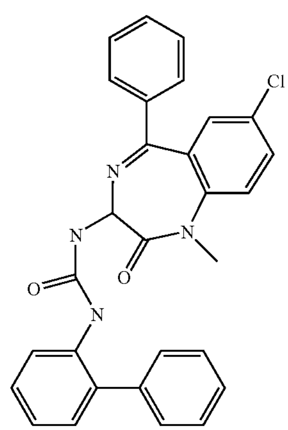 | 494.15 | Yes | 3.73 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 1059 | 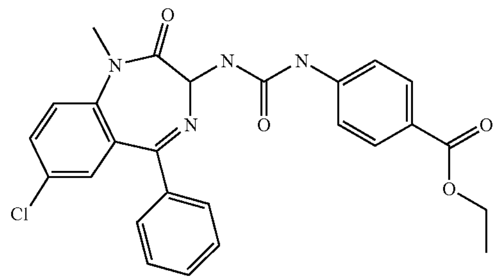 | 490.14 | Yes | 3.52 |
| 1060 | 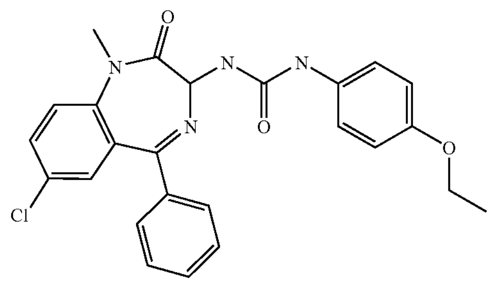 | 462.2 | Yes | 3.24, 3.75 |
| 1061 | 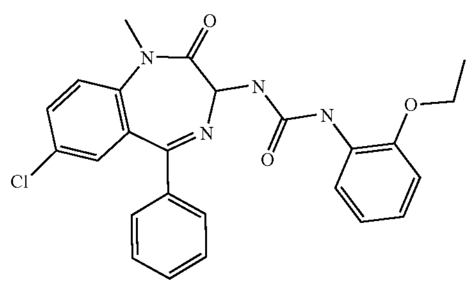 | 462.2 | Yes | 3.43, 4.17 |
| 1062 | 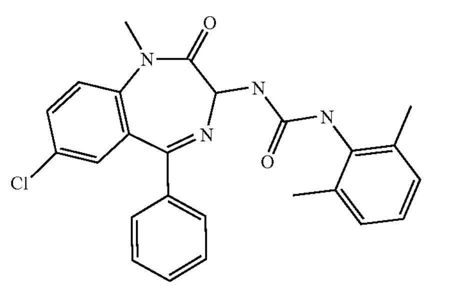 | 446.2 | Yes | 3.21, 3.7 |
| 1063 | 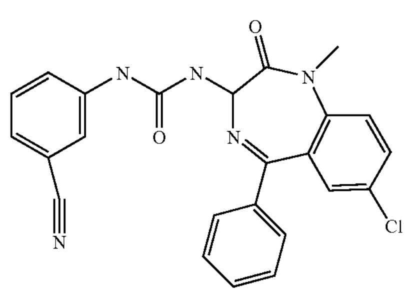 | 443.11 | Yes | 3.08 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 1064 | 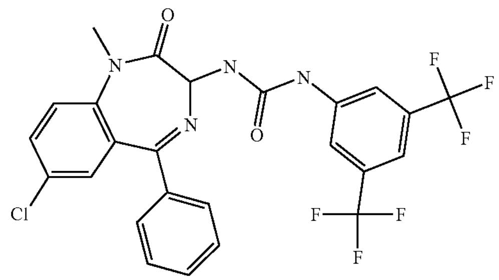 | 554.09 | Yes | 4.59 |
| 1065 | 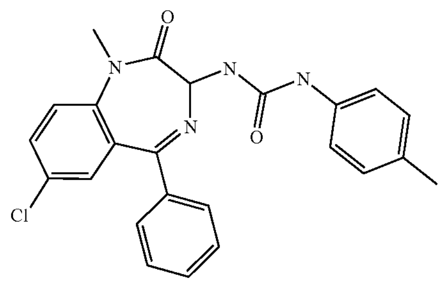 | 432.1 | Tentative | 3.32, 3.82 |
| 1066 | 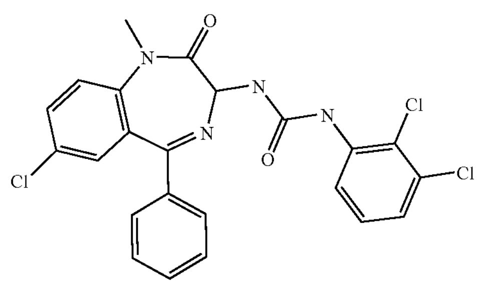 | 486.04 | Yes | 3.85 |
| 1067 | 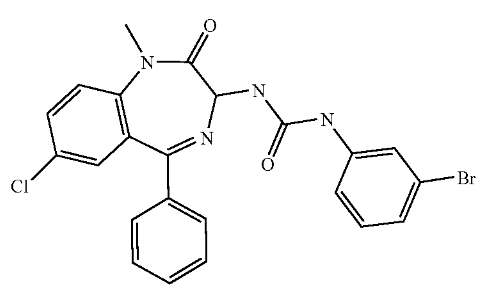 | 496.03 | Yes | 3.65 |
| 1068 | 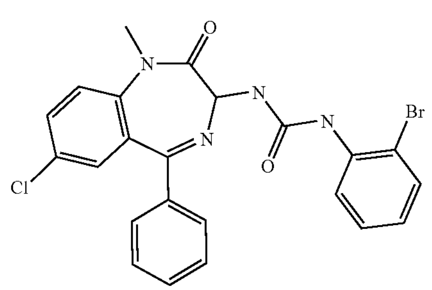 | 496.03 | Yes | 3.39 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 1069 | 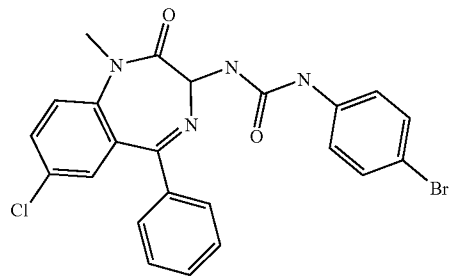 | 496 | Yes | 3.65, 4.15 |
| 1070 | 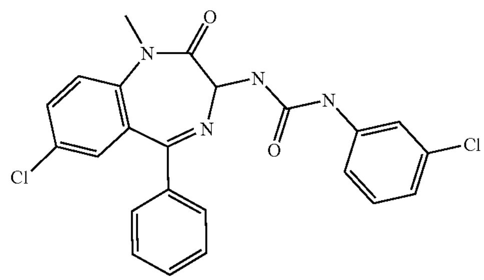 | 452.08 | Yes | 3.55 |
| 1071 | 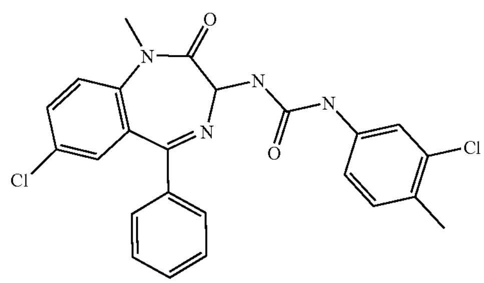 | 466.1 | Yes | 3.83, 6.53 |
| 1072 | 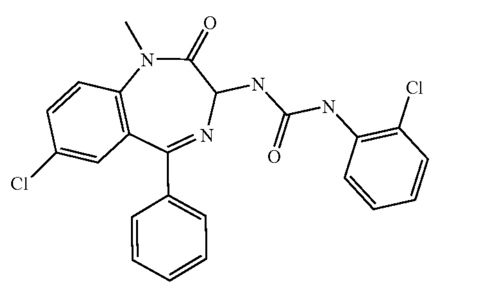 | 452.08 | Yes | 3.37 |
| 1073 | 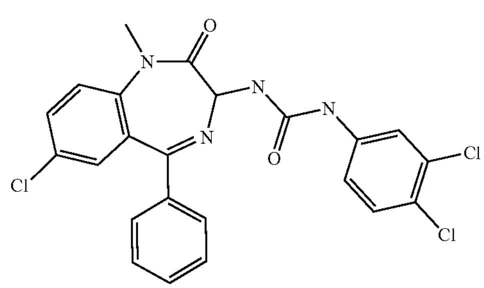 | 486.04 | No | |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 1074 | 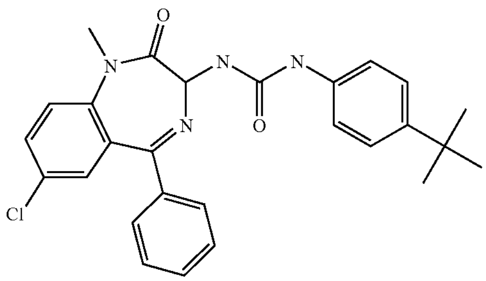 | 474.18 | Yes | 4.14 |
| 1075 | 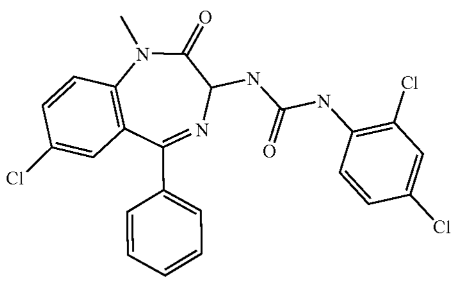 | 486.04 | Yes | 4.01 |
| 1076 | 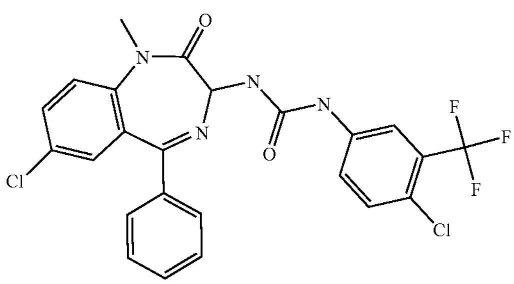 | 520.07 | Yes | 4.15 |
| 1077 | 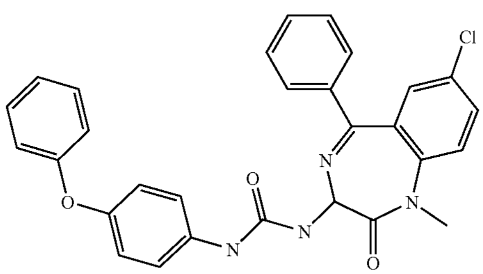 | 510.15 | Yes | 3.96 |
| 1078 | 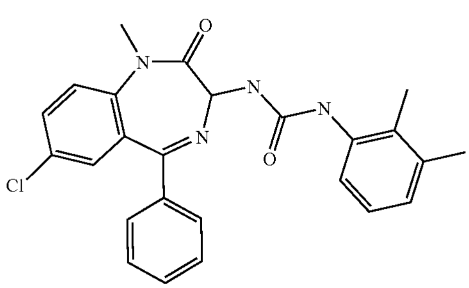 | 446.2 | Yes | 3.31, 3.8 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 1079 | 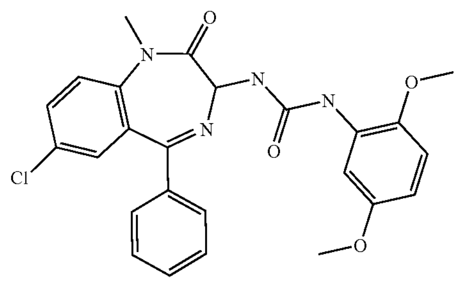 | 478.1 | Yes | 3.2, 3.79 |
| 1080 | 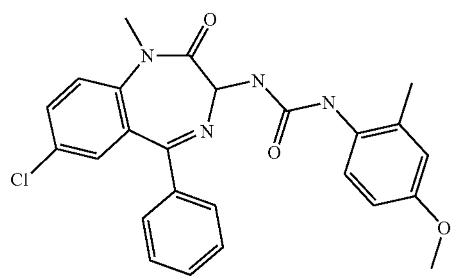 | 462.2 | Yes | 3.04, 3.49 |
| 1081 | 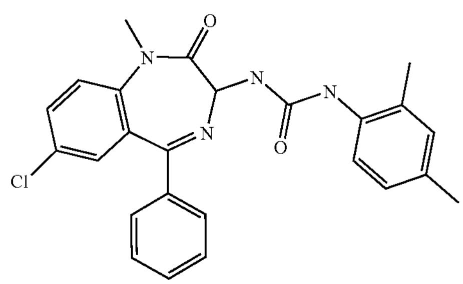 | 446.15 | No | |
| 1082 | 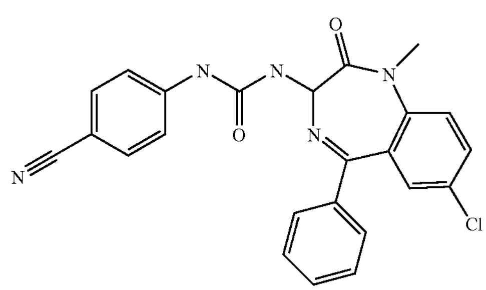 | 443.1 | Yes | 3.07, 3.47 |
| 1083 | 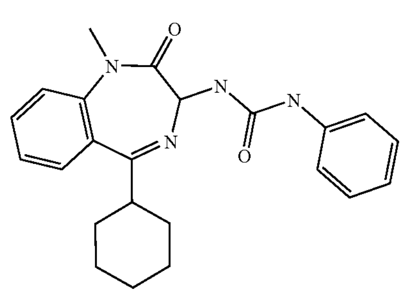 | 390.21 | Tentative | 3.1 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 1084 | 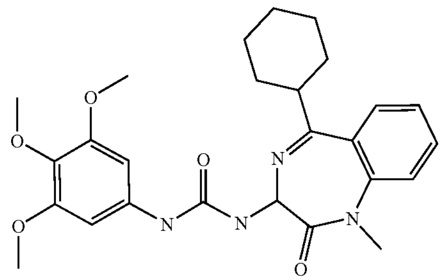 | 480.24 | Yes | 2.71, 3.05 |
| 1085 | 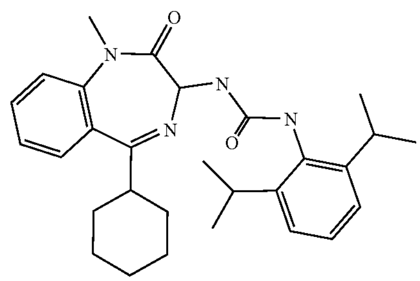 | 474.3 | Yes | 4.39 |
| 1086 | 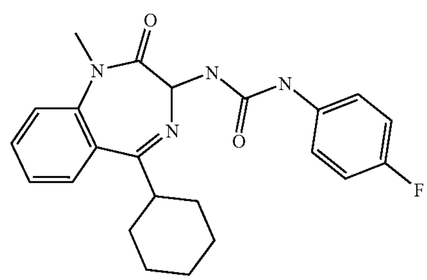 | 408.2 | Tentative | 3.19 |
| 1087 | 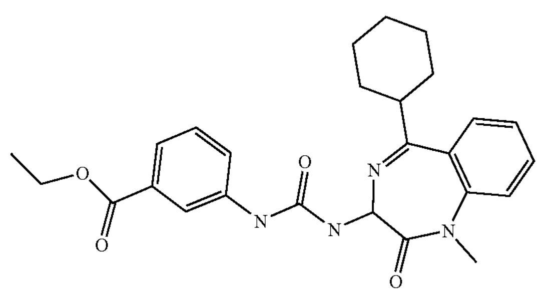 | 462.23 | Yes | 3.5 |
| 1088 | 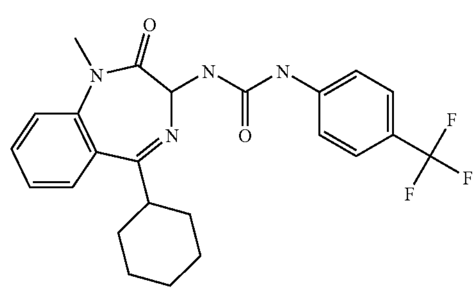 | 458.19 | Yes | 3.77 |

TABLE 1-continued
Spreadsheet of combinatorially prepared compounds with LCMS analysis of the reaction product.
| Compound # | Structure | Target Mass | Mass Found? | Rtn Time (MS) |
|---|---|---|---|---|
| 1089 | 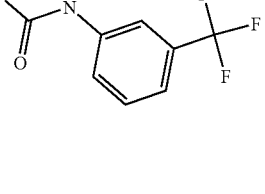 | 458.19 | Yes | 2.7, 3.72 |
| 1090 | 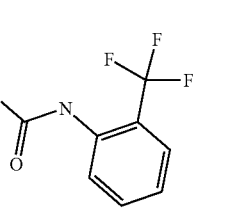 | 458.19 | Yes | 3.38 |
| 1091 | 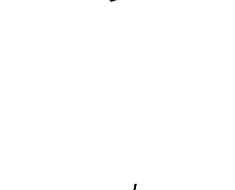 | 404.22 | Tentative | 3.21 |
| 1092 | 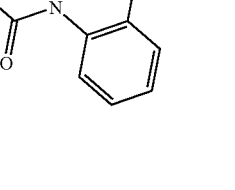 | 450.23 | Yes | 3.12 |
| 1093 | 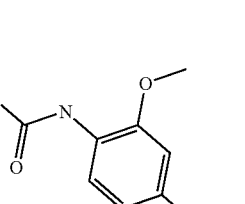 | 440.22 | Yes | 3.48 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 1094 | 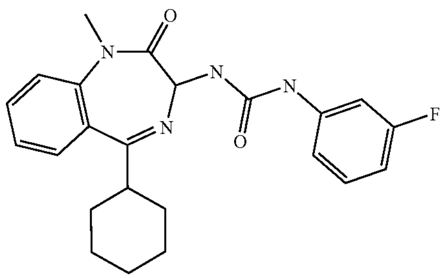 | 408.2 | Tentative | 3.27 |
| 1095 | 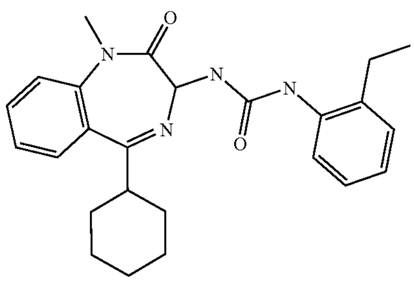 | 418.24 | Yes | 3.44 |
| 1096 | 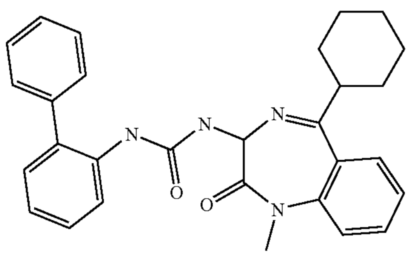 | 466.24 | Yes | 3.81 |
| 1097 | 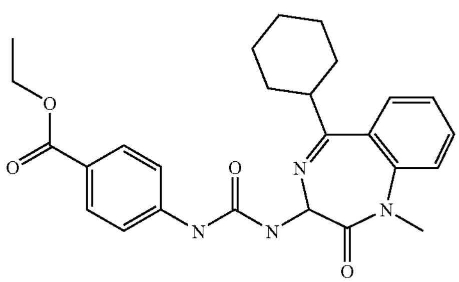 | 462.23 | Yes | 3.53 |
| 1098 | 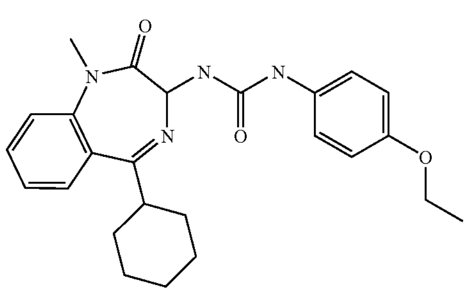 | 434.23 | Yes | 3.28, 6.53 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 1099 | 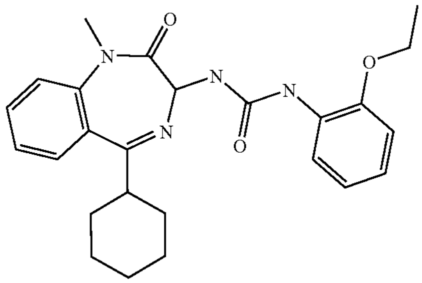 | 434.23 | Yes | 3.45, 6.47 |
| 1100 | 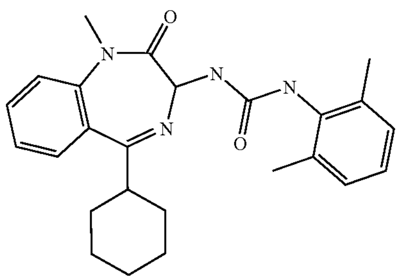 | 418.24 | Tentative | 3.33 |
| 1101 | 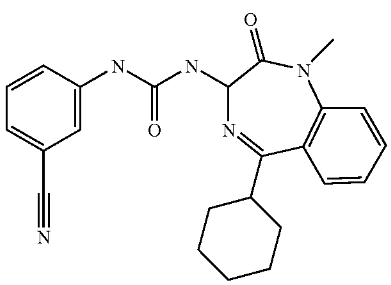 | 415.2 | Tentative | 3.09 |
| 1102 | 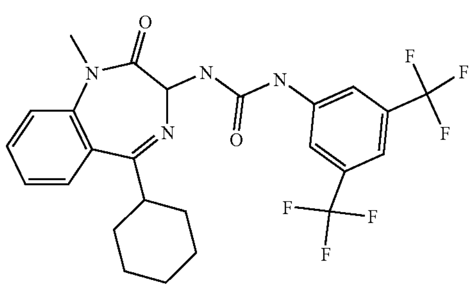 | 526.18 | Tentative | 2.96 |
| 1103 | 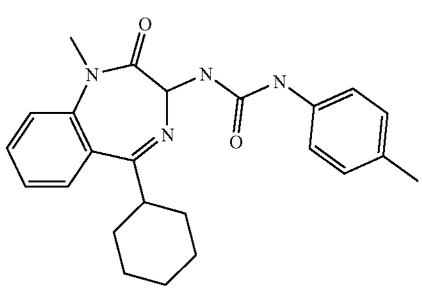 | 404.22 | Tentative | 3.35 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 1104 | 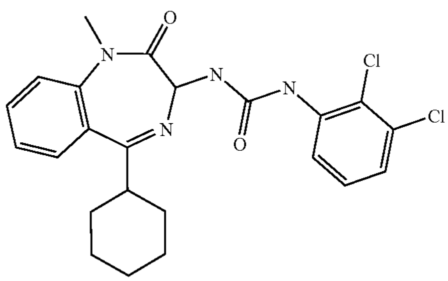 | 458.13 | Yes | 2.7, 3.86 |
| 1105 | 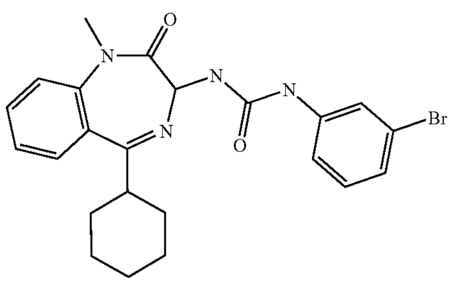 | 468.12 | No | |
| 1106 | 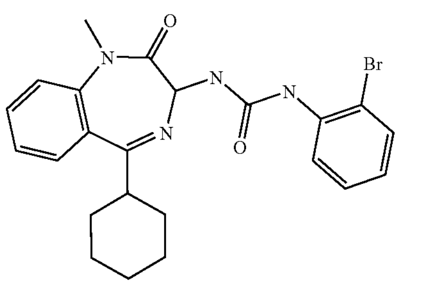 | 468.12 | Yes | 3.42 |
| 1107 | 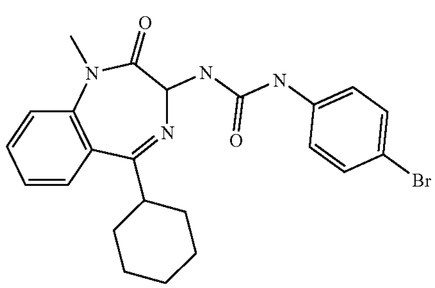 | 468.12 | Yes | 3.64 |
| 1108 | 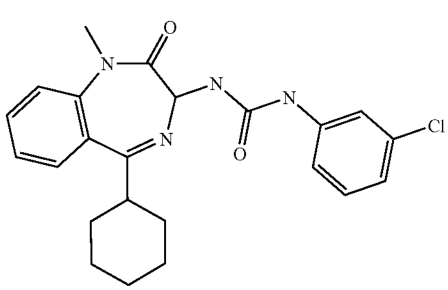 | 424.17 | Yes | 3.55 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 1109 | 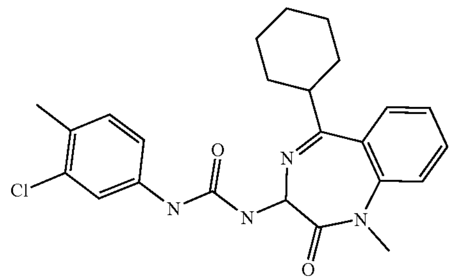 | 438.18 | Yes | 3.83 |
| 1110 | 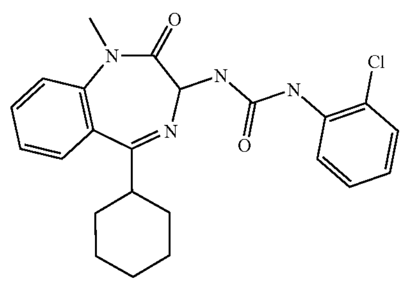 | 424.17 | Yes | 3.4 |
| 1111 | 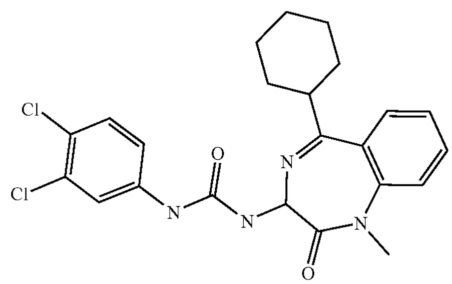 | 458.13 | Yes | 4.01 |
| 1112 | 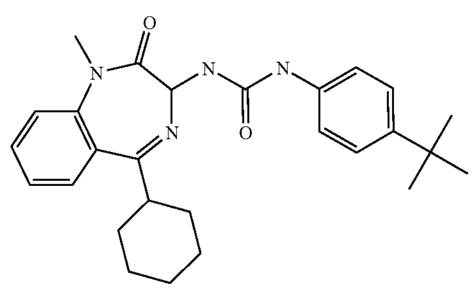 | 446.27 | Yes | 4.17 |
| 1113 | 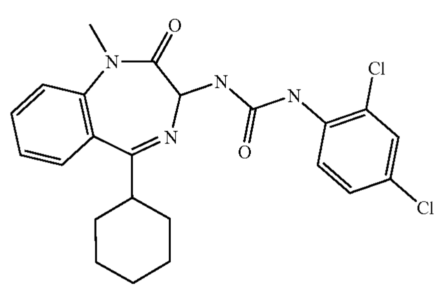 | 458.13 | Yes | 2.7, 4.01 |

TABLE 1-continued
Spreadsheet of combinatorially prepared compounds with LCMS analysis of the reaction product.
| Compound # | Structure | Target Mass | Mass Found? | Rtn Time (MS) |
|---|---|---|---|---|
| 1114 | 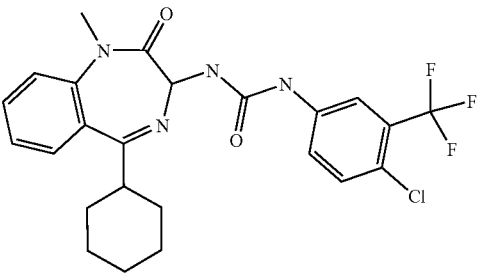 | 492.15 | No | |
| 1115 | 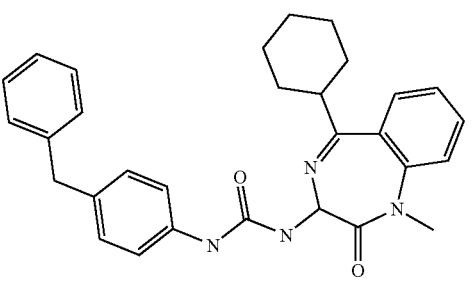 | 482.23 | Yes | 3.98 |
| 1116 | 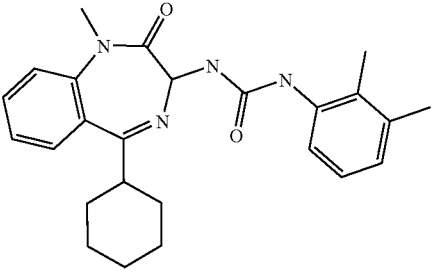 | 418.24 | No | |
| 1117 | 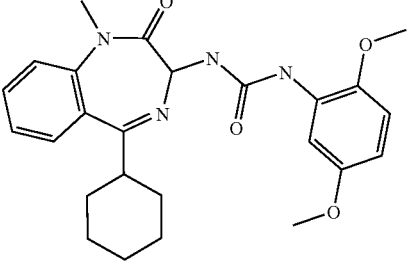 | 450.23 | Yes | 3.23, 6.51 |
| 1118 | 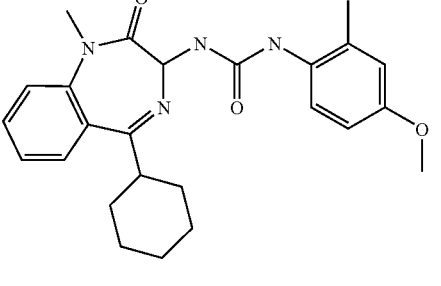 | 434.23 | Tentative | 3.15 |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 1119 | 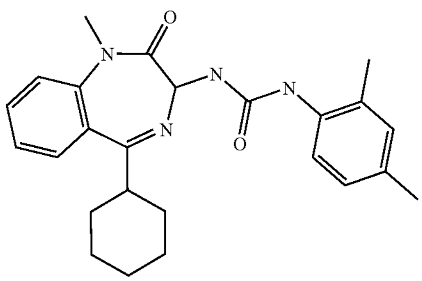 | 418.24 | Tentative | 3.48 |
| 1120 | 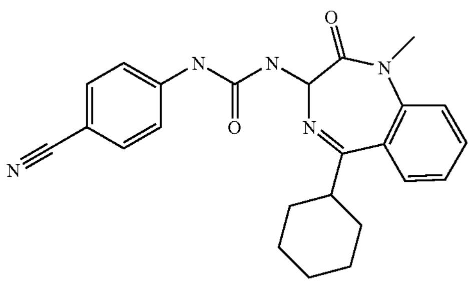 | 415.2 | Yes | 3.09 |

The additional examples below were prepared by individual syntheses.

| | | | | |
|---|---|---|---|---|
| 1121 | | 604.56 | yes | |
| 1122 | | 570.11 | yes | |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 1123 | 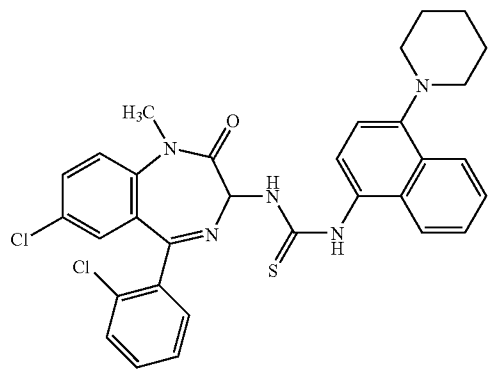 | 602-59 | yes | |
| 1124 | 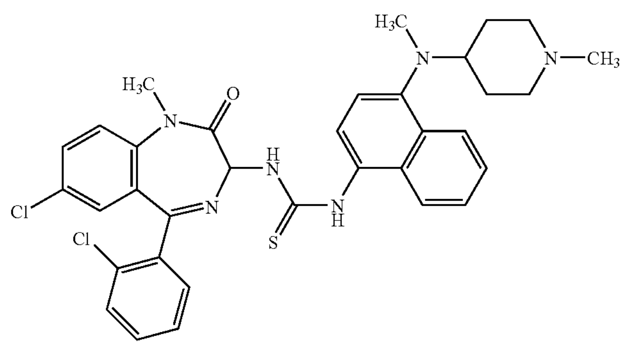 | 645.66 | yes | |
| 1125 | 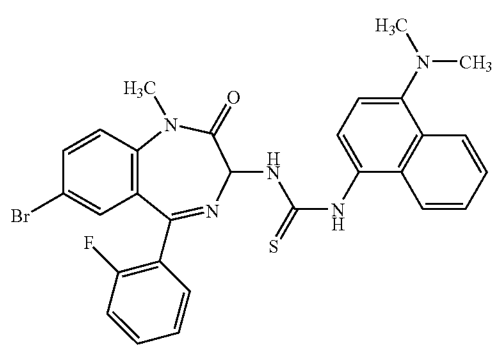 | 590.52 | yes | |
| 1126 | 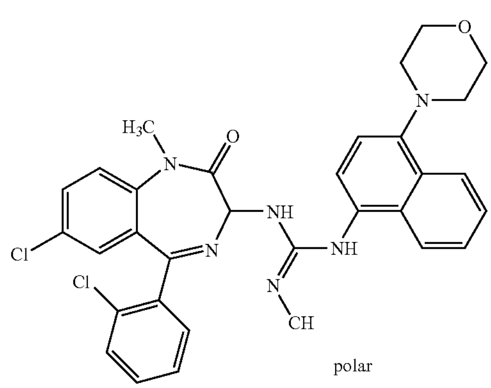 | 612.52 | yes | |

US 7,375,101 B2
463 464
TABLE 1-continued
Spreadsheet of combinatorially prepared compounds with LCMS analysis of the reaction product.
| Compound # | Structure | Target Mass | Mass Found? | Rtn Time (MS) |
|---|---|---|---|---|
| 1127 | 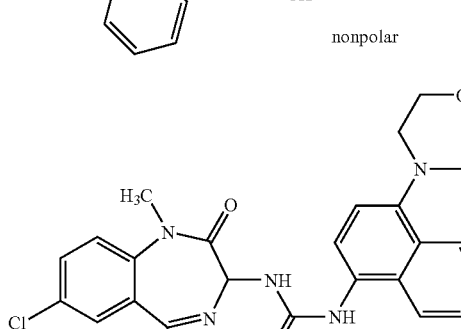 nonpolar | 678.07 | yes | |
| 1128 | 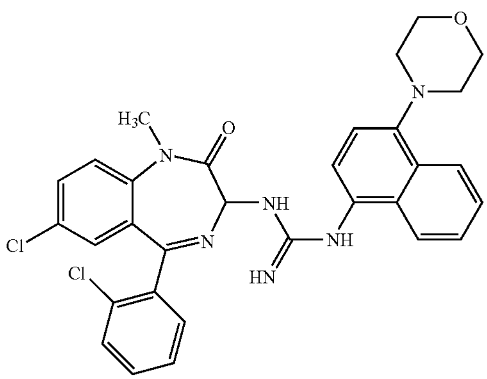 | 587.51 | yes | |
| 1129 | 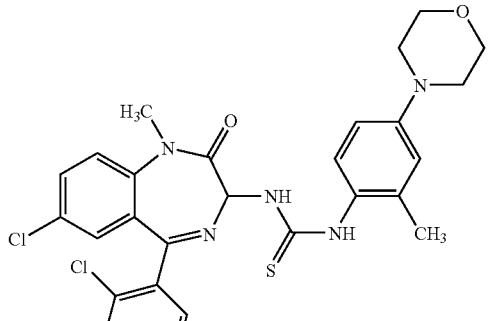 | 568.53 | yes | |
| 1130 | 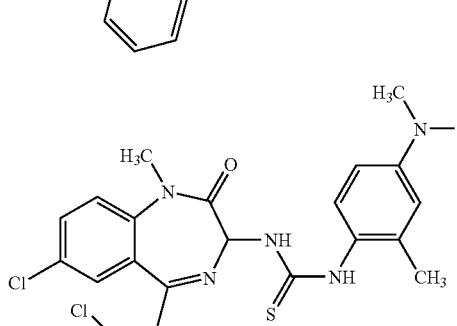 | 526.49 | yes | |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 1131 | 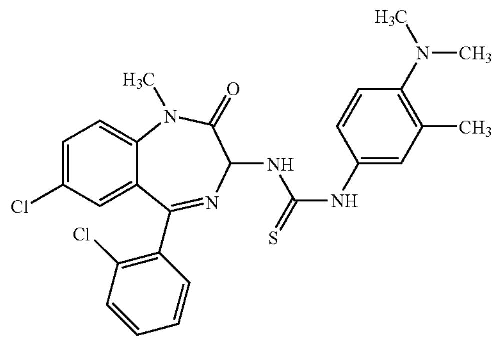 | 526.49 | yes | |
| 1132 | 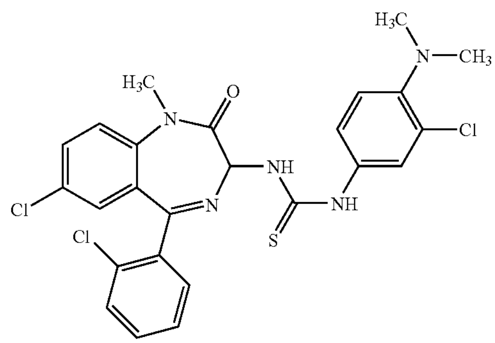 | 546.91 | yes | |
| 1133 | 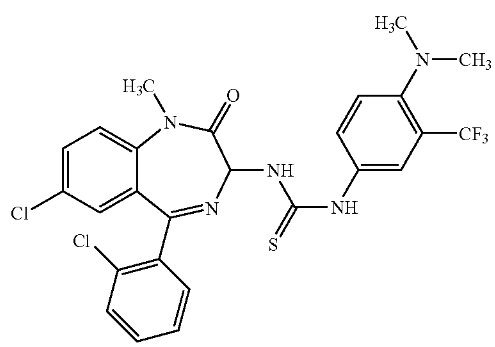 | 580.46 | yes | |
| 1134 | 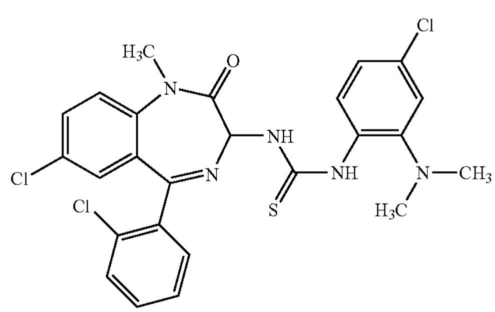 | 546.91 | yes | |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 1135 | 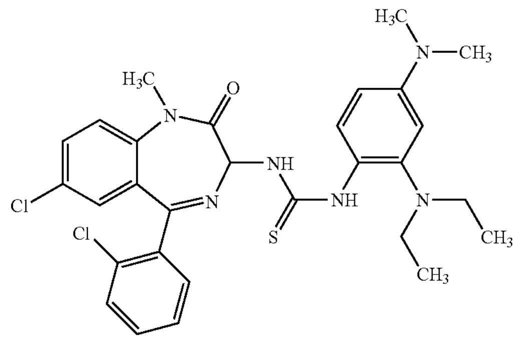 | 583.59 | yes | |
| 1136 | 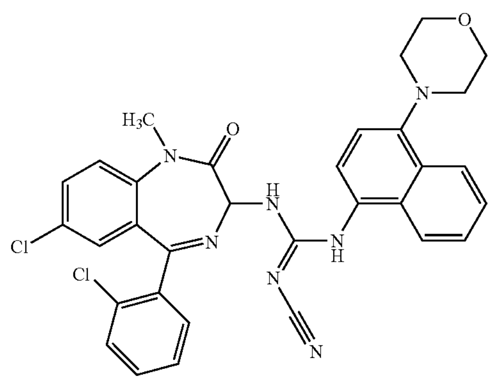 | 612.518 | yes | |
| 1137 | 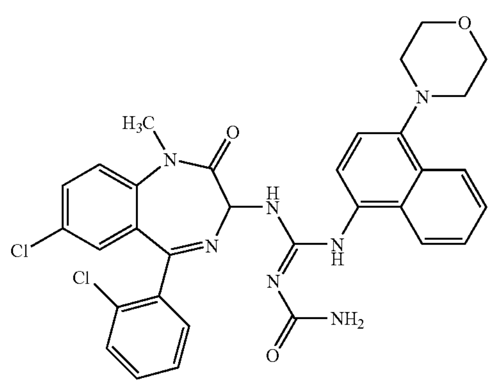 | 630.533 | yes | |
| 1138 | 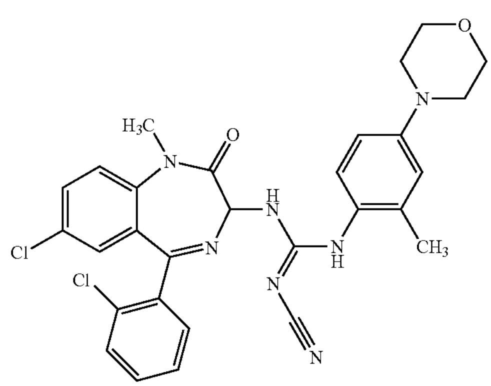 | 576.485 | yes | |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 1139 | 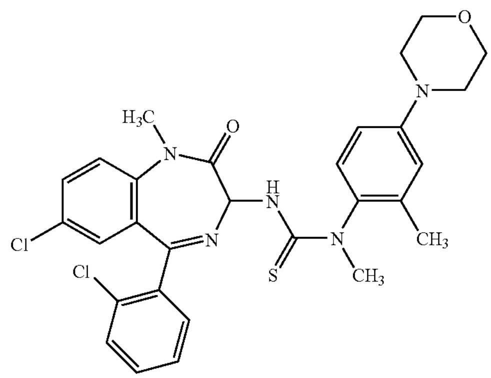 | 582.553 | yes | |
| 1140 | 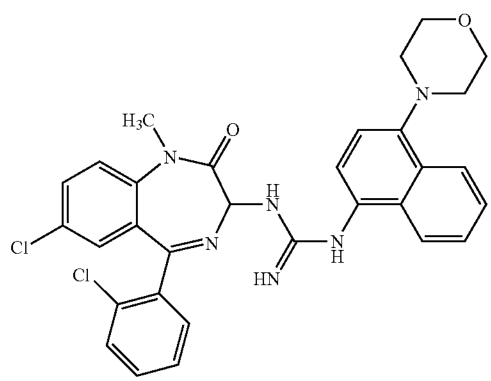 | 587.508 | yes | |
| 1141 | 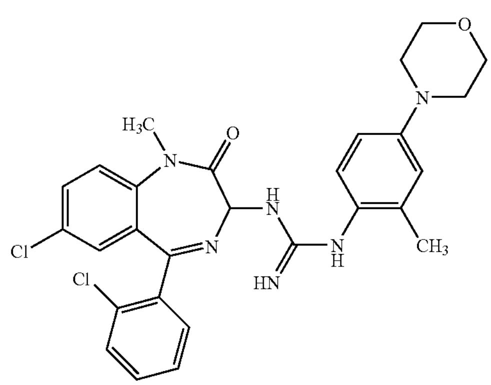 | 551.475 | yes | |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 1142 | 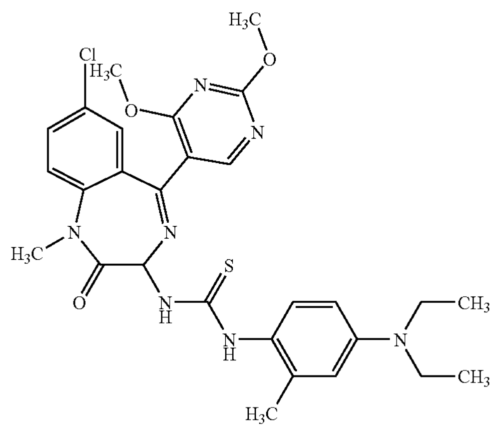 | 582.126 | yes | |
| 1143 | 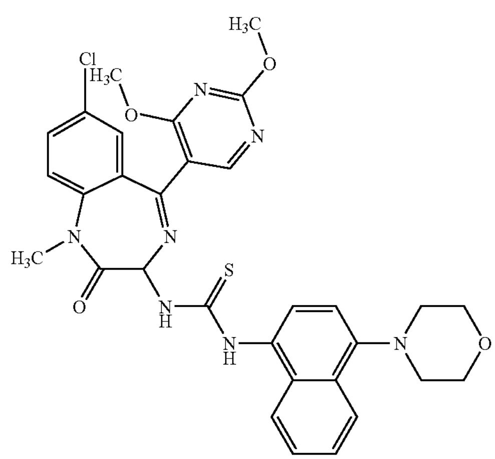 | 632.142 | yes | |
| 1144 | 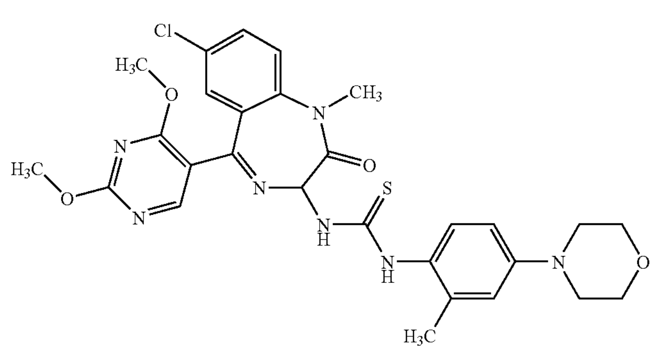 | 596.109 | yes | |

US 7,375,101 B2

473                                                                                                                         474

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 1145 | 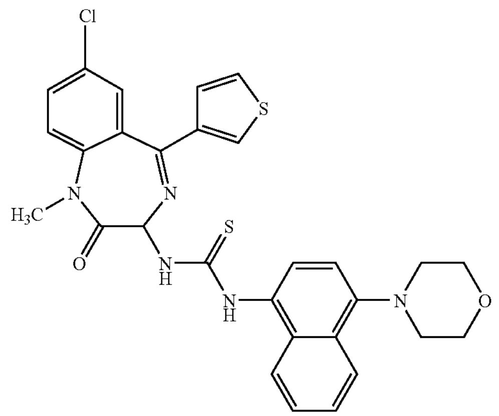 | 576.142 | yes | |
| 1146 | 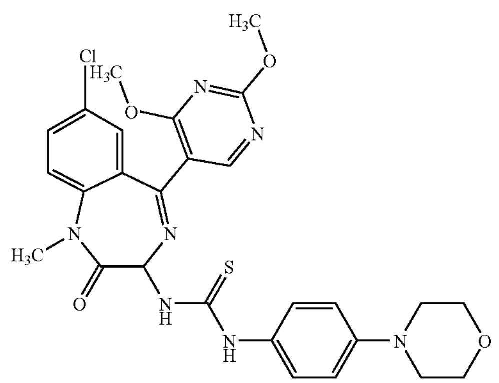 | 582.082 | yes | |
| 1147 | 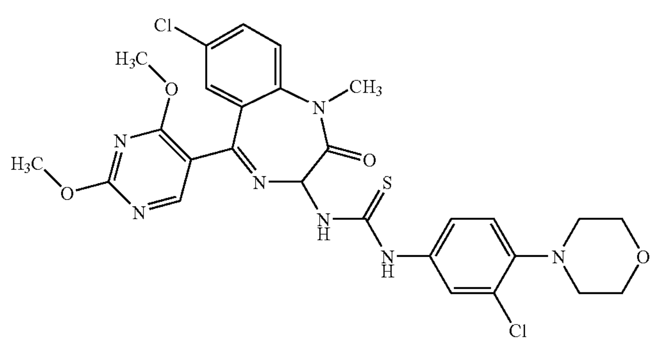 | 616.527 | yes | |
| 1148 | 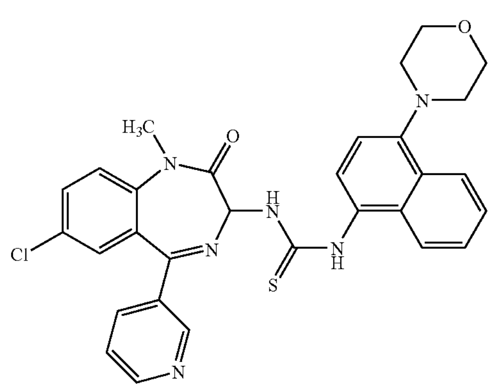 | 571.102 | yes | |

TABLE 1-continued
Spreadsheet of combinatorially prepared compounds with LCMS analysis of the reaction product.
| Compound # | Structure | Target Mass | Mass Found? | Rtn Time (MS) |
|---|---|---|---|---|
| 1149 | 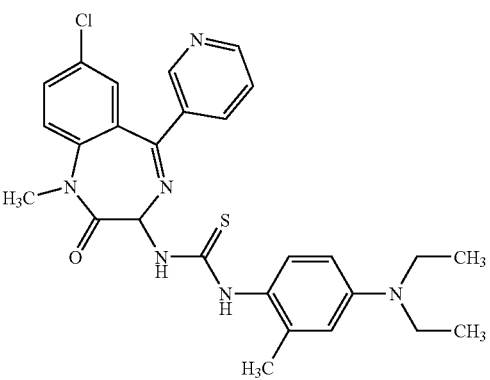 | 521.086 | yes | |
| 1150 | 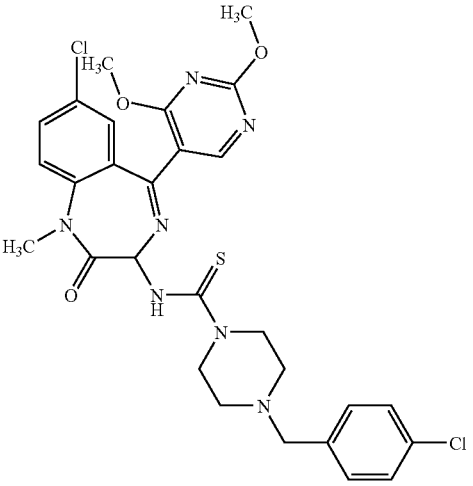 | 614.555 | yes | |
| 1151 | 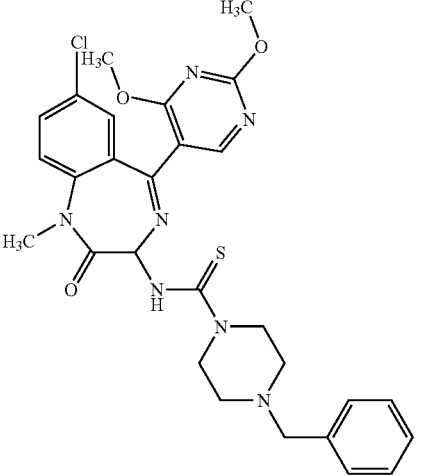 | 580.11 | yes | |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 1152 | 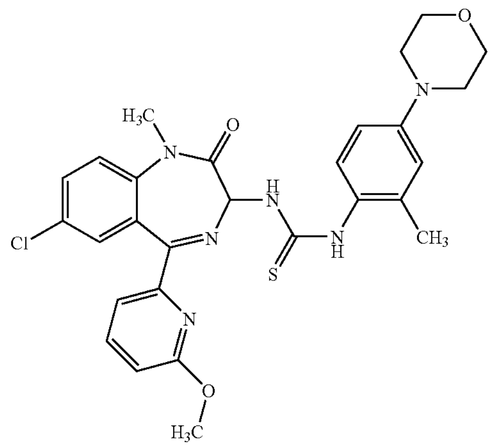 | 565.095 | yes | |
| 1153 | 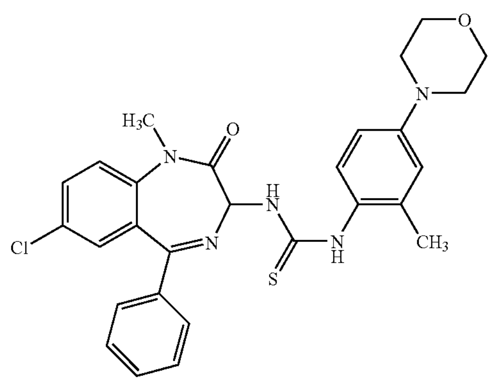 | 534.081 | yes | |
| 1154 | 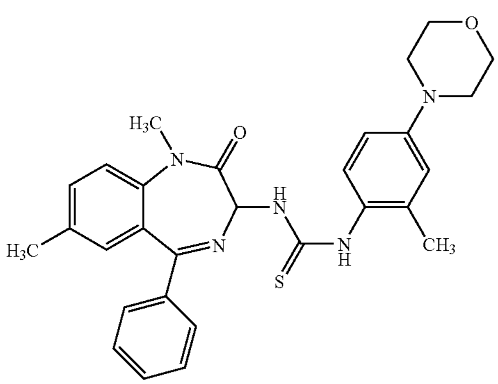 | 513.663 | yes | |

TABLE 1-continued

Spreadsheet of combinatorially prepared compounds with LCMS analysis of the reaction product.

| Compound # | Structure | Target Mass | Mass Found? | Rtn Time (MS) |
|---|---|---|---|---|
| 1155 | 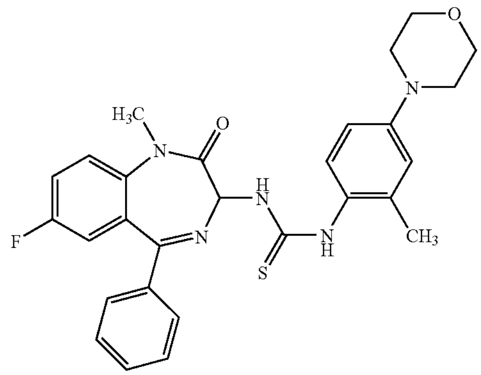 | 517.626 | yes | |
| 1156 | 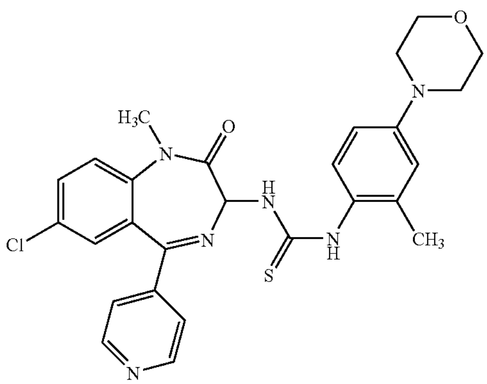 | 535.069 | yes | |

The compounds listed in Table 1, or their pharmaceutically acceptable salts, may be used in the methods described herein to treat or prevent pain.

It will be understood that when compounds of the present invention contain one or more chiral centers, the compounds of the invention may exist in, and be isolated as, enantiomeric or diastereomeric forms, or as a racemic mixture. The present invention includes any possible enantiomers, diastereomers, racemates or mixtures thereof, of a compound of Formula I. The optically active forms of the compound of the invention may be prepared, for example, by chiral chromatographic separation of a racemate, by synthesis from optically active starting materials or by asymmetric synthesis based on the procedures described thereafter.

It will also be appreciated that certain compounds of the present invention may exist as geometrical isomers, for example E and Z isomers of alkenes. The present invention includes any geometrical isomer of a compound of Formula I. It will further be understood that the present invention encompasses tautomers of the compounds of the formula I.

It will also be understood that certain compounds of the present invention may exist in solvated, for example hydrated, as well as unsolvated forms. It will further be understood that the present invention encompasses all such solvated forms of the compounds of the formula I.

Within the scope of the invention are also salts of the compounds of the formula I. Generally, pharmaceutically acceptable salts of compounds of the present invention may be obtained using standard procedures well known in the art, for example by reacting a sufficiently basic compound, for example an alkyl amine with a suitable acid, for example, HCl or acetic acid, to afford a physiologically acceptable anion. It may also be possible to make a corresponding alkali metal (such as sodium, potassium, or lithium) or an alkaline earth metal (such as a calcium) salt by treating a compound of the present invention having a suitably acidic proton, such as a carboxylic acid or a phenol with one equivalent of an alkali metal or alkaline earth metal hydroxide or alkoxide (such as the ethoxide or methoxide), or a suitably basic organic amine (such as choline or meglumine) in an aqueous medium, followed by conventional purification techniques.

In one embodiment, the compound of formula I above may be converted to a pharmaceutically acceptable salt or solvate thereof, particularly, an acid addition salt such as a hydrochloride, hydrobromide, phosphate, acetate, fumarate, maleate, tartrate, citrate, methanesulphonate or p-toluenesulphonate.

The novel compounds of the present invention are useful in therapy, especially for the treatment of various pain conditions such as chronic pain, neuropathic pain, acute pain, cancer pain, pain caused by rheumatoid arthritis, migraine, visceral pain etc. This list should however not be interpreted as exhaustive.

Compounds of the invention are useful in disease states where degeneration or dysfunction of Bradykinin receptors is present or implicated in that paradigm. This may involve the use of isotopically labeled versions of the compounds of the invention in diagnostic techniques and imaging applications such as positron emission tomography (PET).

Compounds of the invention are useful for the treatment of septic shock, pancreatitis, edema, rhinitis, asthma, colitis, arthritis, hepatorenal syndrome, cancer, (including but not restricted to SCLC, prostrate cancer), bacterial and viral infections, ulcerative colitis, and Alzheimer's Disease.

Compounds of the invention are useful as an analgesic agent for use during general anesthesia and monitored anesthesia care. Combinations of agents with different properties are often used to achieve a balance of effects needed to maintain the anesthetic state (e.g. amnesia, analgesia, muscle relaxation and sedation). Included in this combination are inhaled anesthetics, hypnotics, anxiolytics, neuromuscular blockers and opioids.

Also within the scope of the invention is the use of any of the compounds according to the formula I above, for the manufacture of a medicament for the treatment of any of the conditions discussed above.

A further aspect of the invention is a method for the treatment of a subject suffering from any of the conditions discussed above, whereby an effective amount of a compound according to the formula I above, is administered to a patient in need of such treatment.

Thus, the invention provides a compound of formula I, or pharmaceutically acceptable salt or solvate thereof, as hereinbefore defined for use in therapy.

In a further aspect, the present invention provides the use of a compound of formula I, or a pharmaceutically acceptable salt or solvate thereof, as hereinbefore defined in the manufacture of a medicament for use in therapy.

In the context of the present specification, the term "therapy" also includes "prophylaxis" unless there are specific indications to the contrary. The term "therapeutic" and "therapeutically" should be construed accordingly. The term "therapy" within the context of the present invention further encompasses to administer an effective amount of a compound of the present invention, to mitigate either a pre-existing disease state, acute or chronic, or a recurring condition. This definition also encompasses prophylactic therapies for prevention of recurring conditions and continued therapy for chronic disorders.

The compounds of the present invention are useful in therapy, especially for the therapy of various pain conditions including, but not limited to: acute pain, chronic pain, neuropathic pain, acute pain, back pain, cancer pain, and visceral pain.

In use for therapy in a warm-blooded animal such as a human, the compound of the invention may be administered in the form of a conventional pharmaceutical composition by any route including orally, intramuscularly, subcutaneously, topically, intranasally, intraperitoneally, intrathoracially, intravenously, epidurally, intrathecally, intracerebroventricularly and by injection into the joints.

In one embodiment of the invention, the route of administration may be orally, intravenously or intramuscularly.

The dosage will depend on the route of administration, the severity of the disease, age and weight of the patient and other factors normally considered by the attending physician, when determining the individual regimen and dosage level at the most appropriate for a particular patient.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances, which may also act as diluents, flavoring agents, solubilizers, lubricants, suspending agents, binders, or table disintegrating agents; it can also be an encapsulating material.

In powders, the carrier is a finely divided solid, which is in a mixture with the finely divided compound of the invention, or the active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture in then poured into convenient sized moulds and allowed to cool and solidify.

Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term composition is also intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid form compositions include solutions, suspensions, and emulsions. For example, sterile water or water propylene glycol solutions of the active compounds may be liquid preparations suitable for parenteral administration. Liquid compositions can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

Depending on the mode of administration, the pharmaceutical composition will preferably include from 0.05% to 99% w (percent by weight), more preferably from 0.10 to 50% w, of the compound of the invention, all percentages by weight being based on total composition.

A therapeutically effective amount for the practice of the present invention may be determined, by the use of known criteria including the age, weight and response of the individual patient, and interpreted within the context of the disease which is being treated or which is being prevented, by one of ordinary skills in the art.

Within the scope of the invention is the use of any compound of formula I as defined above for the manufacture of a medicament.

Also within the scope of the invention is the use of any compound of formula I for the manufacture of a medicament for the therapy of pain.

Additionally provided is the use of any compound according to Formula I for the manufacture of a medicament for the therapy of various pain conditions including, but not limited to: acute pain, chronic pain, neuropathic pain, acute pain, back pain, cancer pain, and visceral pain.

A further aspect of the invention is a method for therapy of a subject suffering from any of the conditions discussed above, whereby an effective amount of a compound according to the formula I above, is administered to a patient in need of such therapy. Additionally, there is provided a pharmaceutical composition comprising a compound of Formula I, or a pharmaceutically acceptable salt thereof, in association with a pharmaceutically acceptable carrier.

Particularly, there is provided a pharmaceutical composition comprising a compound of Formula I, or a pharmaceutically acceptable salt thereof, in association with a pharmaceutically acceptable carrier for therapy, more particularly for therapy of pain. Further, there is provided a pharmaceutical composition comprising a compound of Formula I, or a pharmaceutically acceptable salt thereof, in association with a pharmaceutically acceptable carrier use in any of the conditions discussed above.

In a further aspect, the present invention provides a method of preparing a compound of formula I.

Methods of Preparation

The compounds listed in Table 1 were prepared as single compounds in a combinatorial array. The Table 1, column 4 designation of "yes" indicates that the target mass of the designated compound was found in >50% abundance in the MS spectrum. Similarly, the designation of "tentative" indicates that the target mass of the designated compound was found in 15-50% abundance in the MS spectrum. Likewise the designation "no" indicates that the target mass of the designated compound was found in <15% abundance in MS 'spectrum. It will be understood by those of ordinary skill in the art that a chemical reaction which fails to efficiently yield the desired product within the context of a combinatorial protocol may nonetheless efficiently yield the desired product when the reaction is performed in a single reaction or parallel reaction format, without undue experimentation on the part of the chemist. In this regard, several of the compounds which were not prepared efficiently in the combinatorial array, were subsequently prepared in separate syntheses as shown in the Examples.

The reaction sequence depicted in Scheme 1, infra, describes a process for preparing compounds of formula (I) wherein X is represented by formula (i) or (ii), comprising reacting a compound of general formula II

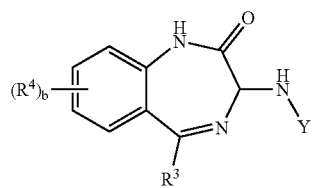

II wherein Y is a protecting group such as CBZ or FMOC, with an alkyl or alkenyl halide, such as allyl bromide in the presence of a base such as cesium carbonate to give compounds of general formula III;

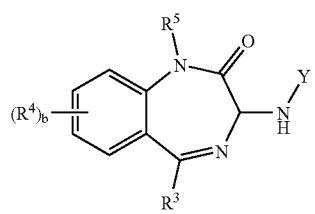

III deprotecting the compounds of formula III under standard conditions and then acylated the deprotected products of formula IV with thiophosgene or phosgene to yield isothiocyanates or isocyanates of formula V, respectively:

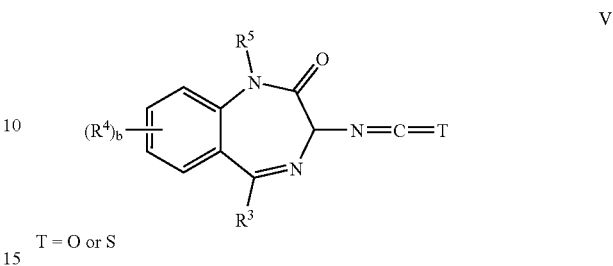

V

T = O or S and subsequently aminating the compounds of formula V combinatorially in a multiwell plate with a selection of different amines to yield compounds of formula I wherein X is represented by formula (i) or (ii) shown above.

The general protocol for the preparation of the combinatorial library is depicted in Scheme 1 and specific experimental details are provided in the Examples below.

Scheme 1

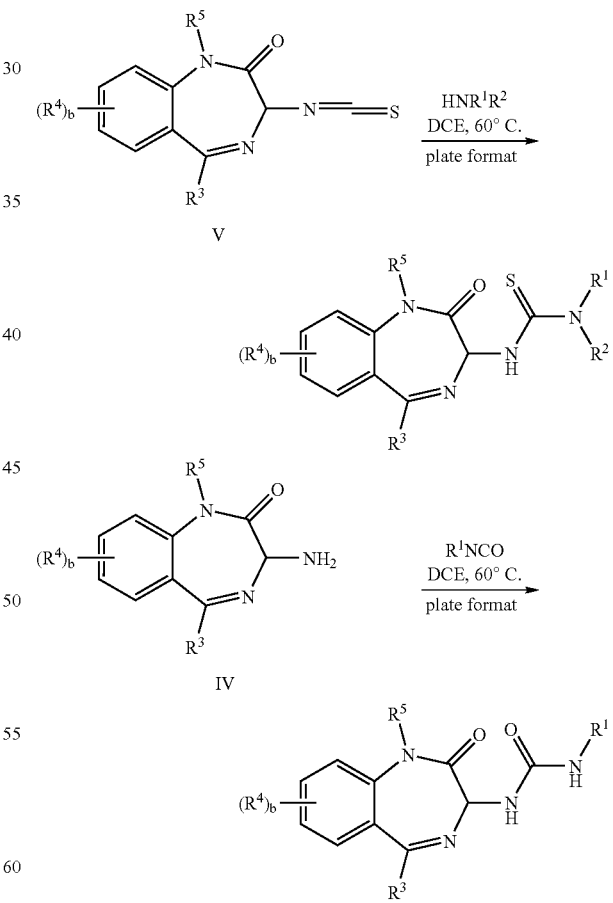

b is 0, 1, or 2; $R^1$, $R^2$, $R^3$, $R^4$, and $R^5$ are as defined above.

In addition, certain compounds of the present invention and certain intermediates used in the preparation of the compounds of the present invention may be prepared according to one or more of the following general procedures, wherein, unless specified otherwise, b, $R^1$, $R^2$, $R^3$, $R^4$ and $R^5$ are defined as above.

General Procedure 1:

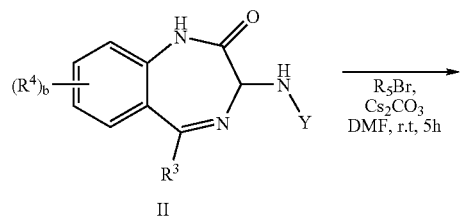

II

Y = protecting goups
such as CBZ or FMOC

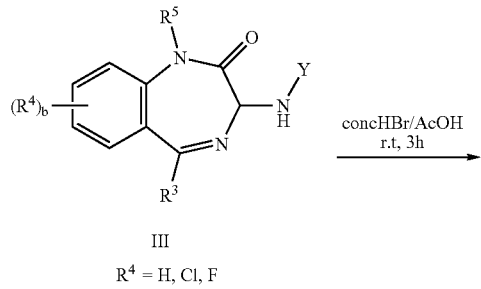

III $R^4$ = H, Cl, F

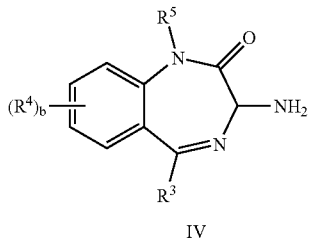

IV $R^5$ = Me, $R^4$ = H, $R^3$ = Cyclohexyl
$R^5$ = Me, $R^4$ = H, $R^3$ = Phenyl
$R^5$ = Me, $R^4$ = Cl, $R^3$ = Phenyl
$R^5$ = Me, $R^4$ = Cl, $R^3$ = 2-ClPhenyl
$R^5$ = Me, $R^4$ = F, $R^3$ = 2-BrPhenyl
$R^5$ = Allyl, $R^4$ = Cl, $R^3$ = Phenyl As illustrated in the scheme above, to a stirred solution of (7-chloro-2,3-dihydro-2-oxo-5-phenyl-1H-1,4-benzodiazepin-3-yl)-, phenylmethyl ester-carbamic acid (10 mmol) in DMF (140 ml) was added cesium carbonate (3.72 g, 11.4 mmol) followed by methyl iodide (2.0 g, 14 mmol). The reaction mixture was stirred at room temperature for 5 hours then concentrated in vacuo. The residue was taken in EtOAc (200 ml) and washed with brine (2×30 ml). The organic phase was then dried over MgSO$_4$, filtered and concentrated in vacuo. The products were purified by flash chromatography using dichloromethane as the eluent. The products (8 mmol) were added with conc HBr (33% in acetic acid) (50 ml) and were stirred at room temperature for 3 hours. The reaction mixture was poured into ether (300 ml), the precipitate was collected, and then taken in dichloromethane (250 ml) and washed with 2N NaOH (2×50 ml). The organic phase was dried over MgSO4, filtered and concentrated in vacuo to provide the desired compound.

General Procedure 2:

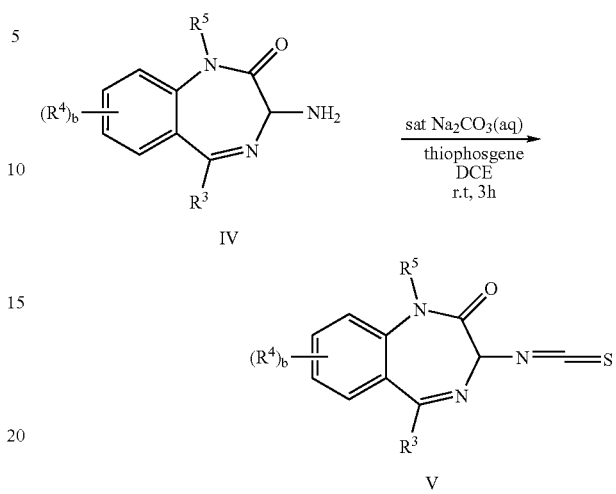

As illustrated in the scheme above, to a solution of 3-aminobenzodiazepines (3 mmol) in dichloroethane (20 ml) and saturated aqueous Na$_2$CO$_3$ (20 ml) was added dropwise thiophosgene (0.7 g, 6 mmol). The reaction mixture was stirred at room temperature for 3 hours. The organic phase was separated and the aqueous phase was extracted with dichloromethane (50 ml). The combined organic phases were dried over MgSO$_4$, filtered and concentrated in vacuo. The product was purified by flash chromatography (100% CH$_2$Cl$_2$) to yield a compound of formula V.

General Procedure 3:

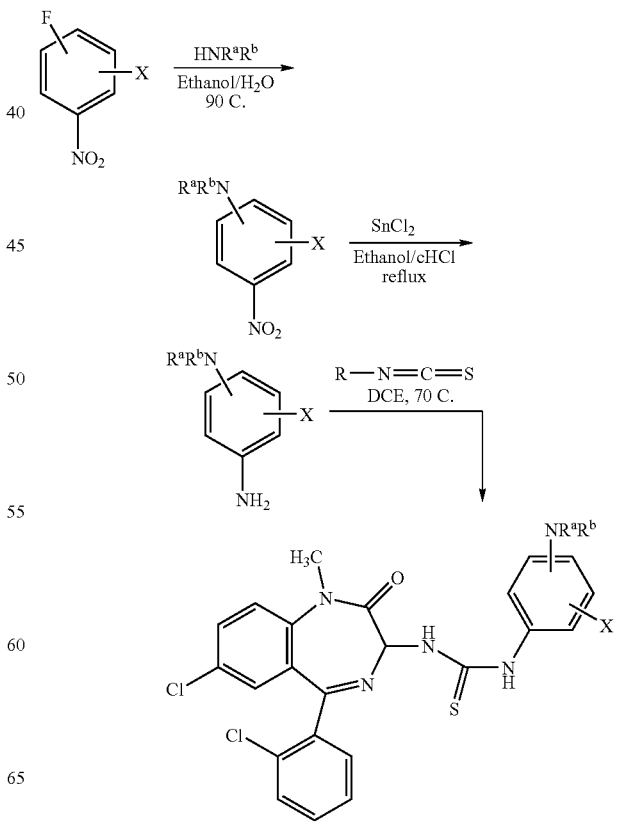

HNR<sup>a</sup>R<sup>b</sup> = 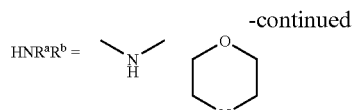

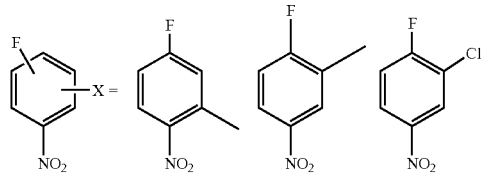

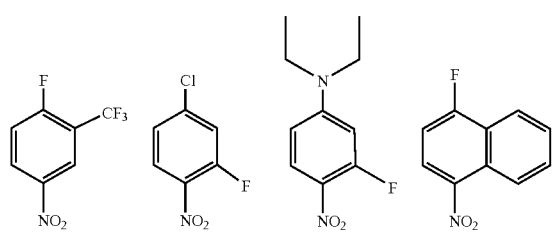

RN=C=S = 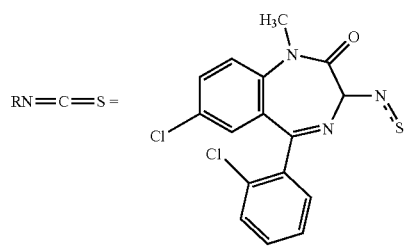

As illustrated in the scheme above, to a solution of 4-fluoro-2-methyl-1-nitro-benzene (0.155 g, 1 mmol) in a 1:1 mixture of ethanol and water (20 ml) was added morpholine (0.435 g, 5 mmol). The reaction mixture was heated at 90° C. for 16 h. The solvent was evaporated in vacuo, the residue was taken in dichloromethane (50 ml) and washed with brine (3×10 ml). The organic phase was dried over MgSO$_4$, filtered, and concentrated in vacuo. The product was taken up in ethanol (20 ml) and heated at reflux. A solution of tin chloride (2M, 2.5 ml) in conc. HCl was added dropwise and heated at reflux for another 30 minutes. The solvent was then evaporated in vacuo, and the residue was treated with a 2M solution of sodium hydroxide until the pH of the solution was >10. The mixture was extracted with dichloromethane (50 ml) and the organic phase was dried over MgSO$_4$, filtered, and concentrated in vacuo. The product (0.032 g, 0.2 mmol) ((ESI) (M+H)$^+$=192) was taken up in dichloroethane (5 ml), and 7-chloro-5-(2-chlorophenyl)-1,3-dihydro-3-isothiocyanato-1-methyl-2H-1,4-benzodiazepin-2-one(0.075 g, 0.2 mmol) was added. The reaction mixture was heated at 70 C for 16 h. The solvent was evaporated in vacuo, and the residue was washed with ether (2×10 ml) to yield the desired compound.

General Procedure 4:

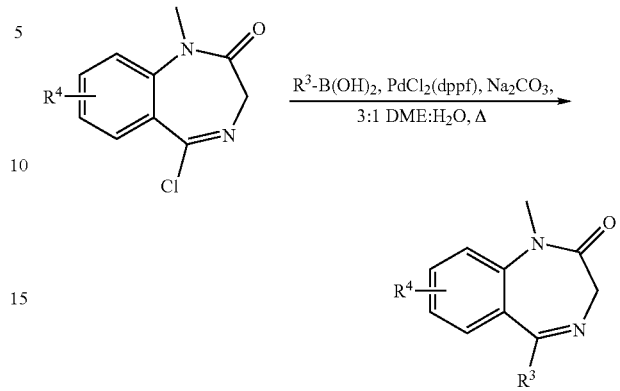

As illustrated in the scheme above, N$_2$ gas was bubbled through both DME and water for at least 3 hours. A solution of the imidoyl chloride (1 equiv.) in DME (1.5 mL/mmol imidoyl chloride) was placed in a N$_2$purged flask. Na$_2$CO$_3$ (1 equiv.), PdCl$_2$(dppf) (0.05 equiv.), boronic acid (1 equiv.) and water (0.5 mL/mmol imidoyl chloride) were added sequentially, and the resulting mixture was heated at 100° C. until the imidoyl chloride was consumed (typically 16 h). The reaction was then cooled, diluted with CH$_2$Cl$_2$ and water, and the layers were separated. The aqueous phase was extracted with CH$_2$Cl$_2$ (3×), and the combined organic phases were dried over Na$_2$SO$_4$, filtered, and concentrated in vacuo. The crude product was purified by silica gel column chromatography to provide the desired compound.

General Procedure 5:

General Procedure 5:

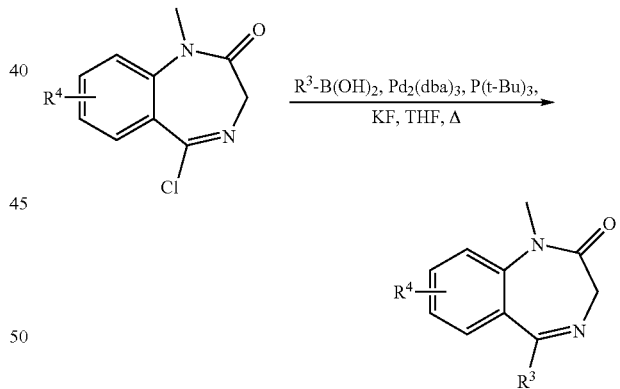

As illustrated in the scheme above, boronic acid (1.15 equiv.), Pd$_2$(dba)$_3$ (0.015 equiv.), and dry KF (3.3 equiv.) were placed in an oven-dried, N$_2$ purged flask. A solution of the imidoyl chloride (1 equiv.) in dry THF (2 mL/mmol imidoyl chloride) was added followed by a solution of P(t-Bu)$_3$ (0.045 equiv., 10% solution in hexanes) in dry THF (1.6 mL/mmol imidoyl chloride). The resulting mixture was heated at reflux until the imidoyl chloride was consumed (typically 16 h). The reaction was then cooled, diluted with EtOAc, and filtered through a small pad of silica gel. The silica was washed well with EtOAc, and the combined organic phases were concentrated in vacuo. The product was purified by silica gel column chromatography to provide the desired compound.

General Procedure 6:

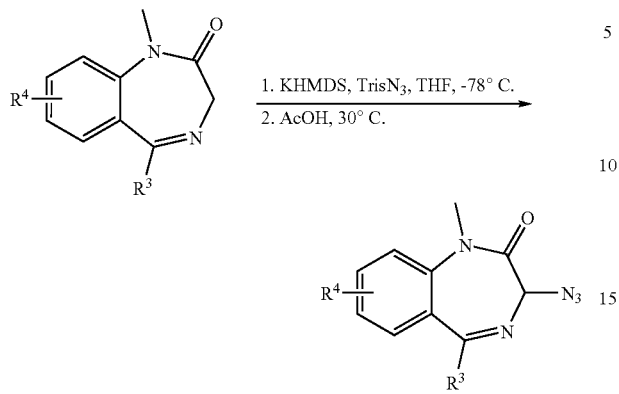

As illustrated in the scheme above, a solution of the benzodiazepine compound (1 equiv.) in dry THF (4 mL/mmol benzodiazepine, or slightly more if solubility was low) was added to a mixture of KHMDS (1.05 equiv., 0.5 M in toluene) and dry THF (2 mL/mmol benzodiazepine) immersed in a −78° C. cooling bath. After stirring for 5 min., a solution of trisyl azide (2.5 equiv) in dry THF (4 mL/mmol benzodiazepine) was added to the reaction, and stirring was continued until all the starting benzodiazepine had been consumed (typically 10 min.). Glacial acetic acid (4.4 equiv) was then added, and the mixture was warmed to 30° C. for 2 h. Saturated NaHCO$_3$ was added, the layers were separated, and the aqueous phase was extracted with CH$_2$Cl$_2$ (4×). The combined organic phases were dried over Na$_2$SO$_4$, filtered, and concentrated in vacuo. The product was purified by silica gel column chromatography to provide the corresponding azide compound.

General Procedure 7:

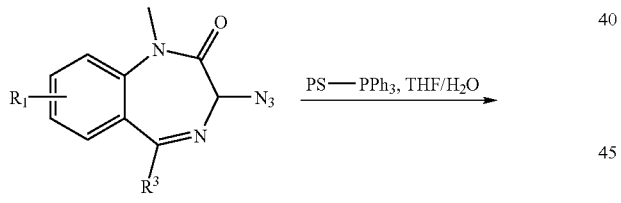

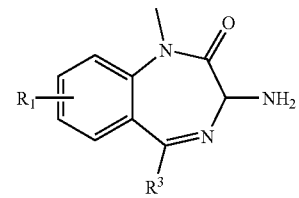

As illustrated in the scheme above, polymer supported triphenylphosphine (Argonaut Technologies, 5-10 equiv) was added to a solution of the azide (1 equiv.) in THF (10 mL/g polymer) and water (0.8 mL/g polymer). The resulting mixture was stirred at room temperature until all of the azide had been consumed (typically overnight). The polymer resin was then removed by filtration, and was washed well with CH$_2$Cl$_2$ and MeOH (3× each). The filtrate was concentrated in vacuo, and the residue was redissolved in CH$_2$Cl$_2$. Any remaining water was removed with the aid of a separatory funnel, and the organic phase was dried over Na$_2$SO$_4$, filtered, and concentrated in vacuo. The amine was purified using a "catch and release" strategy with MP-TsOH resin (Argonaut Technologies): The product was dissolved in CH$_2$Cl$_2$ (10 mL/mmol product), and MP-TsOH resin (2.3 equiv) was added. The mixture was stirred for 1 h, and the solvent was removed by filtration and discarded. The resin was rinsed with CH$_2$Cl$_2$ and MeOH (3× each), and the washings were discarded as well. The product was then released from the resin by washing with 2M NH$_3$ in MeOH and CH$_2$Cl$_2$ (3× each). Concentration of the filtrate in vacuo provided the corresponding amine compound.

Additional compounds of the present invention may also be prepared according to the methods represented in Schemes 2-4 below, wherein, unless specified otherwise, b, $R^1$, $R^2$, $R^3$, $R^4$ and $R^5$ are defined as above.

Scheme 2

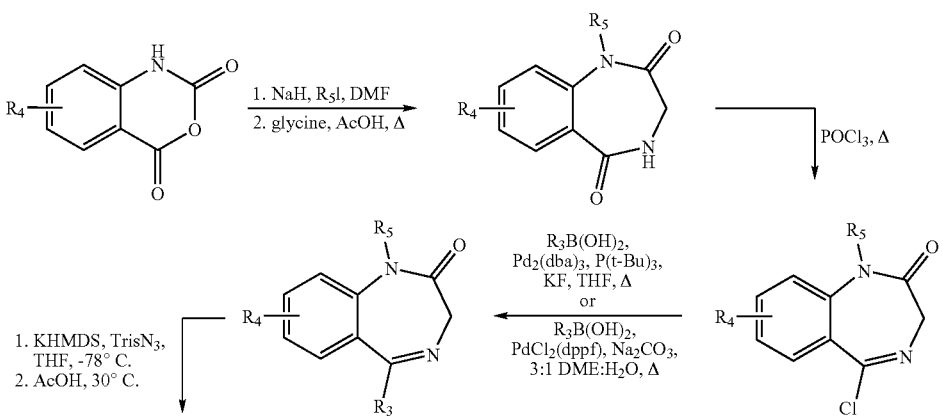

491
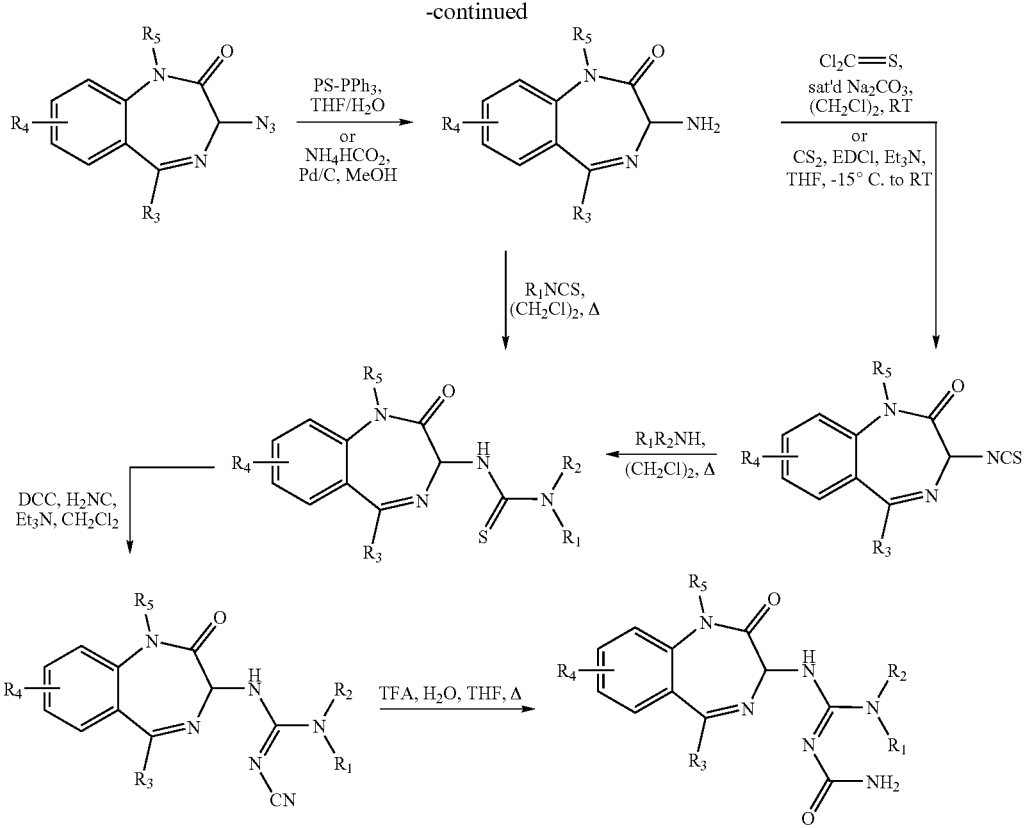
492
Scheme 3
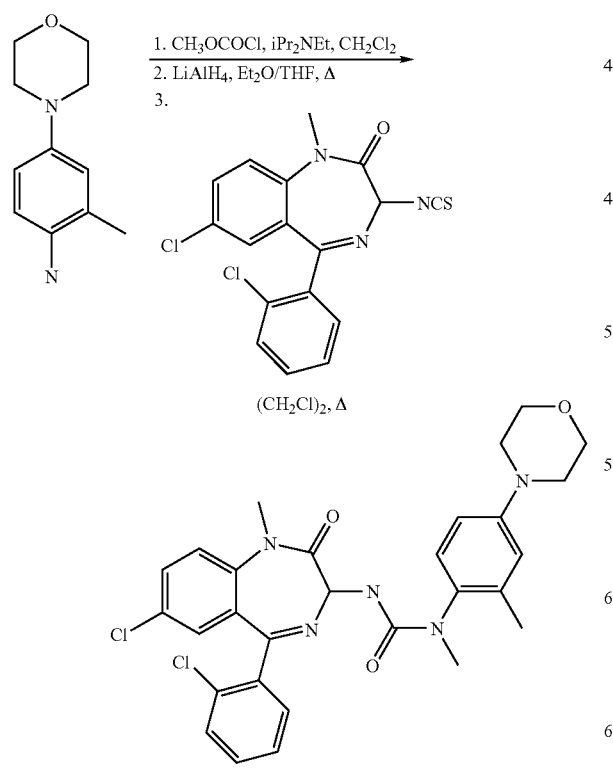
Scheme 4
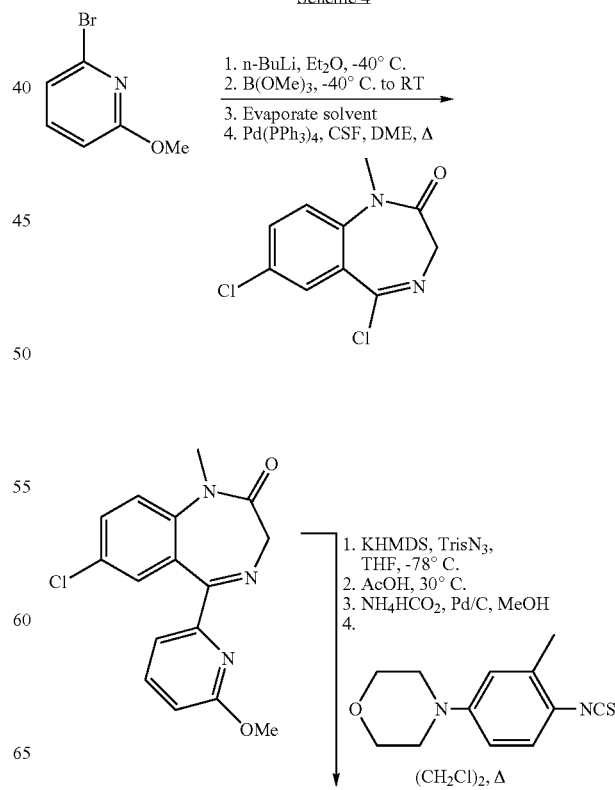

-continued

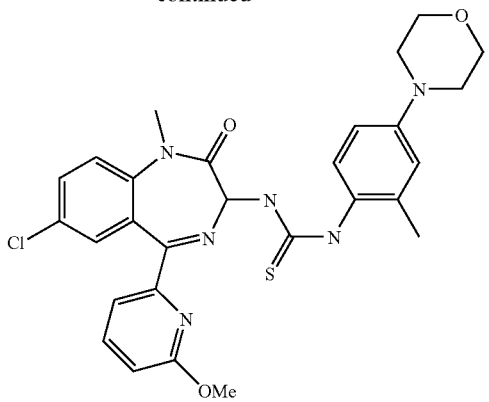

Biological Evaluation

I. B2 Bradykinin Binding Assay

A. Human Bradykinin B2 (hB2) Receptor Expression and Membrane Preparation

The cloned human Bradykinin B2 (hB2) receptor in the pCIN vector was purchased from Receptor Biology. The hB2 receptor was stably transfected into HEK 293 S cells and a clonal cell line was generated. Cells were grown in T-flasks with DMEM culture media containing 10% FBS, 2 mM glutamine, 600 µg/ml neomycin and an antibiotic cocktail (100 IU penicillin, 100 µg/ml streptomycin, 0.25 µg/ml amphotericin B). Membranes, expressing the hB2 receptor, were prepared from this cell line according to this protocol: Cells are harvested at 1 to 1.2 million cells/ml, pelleted, and resuspended in ice-cold lysis buffer (50 mM Tris, pH 7.0, 2.5 mM EDTA, with PMSF added just prior to use to 0.5 mM from a 0.5 M stock in DMSO. After lysis on ice for 15 min, the cells are homogenized with a polytron for 10 sec. The suspension is spun at 1000 g for 10 min at 4° C. The supernatant is saved on ice and the pellets resuspended and spun as before. The supernatants from both spins are combined and spun at 46,000 g for 10-30 min. The pellets are resuspended in cold Tris buffer (50 mM Tris/Cl, pH 7.0) at a dilution of 0.2-1 ml per 40 million cells and spun again. The final pellets are resuspended in membrane buffer (50 mM Tris, 0.32 M sucrose, pH 7.0). Aliquots are frozen in dry ice/ethanol and stored at −70° C. until use. The protein concentrations are determined by a modified Lowry with SDS.

B. hB2 Receptor Binding

Membranes expressing the hB2 receptor are thawed at 37° C., passed 3 times through a 25-gauge blunt-end needle, diluted in the bradykinin binding buffer (50 mM Tris, 3 mM MgCl$_2$, and 1 mg/ml BSA, pH 7.4, 0.02 mg/ml Phenanthroline, 0.25 mg/ml Pefabloc) and 80 µL aliquots containing the appropriate amount of protein (final concentration of 0.25 µg/ml) are distributed in 96-well polystyrene plates (Treff Lab). The IC$_{50}$ of compounds are evaluated from 10-point dose-response curves, where the serial dilutions are done on a final volume of 150 µL, with 70 µL of $^{125}$I-Desamino-TyrHOE140 (Kd=0.05) at 50,000 to 60,000 dpm per well (0.03-0.04 nM) in a final volume of 300 µl. The total and non-specific binding are determined in the absence and presence of 0.1 µM (150 µL) of Bradykinin respectively. The plates are vortexed and incubated for 60 minutes at room temperature, filtered through Unifilters-96 GF/B (Canberra Packard), which were presoaked in 0.1% polyethyleneimine, with a harvester using 3 ml of wash buffer (50 mM Tris, pH 7.0, 3 mM MgCl$_2$). The filters are dried for 1 hour at 55° C. The radioactivity (cpm) is counted in a TopCount (Canberra Packard) after adding 65 µl/well of MS-20 scintillation liquid (Canberra Packard). Compounds of the present invention have demonstrated hB2 receptor binding at concentrations less than 10 µM.

Based on the above assays, the dissociation constant (Ki) for a particular compound of the invention towards a particular receptor is determined using the following equation:

$$Ki=IC_{50}/(1+[rad]/Kd),$$

Wherein IC$_{50}$ is the concentration of the compound of the invention at which 50% displacement has been observed;

[rad] is a standard or reference radioactive ligand concentration at that moment; and Kd is the dissociation constant of the radioactive ligand towards the particular receptor.

II. GTP[γ]$^{35}$S Binding Experiments on Bradykinin (B2) Receptors

A. General Information

The procedures below describe how to perform and interpret GTP[γ]$^{35}$S binding experiments designed to determine the activity of new compounds on the human B2 receptor.

B. General Procedure of the Assay

Human Bradykinin-2 GTP[γ]$^{35}$S Binding

Human Bradykinin-2 membranes (hB2 293s) are thawed at 37° C., passed 3 times through a 25-gauge blunt-end needle and diluted in the GTPγS binding buffer for the assay (50 mM Hepes, pH 7.4; 200 mM NaCl; 1 mM EDTA; 5 mM MgCl$_2$. To this added freshly prepared 1 mM DTT, 0.5% BSA, 1 µM GDP. The EC50 and Emax of compounds are evaluated from 10-point dose-response curves done in 300 µl with the appropriate amount of membrane protein and 100,000-120,000 dpm of GTPγ$^{35}$S per well (0.11-0.14 nM). Bradykinin (1-9) is used as the standard agonist at hB2. The ranges of concentrations tested should include a maximal concentration of 0.1 µM bradykinin in order to establish the E$_{max}$.

The plates are vortexed and incubated for 60 minutes at room temperature, filtered on GF/B Unifilters (presoaked in water) with the Packard harvester using 4 ml/well of wash buffer (50 mM Tris, 5 mM MgCl$_2$, 50 mM NaCl, pH 7.0), minimum. The filters are dried for 1 hour at 55° C. The radioactivity (cpm) is counted in a TopCount (Packard) after adding 65 µl/well of MS-20 scintillation liquid.

Antagonist reversal studies are done in a similar manner except that the compound dose-response curve's are performed in the presence of a constant concentration of agonist (approx. 80% bradykinin E$_{max}$; ~5 nM). A standard B2 Antagonist is used as the reference antagonist at hB2. The ranges of antagonist concentrations tested should include a maximal concentration of 3 µM of the standard B2 Antagonist in order to establish the maximal displacement (D$_{max}$).

C. Radioligand: Preparation of GTP[γ]$^{35}$S

GTP[γ]$^{35}$S is acquired from Perkin-Elmer (250 µCi/20 µl). It is diluted from with 10 mM DTT, 50 mM Tris, pH 7 (dilute in 2 ml, 1.0 mCI/20 µ). Sonicate the solution, filter through a 0.45 μm filter, and freeze aliquots at −70° C. For the experiment, use ~0.3 nM dilution of this tracer in the GTP binding buffer.

D. Data Analysis

The $EC_{50}$ and $E_{max}$ of compounds are evaluated from 10-point dose-response curves done in 300 μl with the appropriate amount of membrane protein and $GTP\gamma^{35}S$ per well and are calculated in Activity base with ExcelFit. The basal and maximal stimulated binding are determined in the absence and presence of standard reference compounds, respectively.

The stimulation (Stim) in the presence of compounds is expressed as the percentage of $D_{max}$ of the reference antagonist. Values of $IC_{50}$, Ki' and $D_{max}$ for ligands capable of competing for agonist stimulated binding are calculated in Activity Base. Mean±S.E.M. values of $IC_{50}$, Ki' and % $D_{max}$ are reported for ligands tested in at least three dose-response curves.

Biological data for particular testing samples (as listed in Table 2) of the compounds of the invention are listed in Table 3 below.

TABLE 2

List of the test samples used in the Biological Evaluation

| Test Sample Nos: | Structure of the Test Sample |
|---|---|
| 1 | |
| 2 | |
| 3 | |

TABLE 2-continued
List of the test samples used in the Biological Evaluation
Test
Sample Nos: Structure of the Test Sample
4
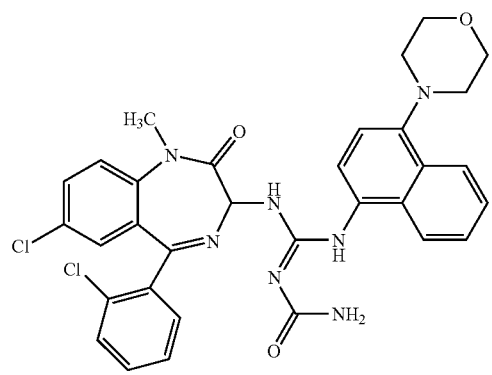
5
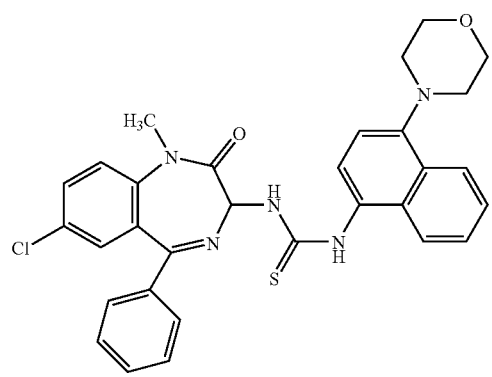
6
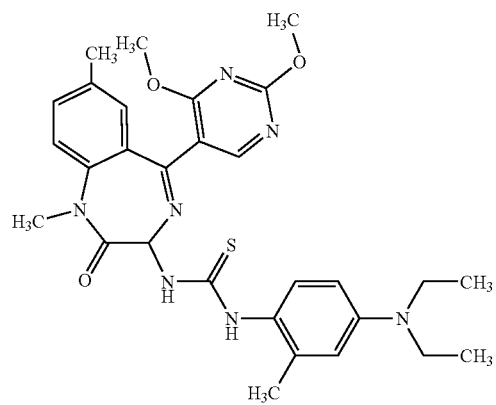

TABLE 2-continued
List of the test samples used in the Biological Evaluation
| Test Sample Nos: | Structure of the Test Sample |
|---|---|
| 7 | 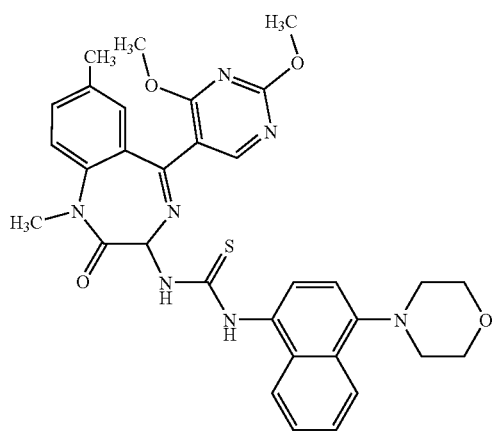 |
| 8 | 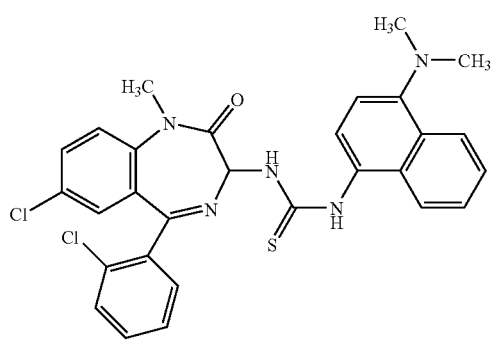 |
| 9 | 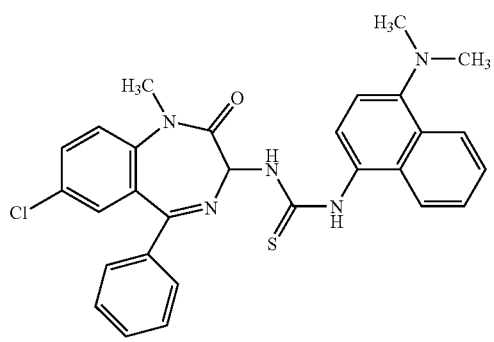 |
| 10 | 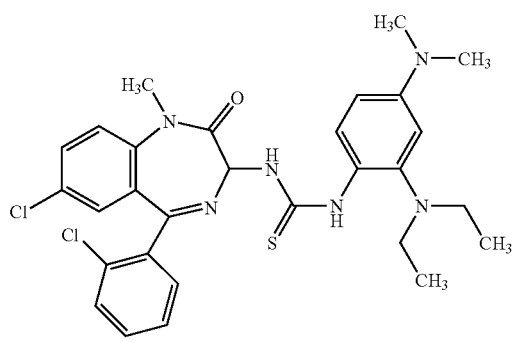 |

TABLE 2-continued
List of the test samples used in the Biological Evaluation
| Test Sample Nos: | Structure of the Test Sample |
|---|---|
| 11 | 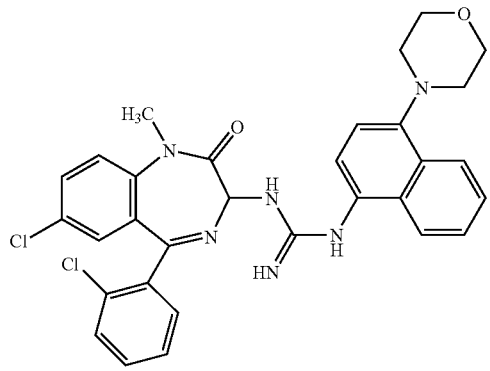 |
| 12 | 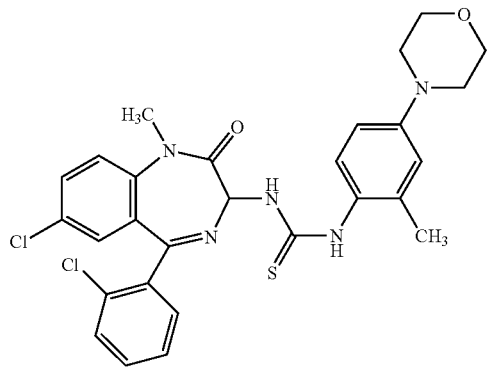 |
| 13 | 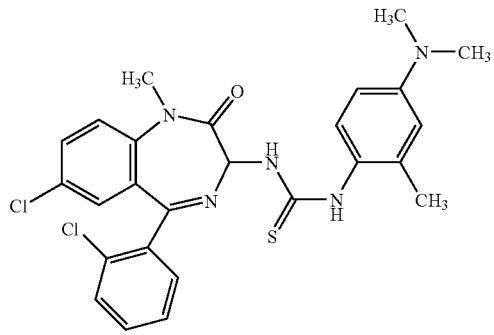 |
| 14 | 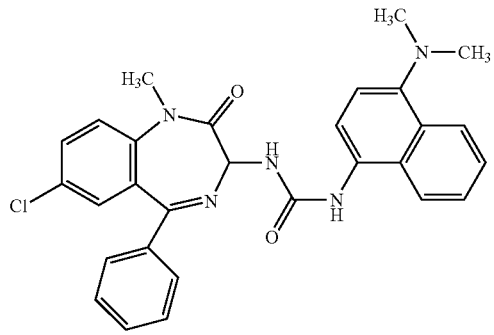 |

TABLE 2-continued
List of the test samples used in the Biological Evaluation
Test
Sample Nos: Structure of the Test Sample
15
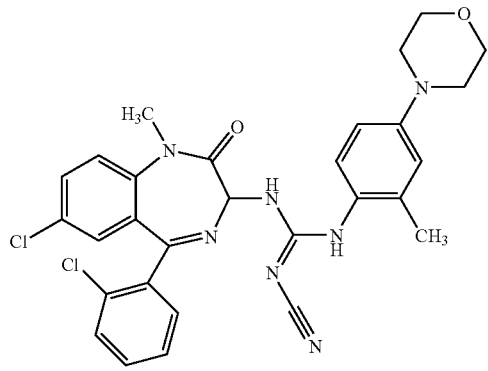
16
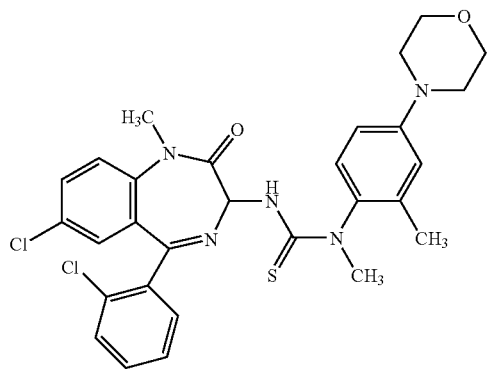
17
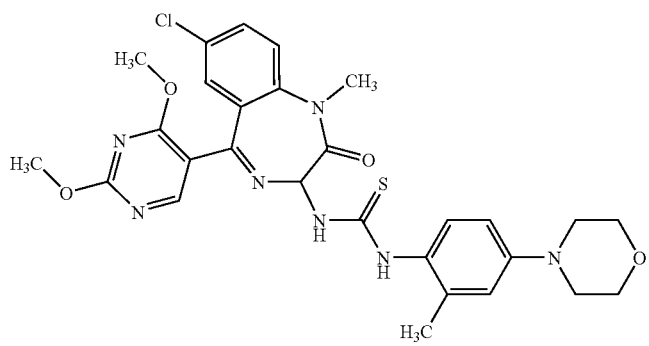
18
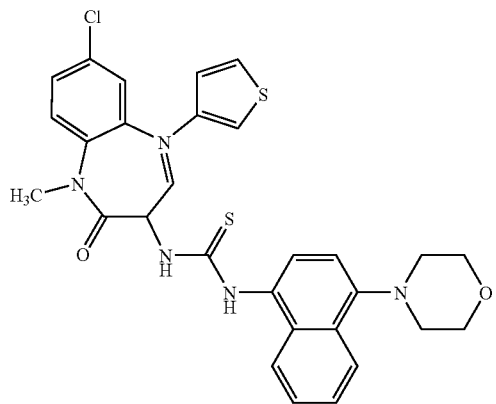

TABLE 2-continued
List of the test samples used in the Biological Evaluation
Test Sample Nos: Structure of the Test Sample
19
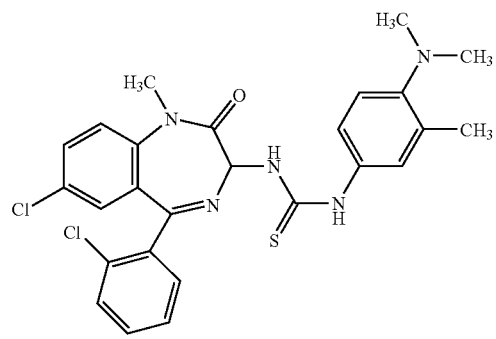
20
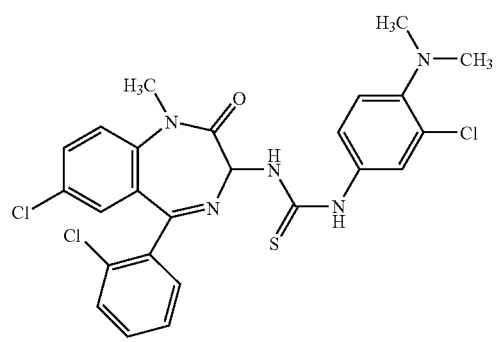
21
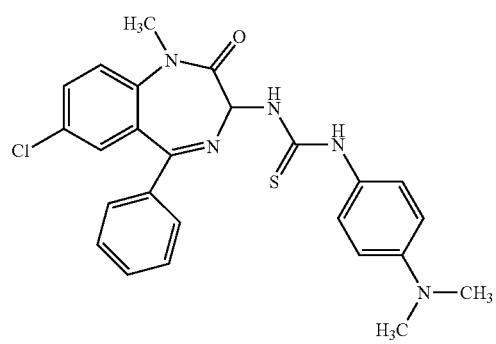
22
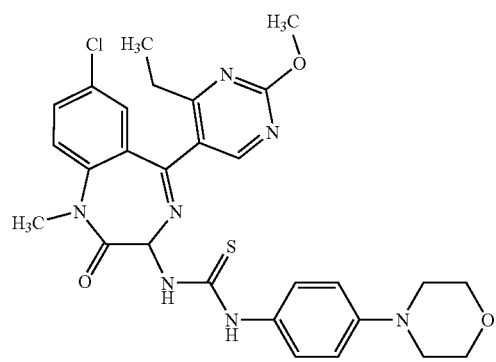

TABLE 2-continued
List of the test samples used in the Biological Evaluation
| Test Sample Nos: | Structure of the Test Sample |
|---|---|
| 23 | 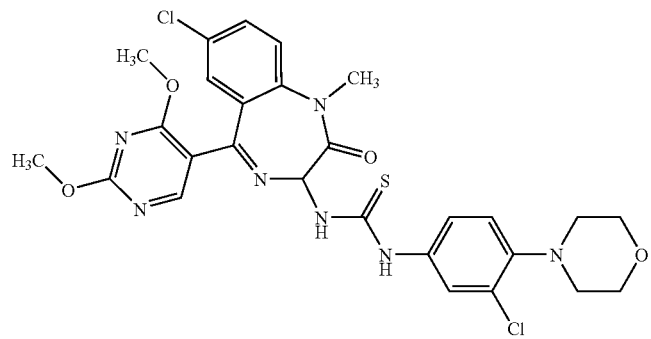 |
| 24 | 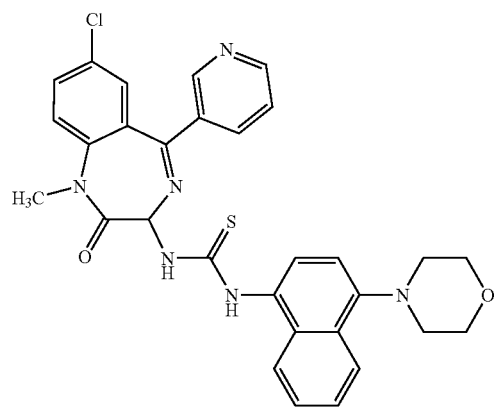 |
| 25 | 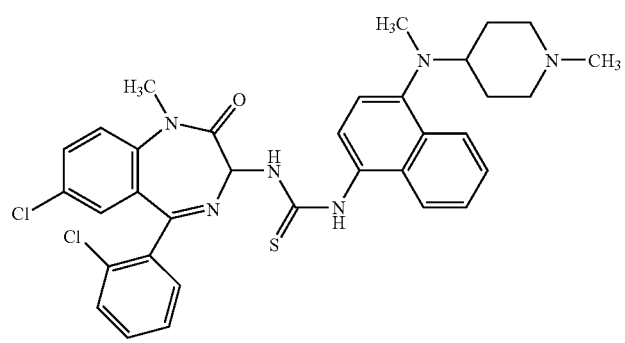 |
| 26 | 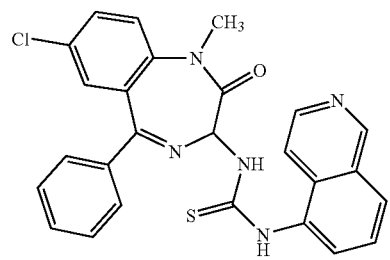 |

TABLE 2-continued
List of the test samples used in the Biological Evaluation
Test
Sample Nos: Structure of the Test Sample
27
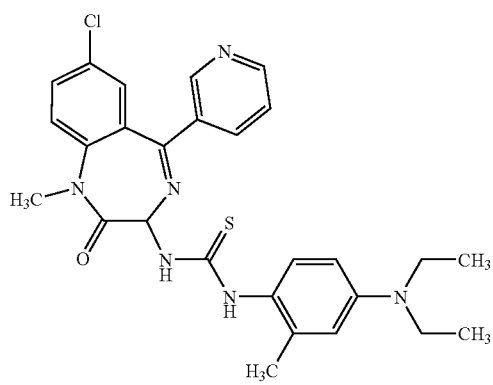
28
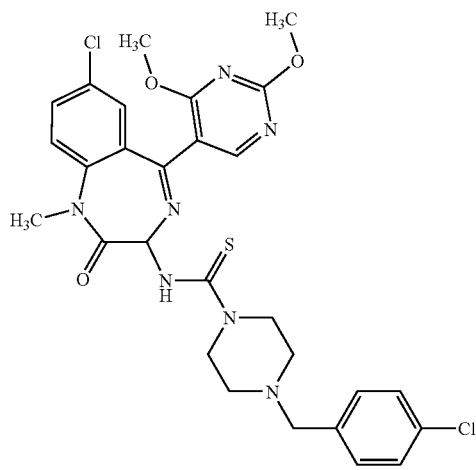
29
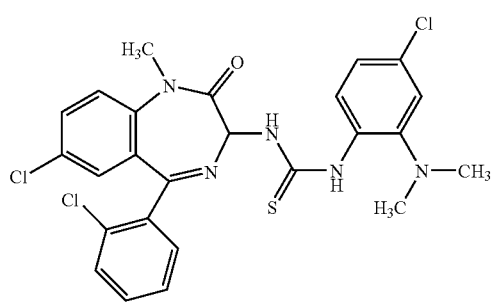
30
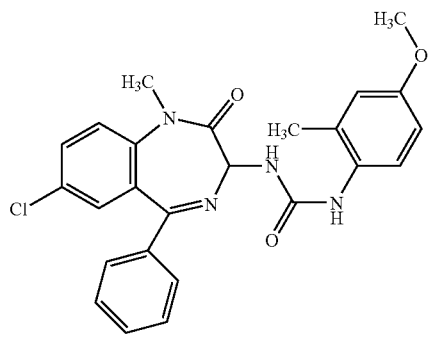

TABLE 2-continued

List of the test samples used in the Biological Evaluation

Test
Sample Nos: Structure of the Test Sample

31

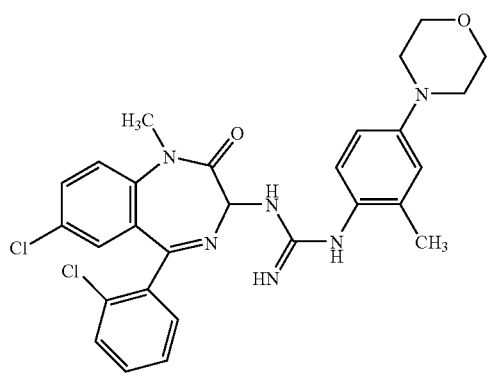

32

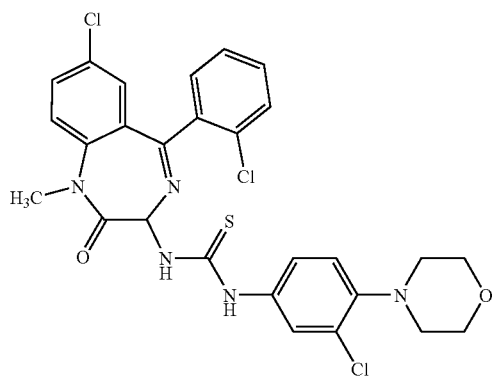

33

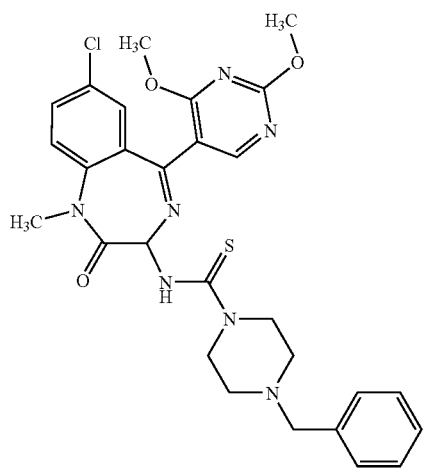

TABLE 3

Biological Data for the testing samples as listed in Table 2

| Test Sample Nos. | Ki (hB2) (nM) |
|---|---|
| 1-33 | 43-3110 |

EXAMPLES

The invention will further be described in more detail by the following Examples which describe methods whereby compounds of the present invention may be prepared, purified, analyzed and biologically tested, and which are not to be construed as limiting the invention.

Intermediate 1

3-amino-7-chloro-1,3-dihydro-1-methyl-5-phenyl-2H-1,4-benzodiazepin-2-one

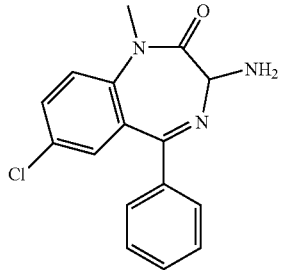

Following General Procedure 1, INTERMEDIATE 1 was obtained as pale brown solid (2.5 g, 77%) and used for the subsequent reaction without further purification. MS (ESI) (M+H)$^+$=300.

Intermediate 2

3-amino-5-(2-bromophenyl)-7-fluoro-1,3-dihydro-1-methyl-2H-1,4-benzodiazepin-2-one

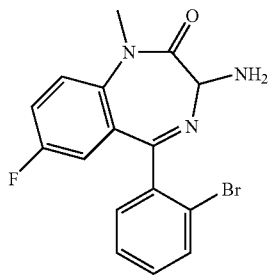

Following General procedure 1, INTERMEDIATE 2 was obtained as a thick pale brown oil (0.5 g, 17%) and used for the subsequent reaction without further purification.

Intermediate 3

3-amino-5-cyclohexyl-1,3-dihydro-1-methyl-2H-1,4-benzodiazepin-2-one

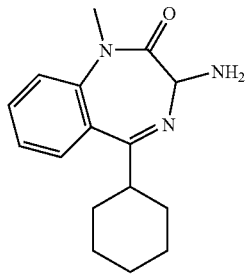

Following General Procedure 1, after flash chromatography (100% EtOAc), INTERMEDIATE 3 was obtained as a pale brown solid (1.25 g, 45%). MS (ESI) (M+H)$^+$=272

Intermediate 4

3-amino-7-chloro-5-(2-chlorophenyl)1,3-dihydro-1-methyl-2H-1,4-benzodiazepin-2-one

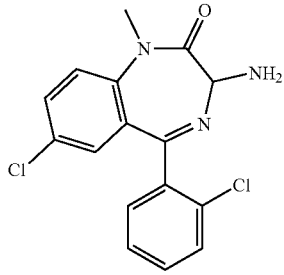

Following General Procedure 1, INTERMEDIATE 4 was obtained as a thick pale brown oil (1.8 g, 65%) and used for the subsequent reaction without further purification. MS (ESI) (M+H)$^+$=334

Intermediate 5

3-amino-1,3-dihydro-1-methyl-5-phenyl-2H-1,4-benzodiazepin-2-one

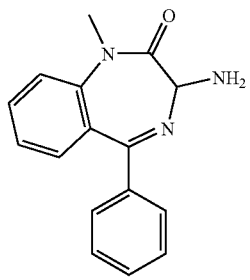

To a stirred solution of (2,3-dihydro-2-oxo-5-phenyl-1H-1,4-benzodiazepin-3-yl)-, phenylmethyl ester-carbamic acid, (4.0 g, 10.3 mmol) in toluene (100 ml) was added Aliquat336 (1.0 g) and 50% aqueous sodium hydroxide (20 ml) followed by methyl iodide (5.0 g, 35 mmol). The reaction mixture was stirred at room temperature for 17 hours. The solvent was evaporated in vacuo and the residue was taken in dichloromethane (150 ml). The organic phase was washed with 2N sodium hydroxide (50 ml) and brine (50 ml); the organic phase was dried over MgSO$_4$, filtered and concentrated in vacuo. The residue was triturated with hexane and the precipitate was treated with conc. HBr as in General Procedure 1. INTERMEDIATE 5 was obtained as a pale brown solid (1.63 g, 59%) and used for the subsequent reaction without further purification. MS (ESI) (M+H)$^+$=266

515

Intermediate 6

3-amino-7-chloro-1,3-dihydro-5-phenyl-1-(2-propenyl)-2H-1,4-benzodiazepin-2-one

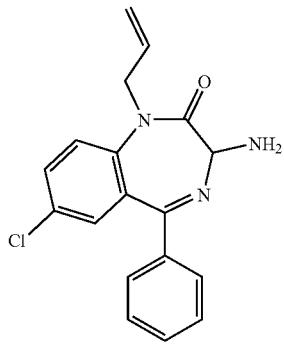

To a stirred solution of (7-chloro-2,3-dihydro-2-oxo-5-phenyl-1-H-1,4-benzodiazepin-3-yl)-, phenylmethyl ester-carbamic acid (1 mmol) in DMF (10 ml) was added cesium carbonate (0.370 g, 1.14 mmol) followed by allyl bromide (0.134 g, 1.1 mmol). The reaction mixture was stirred at room temperature for 5 hours. The solvent was evaporated in vacuo and the residue was taken in EtOAc (50 ml). The organic phase was washed with brine (2×10 ml); the organic phase was dried over MgSO$_4$, filtered and concentrated in vacuo. The crude products were purified by flash chromatography using dichloromethane as the eluent. The crude product was added to conc. HBr (33% in acetic acid) (10 ml) and stirred at room temperature for 3 hours. The reaction mixture was poured into ether (100 ml), the precipitate was collected and then taken in dichloromethane (50 ml) and washed with 2N NaOH (2×10 ml). The organic phase dried over MgSO4, filtered and concentrated in vacuo. The title compound was obtained as a pale yellow solid (0.19 g, 60%) and used for the subsequent reaction without further purification. MS (ESI) (M+H)$^+$=326

Intermediate 7

7-chloro-1,3-dihydro-3-isothiocyanato-1-methyl-5-phenyl-2H-1,4-benzodiazepin-2-one

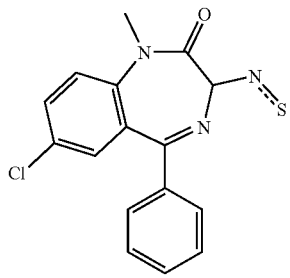

Following General Procedure 2, INTERMEDIATE 7 was obtained as a pale yellow solid (0.7 g, 69%). $^1$H-NMR (CDCl$_3$): δ 7.66-7.64 (m, 2H), 7.60-7.57 (dd, J=2.4 Hz and 8.8 Hz, 1H), 7.55-7.51 (m, 1H), 7.47-7.43 (m, 2H), 7.36-7.34 (m, 2H) and 3.48 (s, 4H) MS (ESI) (M+H)$^+$=342

516

Intermediate 8

7-chloro-5-(2-chlorophenyl)-1,3-dihydro-3-isothiocyanato-1-methyl-2H-1,4-benzodiazepin-2-one

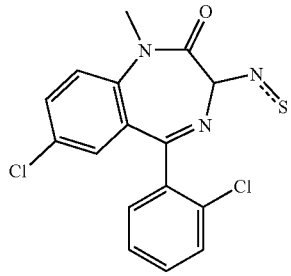

Following General Procedure 2, after flash chromatography (dichloromethane), the title compound was obtained as pate yellow solid (2.2 g, 65%). $^1$H-NMR (CDCl$_3$): δ 7.66-7.64 (m, 1H), 7.56-7.53 (dd, J=2.4 Hz and 8.8 Hz, 1H), 7.46-7.43 (m, 2H), 7.39-7.37 (m, 1H), 7.05 (d, J=2.0 Hz, 1H), 3.73 (s, 1H) and 3.51 (s, 3H). MS (ESI) (M+H)$^+$=376

Example 1

N-(7-chloro-2,3-dihydro-1-methyl-2-oxo-5-phenyl-1H-1,4-benzodiazepin-3-yl)-N'-(5isoquinolinyl)-thiourea

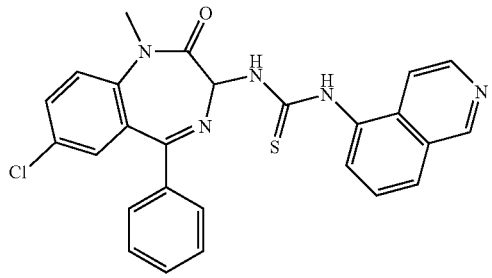

Scheme:

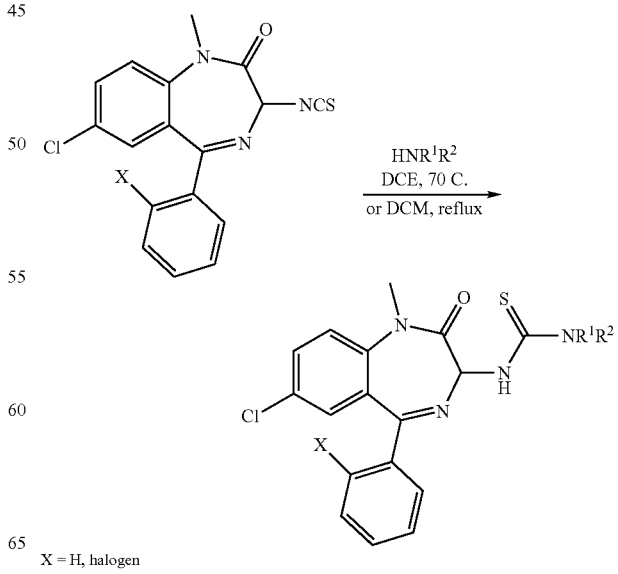

X = H, halogen

As illustrated in the scheme above, to a solution of 7-chloro-1,3-dihydro-3-isothiocyanato-1-methyl-5-phenyl-2H-1,4-benzodiazepin-2-one (INTERMEDIATE 7) (0.035 g, 0.1 mmol) in dichloromethane (5 ml) was added 5-isoquinolinamine (0.015 g, 0.1 mmol). The reaction mixture was heated at reflux for 17 hours. The solvent was evaporated in vacuo, the residue was triturated with ether and the title compound was obtained as a colorless solid (20 mg, 40%). $^1$H-NMR (CDCl$_3$): δ 9.33 and 9.19 (2×s, 1H), 8.63 and 8.49 (2×d, J=5.6 Hz and J=6.0 Hz, 1H), 8.34 (br s, 1H), 8.02 (d, J=8.4 Hz, 1H), 7.92 (t, J=11.6 Hz, 2H), 7.58-7.32 (m, 10H), 6.03 (d, J=7.6 Hz, 1H) and 3.3 (s, 3H). MS (ESI) (M+H)$^+$=486

Example 2

N-(7-chloro-2,3-dihydro-1-methyl-2-oxo-5-phenyl-1H-1,4-benzodiazepin-3-yl)-N'-[4(dimethylamino)phenyl]-thiourea

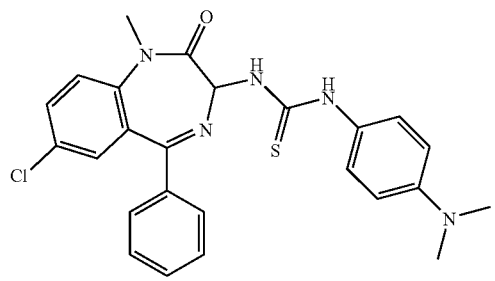

To a solution of 7-chloro-1,3-dihydro-3-isothiocyanato-1-methyl-5-phenyl-2H-1,4-benzodiazepin-2-one (INTERMEDIATE 7) (0.342 g, 1 mmol) in dichloromethane (20 ml) was added N,N-dimethyl-1,4-benzenediamine (0.136 g, 1 mmol). The reaction mixture was heated at reflux for 17 hours. The solvent was evaporated in vacuo, the residue was triturated with ether and the title compound was obtained as a colorless solid (0.167 g, 35%). $^1$H-NMR (CDCl$_3$): δ 7.70-7.22 (m, 10H), 6.75 (d, J=8.8 Hz, 2H), 6.05 (d, J=7.6 Hz, 1H), 3.42 (s, 3H) and 2.98 (s, 6H). MS (ESI) (M+H)$^+$=478.

Example 3

N-(7-chloro-2,3-dihydro-1-methyl-2-oxo-5-phenyl-1H-1,4-benzodiazepin-3-yl)-N'-[4(dimethylamino)-1-naphthalenyl]-N-methyl-thiourea

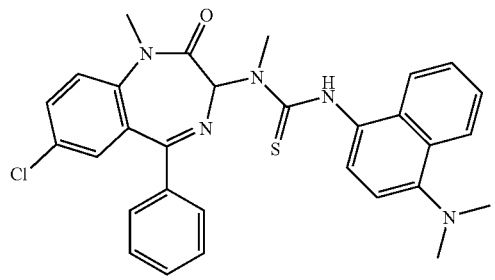

To a stirred solution of carboxybenzyl-3-amino-7-chloro-5-phenyl-2-oxo-1,4-benzodiazepine (EXAMPLE 6) (1 mmol) in DMF(10 ml) was added cesium carbonate (5 mmol) followed by methyl iodide (2.2 mmol). The reaction mixture was stirred at room temperature for 5 hours. The solvent was evaporated in vacuo and the residue was taken in EtOAc (50 ml). The organic phase was washed with brine (2×10 ml); the organic phase was dried over MgSO$_4$, filtered and concentrated in vacuo. The product (0.8 mmol) was added to conc. HBr (35% in acetic acid) (10 ml) and was stirred at room temperature for 3 hours. The reaction mixture was poured into ether (30 ml), the precipitate was collected, and taken in dichloromethane (25 ml) and washed with 2N NaOH (2×10 ml). The organic phase was dried over MgSO$_4$, filtered and concentrated in vacuo. The product was used for the subsequent steps without further purification.

To a solution of the product above (0.03 g, 1 mmol) in dichloroethane (5 ml) was added 4-isothiocyanato-N,N-dimethyl-1-naphthalenamine (0.025 g, 1 mmol). The reaction mixture was stirred at 70 C for 4 hours. The solvent was evaporated in vacuo, the residue was triturated with ether and the title compound was obtained as a colorless solid (28 mg, 52%). $^1$H-NMR (CDCl$_3$): δ 8.24 (m, 1H), 7.92 (m, 1H), 7.67 (d, J=7.2 Hz, 2H), 7.52-7.40 (m, 8H), 7.31 (d, J=1.6 Hz, 1H), 7.05 (d, J=8.0 Hz, 2H), 3.78 (s, 3H), 3.41 (s, 3H) and 2.91 (s, 6H). MS (ESI) (M+H)$^+$=542.

Example 4

N-[7-chloro-5-(2-chlorophenyl)-2,3-dihydro-1-methyl-2-oxo-1H-1,4-benzodiazepin-3-yl]-N'-[4-(dimethylamino)-1-naphthalenyl]-thiourea

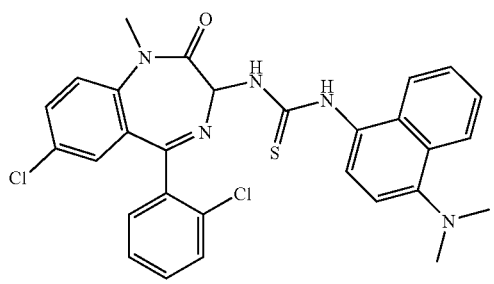

To a solution of 3-amino-7-chloro-5-(2-chlorophenyl)-1,3-dihydro-1-methyl-2H-1,4-benzodiazepin-2-one (INTERMEDIATE 8) (0.03 g, 1 mmol) in dichloroethane (5 ml) was added 4-isothiocyanato-N,N-dimethyl-1-naphthalenamine (0.025 g, 1 mmol). The reaction mixture was stirred at 70° C. for 4 hours. The solvent was evaporated in vacuo, the residue was triturated with ether and the title compound was obtained as a colorless solid (35 mg, 60%). $^1$H-NMR (CDCl$_3$): δ 8.26 (d, J=8.4 Hz, 1H), 8.03 (d, J=7.6 Hz, 1H), 7.93 (br s, 1H), 7.73-7.06 (m, 11H) 6.10 (d, J=7.6 Hz, 1H), 3.40 (s, 3H) and 2.92 (s, 6H). MS (ESI) (M+H)$^+$=562.

Example 5

N-[7-chloro-2,3-dihydro-2-oxo-5-phenyl-1-(2-propenyl)-1H-1,4-benzodiazepin-3-yl]-N'-[4-(dimethylamino)-1-naphthalenyl]-thiourea

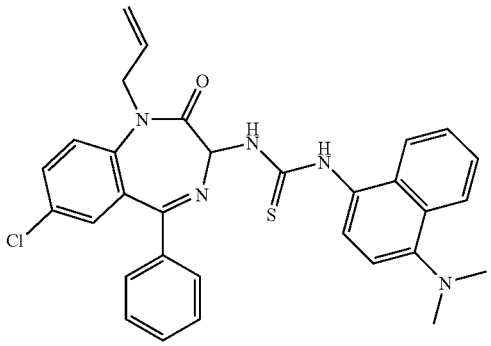

A solution of 3-amino-7-chloro-1,3-dihydro-5-phenyl-1-(2-propenyl)-2H-1,4-benzodiazepin-2-one (INTERMEDIATE 6) (0.162 g, 0.5 mmol) in dichloroethane (5 ml) was added 4-isothiocyanato-N,N-dimethyl-1-naphthalenamine (0.115 g, 0.5 mmol). The reaction mixture was stirred at 70° C. for 4 hours; The solvent was evaporated in vacuo, the residue was triturated with ether and the title compound was obtained as a colorless, solid (0.152 g, 55%). $^1$H-NMR (CDCl$_3$): δ 8.29-8.27 (m, 1H), 8.08-8.06 (m, 1H), 7.90 (s, 1H), 7.60-7.36 (m, 10H), 7.32 (d, J=2.4 Hz, 1H), 7.09 (d, J=8 Hz, 1H), 6.14 (d, J=7.6 Hz, 1H), 5.76-5.69 (m, 1H), 5.15 (s, 1H), 5.12 (dd, J=1.2 and 7.0 Hz, 1H), 4.57-4.39 (m, 2H) and 2.93 (s, 6H). MS (ESI) (M+H)$^+$=554.

Example 6

N-(7-chloro-2,3-dihydro-1-methyl-2-oxo-5-phenyl-1H-1,4-benzodiazepin-3-yl)-N'-[4-(dimethylamino)-1-naphthalenyl]-thiourea

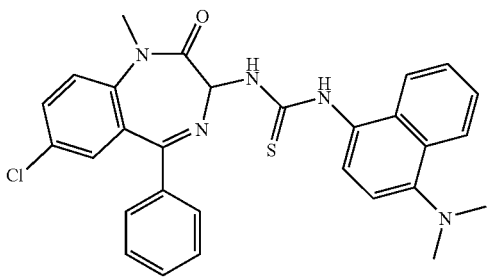

To a solution of 3-amino-7-chloro-5-phenyl-1,3-dihydro-1-methyl-2H-1,4-benzodiazepin-2-one (INTERMEDIATE 1) (0.299 g, 1 mmol) in dichloroethane (15 mi) was added 4-isothiocyanato-N,N-dimethyl-1-naphthalenamine (0.230 g, 1 mmol). The reaction mixture was stirred at room temperature for 17 hours. The solvent was evaporated in vacuo, the residue was triturated with ether and the title compound was obtained as a colorless solid (0.345 g, 65%). $^1$H-NMR (CD$_3$OD): δ 8.25 (d, 8.4 Hz, 2H), 8.00 (d, J=8.4 Hz, 1H), 7.88 (d, J=8.4 Hz, 1H), 7.85-7.81 (m, 2H), 7.77-7.72 (m, 2H), 7.65 (d, J=8.8 Hz, 1H), 7.61-7.58 (m, 4H), 7.51-7.47 (m, 2H), 7.29 (d, J=2.4 Hz, 1H), 6.01 (s, 1H) and 3.49 (s, 9H). MS (ESI) (M+H)$^+$=528.

Example 7

N-(7-chloro-2,3-dihydro-1-methyl-2-oxo-5-phenyl-1H-1,4-benzodiazepin-3-yl)-N'-(4-methoxy-2-methylphenyl)-urea

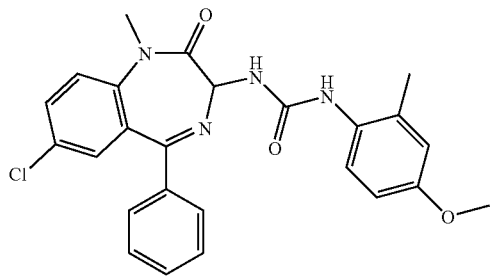

To a solution of 3-amino-7-chloro-5-phenyl-1,3-dihydro-1-methyl-2H-1,4-benzodiazepin-2-one (INTERMEDIATE 1) (0.299 g, 1 mmol) in dichloromethane (15 ml) was added 1-isocyanato-4-methoxy-2-methyl-benzene (0.163 g, 1 mmol). The reaction mixture was stirred at room temperature for 17 hours. The solvent was evaporated in vacuo, the residue was triturated with ether and the title compound was obtained as a colorless solid (0.197 g, 42%). $^1$H-NMR (CDCl$_3$): δ 7.57-7.48 (m, 3H), 7.47-7.44 (m, 1H), 7.39-7.38 (m, 3H), 7.36-7.29 (m, 2H), 6.77-6.73 (m, 2H), 6.71 (d, J=2.8 Hz, 1H), 6.61 (s, 1H), 5.51 (d, J=8.4 Hz, 1H), 3.78 (s, 3H), 3.39 (s, 3H) and 2.29 (s, 3H). MS (ESI) (M+H)$^+$=463.

Example 8

N-(7-chloro-2,3-dihydro-1-methyl-2-oxo-5-phenyl-1H-1,4-benzodiazepin-3-yl)-N'-[4-(dimethylamino)-1-naphthalenyl]-urea

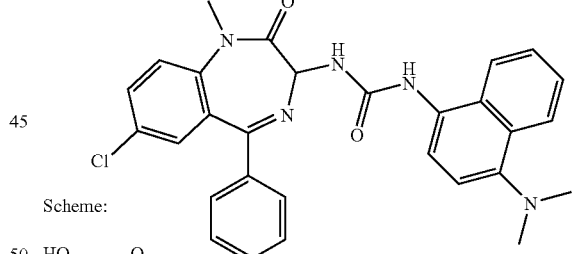

Scheme:

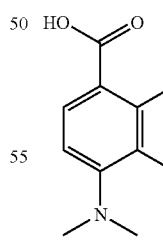

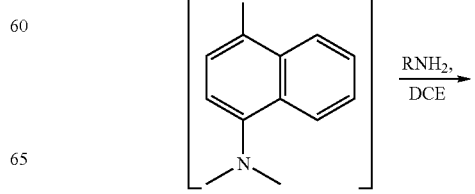

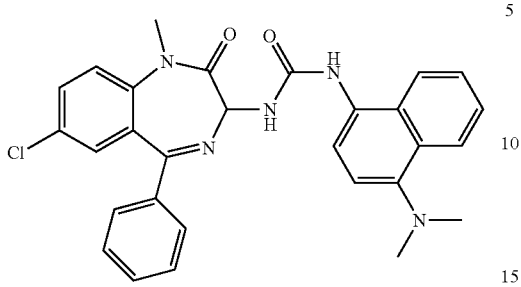

As illustrated in the scheme above, a mixture of 4-(dimethylamino)-1-naphthalenecarboxylic acid (0.1 mmol), diphenylphosphoryl azide (0.15 mmol) and triethylamine (0.3 mmol) in toluene (10 ml) was heated at reflux overnight. The solvent was evaporated in vacuo, and then the residue was redissolved in dichloroethane, added to INTERMEDIATE 1 (0.08 mmol) and heated at 70° C. for 4 hours. The solvent was evaporated in vacuo and the residue was taken in dichloromethane (50 ml). The organic phase was washed with brine (2×10 ml); the organic phase was dried over MgSO$_4$, filtered and concentrated in vacuo. The residue was triturated with ether and the title compound was obtained as a colorless solid (9 mg, 22%); $^1$H-NMR (CDCl$_3$): δ 8.27 (m, 1H), 8.11 (m, 1H), 7.60 (d, J=8 Hz, 1H), 7.77-7.29 (m, 10H), 7.08 (d, J=8.4 Hz, 1H), 6.75 (br s, 2H), 5.56 (d, J=8.4 Hz, 1H), 3.39 (s, 3H) and 2.90 (s, 6H); MS (ESI) (M+H)$^+$=512.

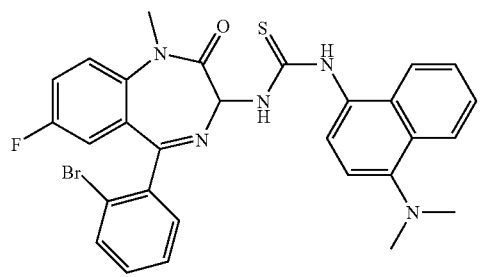

As illustrated in the scheme above, INTERMEDIATE 2 (0.018 g, 0.05 mmol) and 4-isothiocyanato-N,N-dimethyl-1-naphthalenamine (0.011 g, 0.05 mmol) was heated in dichloroethane (4 mL) at 70° C. overnight. The solvent was evaporated in vacuo and the residue was triturated with ether (2×10 ml). The title compound (0.021 g, 72%) was obtained as a colorless solid. $^1$H-NMR (CDCl$_3$): δ 8.26 (m, 1H), 8.06 (m, 1H), 7.85 (s, 1H), 7.79 (m, 1H), 7.69-7.24 (m, 8H), 7.08 (d, J=8.0 Hz, 1H), 7.02 (t, J=8.4 Hz, 1H), 6.06 (d, J=8.0 Hz, 1H), 3.39 (s, 3H), 2.93 (s, 6H). (ESI) (M+H)$^+$=591.

Example 9

N-[5-(2-bromophenyl)-7-fluoro-2,3-dihydro-1-methyl-2-oxo-1H-1,4-benzo-diazepin-3-yl]-N'-[4-(dimethylamino)-1-naphthalenyl]-thiourea

Example 10

N-[7-chloro-5-(2-chlorophenyl)-2,3-dihydro-1-methyl-2-oxo-1H-1,4-benzo-diazepin-3-yl]-N''-cyano-N'-[4-(4-morpholinyl)-1-naphthalenyl]-guanidine (E and Z isomers Separated but not Identified)

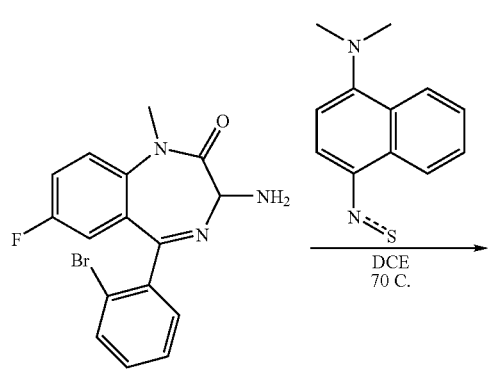

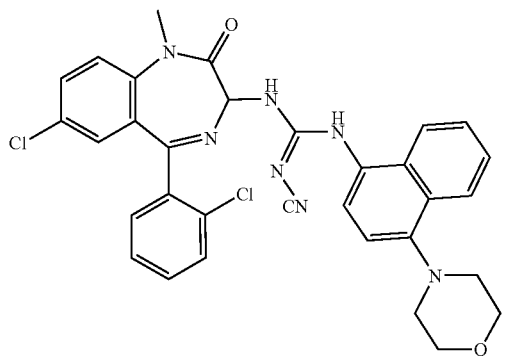

Scheme:

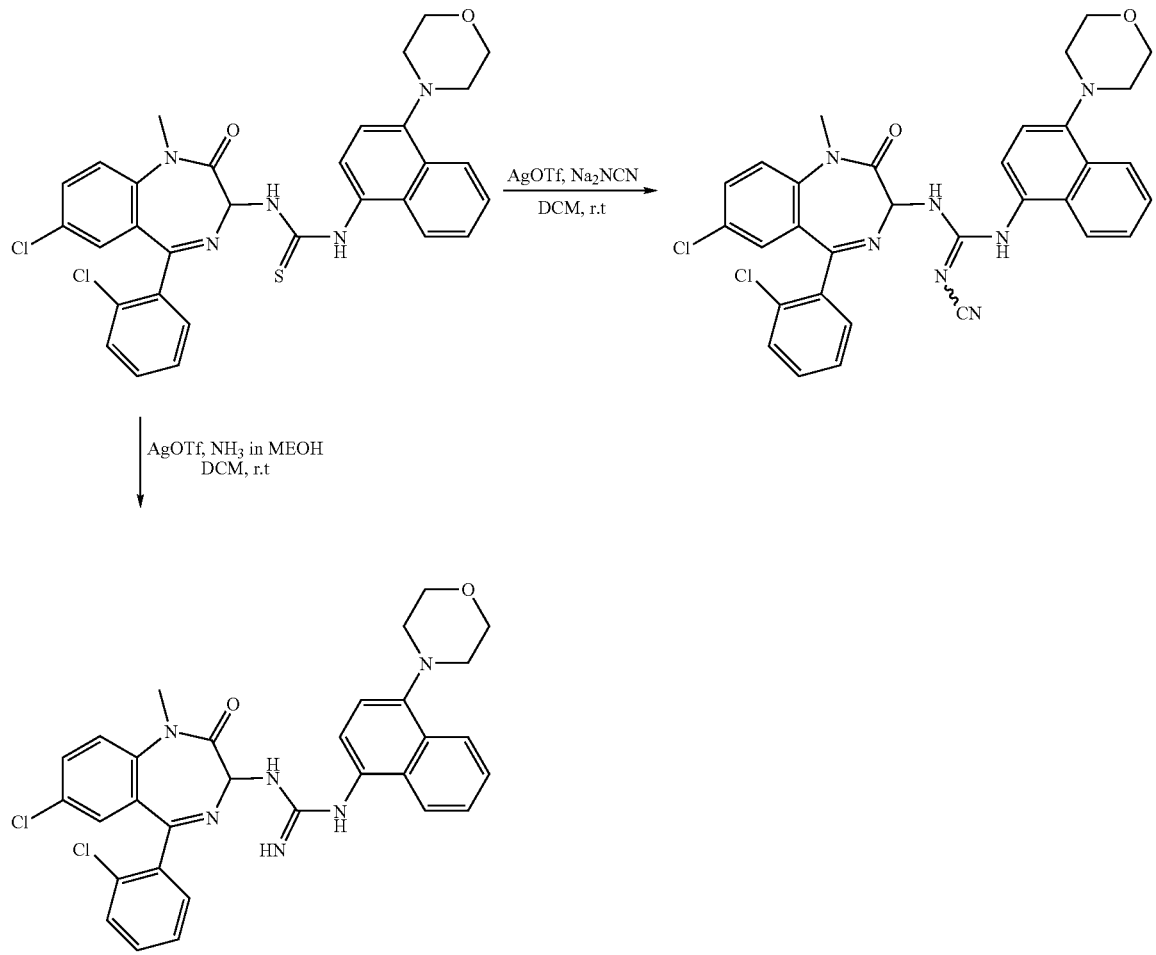

As illustrated in the scheme above, a solution of N-[7-chloro-5-(2-chlorophenyl)-2,3-dihydro-1-methyl-2-oxo-1H-1,4-benzodiazepin-3-yl]-N'-[4-(4-morpholinyl)-1-naphthalenyl]-thiourea (EXAMPLE 11, made according to General Procedure 3) (0.058 g, 0.1 mmol) and silver triflate (0.077 g, 0.3 mmol) in dichloromethane (2 ml) was combined with cyanamide disodium salt (1 mmol) and stirred at room temperature for 3 h. The reaction mixture was then diluted with dichloromethane (10 ml) and washed with brine (2×5 ml). The organic phase was dried over MgSO$_4$, filtered and concentrated in vacuo. The residue was washed with ether (2×10 ml) and the polar isomer of the title compound (0.023 g, 380%) was obtained as pale yellow solid. The ether layer was concentrated in vacuo and purified by column chromatography (1:1 EtOAc:CH$_2$Cl$_2$) to give the non-polar isomer of the title compound (0.009 g, 15%) as a colorless solid.

Example 10A

N-[7-chloro-5-(2-chlorophenyl)-2,3-dihydro-1-methyl-2-oxo-1H-1,4-benzo-diazepin-3-yl]-N''-cyano-N'-[4-(4-morpholinyl)-1-naphthalenyl]-guanidine
(polar isomer)

$^1$H-NMR (CDCl$_3$): δ 8.26 (m, 1H), 7.9 (m, 2H), 7.69 (d, J=12.0 Hz, 2H), 7.53-7.46 (m, 4H), 7.39 (m, 1H), 7.30-7.23 (m, 4H), 7.11 (m, 2H), 3.98 (t, J=9.2 Hz, 2H), 3.48 (s, 3H) and 3.12 (br.s, 6H). (ESI) (M+H)$^+$=612

Example 10B

N-[7-chloro-5(2-chlorophenyl)-2,3-dihydro-1-methyl-2-oxo-1H-1,4-benzo-diazepin-3-yl]-N'''-cyano-N'-[4-(4-morpholinyl)-1-naphthalenyl]-guanidine (nonpolar isomer)

$^1$H-NMR (CDCl$_3$): δ 8.25 (m, 1H), 8.03 (m, 1H), 7.66-7.53 (m, 5H), 7.44-7.40 (m, 3H), 7.39-7.30 (m, 2H), 7.09 (m, 2H), 6.54 (d, J=7.6 Hz, 1H), 5.48 (d, J=7.6 Hz, 1H), 3.99 (t, J=9.2 Hz, 4H), 3.39 (s, 3H) and 3.15 (br.s, 4H). (ESI) (M+H)$^+$=612.

Example 11

N-[7-chloro-5-(2-chlorophenyl)-2,3-dihydro-1-methyl-2-oxo-1H-1,4-benzodiazepin-3-yl]-N'-[4-(4-morpholinyl)-1-naphthalenyl]-thiourea

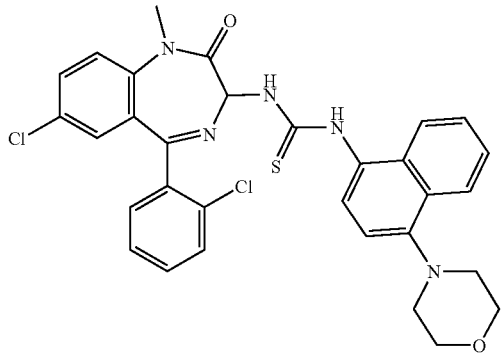

Following General Procedure 3, the title compound (0.078 g, 65%) was obtained as a white solid. $^1$H-NMR (CDCl$_3$): δ 8.4 (m, 1H), 8.08 (m, 2H), 7.72 (m, 1H), 7.64 (d, J=8 Hz, 1H), 7.6-7.5 (m, 4H), 7.39 (t, J=4.4 Hz, 2H), 7.30 (d, J=8.8 Hz, 2H), 7.10 (m, 2H), 6.09 (d, J=7.6 Hz, 1H), 3.98 (t, J=4.4 Hz, 4H) 3.40 (s, 3H), and 3.13 (m, 4H). (ESI) (M+H)$^+$=604.

Example 12

N-[7-chloro-5-(2-chlorophenyl)-2,3-dihydro-1-methyl-2-oxo-1H-1,4-benzo-diazepin-3-yl]-N'-[4(4-morpholinyl)-1-naphthalenyl]-guanidine

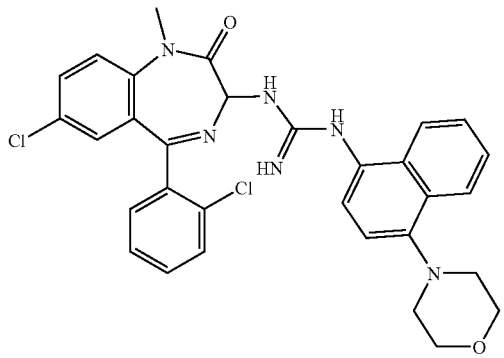

As illustrated in the scheme above, to a solution of N-[7-chloro-5-(2-chlorophenyl)-2,3-dihydro-1-methyl-2-oxo-1H-1,4-benzodiazepin-3-yl]-N'-[4-(4-morpholinyl)-1-naphthalenyl]-thiourea (EXAMPLE 11) (0.029 g, 0.05 mmol) and silver triflate (0.038 g, 0.15 mmol) in dichloromethane (2 ml) was added a solution of ammonia (0.25 ml, 2M in methanol). The reaction mixture was stirred at room temperature for 3 h, diluted with dichloromethane (10 ml) and washed with brine (2×5 ml). The organic layer was dried with MgSO4 filtered, concentrated in vacuo. The residue was triturated with ether to give the title compound (0.008 g, 28%) as a pale yellow solid. $^1$H-NMR (CDCl$_3$): δ 8.22 (d, J=9.2 Hz, 1H), 8.11 (d, J=8.4 Hz, 1H), 7.75 (br.s, 1H), 7.50-7.41 (m, 7H), 7.31 (d, J=8.8 Hz, 1H), 7.04 (m, 2H), 5.8 (br.s, 1H), 3.96 (t, J=9.2 Hz, 4H) 3.51 (s, 3H) and 3.05 (br.s, 4H).). (ESI) (M+H)$^+$=587.

Example 13

N-[7-chloro-5-(2-chlorophenyl)-2,3-dihydro-1-methyl-2-oxo-1H-1,4-benzo-diazepin-3-yl]-N'-[2-methyl-4-(4-morpholinyl)phenyl]-thiourea

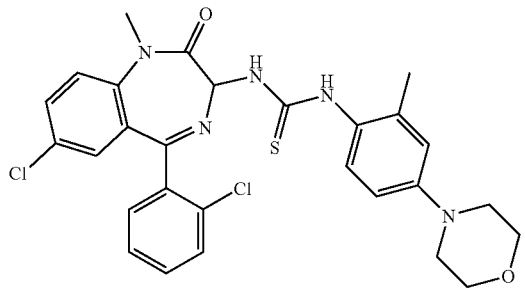

Following General Procedure 3, the title compound (0.096 g, 85%) was obtained as a colorless solid. $^1$H-NMR (CDCl$_3$): δ 7.74 (m, 1H), 7.54 (s, 1H), 7.51 (m, 1H), 7.42-7.39 (m, 3H), 7.34-7.31 (m, 2H), 7.24 (d, J=8.8 Hz, 1H), 7.09 (d, J=2.4 Hz, 1H), 6.80-6.76 (m, 2H), 6.09 (d, J=7.6 Hz, 1H), 3.85 (t, J=9.6 Hz, 4H), 3.44 (s, 3H), 3.17 (t, J=10.0 Hz, 4H) and 2.32 (s, 3H). (ESI) (M+H)$^+$=568.

Example 14

N-[7-chloro-5-(2-chlorophenyl)-2,3-dihydro-1-methyl-2-oxo-1H-1,4-benzo-diazepin-3-yl]-N'-[4-(dimethylamino)-2-methylphenyl]-thiourea

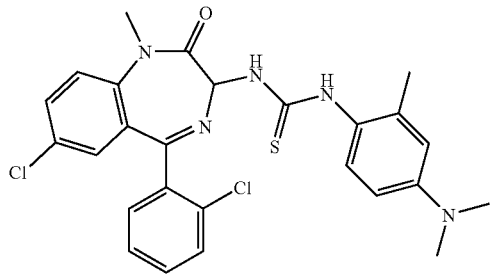

Following the General Procedure 3, the title compound (0.052 g, 51%) was obtained as a pale brown solid. $^1$H-NMR (CDCl$_3$): δ 7.75 (m, 1H), 7.52 (dd, J=8.8 Hz, 1H), 7.47 (s, 1H), 7.42-7.40 (m, 3H), 7.34-7.31 (m, 2H), 7.19 (d, J=8.0 Hz, 1H), 7.09 (d, J=2.0 Hz, 1H), 6.60 (br.s, 1H), 6.58 (br.s, 1H), 6.09 (d, J=8.0 Hz, 1H), 3.44 (s, 3H), 2.97 (s, 6H) and 2.30 (s, 3H). (ESI) (M+H)+=526.

Example 15

N-[7-chloro-5-(2-chlorophenyl)-2,3-dihydro-1-methyl-2-oxo-1H-1,4-benzo-diazepin-3-yl]-N'-[4-(dimethylamino)-3-methylphenyl]-thiourea

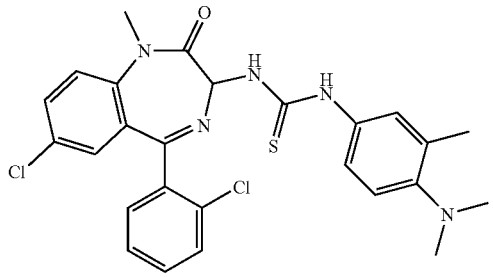

Following General Procedure 3, the title compound (0.034 g, 35%) was obtained as a pale brown solid. $^1$H-NMR (CDCl$_3$): δ 7.86 (d, J=7.6 Hz, 1H), 7.76 (m, 1H), 7.53 (dd, J=8.8 Hz, 1H), 7.42-7.39 (m, 2H), 7.36-7.32 (m, 2H), 7.17 (dd, J=8.8 Hz, 1H), 7.12 (d, J=2.0 Hz, 1H), 7.10 (d, J=2.4 Hz, 1H), 7.06 (d, J=8.4 Hz, 1H), 6.09 (d, J=7.6 Hz, 1H), 3.46 (s, 3H), 2.71 (s, 6H) and 2.33 (s, 3H). (ESI) (M+H)$^+$=526.

Example 16

N-[7-chloro-5-(2-chlorophenyl)-2,3-dihydro-1-methyl-2-oxo-1H-1,4-benzo-diazepin-3-yl]-N'-[3-chloro-4-dimethylamino)phenyl]-thiourea

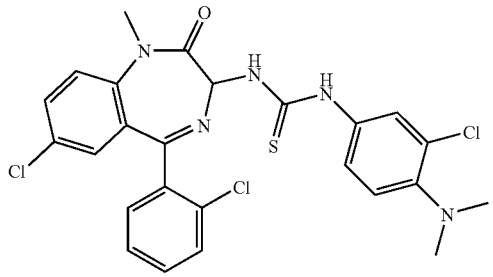

Following the General Procedure 3, the title compound (0.025 g, 23%) was obtained as a pale brown solid. $^1$H-NMR (CDCl$_3$): δ 7.86 (s, 1H), 7.83 (d, J=7.2 Hz, 1H), 7.5 (m, 1H), 7.53 (dd, J=8.8 Hz, 1H), 7.43-7.40 (m, 2H), 7.35-7.33 (m, 2H), 7.28 (m, 1H), 7.10 (s, J=2.0 Hz, 1H), 7.05 (d, J=7.2 Hz, 1H), 6.06 (d, J=7.2 Hz, 1H), 3.47 (s, 3H) and 2.82 (s, 6H). (ESI) (M+H)$^+$=546.

Example 17

N-[7-chloro-5-(2-chlorophenyl)-2,3-dihydro-1-methyl-2-oxo-1H-1,4-benzo-diazepin-3-yl]-N'-[4-(dimethylamino)-3-(trifluoromethyl)phenyl]-thiourea

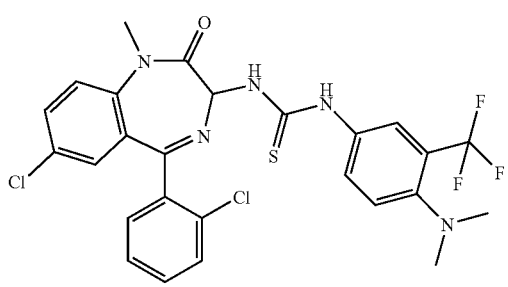

Following General Procedure 3, the title compound (0.017 g, 18%) was obtained as a pale brown solid. $^1$H-NMR (CDCl$_3$): δ 7.93 (s, 1H), 7.85 (d, J=7.2 Hz, 1H), 7.38 (m, 1H), 7.58 (d, J=8.4 Hz, 1H), 7.55-7.53 (m, 2H), 7.42-7.40 (m, 2H), 7.34 (m, 3H), 7.10 (s, J=2.0 Hz, 1H), 6.06 (d, J=7.6 Hz, 1H), 3.47 (s, 3H) and 2.76 (s, 6H). (ESI) (M+H)$^+$=580.

Example 18

N-[7-chloro-5(2-chlorophenyl)-2,3-dihydro-1-methyl-2-oxo-1H-1,4-benzo-diazepin-3-yl]-N'-[4-chloro-2-(dimethylamino)phenyl]-thiourea

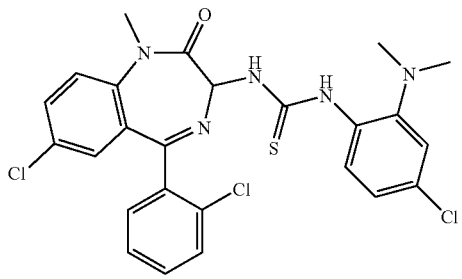

Following the General Procedure 3, the title compound (0.024 g, 22%) was obtained as a pale brown solid. $^1$H-NMR (CDCl$_3$): δ 8.55 (d, J=7.2 Hz, 1H), 7.84 (s, 1H), 7.77 (t, J=4.8 Hz, 1H), 7.53 (dd, J=8.8 Hz, 1H), 7.46 (d, J=8.4 Hz, 1H), 7.42-7.41 (m, 2H), 7.36-7.34 (m, 3H), 7.11-7.02 (m, 2H), 60.6 (d, J=7.2 Hz, 1H), 3.48 (s, 3H) and 2.75 (s, 6H). (ESI) (M+H)$^+$=546.

Example 19

N-[7-chloro-5-(2-chlorophenyl)-2,3-dihydro-1-methyl-2-oxo-1H-1,4-benzo-diazepin-3-yl]-N'-[4-(diethylamino)-2-(dimethylamino)phenyl]-thiourea

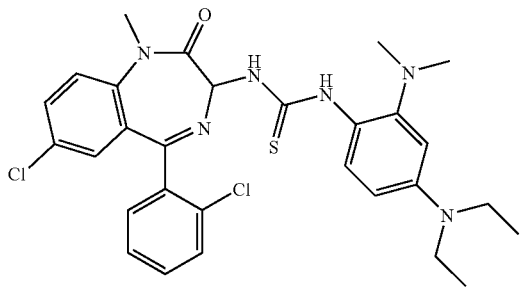

Following the General Procedure 3, the title compound (0.040 g, 35%) was obtained as a pale gray solid. $^1$H-NMR (CDCl$_3$): δ 9.4 (s, 1H), 8.22 (s, 1H), 7.76 (m, 1H), 7.52 (dd, J=8.8 Hz, 1H), 7.40 (m, 2H), 7.35 (m, 2H), 7.10 (d, J=2.4 Hz, 1H), 7.03 (d, J=8.8 Hz, 1H), 6.84 (s, 1H), 6.49 (dd, J=8.8 Hz, 1H), 6.11 (d, J=7.2 Hz, 1H), 3.47 (s, 3H) 3.33 (m, 4H), 2.65 (s, 6H) and 1.38 (t, J=14.0 Hz, 6H). ESI (M+H)$^+$=583.

Example 20

N-[(1E)-[[7-Chloro-5-(2-chlorophenyl)-2,3-dihydro-1-methyl-2-oxo-1H-1,4-benzodiazepin-3-yl]amino][[4-(4-morpholinyl)-1-naphthalenyl]amino]methylene]urea

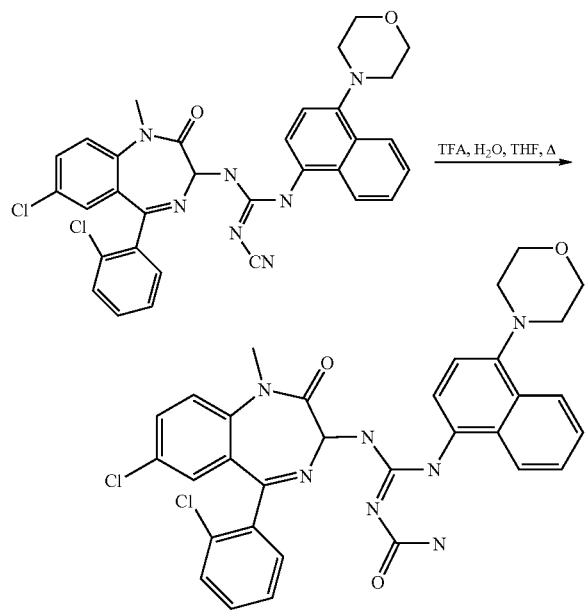

A mixture of N-[7-chloro-5-(2-chlorophenyl)-2,3-dihydro-1-methyl-2-oxo-1H-1,4-benzodiazepin-3-yl]-N''-cyano-N'-[4-(4-morpholinyl)-1-naphthalenyl]guanidine (EXAMPLE 10) (21.9 mg, 35.8 μmol), water (4.6 μL, 260 μmol) and trifluoroacetic acid (19.8 μL, 257 μmol) in THF (3 mL) was heated to reflux for 43 h. The reaction was concentrated in vacuo, and the residue was purified by reverse phase HPLC (gradient 20-70% CH$_3$CN in H$_2$O) to provide the title compound (0.0092 g, 35%) as its TFA salt. $^1$H-NMR (CD$_3$OD): δ 8.37 (br s, 1H), 8.06 (br s, 1H), 7.75-7.41 (br m, 9H), 7.26 (br s, 1H), 7.04 (br s, 1H), 5.66 (br s, 1H), 4.00 (br s, 4H), 3.58 (br s, 3H), 3.17 (br s, 4H). HRMS calculated for (C$_{32}$H$_{29}$Cl$_2$N$_7$O$_3$+H) (M+H)$^+$: 630.1787. Found (ESI): 630.1800.

Example 21

N'-[7-Chloro-5-(2-chlorophenyl)-2,3-dihydro-1-methyl-2-oxo-1H-1,4-benzodiazepin-3-yl]-N-methyl-N-[2-methyl-4-(4-morpholinyl)phenyl]thiourea

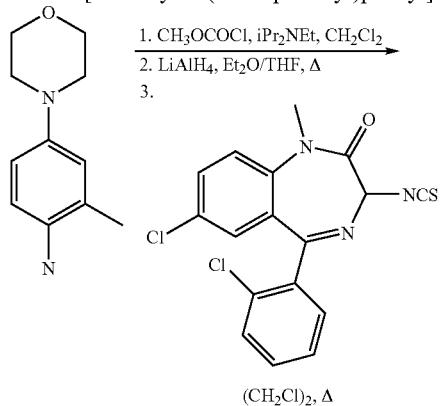

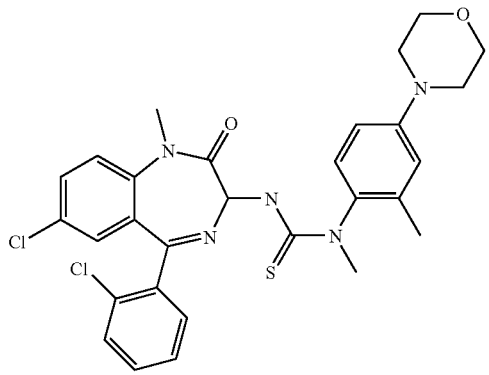

A solution of 2-methyl-4-(4-morpholinyl)benzenamine (53.3 mg, 0.277 mmol) and diisopropylethylamine (0.063 mL, 0.36 mmol) in CH$_2$Cl$_2$ (1 mL) was cooled to 0° C. Methyl chloroformate (0.024 mL, 0.31 mmol) was added dropwise, and then the reaction was allowed to warm to room temperature and stir overnight. The reaction was diluted with CH$_2$Cl$_2$ (20 mL) and washed with brine (10 mL). The organic phase was dried over Na$_2$SO$_4$, filtered, and concentrated in vacuo. The crude product was then suspended in a 1:2 mixture of Et$_2$O:THF (6 mL). A solution of LiAlH$_4$ in Et$_2$O (0.34 mL of a 1 M solution, 0.34 mmol) was added dropwise, and then the reaction mixture was heated to reflux for 1.5 h. The reaction was cooled, diluted with additional Et$_2$O (8 mL), and quenched with Na$_2$SO$_4$5H$_2$O (0.98 g, 4.2 mmol). After stirring for 15 minutes, the mixture was filtered and the reaction was concentrated in vacuo. A portion of this crude aniline (0.0580 g, 0.281 mmol) was dissolved in (CH$_2$Cl)$_2$ (8 mL), and 7-chloro-5-(2-chlorophenyl)-1,3-dihydro-3-isothiocyanato-1-methyl-2H-1,4-benzodiazepin-2-one (0.106 g, 0.281 mmol) was added. The resulting mixture was heated at 70° C. for 14 h. The reaction was cooled and concentrated in vacuo, and the residue was purified by silica gel column chromatography (7:1 CH$_2$Cl$_2$:EtOAc) to provide the title compound (0.1211 g, 74%). Due to hindered rotation about one of the bonds, rotamers were observed in the $^1$H-NMR spectrum. $^1$H-NMR (CDCl$_3$): δ 7.77-7.68 (m, 1H), 7.51 (dd, J=2.4 Hz, J=8.8 Hz, 1H), 7.43-7.36 (m, 2H), 7.34-7.28 (m, 2H), 7.16 (t, J=8.4 Hz, 1H), 7.10-7.01 (m, 2H), 6.86-6.76 (m, 2H), 6.14 and 6.10 (2×d, J=8.0 Hz, J=7.6 Hz, 1H), 3.88-3.82 (br m, 4H), 3.60 and 3.59 (2×s, 3H), 3.41 (s, 3H), 3.19 (br s, 4H), 2.24 and 2.23 (2×s, 3H). MS (ESI) (M+H)$^+$=582. HRMS calculated for (C$_{29}$H$_{29}$Cl$_2$N$_5$O$_2$S+H) (M+H)$^+$: 582.1497. Found (ESI): 582.1448.

Intermediate 9

6-Chloro-1-methyl-2H-3,1-benzoxazine-2,4(1H)-dione

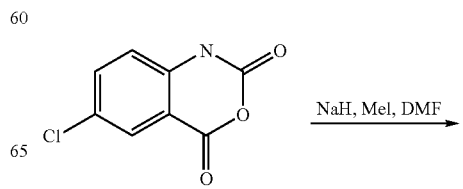

-continued

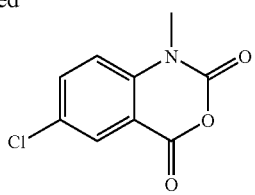

As illustrated in the scheme above, NaH (2.43 g of a 60% dispersion, 60.8 mmol) was added to a solution of 6-chloro-2H-3,1-benzoxazine-2,4(1H)-dione (10.0 g, 50.6 mmol) dissolved in DMF (200 mL). The resulting mixture was stirred at room temperature for 30 min., and then methyl iodide (6.3 mL, 101 mmol) was added dropwise. After the reaction had stirred at room temperature overnight, it was concentrated in vacuo. Water and brine were added to the residue, and the aqueous layer was extracted with $CH_2Cl_2$ (2×). The combined organic phases were dried over $Na_2SO_4$, filtered, and concentrated in vacuo. The crude product was triturated with 3:1 hexanes:EtOAc. The solvent was removed by filtration, and the resulting solid was washed with additional 3:1 hexanes:EtOAc, followed by 100% hexanes. The product was dried briefly under vacuum to produce the title compound as a pale yellow solid. (8.59 g, 80%). $^1$H-NMR (DMSO-$d_6$): δ 7.96 (d, J=2.6 Hz, 1H), 7.89 (dd, J=2.6 Hz, J=9.0 Hz, 1H), 7.48 (d, J=9.0 Hz, 1H), 3.45 (s, 3H). MS (ESI) (M+H)$^+$=212.

Intermediate 10

7-Chloro-3,4-dihydro-1-methyl-1H-1,4-benzodiazepine-2,5-dione

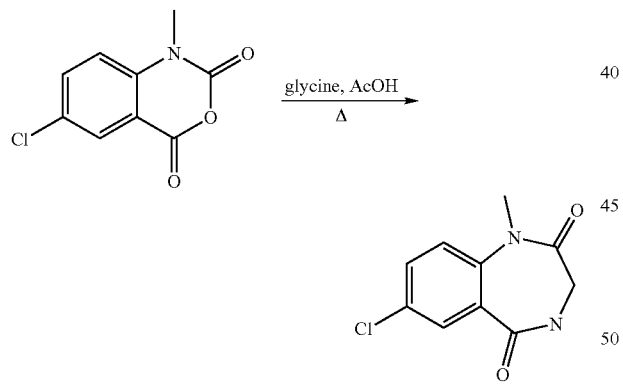

As illustrated in the scheme above, a mixture of 6-chloro-1-methyl-2H-3,1-benzoxazine-2,4(1H)-dione (6.00 g, 28.4 mmol) and glycine (2.14 g, 28.4 mmol) in glacial acetic acid (72 mL) was heated at reflux for 4 h. The reaction was cooled and concentrated in vacuo. Water was added to the residue, and the mixture was cooled to 0° C. NaHCO$_3$ was added to adjust the pH of the aqueous layer to approximately 8, and then the aqueous layer was extracted with $CH_2Cl_2$ (3×). The combined organic phases were dried over $Na_2SO_4$, filtered, and concentrated in vacuo. The crude product was triturated with Et$_2$O, the solvent was removed by filtration, and the resulting solid was washed with additional Et$_2$O to provide the title compound as a slightly yellow solid (5.657 g, 89%). $^1$H-NMR (CDCl$_3$): δ 7.88 (d, J=2.5 Hz, 1H), 7.57 (br s, 1H), 7.53 (dd, J=2.6 Hz, J=8.7 Hz, 1H), 7.19 (d, J=8.6 Hz, 1H), 3.84 (d, J=6.1 Hz, 2H), 3.39 (s, 3H). MS (ESI) (M+H)$^+$=225.

Intermediate 11

5,7-Dichloro-1,3-dihydro-1-methyl-2H-1,4benzodiazepin-2-one

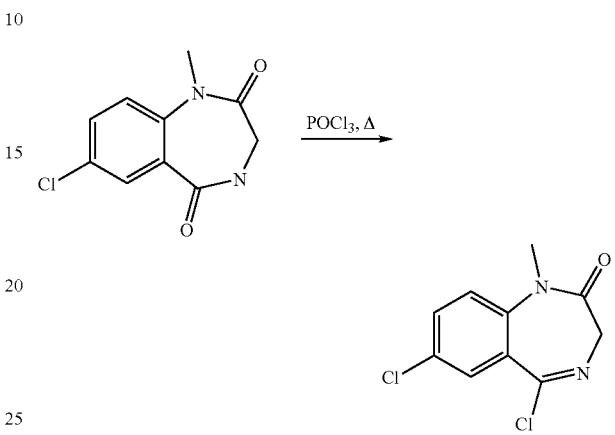

As illustrated in the scheme above, 7-chloro-3,4-dihydro-1-methyl-1H-1,4-benzodiazepine-2,5-dione (5.00 g, 22.3 mmol) was suspended in POCl$_3$ (100 mL) and heated at 100° C. for 30 min. The reaction was cooled and concentrated in vacuo. Traces of POCl$_3$ were removed by adding toluene and concentrating the mixture in vacuo (2×). The residue was dissolved in $CH_2Cl_2$, the solution was cooled to 0° C., and Et$_3$N (6.8 mL, 48.8 mmol) was added dropwise. The mixture was stirred for 1 h and allowed to slowly warm to room temperature, and was then concentrated in vacuo once again. The residue was purified by silica gel column chromatography (5:1 $CH_2Cl_2$:EtOAc+0.5% Et$_3$N) to provide the title compound as an orange solid (4.68 g, 86%). $^1$H-NMR (CDCl$_3$): δ 7.79 (d, J=2.5 Hz, 1H), 7.55 (dd, J=2.4 Hz, J=8.9 Hz, 1H), 7.23 (d, J=8.8 Hz, 1H), 4.67 (br s, 1H), 3.72 (br s, 1H), 3.39 (s, 3H). MS (ESI) (M+H)$^+$=243.

Intermediate 12

7-Chloro-5-(2,4-dimethoxy-5-pyrimidinyl)-1,3-dihydro-1-methyl-2H-1,4-benzodiazepin-2-one

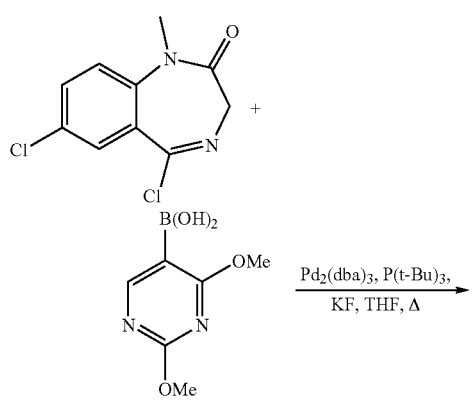

-continued

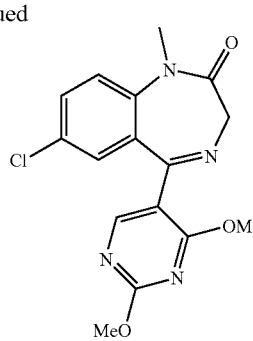

As illustrated in the scheme above and following General Procedure 5, (2,4-dimethoxy-5-pyrimidinyl)boronic acid (0.939 g, 5.10 mmol), Pd$_2$(dba)$_3$ (0.064 g, 0.07 mmol), dry KF (0.890 g, 15.3 mmol), 5,7-dichloro-1,3-dihydro-1-methyl-2H-1,4-benzodiazepin-2-one (1.12 g, 4.61 mmol) and P(t-Bu)$_3$ (0.42 mL of a 10% solution in hexanes, 0.21 mmol) were combined and heated for 20 h. After workup, purification of the crude product by silica gel column chromatography (1:3 hexanes:EtOAc) provided the title compound as a pale orange solid (1.20 g, 75%). $^1$H-NMR (CDCl$_3$): δ 8.50 (s, 1H), 7.49 (dd, J=2.4 Hz, J=8.8 Hz, 1H), 7.29 (d, J=8.8 Hz, 1H), 7.13 (d, J=2.4 Hz, 1H), 4.84 (d, J=10.8 Hz, 1H), 4.06 (s, 3H), 3.79 (s, 3H), 3.76 (d, J=10.8 Hz, 1H), 3.42 (s, 3H). MS (ESI) (M+H)$^+$=347.

Intermediate 13

3-Azido-7-chloro-5-(2,4-dimethoxy-5-pyrimidinyl)-1,3-dihydro-1-methyl-2H-1,4-benzodiazepin-2-one

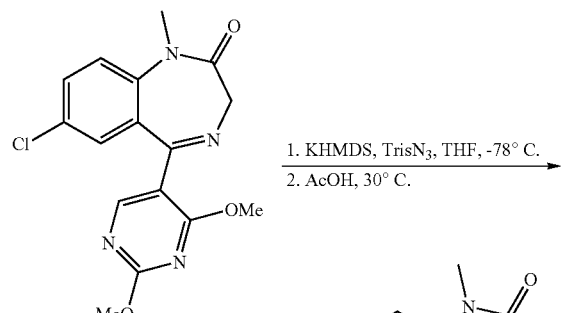

As illustrated in the scheme above and following General Procedure 6, KHMDS (7.0 mL of 0.5 M in toluene, 3.5 mmol), 7-chloro-5-(2,4-dimethoxy-5-pyrimidinyl)-1,3-dihydro-1-methyl-2H-1,4-benzodiazepin-2-one (1.16 g, 3.35 mmol), trisyl azide (2.60 g, 8.40 mmol) and acetic acid (0.85 mL, 14.8 mmol) were combined. After workup, purification of the crude product by silica gel column chromatography (2:3 hexanes:EtOAc) provided the title compound as a pale yellow solid (1.23 g, 95%). $^1$H-NMR (CDCl$_3$): δ 8.64 (s, 1H), 7.54 (dd, J=2.3 Hz, J=8.8 Hz, 1H), 7.33 (d, J=8.8 Hz, 1H), 7.19 (d, J=2.3 Hz, 1H), 4.51 (s, 1H), 4.08 (s, 3H), 3.78 (s, 3H), 3.47 (s, 3H). MS (ESI) (M+H)$^+$388.

Intermediate 14

3-Amino-7-chloro-5-(2,4-dimethoxy-5-pyrimidinyl)-1,3-dihydro-1-methyl-2H-1,4-benzodiazepin-2-one

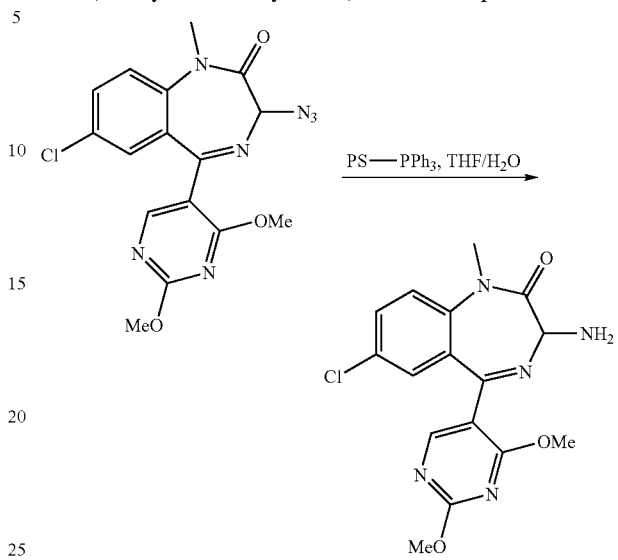

As illustrated in the scheme above and following General Procedure 7, 3-azido-7-chloro-5-(2,4-dimethoxy-5-pyrimidinyl)-1,3-dihydro-1-methyl-2H-1,4-benzodiazepin-2-one (1.22 g, 3.15 mmol) and PS—PPh$_3$ (23.0 g of 1.37 mmol/g, 31.5 mmol) were combined. After workup and purification by "catch and release," the title compound was obtained as a brown solid (1.15 g, quantitative). 1H-NM (CDCl$_3$): δ 8.56 (s, 1H), 7.50 (dd, J=2.4 Hz, J=8.9 Hz, 1H), 7.30 (d, J=8.8 Hz, 1H), 7.15 (d, J=2.5 Hz, 1H), 4.46 (s, 1H), 4.06 (s, 3H), 3.77 (s, 3H), 3.46 (s, 3H), 2.85-2.12 (br s, 2H). MS (ESI) (M+H)$^+$=362.

Intermediate 15

7-Chloro-5-(2,4-dimethoxy-5-pyrimidinyl)-1,3-dihydro-3-isothiocyanato-1-methyl-2H-1,4-benzodiazepin-2-one

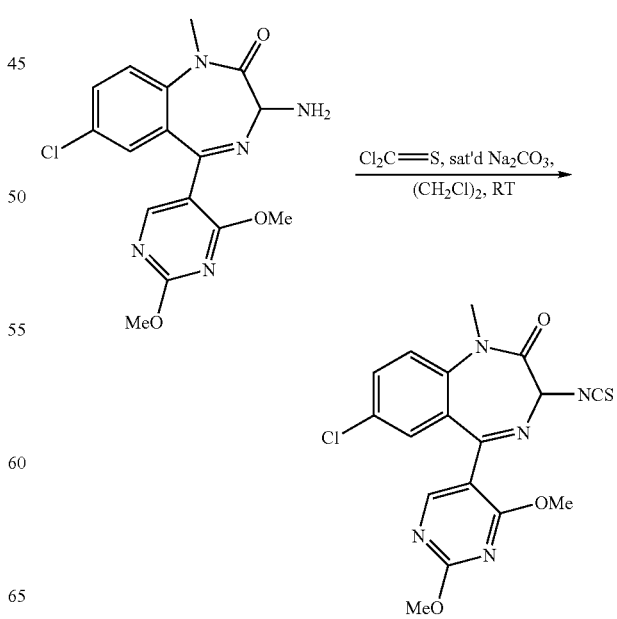

As illustrated in the scheme above and following General Procedure 2, 3-amino-7-chloro-5-(2,4-dimethoxy-5-pyrimidinyl)-1,3-dihydro-1-methyl-2H-1,4-benzodiazepin-2-one (1.15 g, 3.18 mmol) and thiophosgene (0.49 mL, 6.4 mmol) were combined. Purification of the crude product by silica gel column chromatography (9:1 $CH_2Cl_2$:EtOAc) provided the title compound as a viscous dark yellow oil (0.560 g, 44%). $^1$H-NMR ($CDCl_3$): δ 8.60 (s, 1H), 7.55 (dd, J=2.5 Hz, J=8.8 Hz, 1H), 7.33 (d, J=8.8 Hz, 1H), 7.17 (d, J=2.5 Hz, 1H), 5.16 (s, 1H), 4.07 (s, 3H), 3.78 (s, 3H), 3.49 (s, 3H). MS (ESI) $(M+H)^+$=404.

Example 22

N-[7-chloro-5-(2,4-dimethoxy-5-pyrimidinyl)-2,3-dihydro-1-methyl-2-oxo-1H-1,4-benzodiazepin-3-yl]-N'-[4-(diethylamino)-2-methylphenyl]-thiourea

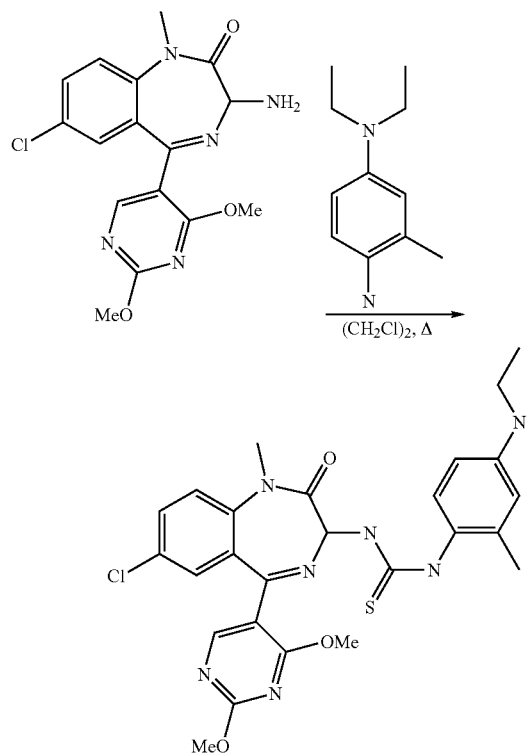

As illustrated in the scheme above, a solution of 7-chloro-5-(2,4-dimethoxy-5-pyrimidinyl)-1,3-dihydro-3-isothiocyanato-1-methyl-2H-1,4-benzodiazepin-2-one (0.069 g, 0.146 mmol) and $N^4,N^4$-diethyl-2-methyl-1,4benzenediamine (0.029 g, 0.161 mmol) in $(CH_2Cl)_2$ (5.0 mL) was heated at 70° C. for 16 h. The reaction was cooled and concentrated in vacuo, and the residue was purified by silica gel column chromatography (7:3 $CH_2Cl_2$:EtOAc) to provide the title compound as a light orange solid (0.074 g, 87%). $^1$H-NMR ($CDCl_3$): δ 8.64 (s, 1H), 7.52 (dd, J=2.5 Hz, J=8.8 Hz, 1H), 7.40 (s, 1H), 7.35 (d, J=7.8 Hz, 1H), 7.32 (d, J=9.0 Hz, 1H), 7.20 (d, J=2.2 Hz, 1H), 7.17-7.13 (m, 1H), 6.54-6.51 (m, 2H), 6.06 (d, J=8.0 Hz, 1H), 4.05 (s, 3H), 3.74 (s, 3H), 3.42 (s, 3H), 3.40-3.27 (m, 4H), 2.30 (s, 3H), 1.17 (t, J=7.1 Hz, 6H). HRMS calculated for $(C_{28}H_{32}ClN_7O_3S+H)$ $(M+H)^+$: 582.2054. Found (ESI): 582.2076.

Intermediate 16

7-Chloro-1,3-dihydro-1-methyl-5-(3-thienyl)-2H-1,4-benzodiazepin-2-one

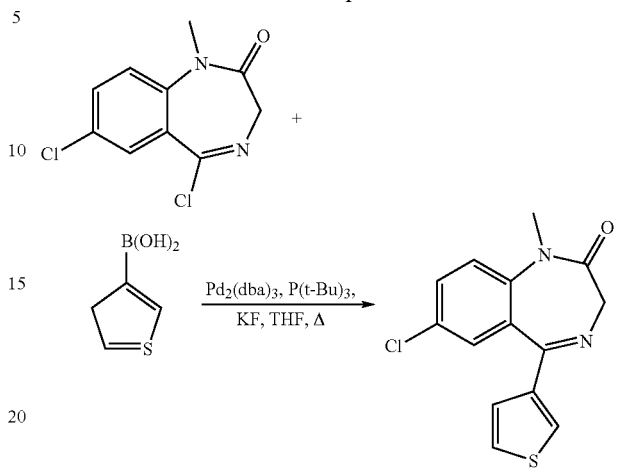

As illustrated in the scheme above and following General Procedure 5,3-thienylboronic acid (1.15 g, 9.01 mmol), $Pd_2(dba)_3$ (0.113 g, 0.123 mmol), dry KF (1.57 g, 27.0 mmol), 5,7-dichloro-1,3-dihydro-1-methyl-2H-1,4-benzodiazepin-2-one (1.98 g, 8.15 mmol) and $P(t-Bu)_3$ (0.75 mL of a 10% solution in hexanes, 0.37 mmol) were combined and heated for 16 h. After workup, purification of the crude product by silica gel column chromatography (9:1 $CH_2Cl_2$: EtOAc) provided the title compound as a yellow solid (1.44 g, 61%). $^1$H-NMR ($CDCl_3$): δ 7.54-7.49 (m, 4H), 7.37 (dd, J=3.0 Hz, J=5.0 Hz, 1H), 7.29 (d, J=9.4 Hz, 1H), 4.76 (d, J=10.9 Hz, 1H), 3.77 (d, J=10.9 Hz, 1H), 3.38 (s, 3H). MS (ESI) $(M+H)^+$=291.

Intermediate 17

3-Azido-7-chloro-1,3-dihydro-1-methyl-5-(3-thienyl)-2H-1,4-benzodiazepin-2-one

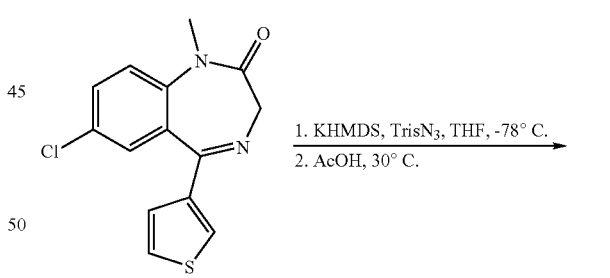

As illustrated in the scheme above and following General Procedure 6, KHMDS (10.4 mL of 0.5 M in toluene, 5.20 mmol), 7-chloro-1,3-dihydro-1-methyl-5-(3-thienyl)-2H-1,4-benzodiazepin-2-one (1.44 g, 4.95 mmol), trisyl azide (3.83 g, 12.4 mmol) and acetic acid (1.25 mL, 21.8 mmol) were combined. After workup, purification of the crude product by silica gel column chromatography (7:3 hexanes: EtOAc) provided the title compound as a pale yellow solid (1.60 g, 98%). ¹H-NMR (CDCl₃): δ 7.61-7.55 (m, 4H), 7.40 (dd, J=2.9 Hz, J=5.1 Hz, 1H), 7.33 (dd, J=1.0 Hz, J=8.2 Hz, 1H), 4.54 (s, 1H), 3.44 (s, 3H). MS (ESI) (M+H)⁺=332.

Intermediate 18

3-Amino-7-chloro-1,3-dihydro-1-methyl-5-(3-thienyl)-2H-1,4-benzodiazepin-2-one

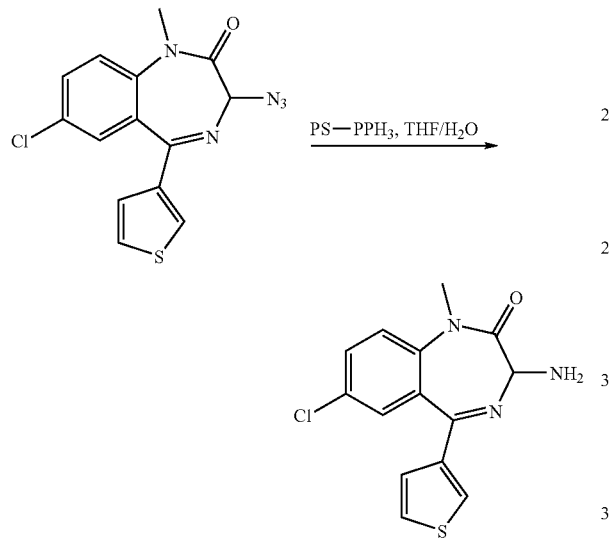

As illustrated in the scheme above and following General Procedure 7, 3-azido-7-chloro-1,3-dihydro-1-methyl-5-(3-thienyl)-2H-1,4-benzodiazepin-2-one (1.60 g, 4.82 mmol) and PS—PPh₃ (30.0 g of 1.37 mmol/g, 41.1 mmol) were combined. After workup and purification by "catch and release," the title compound was obtained as a brown solid (1.35 g, 92%). ¹H-NMR (CDCl₃): δ 7.56-7.50 (m, 4H), 7.36 (dd, J=3.1 Hz, J=4.9 Hz, 1H), 7.29 (d, J=8.8 Hz, 1H), 4.46 (s, 1H), 3.43 (s, 3H), 2.35-2.15 (br s, 2H). MS (ESI) (M+H)⁺=306.

Intermediate 19

7-Chloro-1,3-dihydro-3-isothiocyanato-1-methyl-5-(3-thienyl)-2H-1,4-benzodiazepin-2-one

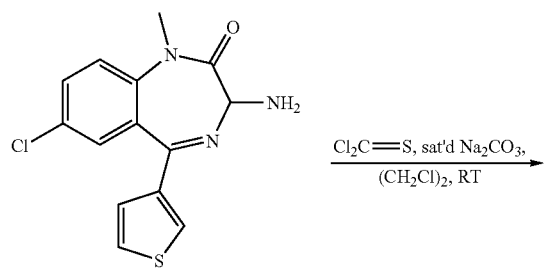

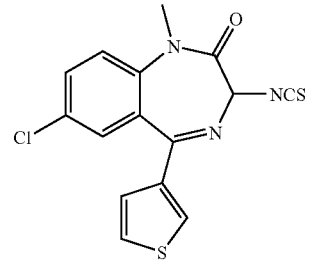

As illustrated in the scheme above and following General Procedure 2, 3-amino-7-chloro-1,3-dihydro-1-methyl-5-(3-thienyl)-2H-1,4-benzodiazepin-2-one (1.35 g, 4.41 mmol) and thiophosgene (0.67 mL, 8.8 mmol) were combined. Purification of the crude product by silica gel column chromatography (100% CH₂Cl₂) provided the title compound as a yellow solid (1.04 g, 68%). ¹H-NMR (CDCl₃): δ 7.61-7.54 (m, 4H), 7.39 (dd, J=2.9 Hz, J=5.3 Hz, 1H), 7.33 (d, J=8.8 Hz, 1H), 5.20 (s, 1H), 3.46 (s, 3H). MS (ESI) (M+H)⁺=348.

Example 23

N-[7-Chloro-2,3-dihydro-1-methyl-2-oxo-5-(3-thienyl)-1H-1,4-benzodiazepin-3-yl]-N'-[4-(4-morpholinyl)-1-naphthalenyl]thiourea

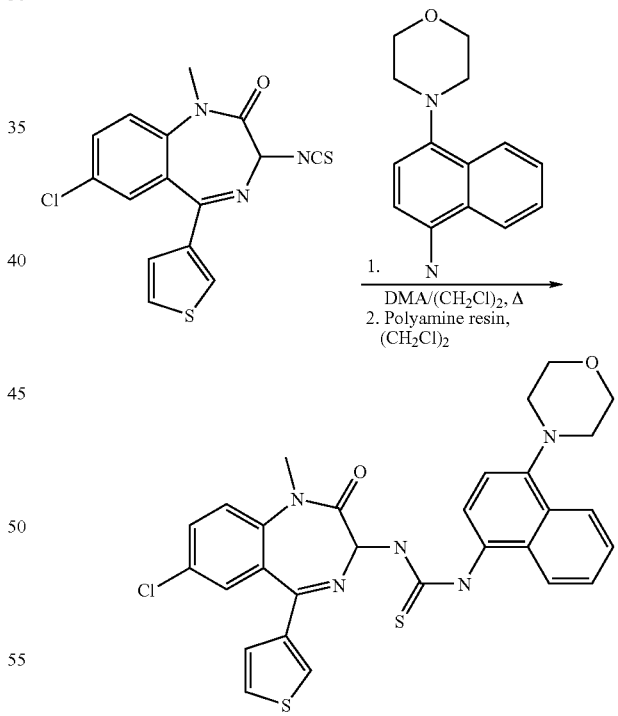

This reaction was carried out in a multiwell plate. As illustrated in the scheme above, aA mixture of 7-chloro-1,3-dihydro-3-isothiocyanato-1-methyl-5-(3-thienyl)-2H-1,4-benzodiazepin-2-one (156 µL of a 0.128 M solution in (CH₂Cl)₂, 0.020 mmol), 4-(4-morpholinyl)-1-naphthalenamine (44 µL of a 0.5 M solution in DMA, 0.022 mmol), and (CH₂Cl)₂ (300 µL) was agitated and heated at 70° C. for 22 h. The reaction was cooled and concentrated in vacuo, and the residue was redissolved in DMA (25 µL) and (CH₂Cl)₂ (275 µL). Polyamine resin HL (NovaBiochem) was added (20 mg of 4.53 mmol/g, 0.091 mmol), and the mixture was agitated at room temperature overnight. The resin was removed by filtration and washed with additional (CH₂Cl)₂ and MeOH. The filtrate was concentrated in vacuo to provide the title compound. MS (ESI) (M+H)⁺=576.

Intermediate 20

7-Chloro-1,3dihydro-1-methyl-5-(3-pyridinyl)-2H-1,4-benzodiazepin-2-one

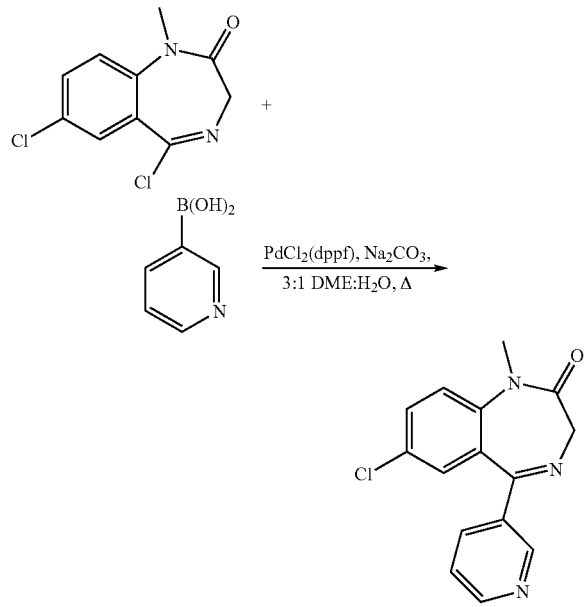

As illustrated in the scheme above and following General Procedure 4,5,7-dichloro-1,3-dihydro-1-methyl-2H-1,4-benzodiazepin-2-one (1.99 g, 8.19 mmol), Na₂CO₃ (0.868 g, 8.19 mmol), PdCl₂(dppf) (0.335 g, 0.410 mmol) and (3-pyridinyl)boronic acid (1.01 g, 8.19 mmol) were combined and heated for 14 h. After workup, purification of the crude product by silica gel column chromatography (100% EtOAc) provided the title compound (1.51 g, 64%). ¹H-NMR (CDCl₃): δ 8.78 (d, J=1.6 Hz, 1H), 8.72 (dd, J=1.6 Hz, J=4.8 Hz, 1H), 8.02 (dt, J=1.6 Hz J=8.0 Hz, 1H),7.56 (dd, J=2.4 Hz, J=8.8 Hz,1H), 7.39 (dd, J=4.8 Hz, J=8.0 Hz, 1H), 7.34 (d, J=8.8 Hz, 1H), 7.28 (d, J=2.4 Hz, 1H), 4.89 (d, J=10.4 Hz, 1H), 3.80 (d, J=10.8 Hz, 1H), 3.41 (s, 3H); MS (ESI) (M+H)⁺=286.

Intermediate 21

3-Azido-7-chloro-1,3-dihydro-1-methyl-5-(3-pyridinyl)-2H-1,4benzodiazepin-2-one

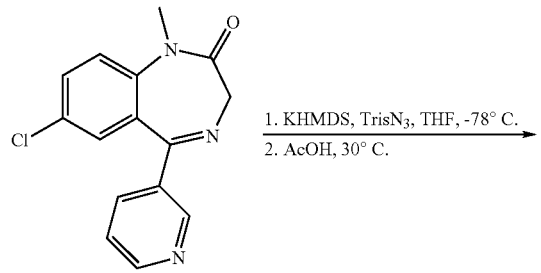

1. KHMDS, TrisN₃, THF, -78° C.
2. AcOH, 30° C.

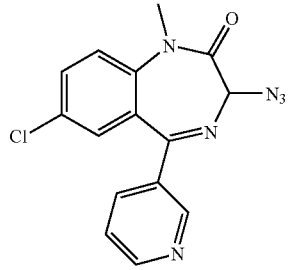

As illustrated in the scheme above and following General Procedure 6, KHMDS (10.5 mL of 0.5 M in toluene, 5.25 mmol), 7-chloro-1,3-dihydro-1-methyl-5-(3-pyridinyl)-2H-1,4-benzodiazepin-2-one (1.43 g, 4.99 mmol), trisyl azide (3.86 g, 12.5 mmol) and acetic acid (1.26 mL, 22.0 mmol) were combined. After workup, purification of the crude product by silica gel column chromatography (1:1 CH₂Cl₂:EtOAc) provided the title compound as a yellow foam (1.47 g, 90%). ¹H-NMR (CDCl₃): δ 8.80 (s, 1H), 8.76 (d, J=3.6 Hz, 1H), 8.14 (dt, J=1.6 Hz, J=8.0 Hz, 1H), 7.61 (dd, J=2.0 Hz, J=8.4 Hz, 1H), 7.44 (ddd, J=0.8 Hz, J=4.8 Hz, J=8.0 Hz, 1H), 7.38 (d, J=8.8 Hz, 1H), 7.35 (d, J=2.4 Hz, 1H), 4.56 (s, 1H), 3.48 (s, 3H). MS (ESI) (M+H)⁺=327.

Intermediate 22

3-Amino-7-chloro-1,3-dihydro-1-methyl-5-(3-pyridinyl)-2H-1,4-benzodiazepin-2-one

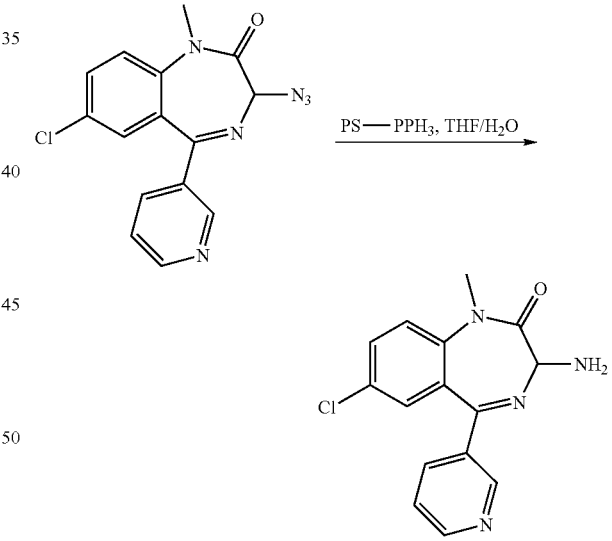

As illustrated in the scheme above and following General Procedure 7, 3-azido-7-chloro-1,3-dihydro-1-methyl-5-(3-pyridinyl)-2H-1,4-benzodiazepin-2-one (1.47 g, 4.49 mmol) and PS—PPh₃ (16.4 g of 1.37 mmol/g, 22.4 mmol) were combined. After workup and purification by "catch and release," the title compound was obtained as a slightly brown solid (1.46 g, quantitative). ¹H-NMR (CDCl₃): δ 8.76 (d, J=2.4 Hz, 1H), 8.72 (dd, J=1.6 Hz, J=5.2 Hz, 1H), 8.06 (dt, J=2.4 Hz, J=7.6 Hz, 1H), 7.58 (dd, J=2.4 Hz, J=8.8 Hz, 1H), 7.40 (dd, J=4.8 Hz, J=8.0 Hz, 1H), 7.35 (d, J=8.8 Hz, 1H), 7.29 (d, J=2.4 Hz, 1H), 4.51 (s, 1H), 3.46 (s, 3H), 2.41 (br s, 2H). MS (ESI) (M+H)⁺=301.

Intermediate 23

7-Chloro-1,3-dihydro-3-isothiocyanato-1-methyl-5-(3-pyridinyl)-2H-1,4-benzodiazepin-2-one

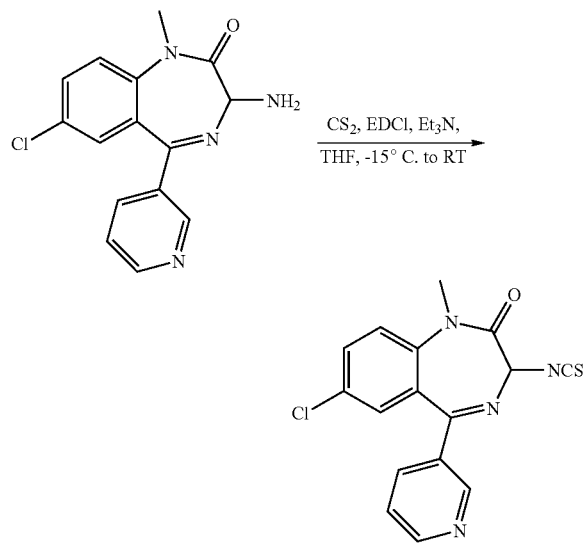

As illustrated in the scheme above, a solution of 3-amino-7-chloro-1,3-dihydro-1-methyl-5-(3-pyridinyl)-2H-1,4benzodiazepin-2-one (1.36 g, 4.52 mmol) in dry THF (55 mL) was cooled to −15° C. Carbon disulfide (2.7 mL, 45 mmol) was added, followed by EDCI (1.73 g, 9.03 mmol). The mixture was stirred for 10 min., and then Et$_3$N (1.26 mL, 9.04 mmol) was added. The reaction was stirred for 16 h while it was allowed to slowly warm to room temperature. The precipitated solid was removed by filtration and was washed well with CH$_2$Cl$_2$ and then discarded. The filtrate was concentrated in vacuo, and the residue was dissolved in CH$_2$Cl$_2$. The organic phase was washed with water, saturated NaHCO$_3$, and brine, and was then dried over Na$_2$SO$_4$, filtered, and concentrated in vacuo. Purification of the crude product by silica gel column chromatography (3:1 CH$_2$Cl$_2$:EtOAc) provided the title compound as a solid (0.652 g, 42%). $^1$H-NMR (CDCl$_3$): δ 8.75 (s, 2H), 8.12 (dt, J=2.0 Hz, J=8.0 Hz, 1H), 7.63 (dd, J=2.0 Hz, J=8.8 Hz, 1H), 7.43 (dd, J=4.8 Hz, J=8.0 Hz, 1H), 7.39 (d, J=8.8 Hz, 1H), 7.33 (d, J=2.4 Hz, 1H), 5.22 (s, 1H), 3.50 (s, 3H). MS (ESI) (M+H)$^+$=343.

Example 24

N-[7-Chloro-2,3-dihydro-1-methyl-2-oxo-5-(3-pyridinyl)-1H-1,4-benzodiazepin-3-yl]-N'-[4-(4-morpholinyl)-1-naphthalenyl]thiourea

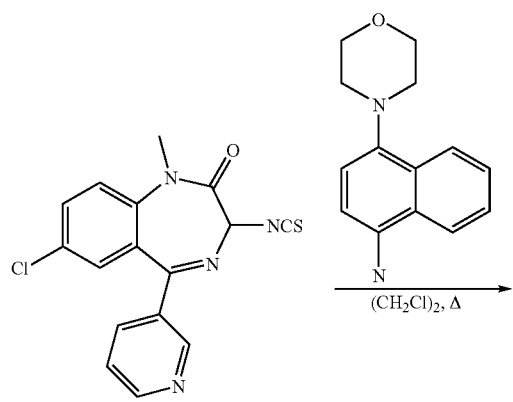

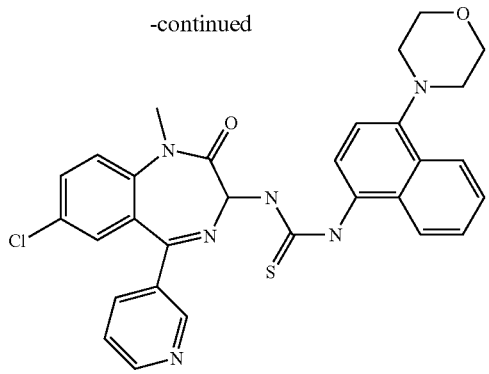

A solution of 7-chloro-1,3-dihydro-3-isothiocyanato-1-methyl-5-(3-pyridinyl)-2H-1,4-benzodiazepin-2-one (0.0282 g, 0.0823 mmol) and 4-(4-morpholinyl)-1-naphthalenamine (0.0188 g, 0.0823 mmol) in (CH$_2$Cl)$_2$ (2.5 mL) was heated at 70° C. for 24 h. The reaction was cooled and concentrated in vacuo, and the residue was purified by silica gel column chromatography (1:2 CH$_2$Cl$_2$:EtOAc) to provide the title compound (0.0263 g, 56%). $^1$H-NMR (CDCl$_3$): δ 8.72-8.68 (m, 2H), 8.29-8.25 (m, 1H), 8.11-8.07 (m, 1H), 8.05-8.00 (m, 2H), 7.64-7.55 (m, 5H), 7.38-7.33 (m, 3H), 7.15 (d, J=8.0 Hz, 1H), 6.08 (d, J=7.6 Hz, 1H), 4.03-3.96 (br m, 4H), 3.39 (s, 3H), 3.15 (br s, 4H). HRMS calculated for (C$_{30}$H$_{27}$ClN$_6$O$_2$S+H) (M+H)$^+$: 571.1683. Found (ESI): 571.1699. Anal. Calcd for C$_{30}$H$_{27}$ClN$_6$O$_2$S+0.7 H$_2$O: C, 61.73; H, 4.90; N, 14.40. Found: C, 61.93; H, 4.79; N, 13.87.

Intermediate 24

6-Fluoro-1-methyl-2H-3,1-benzoxazine-2,4(1H)-dione

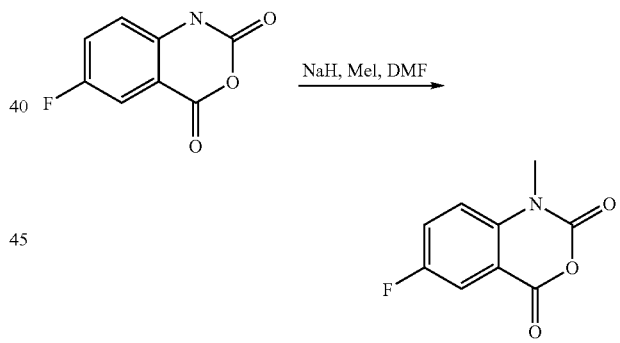

As illustrated in the scheme above, NaH (0.312 g of a 60% dispersion, 7.80 mmol) was added to a solution of 6-fluoro-2H-3,1-benzoxazine-2,4(1H)-dione (1.176 g, 6.49 mmol) dissolved in DMF (60 mL). The resulting mixture was stirred at room temperature for 30 min., and then methyl iodide (0.81 mL, 13 mmol) was added dropwise. After the reaction had stirred at room temperature overnight, it was concentrated in vacuo. Water and brine were added to the residue, and the aqueous layer was extracted with CH$_2$Cl$_2$ (3×). The combined organic phases were dried over Na$_2$SO$_4$, filtered, and concentrated in vacuo. The crude product was triturated with Et$_2$O. The solvent was removed by filtration, and the resulting solid was washed with additional Et$_2$O. The product was dried briefly under vacuum to produce the title compound as a white solid (1.00 g, 79%). $^1$H-NMR (CDCl$_3$): δ 7.86-7.82 (m, 1H), 7.55-7.48 (m, 1H), 7.22-7.17 (m, 1H), 3.61 (s, 3H). MS (ESI) (M+H)$^+$=196.

Intermediate 25

7-Fluoro-3,4-dihydro-1-methyl-1H-1,4-benzodiazepine-2,5-dione

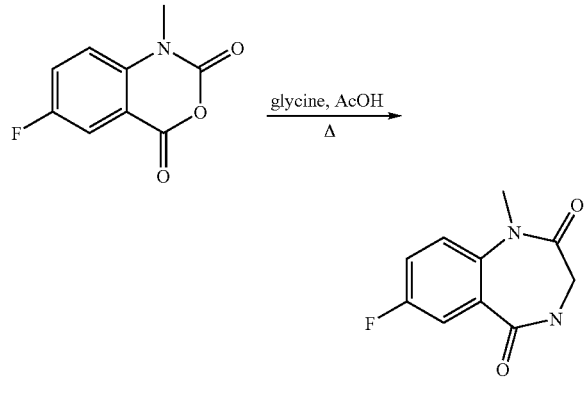

As illustrated in the scheme above, a mixture of 6-fluoro-1-methyl-2H-3,1-benzoxazine-2,4(1H)-dione (1.00 g, 5.12 mmol) and glycine (0.385 g, 5.13 mmol) in glacial acetic acid (13 mL) was heated at reflux for 4 h. The reaction was cooled and concentrated in vacuo. Water was added to the residue, and the mixture was cooled to 0° C. NaHCO$_3$ was added to adjust the pH of the aqueous layer to approximately 8, and then the aqueous layer was extracted with CH$_2$Cl$_2$ (4×). The combined organic phases were dried over Na$_2$SO$_4$, filtered, and concentrated in vacuo. The crude product was triturated with Et$_2$O, the solvent was removed by filtration, and the resulting solid was washed with additional Et$_2$O to provide the title compound as a slightly yellow solid (0.560 g, 52%). $^1$H-NMR (DMSO-d$_6$): δ 8.80 (br s, 1H), 7.49-7.38 (m, 3H), 3.76 (br d, 1H), 3.47 (br d, 1H), 3.26 (s, 3H). MS (ESI) (M+H)$^+$=209.

Intermediate 26

5-Chloro-7-fluoro-1,3-dihydro-1-methyl-2H-1,4-benzodiazepin-2-one

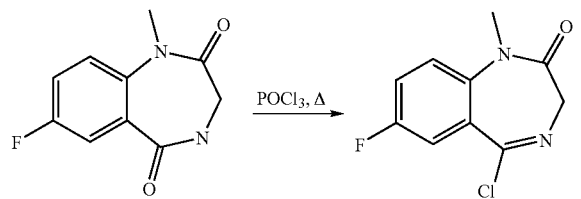

As illustrated in the scheme above, 7-fluoro-3,4-dihydro-1-methyl-1H-1,4-benzodiazepine-2,5-dione (0.495 g, 2.38 mmol) was suspended in POCl$_3$ (10.6 mL) and heated at 100° C. for 30 min. The reaction was cooled and concentrated in vacuo. Traces of POCl$_3$ were removed by adding toluene and concentrating the mixture in vacuo (2×). The residue was dissolved in CH$_2$Cl$_2$, the solution was cooled to 0° C., and Et$_3$N (0.75 mL, 5.4 mmol) was added dropwise. The mixture was stirred for 0.5 h and allowed to slowly warm to room temperature, and was then concentrated in vacuo once again. The residue was purified by silica gel column chromatography (9:1 CH$_2$Cl$_2$:EtOAc+0.5% Et$_3$N) to provide the title compound as a light tan solid (0.422 g, 78%). $^1$H-NMR (CDCl$_3$): δ 7.53-7.48 (m, 1H), 7.34-7.24 (m, 2H), 4.66 (br s, 1H), 3.72 (br s, 1H), 3.39 (s, 3H). MS (ESI) (M+H)$^+$=227.

Intermediate 27

7-Fluoro-1,3-dihydro-1-methyl-5-phenyl-2H-1,4-benzodiazepin-2-one

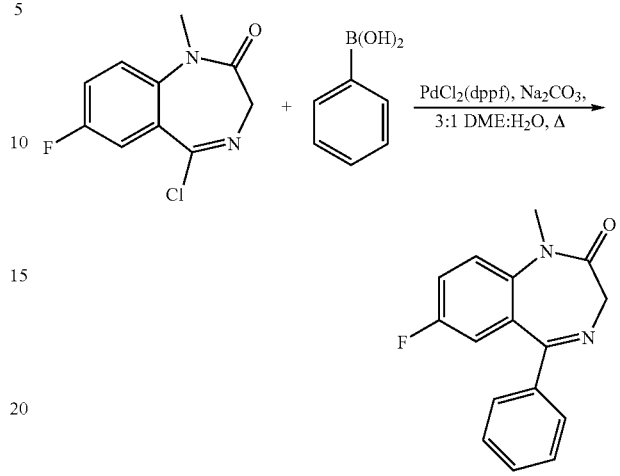

As illustrated in the scheme above and following General Procedure 4, 5-chloro-7-fluoro-1,3-dihydro-1-methyl-2H-1,4-benzodiazepin-2-one (0.201 g, 0.887 mmol), Na$_2$CO$_3$ (0.0940 g, 0.887 mmol), PdCl$_2$(dppf) (0.0362. g, 0.0443 mmol) and phenylboronic acid (0.108 g, 0.886 mmol) were combined and heated for 13 h. After workup, purification of the crude product by silica gel column chromatography (3:1 CH$_2$Cl$_2$:EtOAc) provided the title compound (0.180 g, 76%). $^1$H-NMR (CDCl$_3$): δ 7.64-7.60 (m, 2H), 7.51-7.45 (m, 1H), 7.44-7.39 (m, 2H), 7.34 (dd, J=4.8 Hz, J=9.2 Hz, 1H), 7.31-7.25 (m, 1H), 7.02 (dd, J=2.8 Hz, J=8.8 Hz, 1H), 4.84 (d, J=10.8 Hz, 1H), 3.78 (d, J=10.8 Hz, 1H), 3.40 (s, 3H). MS (ESI) (M+H)$^+$=269.

Intermediate 28

3-Azido-7-fluoro-1,3-dihydro-1-methyl-5-phenyl-2H-1,4-benzodiazepin-2-one

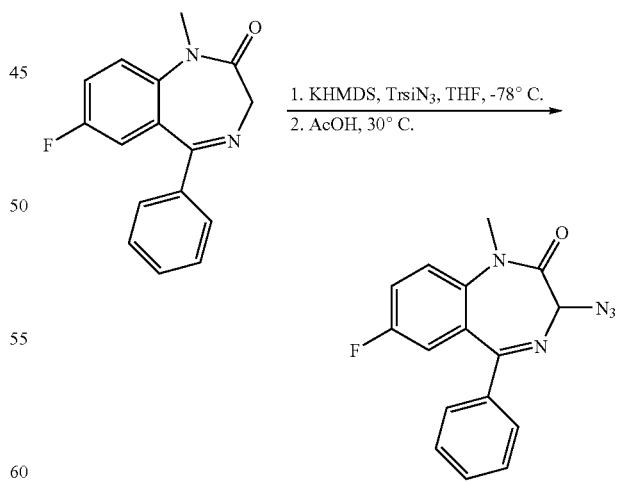

As illustrated in the scheme above and following General Procedure 6, KHMDS (1.34 mL of 0.5 M in toluene, 0.670 mmol), 7-fluoro-1,3-dihydro-1-methyl-5-phenyl-2H-1,4-benzodiazepin-2-one (0.171 g, 0.637 mmol), trisyl azide (0.493 g, 1.59 mmol) and acetic acid (0.16 mL, 2.8 mmol) were combined. After workup, purification of the crude product by silica gel column chromatography (100% CH$_2$Cl$_2$ to 9:1 CH$_2$Cl$_2$:EtOAc) provided the title compound as a pale yellow solid (0.163 g, 83%). $^1$H-NMR (CDCl$_3$): δ 7.72-7.67 (m, 2H), 7.54-7.49 (m, 1H), 7.47-7.42 (m, 2H), 7.39 (dd, J=4.8 Hz, J=9.2 Hz, 1H), 7.36-7.30 (m, 1H), 7.08 (dd, J=2.8 Hz, J=8.4 Hz, 1H), 4.55 (s, 1H), 3.45 (s, 3H). MS (ESI) (M+H)$^+$=310.

Intermediate 29

3-Amino-7-fluoro-1,3-dihydro-1-methyl-5-phenyl-2H-1,4-benzodiazepin-2-one

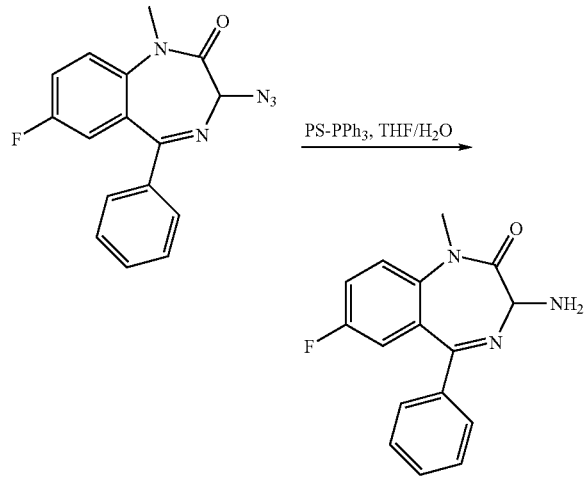

As illustrated in the scheme above and following General Procedure 7, 3-azido-7-fluoro-1,3-dihydro-1-methyl-5-phenyl-2H-1,4-benzodiazepin-2-one (0.0826 g, 0.267 mmol) and PS—PPh$_3$ (1.63 g of 1.64 mmol/g, 2.67 mmol) were combined. After workup and purification by "catch and release," the title compound was obtained as a slightly yellow solid (0.0450 g, 59%). $^1$H-NMR (CDCl$_3$): δ 7.65-7.60 (m, 2H), 7.51-7.46 (m, 1H), 7.44-7.39 (m, 2H), 7.36 (dd, J=4.8 Hz, J=9.2 Hz, 1H), 7.33-7.26 (m, 1H), 7.03 (dd, J=2.4 Hz, J=8.4 Hz, 1H), 4.48 (s, 1H), 3.45 (s, 3H), 2.30-1.60 (br s, 2H). MS (ESI) (M+H)$^+$=284.

Example 25

N-(7-Fluoro-2,3-dihydro-1-methyl-2-oxo-5-phenyl-1H-1,4-benzodiazepin-3-yl)-N'-[2-methyl-4-(4-morpholinyl)phenyl]thiourea

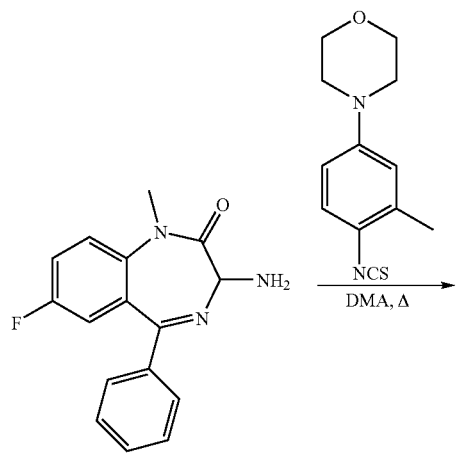

-continued

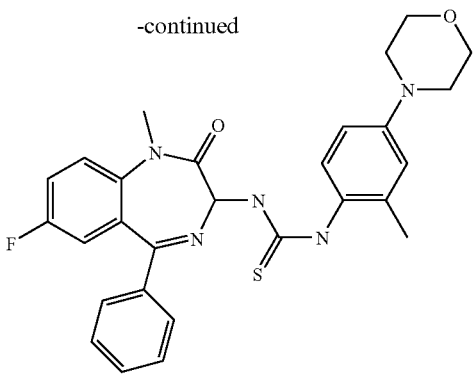

As illustrated in the scheme above, a solution of 3-amino-7-fluoro-1,3-dihydro-1-methyl-5-phenyl-2H-1,4-benzodiazepin-2-one (0.0056 g, 0.020 mmol) and 4-(4-isothiocyanato-3-methylphenyl)morpholine (0.0048 g, 0.020 mmol) in DMA (0.5 mL) was heated at 70° C. for 16 h. The reaction was cooled and concentrated in vacuo, and the residue was lyophilized to provide the title compound (0.0104 g, quantitative). $^1$H-NMR (CDCl$_3$): δ 7.63-7.58 (m, 2H), 7.50-7.45 (m, 1H), 7.44-7.36 (m, 4H), 7.36-7.26 (m, 3H), 7.09 (dd, J=2.4 Hz, J=8.4 Hz, 1H), 6.85-6.78 (m, 2H), 6.09-6.05 (m, 1H), 3.90-3.83 (br m, 4H), 3.41 (s, 3H), 3.21-3.15 (br s, 4H), 2.36 (s, 3H). MS (ESI) (M+H)$^+$=518. HRMS calculated for (C$_{28}$H$_{28}$FN$_5$O$_2$S+H) (M+H)$^+$: 518.2026. Found (ESI): 518.2117.

Intermediate 30

7-Chloro-1,3-dihydro-5-(6-methoxy-2-pyridinyl)-1-methyl-2H-1,4-benzodiazepin-2-one

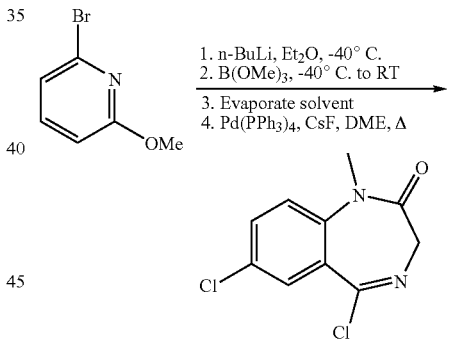

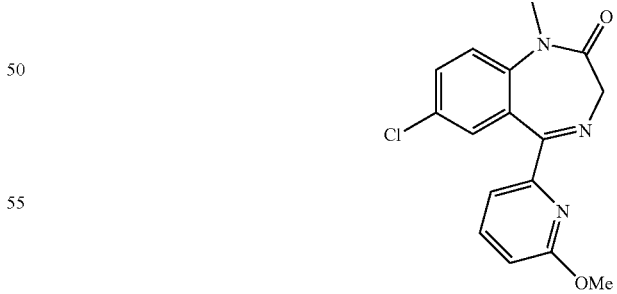

As illustrated in the scheme above, absolution of 2-bromo-6-methoxypyridine (0.022 mL, 0.18 mmol) in dry Et$_2$O (0.3 mL) was added to a solution of n-BuLi (0.12 mL of 1.6 M in hexanes, 0.19 mmol) maintained at −40° C. The reaction was stirred at −40° C. for 20 min., and then B(OMe)$_3$ (0.022 mL, 0.19 mmol) was added dropwise. The reaction was stirred at −40° C. for 30 min., and then at room temperature for 3.5 h. The reaction was concentrated in vacuo, anhydrous MeOH was added to the residue, and the reaction was concentrated in vacuo once again. Dry DME (0.8 mL), 5,7-dichloro-1,3-dihydro-1-methyl-2H-1,4-benzodiazepin-2-one (0.0392 g, 0.161 mmol), Pd(PPh$_3$)$_4$ (0.0093 g, 0.0080 mmol) and CsF (0.0612 g, 0.403 mmol) were added to the residue, and the mixture was heated to reflux for 15 h. Water (5 mL) and CH$_2$Cl$_2$ (5 mL) were added to the reaction mixture, and the layers were separated. The aqueous phase was extracted with additional CH$_2$Cl$_2$ (3×), and the combined organic phases were dried over Na$_2$SO$_4$, filtered, and concentrated in vacuo. Purification of the crude product by silica gel column chromatography (2:1 CH$_2$Cl$_2$:EtOAc) provided the title compound (0.029 g, 57%). $^1$H-NMR (CDCl$_3$): δ 7.77 (d, J=7.6 Hz, 1H), 7.71-7.64 (m, 2H), 7.49 (dd, J=2.4 Hz, J=8.8 Hz, 1H), 7.27 (d, J=8.8 Hz, 1H), 6.83 (d, J=8.0 Hz, 1H), 4.85 (d, J=10.8 Hz, 1H), 3.86 (d, J=10.4 Hz, 1H), 3.81 (s, 3H), 3.39 (s, 3H). MS (ESI) (M+H)$^+$=316.

Intermediate 31

3-Azido-7-chloro-1,3-dihydro-5-(6-methoxy-2-pyridinyl)-1-methyl-2H-1,4-benzodiazepin-2-one

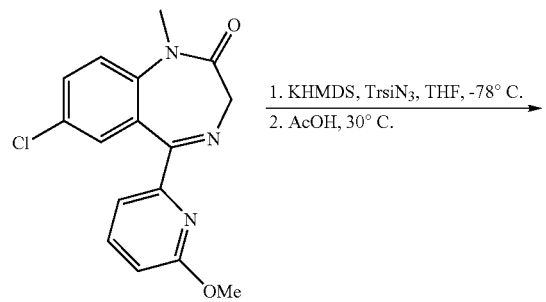

As illustrated in the scheme above and following General Procedure 6, KHMDS (0.19 mL of 0.5 M in toluene, 0.095 mmol), 7-chloro-1,3-dihydro-5-(6-methoxy-2-pyridinyl)-1-methyl-2H-1,4-benzodiazepin-2-one (0.0290 g, 0.0918 mmol), trisyl azide (0.0710 g, 0.229 mmol) and acetic acid (0.023 mL, 0.40 mmol) were combined. After workup, purification of the crude product by silica gel column chromatography (49:1 CH$_2$Cl$_2$:EtOAc) provided the title compound (0.0204 g, 62%). $^1$H-NMR (CDCl$_3$): δ 7.95 (d, J=7.2 Hz, 1H), 7.78-7.70 (m, 2H), 7.54 (dd, J=2.4 Hz, J=8.8 Hz, 1H), 7.31 (d, J=8.8 Hz, 1H), 6.87 (d, J=8.4 Hz, 1H), 4.64 (s, 1H), 3.80 (s, 3H), 3.44 (s, 3H). MS (ESI) (M+H)$^+$=357.

Intermediate 32

3-Amino-7-chloro-1,3-dihydro-5-(6-methoxy-2-pyridinyl)-1-methyl-2H-1,4-benzodiazepin-2-one

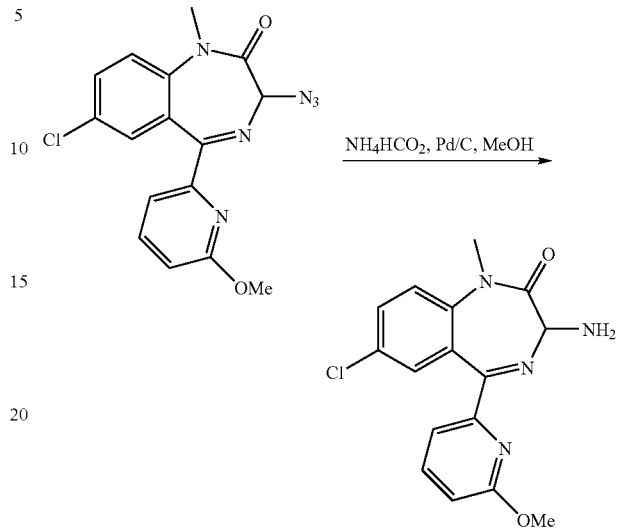

As illustrated in the scheme above, a suspension of Pd/C (0.005 g of 10% on C) in MeOH (0.5 mL) under N$_2$ was treated with ammonium formate (0.0252 g, 0.400 mmol). The mixture was stirred for 10 min. and then transferred via Pasteur pipette to a suspension of 3-azido-7-chloro-1,3-dihydro-5-(6-methoxy-2-pyridinyl)-1-methyl-2H-1,4-benzodiazepin-2-one (0.0204 g, 0.0572 mmol) in MeOH (1.2 mL). The resulting mixture was stirred at room temperature for 3 h and was then filtered through a small pad of Celite. The filtrate was concentrated in vacuo, and the residue was purified by silica gel column chromatography (100% EtOAc, followed by 4:1 CH$_2$Cl$_2$:EtOAc) to provide the title compound (0.0148 g, 78%). $^1$H-NMR (CDCl$_3$): δ 7.82 (dd, J=0.8 Hz, J=7.6 Hz, 1H), 7.71-7.66 (m, 2H), 7.51 (dd, 2.4 Hz, J=8.8 Hz, 1H), 7.28 (d, J=8.8 Hz, 1H), 6.83 (dd, J=0.8 Hz, J=8.4 Hz, 1H), 4.56 (s, 1H), 3.80 (s, 3H), 3.44 (s, 3H), 2.53 (br s, 2H). MS (ESI) (M+H)$^+$=331.

Example 26

N-[7-Chloro-2,3-dihydro-5-(6-methoxy-2-pyridinyl)-1-methyl-2-oxo-1H-1,4-benzodiazepin-3-yl]-N'-[2-methyl-4-(4-morpholinyl)phenyl]thiourea

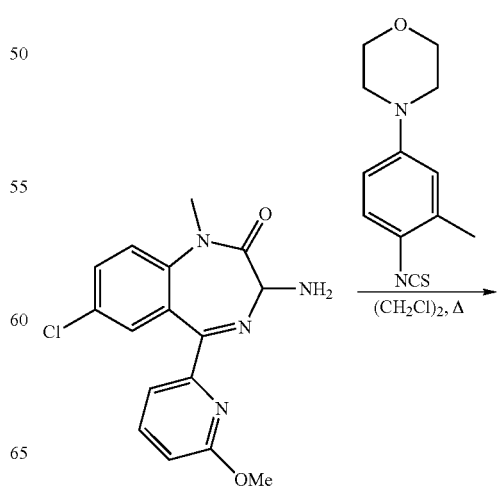

-continued

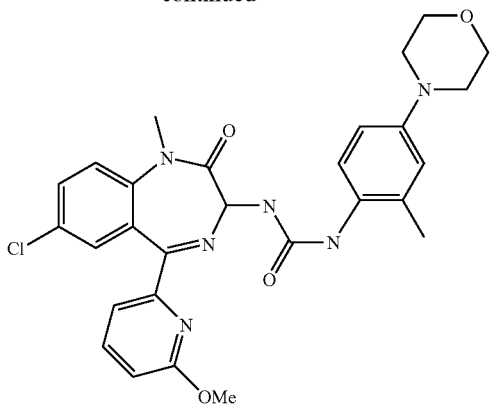

As illustrated in the scheme above, a solution of 3-amino-7-chloro-1,3-dihydro-5-(6-methoxy-2-pyridinyl)-1-methyl-2H-1,4-benzodiazepin-2-one (0.0113 g, 0.0342 mmol) and 4-(4-isothiocyanato-3-methylphenyl)morpholine (0.0080 g, 0.034 mmol) in $(CH_2Cl)_2$ (0.9 mL) was heated at 70° C. for 20 h. The reaction was cooled and concentrated in vacuo, and the residue was purified by silica gel column chromatography (2:1 $CH_2Cl_2$:EtOAc) to provide the title compound (0.0172 g, 89%) as a slightly yellow solid. $^1$H-NMR ($CDCl_3$): δ 7.79 (dd, J=0.8 Hz, J=7.2 Hz, 1H), 7.70-7.65 (m, 2H), 7.54 (dd, J=2.4 Hz, J=8.8 Hz, 1H), 7.42 (br s, 1H), 7.30 (d, J=8.8 Hz, 1H), 7.28-7.25 (m partially hidden under $CHCl_3$, 2H), 6.85-6.80 (m, 3H), 6.14 (m, 1H), 3.88-3.85 (m, 4H), 3.78 (s, 3H), 3.40 (s, 3H), 3.22-3.18 (m, 4H), 2.36 (s, 3H). MS (M+H$^+$=565.

What is claimed is:

1. A compound of Formula (I), or pharmaceutically acceptable salt, diastereomer, or enantiomer thereof:

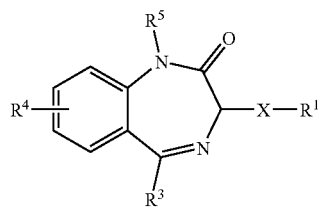

(I)

wherein $R^1$ is selected from optionally substituted acyl, optionally substituted alkyloxycarbonyl, optionally substituted alkyl, optionally substituted heteroalkyl, optionally substituted cycloalkyl, optionally substituted naphthyl, optionally substituted isoquinolyl, optionally substituted acridinyl, optionally substituted coumarinyl, optionally substituted carbazolyl, optionally substituted heterocyclyl, optionally substituted aryl-$C_{1-6}$alkyl, and optionally substituted heterocyclyl-$C_{1-6}$alkyl;

X is —NHC(=S)N($R^2$)—;

$R^3$ is substituted aryl, optionally substituted $C_{1-12}$alkyl, optionally substituted $C_{3-12}$cycloalkyl, or optionally substituted heterocyclyl;

$R^4$ is, at each position, independently halogen, optionally substituted alkyl, optionally substituted heteroalkyl, nitro, cyano, hydroxy, —OR$^6$, —SR$^6$, —S(=O)R$^6$, —S(=O)$_2$R$^6$, —C(=O)R$^6$, —C(=S)R$^6$, —NR$^7$R$^6$, —C(=O)NR$^7$R$^6$, —NR$^7$C(=O)R$^6$, —SO$_2$NR$^7$R$^6$, —NR$^7$SO$_2$R$^6$, or —C(=O)OR$^6$;

$R^5$, $R^6$ and $R^7$ are independently —H, or optionally substituted $C_{1-6}$alkyl; and $R^2$ is selected from —H, optionally substituted $C_{1-12}$alkyl, optionally substituted $C_{1-12}$heteroalkyl, substituted aryl, and optionally substituted heterocyclyl.

2. The compound of claim 1, or pharmaceutically acceptable salt, diastereomer, or enantiomer thereof wherein:

$R^1$ is optionally substituted naphthyl, optionally substituted isoquinolyl, optionally substituted acridinyl, optionally substituted coumarinyl, or optionally substituted carbazolyl, wherein said naphthyl, isoquinolyl, acridinyl, coumarinyl, and carbazolyl are optionally substituted by $C_{1-6}$alkyl, $C_{1-6}$heterocyclyl or amino;

$R^2$ is —H or $C_{1-3}$alkyl;

$R^3$ is substituted aryl, optionally substituted heteroaryl or optionally substituted cycloalkyl;

$R^4$ is halogen, or $C_{1-3}$alkyl; and $R^5$ is $C_{1-3}$alkyl.

3. The compound of claim 2, or pharmaceutically acceptable salt, diastereomer, or enantiomer thereof, wherein:

$R^1$ is optionally substituted naphthyl or optionally substituted isoquinolyl, wherein said naphthyl, and isoquinolyl are optionally substituted by $C_{1-6}$alkyl, $C_{1-6}$heterocyclyl or amino;

$R^2$ is —H or $C_{1-3}$alkyl;

$R^3$ is optionally substituted cyclohexyl, optionally substituted pyridyl, optionally substituted thienyl, or optionally substituted pyrimidinyl, wherein said cyclohexyl, pyridyl, thienyl, and pyrimidinyl are optionally substituted by halogen, methoxy, or $C_{1-3}$alkyl;

$R^4$ is halogen; and $R^5$ is methyl.

4. The compound of claim 1, or pharmaceutically acceptable salt, diastereomer, or enantiomer thereof, wherein:

$R^1$ is optionally substituted naphthyl or, optionally substituted isoquinolyl, wherein said naphthyl, and isoquinolyl are optionally substituted by $C_{1-6}$alkyl, $C_{1-6}$heterocyclyl or amino;

$R^2$ is $C_{1-3}$alkyl;

$R^3$ is optionally substituted cyclohexyl, substituted phenyl, substituted pyridyl, substituted thienyl, or substituted pyrimidinyl, wherein said cyclohexyl is optionally substituted by halogen, methoxy, or $C_{1-3}$alkyl;

$R^4$ is halogen; and $R^5$ is methyl.

5. The compound of claim 1, or pharmaceutically acceptable salt, diastereomer, or enantiomer thereof, wherein $R^5$ is —H or substituted $C_{1-6}$alkyl.

6. The compound of claim 1, or pharmaceutically acceptable salt, diastereomer, or enantiomer thereof, wherein:

$R^1$ is optionally substituted naphthy or optionally substituted isoquinolyl, wherein said naphthyl, and isoquinolyl are optionally substituted by $C_{1-6}$alkyl, $C_{1-6}$heterocyclyl or amino;

$R^2$ is —H or $C_{1-3}$alkyl;

$R^3$ is optionally substituted cyclohexyl, substituted phenyl, substituted pyridyl, substituted thienyl, or substituted pyrimidinyl, wherein said cyclohexyl is optionally substituted by halogen, methoxy, or $C_{1-3}$alkyl;

$R^4$ is halogen; and $R^5$ is substituted $C_{1-3}$alkyl.

7. A compound of Formula I, or pharmaceutically acceptable salt, diastereomer, or enantiomer thereof:

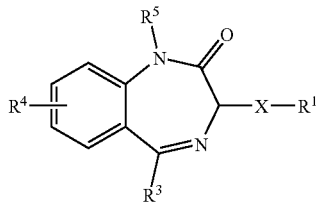

wherein:
  $R^1$ is optionally substituted phenyl, optionally substituted naphthyl, optionally substituted isoquinolyl, optionally substituted acridinyl, optionally substituted coumarinyl, optionally substituted carbazolyl, or a first divalent group selected from optionally substituted $C_{1-12}$alkylene and optionally substituted $C_{1-12}$heteroalkylene; wherein said naphthyl, isoquinolyl, acridinyl, coumarinyl, and carbazolyl are optionally substituted by $C_{1-6}$alkyl, $C_{1-6}$heterocyclyl or amino, wherein said $C_{1-12}$alkylene and $C_{1-12}$heteroalkylene are optionally substituted by $C_{1-6}$alkyl, aryl-$C_{1-6}$alkyl, aryl or heterocyclyl;
  X is —NHC(=S)N($R^2$)—;
  $R^2$ is —H, $C_{1-3}$alkyl, or a second divalent group selected from a single bond, an optionally substituted alkylene and an optionally substituted heteroalkylene;
  wherein said second divalent group together with said first divalent group forms a portion of a ring;
  $R^3$ is substituted aryl, optionally substituted heteroaryl or optionally substituted cycloalkyl;
  $R^4$ is halogen, or $C_{1-3}$alkyl; and
  $R^5$ is $C_{1-3}$alkyl.

8. The compound of claim 7, or pharmaceutically acceptable salt, diastereomer, or enantiomer thereof, wherein:
  $R^1$ is optionally substituted naphthyl, optionally substituted isoquinolyl, wherein said naphthyl, and isoquinolyl are optionally substituted by $C_{1-6}$alkyl, $C_{1-6}$heterocyclyl or amino;
  $R^1$ is —H or $C_{1-3}$alkyl;
  $R^3$ is optionally substituted cyclohexyl, substituted phenyl, substituted pyridyl, substituted thienyl, or substituted pyrimidinyl, wherein said cyclohexyl is optionally substituted by halogen, methoxy, or $C_{1-3}$alkyl;
  $R^4$ is halogen; and
  $R^5$ methyl.

9. The compound of claim 1, or pharmaceutically acceptable salt, diastereomer, or enantiomer thereof, wherein:
  $R^1$ is optionally substituted naphthyl, optionally substituted isoquinolyl, wherein said naphthyl and isoquinolyl are optionally substituted by $C_{1-6}$alkyl, $C_{1-6}$heterocyclyl or amino;
  $R^2$ is —H or $C_{1-3}$alkyl;
  $R^3$ is optionally substituted cyclohexyl, substituted phenyl, substituted pyridyl, substituted thienyl, or substituted pyrimidinyl, wherein said cyclohexyl is optionally substituted by halogen, methoxy, or $C_{1-3}$alkyl;
  $R^4$ is halogen; and
  $R^5$ methyl.

10. A mixture of two or more compounds selected from a compound of claim 1, a pharmaceutically acceptable salt thereof, a diasteromer thereof, and an enantiomer thereof.

11. A compound of Formula I, or pharmaceutically acceptable salt, diastereomer, or enantiomer thereof:

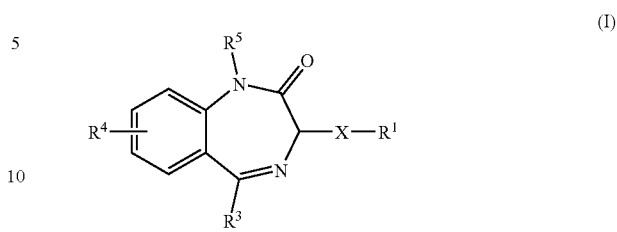

wherein;
  —X—$R^1$, in combination, is selected from —NHC(=S)N($R^2$)($R^1$) and

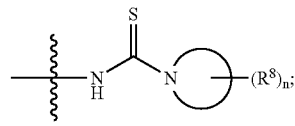

$R^1$ is optionally substituted phenyl, optionally substituted naphthyl, optionally substituted isoquinolyl, wherein said phenyl, naphthyl and isoquinolyl are optionally substituted by $C_{1-6}$alkyl, $C_{1-6}$heterocyclyl or amino;
  $R^2$ is —H, or $C_{1-3}$alkyl;

" 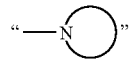 "

is a nitrogen containing heterocyclyl, which is optionally substituted by one or more —$R^8$, and which includes a bond on the nitrogen that links to other group of formula (I);
  $R^8$ is —H, optionally substituted aryl, optionally substituted heterocyclyl, optionally substituted $C_{1-6}$alkyl, —OH, or $C_{1-6}$alkoxy, wherein $R^8$ is optionally fused with the ring of " 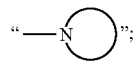 ";

$R^3$ is optionally substituted $C_{3-12}$cyclohexyl, substituted phenyl, optionally substituted pyridyl, optionally substituted thienyl, or optionally substituted pyrimidinyl, wherein said $C_{3-12}$cyclohexyl, phenyl, pyridyl, thienyl and pyrimidinyl are optionally substituted by halogen, methoxy, or $C_{1-3}$alkyl;
  $R^4$ is halogen; and
  $R^5$ is methyl.

12. A compound as claimed in claim 11, wherein said nitrogen containing heterocyclyl is selected from piperazinyl, morpholinyl, piperidyl, and pyrrolidinyl.

* * * * *